US008541475B2

(12) United States Patent
McElroy et al.

(10) Patent No.: US 8,541,475 B2
(45) Date of Patent: Sep. 24, 2013

(54) MAO-B INHIBITORS USEFUL FOR TREATING OBESITY

(75) Inventors: John Francis McElroy, Wilmington, DE (US); Robert J. Chorvat, West Chester, PA (US); Parthasarathi Rajagopalan, Chennai (IN)

(73) Assignee: Jenrin Discovery, Inc., Wilmington, DE (US)

( * ) Notice: Subject to any disclaimer, the term of this patent is extended or adjusted under 35 U.S.C. 154(b) by 104 days.

(21) Appl. No.: 12/650,642

(22) Filed: Dec. 31, 2009

(65) Prior Publication Data

US 2010/0168068 A1      Jul. 1, 2010

Related U.S. Application Data

(62) Division of application No. 11/445,044, filed on Jun. 1, 2006, now Pat. No. 7,649,115.

(60) Provisional application No. 60/686,585, filed on Jun. 2, 2005.

(51) Int. Cl.
*A61K 31/135* (2006.01)
*C07C 211/42* (2006.01)

(52) U.S. Cl.
USPC .......................................... 514/657; 564/428

(58) Field of Classification Search
USPC .......................................... 564/428; 514/657
See application file for complete search history.

(56) References Cited

U.S. PATENT DOCUMENTS

| | | | |
|---|---|---|---|
| 3,201,470 | A | 8/1965 | Huebner |
| 3,253,037 | A | 5/1966 | Huebner |
| 3,513,244 | A | 5/1970 | Gittos et al. |
| 5,786,390 | A | 7/1998 | Youdim |
| 6,271,263 | B1 | 8/2001 | Sklarz et al. |
| 6,303,650 | B1 | 10/2001 | Chorev et al. |
| 6,462,222 | B1 | 10/2002 | Chorev |
| 6,528,685 | B2 | 3/2003 | Cohen et al. |
| 2004/0010038 | A1 | 1/2004 | Blaugrund et al. |
| 2004/0068016 | A1 | 4/2004 | Haehne |
| 2005/0197365 | A1 | 9/2005 | Sterling et al. |
| 2006/0199974 | A1 | 9/2006 | Boulton et al. |

FOREIGN PATENT DOCUMENTS

| | | |
|---|---|---|
| EP | 0 538 134 A2 | 4/1993 |
| EP | 1 078 632 A1 | 2/2001 |
| GB | 1003686 | 9/1965 |
| WO | 96/21640 A1 | 7/1996 |
| WO | 03/072055 A2 | 9/2003 |
| WO | 2005/084205 A2 | 9/2005 |

OTHER PUBLICATIONS

Visentin, V. et al; Inhibition of Rat Fat Cell Lipolysis by Monoamine Oxidase and Semicarbazide-Sensitive Amine Oxidase Substrates; European Journal of Pharmacology 466 (2003) 235-243.
Visentin, V. et al; Alteration of Amine Oxidase Activity in the Adipose Tissue of Obese Subjects; Obesity Research vol. 12 No. 3 Mar. 2004 547-555.
Hubalek, F.; Inactivation of Purified Human Recombinant Monoamine Oxidases A and B by Rasagiline and Its Analogues; 2004 American Chemical Society; J. Med. Chem. 2004, 47, 1760-1766.
Binda, C.; Binding of E-Rasagiline-Related Inhibitors to Human Monoamine Oxidase: A Kinetic and Crystallographic Analysis; 2005 American Chemical Society; J. Med. Chem. 2005, 48, 8148-8154.
Tipton, K.F.; Inhibition of Rat Liver Monoamine Oxidase by -Methyl—and N-Propargyl-Amine Derivatives; Biochmeical Pharmacology, vol. 31, No. 7, pp. 1251-1255, 1982, Pergamon Press Ltd.
Diabetes Mellitus {DM} [online], [retrieved on Apr. 17, 2007]. Rerieved from the internet, URL; http://www.merck.com/mmpe/print/sec12/ch158/ch158b.html.
Cecil Textbook of Medicine, 20th edition (1996), vol. 2 pp. 2050-2057.
Cecil Textbook of Medicine, 29th edition (1996), vol. 2, p. 1992-1996.
FDA mulls drug to slow late-stage Alzheimer's [online], [retrieved on Sep. 23, 2003], retrieved from the internet, URL; http://www.cnn.com/2003/HEALTH/conditions/09/24/alzheimers.drug/ap/indexhtml>.
Extended European Search Report for EP 06771748.8-2103/1890690 (PCT/US2006/021142).

Primary Examiner — Shawquia Young
(74) Attorney, Agent, or Firm — Vance Intellectual Property, PC

(57) ABSTRACT

The invention provides novel compounds of formulae I and II:

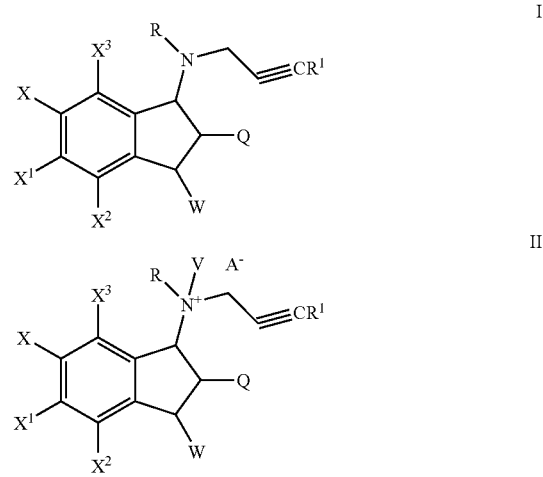

that are monoamine oxidase-B inhibitors, which can be useful in treating obesity, diabetes, and/or cardiometabolic disorders (e.g., hypertension, dyslipidemias, high blood pressure, and insulin resistance).

21 Claims, No Drawings

MAO-B INHIBITORS USEFUL FOR TREATING OBESITY

CROSS-REFERENCE TO RELATED APPLICATIONS

This application claims the priority benefit of U.S. Provisional Application No. 60/686,585 filed Jun. 2, 2005, now pending, which is incorporated herein by reference.

FIELD OF THE INVENTION

The present invention provides relates to compounds and pharmaceutical compositions thereof and methods of using the same for treating obesity. More particularly, the present invention relates to a novel method for treating obesity using an MAO-B inhibitor.

BACKGROUND OF THE INVENTION

L-Selegiline is a monoamine oxidase (MAO) inhibitor that was developed for the treatment of neurological disorders and is primarily used to treat Parkinson's disease. MAO is an enzyme responsible for metabolizing biogenic monoamines including serotonin, dopamine, histamine, and phenylethylamine. By inhibiting MAO located in the central nervous system (CNS), MAO inhibitors and their analogues increase the concentration of monoamines present within the brain synapses. This enhances monoamine-mediated neurotransmission, effectively treating neurological disorders such as Parkinson's disease and depression.

MAO enzymes are also located in a number of peripheral (non-CNS) tissues, including adipocytes, the cells that comprise body fat. The function of MAO enzymes in adipocytes has not been established. Currently, the only approved clinical use of L-selegiline and other MAO inhibitors is for the treatment of neurological disorders such as Parkinson's disease and depression.

Obesity is associated with an increase in the overall amount of adipose tissue (i.e., body fat), especially adipose tissue localized in the abdominal area. Obesity has reached epidemic proportions in the United States. The prevalence of obesity has steadily increased over the years among all racial and ethnic groups. According to the United States Surgeon General, 61% of the adult population and 14% of children are obese or overweight. Forty four million Americans are obese, with an additional eighty million deemed medically overweight. Obesity is responsible for more than 300,000 deaths annually, and will soon overtake tobacco usage as the primary cause of preventable death in the United States. Obesity is a chronic disease that contributes directly to numerous dangerous co-morbidities, including type 2 diabetes, cardiovascular disease, inflammatory diseases, premature aging, and some forms of cancer. Type 2 diabetes, a serious and life-threatening disorder with growing prevalence in both adult and childhood populations, is currently the $7^{th}$ leading cause of death in the United States. Since more than 80% of patients with type 2 diabetes are overweight, obesity is the greatest risk factor for developing type 2 diabetes. Increasing clinical evidence indicates that the best way to control type 2 diabetes is to reduce weight.

The most popular over-the counter drugs for the treatment of obesity, phenylpropanolamine and ephedrine, and the most popular prescription drug, fenfluramine, were removed from the marketplace as a result of safety concerns. Drugs currently approved for the long-term treatment of obesity fall into two categories: (a) Central Nervous System (CNS) appetite suppressants such as sibutramine and (b) gut lipase inhibitors such as orlistat. CNS appetite suppressants reduce eating behavior through activation of the 'satiety center' in the brain and/or by inhibition of the 'hunger center' in the brain. Gut lipase inhibitors reduce the absorption of dietary fat from the gastrointestinal (GI) tract. Although sibutramine and orlistat work through very different mechanisms, they share in common the same overall goal of reducing body weight secondary to reducing the amount of calories that reach the systemic circulation. Unfortunately, these indirect therapies produce only a modest initial weight loss (approximately 5% compared to approximately 2% with placebo) that is usually not maintained. After one or two years of treatment, most patients return to or exceed their starting weight. In addition, most approved anti-obesity therapeutics produce undesirable and often dangerous side effects that can complicate treatment and interfere with a patient's quality of life.

The lack of therapeutic effectiveness, coupled with the spiraling obesity epidemic, positions the 'treatment of obesity' as one of the largest and most urgent unmet medical needs. There is, therefore, a real and continuing need for the development of improved medications that treat or prevent obesity.

General MAO-B inhibitors such as selegiline have been clinically useful in the treatment of CNS disorders. They have now unexpectedly been discovered to also have anti-obesity activity. Even more surprising is that the anti-obesity activity mediated by these agents is outside of the CNS. This new discovery provides a novel approach for the prevention or treatment of obesity. Moreover, if the CNS effects of these compounds can be eliminated, their peripherally mediated anti-obesity properties should provide therapeutic agents with greater safety. It has, as a result, become highly desirable to find MAO-B inhibitors with limited or no CNS effects. Compounds of this sort are expected to be useful in treating obesity and the variety of co-morbidities to which it contributes.

SUMMARY OF THE INVENTION

Accordingly, in an aspect, the present invention provides novel MAO-B inhibitors or pharmaceutically acceptable salts that are useful to treat obesity, diabetes, and/or cardiometabolic disorders (e.g., hypertension, dyslipidemias, high blood pressure, and insulin resistance).

In another aspect, the present invention provides novel pharmaceutical compositions, comprising: a pharmaceutically acceptable carrier and a therapeutically effective amount of at least one of the compounds of the present invention or a pharmaceutically acceptable salt form thereof.

In another aspect, the present invention provides novel methods for treating obesity, diabetes, and/or cardiometabolic disorders (e.g., hypertension, dyslipidemias, high blood pressure, and insulin resistance), comprising: administering to a patient in need thereof a therapeutically effective amount of at least one of the compounds of the present invention or a pharmaceutically acceptable salt form thereof.

In another aspect, the present invention provides novel methods for treating CNS disorders, comprising: administering to a patient in need thereof a therapeutically effective amount of at least one of the compounds of the present invention or a pharmaceutically acceptable salt form thereof.

In another aspect, the present invention provides processes for preparing novel compounds.

In another aspect, the present invention provides novel compounds or pharmaceutically acceptable salts for use in therapy.

In another aspect, the present invention provides the use of novel compounds for the manufacture of a medicament for the treatment of obesity, diabetes, and/or cardiometabolic disorders.

These and other objects, which will become apparent during the following detailed description, have been achieved by the inventors' discovery that the presently claimed compounds or pharmaceutically acceptable salt forms thereof are expected to be effective MAO-B inhibitors.

DETAILED DESCRIPTION OF THE INVENTION

The present invention is based on the unexpected finding that an MAO-B inhibitor is capable of reducing the amount of adipose tissue (i.e., body fat) in a warm-blooded mammal. This finding was unexpected because body fat can be reduced despite little, if any, concomitant reduction in food intake.

In an embodiment, the present invention provides novel compound A or a stereoisomer or a pharmaceutically acceptable salt thereof:

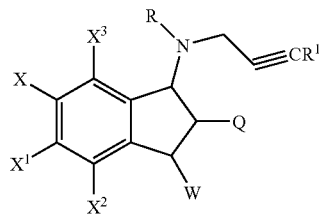

A wherein: Q, R, $R^1$, W, X, $X^1$, $X^2$, and $X^3$ are all independently selected from H and a group capable of reducing or limiting the CNS activity of compound A; and, provided that at least one of Q, R, $R^1$, W, X, $X^1$, $X^2$, and $X^3$ is other than H.

[1] In another embodiment, the present invention provides a novel compound of formula I or II, or a stereoisomer or pharmaceutically acceptable salt thereof:

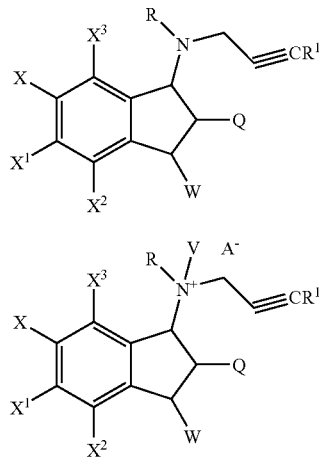

wherein:

R, at each occurrence, is independently selected from H, $C_{1-6}$ alkyl, $C_{2-6}$ alkenyl, and $C_{2-6}$ alkynyl;

$R^1$ is selected from H, $C_{1-6}$ alkyl, $C_{2-6}$ alkenyl, $C_{2-6}$ alkynyl, $(CH_2)_mCO_2R$, $C_{2-6}$ alkenyl-$CO_2R$, $CH_2CH(NHAc)CO_2R$, $CH_2CH(NHR)CO_2R$, and, $(CH_2)_nPO(OR)_2$;

$A^-$ is a counter ion;

V is selected from $O^-$, $C_{1-4}$ alkyl, $C_{2-4}$ alkenyl, and $C_{2-4}$ alkynyl;

X, $X^1$, $X^2$, and $X^3$ are independently selected from H, OR, $C_{1-6}$ alkyl, $C_{2-6}$ alkenyl, $C_{2-6}$ alkynyl, halogen, $CF_3$, nitro, —CN, $N(R)_2$, $(CH_2)_m$-tetrazole, $(CH_2)_nCO_2R$, $(CH_2)_nCONR_2$, $(CH_2)_nCN$, $O(CH_2)_nCN$, $O(CH_2)_n$-tetrazole, $O(CH_2)_nCO_2R$, $O(CH_2)_nCON(R)_2$, O—$C_{2-6}$ alkenyl-$CO_2R$, $O(CH_2)_nPO(OR)_2$, NR—$C_{2-4}$ alkenyl, $NRSO_2CH_3$, $NR(CH_2)_nCO_2R$, $NR(CH_2)_nCON(R)_2$, NR—$C_{2-4}$ alkenyl-$CO_2R$, $NR(CH_2)_nPO(OR)_2$, $NR(CH_2)_nSO_2OR$, $NR(CH_2)_n$-tetrazole, $SO_2NRCH_3$, $OCH_2CHMCONRCH_2CO_2R$, $CH_2$-aryl, $O(CH_2)_nPO(OR)_2$, $O(CH_2)_nSO_2OR$, $OCH_2(CH_2)_nN^+(CH_3)_3A^-$, $O(CH_2)_n$-biphenyl, $O(CH_2)_n$-biphenyl-$(CH_2)_mCO_2R$, $O(CH_2)_n$-biphenyl-$(CH_2)_m$tetrazole, $O(CH_2)_n$-biphenyl-$(CH_2)_mCN$, $O(CH_2)_n$-biphenyl-$(CH_2)_mCON(R)_2$, $NR(CH_2)_n$-biphenyl, $NR(CH_2)_n$-biphenyl-$(CH_2)_mCO_2R$, $NR(CH_2)_n$-biphenyl-$(CH_2)_m$tetrazole, $NR(CH_2)_n$-biphenyl-$(CH_2)_mCN$, $NR(CH_2)_n$-biphenyl-$(CH_2)_mCON(R)_2$, $O(CH_2)_n$-aryl, $O(CH_2)_n$-heteroaryl, $NR(CH_2)_n$-aryl, $NR(CH_2)_n$-heteroaryl, $O(CH_2)_n$-aryl$(CH_2)_mCO_2R$, $O(CH_2)_n$-aryl-$C_{2-6}$ alkenyl-$CO_2R$, $O(CH_2)_n$-aryl$(CH_2)_m$-tetrazole, $O(CH_2)_n$-aryl$(CH_2)_mCN$, $O(CH_2)_n$-aryl$(CH_2)_mCON(R)_2$, $O(CH_2)_n$-aryl$(CH_2)_m$—PO$(OR)_2$, $O(CH_2)_n$-aryl-$O(CH_2)_nCO_2R$, $O(CH_2)_n$-aryl-O—$C_{2-6}$ alkenyl-$CO_2R$, $O(CH_2)_n$-arylO$(CH_2)_n$-tetrazole, $O(CH_2)_n$-arylO$(CH_2)_nCN$, $O(CH_2)_n$-arylO$(CH_2)_nCON(R)_2$, $O(CH_2)_n$-arylO$(CH_2)_n$—PO$(OR)_2$, $O(CH_2)_n$-aryl-$NR(CH_2)_nCO_2R$, $O(CH_2)_n$-aryl-$NRC_{2-6}$ alkenyl-$CO_2R$, $O(CH_2)_n$-aryl-$NR(CH_2)_n$-tetrazole, $O(CH_2)_n$-aryl-$NR(CH_2)_nCN$, $O(CH_2)_n$-aryl-$NR(CH_2)_nCON(R)_2$, $O(CH_2)_n$-aryl-$NR(CH_2)_n$—PO$(OR)_2$, $NR(CH_2)_n$-aryl$(CH_2)_mCO_2R$, $NR(CH_2)_n$-aryl-$C_{2-6}$ alkenyl-$CO_2R$, $NR(CH_2)_n$-aryl$(CH_2)_m$-tetrazole, $NR(CH_2)_n$-aryl$(CH_2)_m$CN, $NR(CH_2)_n$-aryl$(CH_2)_mCON(R)_2$, $NR(CH_2)_n$-aryl$(CH_2)_m$—PO$(OR)_2$, $NR(CH_2)_n$-aryl-$NR(CH_2)_nCO_2R$, $NR(CH_2)_n$-aryl-NR—$C_{2-6}$ alkenyl-$CO_2R$, $NR(CH_2)_n$-aryl-$NR(CH_2)_n$ tetrazole, $NR(CH_2)_n$-aryl-$NR(CH_2)_nCN$, $NR(CH_2)_n$-aryl-$NR(CH_2)_nCON(R)_2$, $NR(CH_2)_n$-aryl-NR$(CH_2)_nPO(OR)_2$, $NR(CH_2)_n$-arylO$(CH_2)_nCO_2R$, $NR(CH_2)_n$-aryl-O—$C_{2-6}$ alkenyl-$CO_2R$, $NR(CH_2)_n$-aryl-O$(CH_2)_n$ tetrazole, $NR(CH_2)_n$-arylO$(CH_2)_nCN$, $NR(CH_2)_n$-aryl-O$(CH_2)_nCON(R)_2$, $NR(CH_2)_n$-arylO$(CH_2)_nPO(OR)_2$, $O(CH_2)_n$-heteroaryl$(CH_2)_mCO_2R$, $O(CH_2)_n$-heteroaryl-$C_{2-6}$ alkenyl-$CO_2R$, $O(CH_2)_n$-heteroaryl$(CH_2)_m$-tetrazole, $O(CH_2)_n$-heteroaryl-$(CH_2)_mCN$, $O(CH_2)_n$-heteroaryl$(CH_2)_mCON(R)_2$, $O(CH_2)_n$-heteroaryl$(CH_2)_m$—PO$(OR)_2$, $O(CH_2)_n$-heteroaryl-O$(CH_2)_nCO_2R$, $O(CH_2)_n$-heteroaryl-O—$C_{2-6}$ alkenyl-$CO_2R$, $O(CH_2)_n$-heteroarylO$(CH_2)_n$-tetrazole, $O(CH_2)_n$-heteroaryl $O(CH_2)_nCN$, $O(CH_2)_n$-heteroarylO$(CH_2)_nCON(R)_2$, $O(CH_2)_n$-heteroarylO$(CH_2)_n$—PO$(OR)_2$, $O(CH_2)_n$-heteroaryl-$NR(CH_2)_nCO_2R$, $O(CH_2)_n$-heteroaryl-NR—$C_{2-6}$ alkenyl-$CO_2R$, $O(CH_2)_n$-heteroaryl-$NR(CH_2)_n$-tetrazole, $O(CH_2)_n$-heteroaryl-$NR(CH_2)_nCN$, $O(CH_2)_n$-heteroaryl-$NR(CH_2)_nCON(R)_2$, $O(CH_2)_n$-heteroaryl-$NR(CH_2)_n$—PO$(OR)_2$, $NR(CH_2)_n$-heteroaryl$(CH_2)_mCO_2R$, $NR(CH_2)_n$-heteroaryl-$C_{2-6}$ alkenyl-$CO_2R$, $NR(CH_2)_n$-heteroaryl$(CH_2)_m$-tetrazole, $NR(CH_2)_n$-heteroaryl$(CH_2)_mCN$, $NR(CH_2)_n$-heteroaryl$(CH_2)_mCON(R)_2$, $NR(CH_2)_n$-heteroaryl$(CH_2)_m$—PO$(OR)_2$, $NR(CH_2)_n$-heteroaryl-$NR(CH_2)_nCO_2R$, $NR(CH_2)_n$-heteroaryl-NR—$C_{2-6}$ alkenyl-$CO_2R$, $NR(CH_2)_n$-heteroaryl-$NR(CH_2)_n$-tetrazole, $NR(CH_2)_n$ heteroaryl-NR$(CH_2)_nCN$, $NR(CH_2)_n$-heteroaryl-$NR(CH_2)_nCON(R)_2$, $NR(CH_2)_n$-heteroaryl-$NR(CH_2)_nPO(OR)_2$, $NR(CH_2)_n$-heteroaryl-O$(CH_2)_nCO_2R$, $NR(CH_2)_n$-heteroaryl-O—$C_{2-6}$ alkenyl-$CO_2R$, $NR(CH_2)_n$-heteroaryl-O$(CH_2)_n$-tetrazole, NR(CH$_2$)$_n$-heteroaryl-O(CH$_2$)$_n$CN, NR(CH$_2$)$_n$-heteroaryl-O(CH$_2$)$_n$CON(R)$_2$, NR(CH$_2$)$_n$-heteroarylO(CH$_2$)$_n$PO(OR)$_2$, where heteroaryl is a 5-12 membered ring system consisting of carbon atoms and from 1-4 heteroatoms selected from N, O, and S, and wherein aryl and heteroaryl are substituted with 1-2 X$^4$ and tetrazole is substituted with 0-1 R;

X$^4$ is selected from H, OR, O—C$_{2-6}$ alkenyl, C$_{1-6}$ alkyl, C$_{2-6}$ alkenyl, C$_{2-6}$ alkynyl, halogen, CF$_3$, nitro, —CN, C(O)NR$_2$, NRSO$_2$CH$_3$, and, SO$_2$N(R)C$_{1-6}$alkyl;

Q is selected from H, OH, C$_{1-6}$ alkoxy, O(CH$_2$)$_n$CO$_2$R, O(CH$_2$)$_n$CON(R)$_2$, O—C$_{2-6}$ alkenyl, O—C$_{2-6}$ alkenyl-CO$_2$R, OCH$_2$CH$_2$CONRCH$_2$CO$_2$R, OCH$_2$CHMCONRCH$_2$CO$_2$R, O(CH$_2$)$_n$PO(OR)$_2$, O(CH$_2$)$_n$SO$_2$OR, OCH$_2$CH(NHAc)CO$_2$R, OCH$_2$CH(NHR)CO$_2$R, O(CH$_2$)$_n$-aryl, and O(CH$_2$)$_n$-5-12 membered heteroaryl consisting of carbon atoms and from 1-4 heteroatoms selected from N, O, and S;

W is selected from H, CO$_2$R, CON(R)$_2$, CH$_2$OH, CH$_2$OC$_{1-6}$ alkyl, CH$_2$OC$_{2-6}$ alkenyl, CH$_2$O(CH$_2$)$_n$CO$_2$R, CH$_2$O(CH$_2$)$_n$CON(R)$_2$, CH$_2$O—C$_{2-6}$ alkenyl-CO$_2$R, CH$_2$OCH$_2$CH$_2$CONRCH$_2$CO$_2$R, CH$_2$OCH$_2$CHMCONRCH$_2$CO$_2$R, CH$_2$O(CH$_2$)$_n$PO(OR)$_2$, CH$_2$O(CH$_2$)$_n$SO$_2$OR, CH$_2$OCH$_2$CH(NHAc)CO$_2$R, CH$_2$OCH$_2$CH(NHR)CO$_2$R, CH$_2$O—C$_{2-6}$ alkenyl, and CH$_2$O(CH$_2$)$_n$CONH$_2$, CH$_2$O(CH$_2$)$_n$-aryl, and CH$_2$O(CH$_2$)$_n$-5-12 membered heteroaryl consisting of carbon atoms and from 1-4 heteroatoms selected from N, O, and S, and wherein heteroaryl is substituted with 1-2 X$^4$;

M is independently selected from H, C$_{1-6}$ alkyl, C$_{3-8}$ cycloalkyl, C$_{2-6}$ alkenyl, C$_{2-6}$ alkynyl, aryl, (CH$_2$)$_n$-aryl, heteroaryl, and (CH$_2$)$_n$-heteroaryl, where heteroaryl is a 5-12 membered ring system consisting of carbon atoms and from 1-4 heteroatoms selected from N, O, and S, and wherein aryl and heteroaryl are substituted with 1-2 X$^4$;

m is independently selected from 0, 1, 2, 3, and 4; and, n is independently selected from 1, 2, 3, and 4;

provided that at least one of X, X$^1$, X$^2$, and X$^3$ is other than H, alkyl, alkoxy, hydroxyl, and halo.

In another variant, the compounds of the present invention have no more than one acid functionality.

[2] In another embodiment, the present invention provides a novel compound of formula I$_1$ or II$_1$, or a stereoisomer or pharmaceutically acceptable salt thereof:

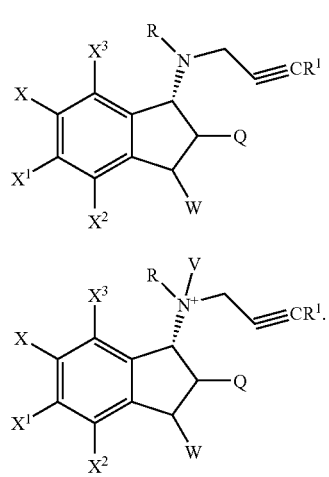

[3] In another embodiment, the present invention provides a novel compound of formula Ia, or a stereoisomer or pharmaceutically acceptable salt thereof:

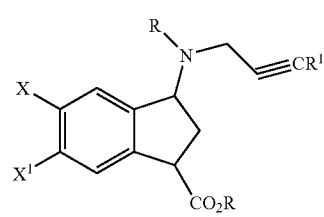

wherein:

R, at each occurrence, is independently selected from H and C$_{1-4}$ alkyl;

R$^1$ is selected from H and C$_{1-4}$ alkyl;

X and X$^1$ are independently selected from H, OR, C$_{1-4}$ alkyl, C$_{2-4}$ alkenyl, C$_{2-4}$ alkenyl, C$_{2-4}$ alkynyl, halogen, CF$_3$, nitro, —CN, O(CH$_2$)$_n$CON(R)$_2$, O—C$_{2-4}$ alkenyl, N(R)$_2$, NRSO$_2$CH$_3$, SO$_2$NRCH$_3$, CH$_2$N(C$_{1-4}$ alkyl)$_2$, CH$_2$-aryl, CH$_2$-heteroaryl, O(CH$_2$)$_n$-aryl, O(CH$_2$)$_n$-heteroaryl, NR(CH$_2$)$_n$-aryl, NR(CH$_2$)$_n$-heteroaryl, O(CH$_2$)$_n$-aryl-(CH$_2$)$_m$CON(R)$_2$, O(CH$_2$)$_n$-aryl-O(CH$_2$)$_n$CON(R)$_2$, O(CH$_2$)$_n$-aryl-NR(CH$_2$)$_n$CON(R)$_2$, O(CH$_2$)$_n$heteroaryl-(CH$_2$)$_m$CON(R)$_2$, O(CH$_2$)$_n$-heteroaryl-O(CH$_2$)$_n$CON(R)$_2$, O(CH$_2$)$_n$-heteroaryl-NR(CH$_2$)$_n$CON(R)$_2$, NR(CH$_2$)$_n$-aryl-(CH$_2$)$_m$CON(R)$_2$, NR(CH$_2$)$_n$-aryl-O(CH$_2$)$_n$CON(R)$_2$, NR(CH$_2$)$_n$-aryl-NR(CH$_2$)$_n$CON(R)$_2$, NR(CH$_2$)$_n$-heteroaryl-O(CH$_2$)$_n$CON(R)$_2$, NR(CH$_2$)$_n$-heteroaryl-(CH$_2$)$_n$CON(R)$_2$, NR(CH$_2$)$_n$-heteroaryl-NR(CH$_2$)$_n$CON(R)$_2$, O(CH$_2$)$_n$-biphenyl, O(CH$_2$)$_n$-biphenyl-CN, O(CH$_2$)$_n$-biphenyl-CONH$_2$, NR(CH$_2$)$_n$-biphenyl, NR(CH$_2$)$_n$-biphenyl-CN, and NR(CH$_2$)$_n$-biphenyl-CONH$_2$, where heteroaryl is a 5-10 membered ring system consisting of carbon atoms and from 1-4 heteroatoms selected from N, O, and S, and wherein aryl and heteroaryl are substituted with 1-2 X$^4$;

X$^4$ is selected from H, OH, C$_{1-4}$ alkoxy, C$_{1-4}$ alkyl, C$_{2-4}$ alkenyl, C$_{2-4}$ alkynyl, halogen, CF$_3$, nitro, —CN, C(O)NR$_2$, NRSO$_2$CH$_3$, and, SO$_2$N(R)C$_{1-6}$alkyl;

n is independently selected from 1, 2, and 3;

provided that at least one of X and X$^1$ is other than H, alkyl, alkoxy, hydroxyl, and halo.

[3a] In another embodiment, the present invention provides a novel compound of formula Ia, or a stereoisomer or pharmaceutically acceptable salt thereof, wherein:

one of X and X$^1$ is H and the other is selected from OH, C$_{1-4}$ alkyl, C$_{2-4}$ alkenyl, C$_{2-4}$ alkynyl, halogen, CF$_3$, nitro, —CN, C$_{1-4}$ alkoxy, O(CH$_2$)$_n$CON(R)$_2$, O—C$_{2-4}$ alkenyl, N(R)$_2$, NRSO$_2$CH$_3$, SO$_2$NRCH$_3$, CH$_2$N(C$_{1-4}$ alkyl)$_2$, CH$_2$-aryl, CH$_2$-heteroaryl, O(CH$_2$)$_n$-aryl, O(CH$_2$)$_n$-heteroaryl, NR(CH$_2$)$_n$-aryl, NR(CH$_2$)$_n$-heteroaryl, O(CH$_2$)$_n$-aryl-(CH$_2$)$_m$CON(R)$_2$, O(CH$_2$)$_n$-aryl-O(CH$_2$)$_n$CON(R)$_2$, O(CH$_2$)$_n$-aryl-NR(CH$_2$)$_n$CON(R)$_2$, O(CH$_2$)$_n$-heteroaryl-(CH$_2$)$_m$CON(R)$_2$, O(CH$_2$)$_n$-heteroaryl-O(CH$_2$)$_n$CON(R)$_2$, O(CH$_2$)$_n$-heteroaryl-NR(CH$_2$)$_n$CON(R)$_2$, NR(CH$_2$)$_n$-aryl-(CH$_2$)$_m$CON(R)$_2$, NR(CH$_2$)$_n$-aryl-O(CH$_2$)$_n$CON(R)$_2$, NR(CH$_2$)$_n$-aryl-NR(CH$_2$)$_n$CON(R)$_2$, NR(CH$_2$)$_n$-heteroaryl-O(CH$_2$)$_n$CON(R)$_2$, NR(CH$_2$)$_n$-heteroaryl-(CH$_2$)$_m$CON(R)$_2$, NR(CH$_2$)$_n$-heteroaryl-NR(CH$_2$)$_n$CON(R)$_2$, O(CH$_2$)$_n$-biphenyl, O(CH$_2$)$_n$-biphenyl-CN, O(CH$_2$)$_n$-biphenyl-CONH$_2$, NR(CH$_2$)$_n$-biphenyl, NR(CH$_2$)$_n$-biphenyl-CN, and NR(CH$_2$)$_n$-biphenyl-CONH$_2$, where heteroaryl is a 5-10 membered ring system consisting of carbon atoms and from 1-4 heteroatoms selected from N, O, and S, and wherein aryl and heteroaryl are substituted with 1-2 $X^4$;

provided that at least one of X and $X^1$ is other than H, alkyl, alkoxy, hydroxyl, and halo.

[4] In another embodiment, the present invention provides a novel compound of formula $Ia_1$, or a stereoisomer or pharmaceutically acceptable salt thereof:

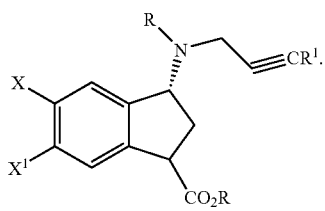

[5] In another embodiment, the present invention provides a novel compound of formula Ib, or a stereoisomer or pharmaceutically acceptable salt thereof:

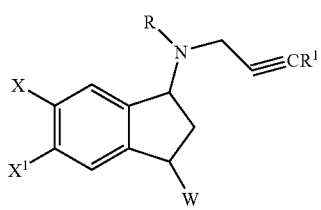

wherein:

R, at each occurrence, is independently selected from H and $C_{1-4}$ alkyl;

$R^1$ is selected from H, $C_{1-4}$ alkyl, $(CH_2)_mCO_2R$, $C_{2-4}$ alkenyl-$CO_2R$, $CH_2CH(NHAc)CO_2R$, $CH_2CH(NHR)CO_2R$, and, $(CH_2)_nPO(OR)_2$;

X and $X^1$ are independently selected from H, OR, $C_{1-4}$ alkyl, $C_{2-4}$ alkenyl, $C_{2-4}$ alkynyl, halogen, $CF_3$, nitro, —CN, $O(CH_2)_nCON(R)_2$, O—$C_{2-4}$ alkenyl, $N(R)_2$, $NRSO_2CH_3$, $SO_2NRCH_3$, $CH_2N(C_{1-4}$ alkyl$)_2$, $CH_2$-aryl, $CH_2$-heteroaryl, $O(CH_2)_n$-aryl, $O(CH_2{\bf 0}_n$-heteroaryl, $NR(CH_2)_n$-aryl, $NR(CH_2)_n$-heteroaryl, $O(CH_2)_n$-aryl-$(CH_2)_mCON(R)_2$, $O(CH_2)_n$-aryl-$O(CH_2)_nCON(R)_2$, $O(CH_2)_n$-aryl-$NR(CH_2)_nCON(R)_2$, $O(CH_2)_n$-heteroaryl-$(CH_2)_mCON(R)_2$, $O(CH_2)_n$-heteroaryl-$O(CH_2)_nCON(R)_2$, $O(CH_2)_n$-heteroaryl-$NR(CH_2)_nCON(R)_2$, $NR(CH_2)_n$-aryl-$(CH_2)_mCON(R)_2$, $NR(CH_2)_n$-aryl-$O(CH_2)_nCON(R)_2$, $NR(CH_2)_n$-aryl-$NR(CH_2)_nCON(R)_2$, $NR(CH_2)_n$-heteroaryl-$O(CH_2)_nCON(R)_2$, $NR(CH_2)_n$-heteroaryl-$(CH_2)_mCON(R)_2$, $NR(CH_2)_n$-heteroaryl-$NR(CH_2)_nCON(R)_2$, $O(CH_2)_n$-biphenyl, $O(CH_2)_n$-biphenyl-CN, $O(CH_2)_n$-biphenyl-$CONH_2$, $NR(CH_2)_n$-biphenyl, $NR(CH_2)_n$-biphenyl-CN, $NR(CH_2)_n$-biphenyl-$CONH_2$, where heteroaryl is a 5-10 membered ring system consisting of carbon atoms and from 1-4 heteroatoms selected from N, O, and S, and wherein aryl and heteroaryl are substituted with 1-2 $X^4$;

$X^4$ is selected from H, OH, $C_{1-4}$ alkoxy, $C_{1-4}$ alkyl, $C_{2-4}$ alkenyl, $C_{2-4}$ alkynyl, halogen, $CF_3$, nitro, —CN, $C(O)NR_2$, $NRSO_2CH_3$, and, $SO_2N(R)C_{1-6}$alkyl;

W is selected from H, $CH_2OH$, $CH_2OC_{1-4}$ alkyl, $CH_2OC_{2-4}$ alkenyl, $CH_2O(CH_2)_nCO_2R$, $CH_2O$—$C_{2-4}$ alkenyl-$CO_2R$, $CH_2O(CH_2)_nCON(R)_2$, $CH_2O(CH_2)_nPO(OR)_2$, $CH_2O(CH_2)_n$-aryl, and $CH_2O(CH_2)_n$-5-10 membered heteroaryl consisting of carbon atoms and from 1-4 heteroatoms selected from N, O, and S;

m is independently selected from 0, 1, and 2; and,
n is independently selected from 1, 2, and 3;

provided that at least one of X and $X^1$ is other than H, alkyl, alkoxy, hydroxyl, and halo.

[5a] In another embodiment, the present invention provides a novel compound of formula Ib, or a stereoisomer or pharmaceutically acceptable salt thereof, wherein:

one of X and $X^1$ is H and the other is selected from OH, $C_{1-4}$ alkyl, $C_{2-4}$ alkenyl, $C_{2-4}$ alkynyl, halogen, $CF_3$, nitro, —CN, $C_{1-4}$ alkoxy, $O(CH_2)_nCON(R)_2$, O—$C_{2-4}$ alkenyl, $N(R)_2$, $NRSO_2CH_3$, $SO_2NRCH_3$, $CH_2N(C_{1-4}$ alkyl$)_2$, $CH_2$-aryl, $CH_2$-heteroaryl, $O(CH_2)_n$-aryl, $O(CH_2)_n$-heteroaryl, $NR(CH_2)_n$-aryl, $NR(CH_2)_n$-heteroaryl, $O(CH_2)_n$-aryl-$(CH_2)_mCON(R)_2$, $O(CH_2)_n$-aryl-$O(CH_2)_nCON(R)_2$, $O(CH_2)_n$-aryl-$NR(CH_2)_nCON(R)_2$, $O(CH_2)_n$-heteroaryl-$(CH_2)_mCON(R)_2$, $O(CH_2)_n$-heteroaryl-$O(CH_2)_nCON(R)_2$, $O(CH_2)_n$-heteroaryl-$NR(CH_2)_nCON(R)_2$, $NR(CH_2)_n$-aryl-$(CH_2)_mCON(R)_2$, $NR(CH_2)_n$-aryl-$O(CH_2)_nCON(R)_2$, $NR(CH_2)_n$-aryl-$NR(CH_2)_nCON(R)_2$, $NR(CH_2)_n$-heteroaryl-$O(CH_2)_nCON(R)_2$, $NR(CH_2)_n$-heteroaryl-$(CH_2)_mCON(R)_2$, $NR(CH_2)_n$-heteroaryl-$NR(CH_2)_nCON(R)_2$, $O(CH_2)_n$-biphenyl, $O(CH_2)_n$-biphenyl-CN, $O(CH_2)_n$-biphenyl-$CONH_2$, $NR(CH_2)_n$-biphenyl, $NR(CH_2)_n$-biphenyl-CN, $NR(CH_2)_n$-biphenyl-$CONH_2$, where heteroaryl is a 5-10 membered ring system consisting of carbon atoms and from 1-4 heteroatoms selected from N, O, and S, and wherein aryl and heteroaryl are substituted with 1-2 $X^4$;

provided that at least one of X and $X^1$ is other than H, alkyl, alkoxy, hydroxyl, and halo.

[6] In another embodiment, the present invention provides a novel compound of formula $Ib_1$, or a stereoisomer or pharmaceutically acceptable salt thereof:

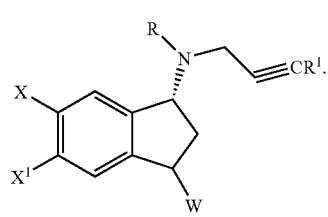

[7] In another embodiment, the present invention provides a novel compound of formula Ic, or a stereoisomer or pharmaceutically acceptable salt thereof:

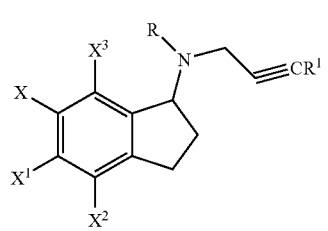

wherein:

R, at each occurrence, is independently selected from H, $C_{1-4}$ alkyl, $C_{2-4}$ alkenyl, and $C_{2-4}$ alkynyl;

$R^1$ is selected from H and $C_{1-4}$ alkyl;

X, $X^1$, $X^2$, and $X^3$ are independently selected from H, OR, $C_{1-4}$ alkyl, $C_{2-4}$ alkenyl, $C_{2-4}$ alkynyl, halogen, $CF_3$, nitro, —CN, $N(R)_2$, $(CH_2)_m$-tetrazole, $(CH_2)_nCO_2R$, $(CH_2)_nCONR_2$, $(CH_2)_nCN$, $O(CH_2)_nCN$, $O(CH_2)_n$-tetrazole, $O(CH_2)_nCO_2R$, $O(CH_2)_nCON(R)_2$, O—$C_{2-4}$ alkenyl-$CO_2R$, $O(CH_2)_nPO(OR)_2$, NR—$C_{2-4}$ alkenyl, $NRSO_2CH_3$, $NR(CH_2)_nCO_2R$, $NR(CH_2)_nCON(R)_2$, NR—$C_{2-4}$ alkenyl-$CO_2R$, $NR(CH_2)_nPO(OR)_2$, $NR(CH_2)_nSO_2OR$, $NR(CH_2)_n$-tetrazole, $SO_2NRCH_3$, $OCH_2CHMCONRCH_2CO_2R$, $CH_2$-aryl, $O(CH_2)_nPO(OR)_2$, $O(CH_2)_nSO_2OR$, $OCH_2(CH_2)_nN^+(CH_3)_3A^-$, $O(CH_2)_n$-biphenyl, $O(CH_2)_n$-biphenyl-$(CH_2)_mCO_2R$, $O(CH_2)_n$-biphenyl-$(CH_2)_m$tetrazole, $O(CH_2)_n$-biphenyl-$(CH_2)_mCN$, $O(CH_2)_n$-biphenyl-$(CH_2)_mCON(R)_2$, $NR(CH_2)_n$-biphenyl, $NR(CH_2)_n$-biphenyl-$(CH_2)_mCO_2R$, $NR(CH_2)_n$-biphenyl-$(CH_2)_m$tetrazole, $NR(CH_2)_n$-biphenyl-$(CH_2)_mCN$, $NR(CH_2)_n$-biphenyl-$(CH_2)_mCON(R)_2$, $O(CH_2)_n$-aryl, $O(CH_2)_n$-heteroaryl, $NR(CH_2)_n$-aryl, $NR(CH_2)_n$-heteroaryl, $O(CH_2)_n$-aryl$(CH_2)_mCO_2R$, $O(CH_2)_n$-aryl-$C_{2-4}$ alkenyl-$CO_2R$, $O(CH_2)_n$-aryl$(CH_2)_m$-tetrazole, $O(CH_2)_n$-aryl$(CH_2)_mCN$, $O(CH_2)_n$-aryl$(CH_2)_mCON(R)_2$, $O(CH_2)_n$-aryl$(CH_2)_m$—PO$(OR)_2$, $O(CH_2)_n$-aryl-$O(CH_2)_nCO_2R$, $O(CH_2)_n$-aryl-O—$C_{2-4}$ alkenyl-$CO_2R$, $O(CH_2)_n$-arylO$(CH_2)_n$-tetrazole, $O(CH_2)_n$-arylO$(CH_2)_nCN$, $O(CH_2)_n$-arylO$(CH_2)_{nCON(R)2}$, $O(CH_2)_n$-arylO$(CH_2)_nPO(OR)_2$, $O(CH_2)_n$-aryl-$NR(CH_2)_nCO_2R$, $O(CH_2)_n$-aryl-$NRC_{2-4}$ alkenyl-$CO_2R$, $O(CH_2)_n$-aryl-$NR(CH_2)_n$-tetrazole, $O(CH_2)_n$-aryl-$NR(CH_2)_nCN$, $O(CH_2)_n$-aryl-$NR(CH_2)_nCON(R)_2$, $O(CH_2)_n$-aryl-$NR(CH_2)_n$—PO$(OR)_2$, $NR(CH_2)_n$-aryl$(CH_2)_mCO_2R$, $NR(CH_2)_n$-aryl-$C_{2-4}$ alkenyl-$CO_2R$, $NR(CH_2)_n$-aryl$(CH_2)_m$-tetrazole, $NR(CH_2)_n$-aryl$(CH_2)_mCN$, $NR(CH_2)_n$-aryl$(CH_2)_mCON(R)_2$, $NR(CH_2)_n$-aryl$(CH_2)_m$—PO$(OR)_2$, $NR(CH_2)_n$-aryl-$NR(CH_2)_nCO_2R$, $NR(CH_2)_n$-aryl-NR-$C_{2-4}$alkenyl-$CO_2R$, $NR(CH_2)_n$-aryl-$NR(CH_2)_n$-tetrazole, $NR(CH_2)_n$-aryl-$NR(CH_2)_nCN$, $NR(CH_2)_n$-aryl-$NR(CH_2)_nCON(R)_2$, $NR(CH_2)_n$-aryl-$NR(CH_2)_nPO(OR)_2$, $NR(CH_2)_n$-arylO$(CH_2)_nCO_2R$, $NR(CH_2)_n$-aryl-O—$C_{2-4}$ alkenyl-$CO_2R$, $NR(CH_2)_n$-aryl-O$(CH_2)_n$-tetrazole, $NR(CH_2)_n$-arylO$(CH_2)_nCN$, $NR(CH_2)_n$-aryl-O$(CH_2)_nCON(R)_2$, $NR(CH_2)_n$-arylO$(CH_2)_nPO(OR)_2$, $O(CH_2)_n$-heteroaryl$(CH_2)_mCO_2R$, $O(CH_2)_n$-heteroaryl-$C_{2-4}$ alkenyl-$CO_2R$, $O(CH_2)_n$-heteroaryl$(CH_2)_m$-tetrazole, $O(CH_2)_n$-heteroaryl-$(CH_2)_mCN$, $O(CH_2)_n$-heteroaryl$(CH_2)_mCON(R)_2$, $O(CH_2)_n$-heteroaryl$(CH_2)_m$—PO$(OR)_2$, $O(CH_2)_n$-heteroaryl-$O(CH_2)_nCO_2R$, $O(CH_2)_n$-heteroaryl-O—$C_{2-4}$ alkenyl-$CO_2R$, $O(CH_2)_n$-heteroarylO$(CH_2)_n$-tetrazole, $O(CH_2)_n$-heteroaryl O$(CH_2)_nCN$, $O(CH_2)_n$-heteroarylO$(CH_2)_nCON(R)_2$, $O(CH_2)_n$-heteroarylO$(CH_2)_n$—PO$(OR)_2$, $O(CH_2)_n$-heteroaryl-$NR(CH_2)_nCO_2R$, $O(CH_2)_n$-heteroaryl-NR—$C_{2-4}$ alkenyl-$CO_2R$, $O(CH_2)_n$-heteroaryl-$NR(CH_2)_n$-tetrazole, $O(CH_2)_n$-heteroaryl-$NR(CH_2)_nCN$, $O(CH_2)_n$-heteroaryl-$NR(CH_2)_nCON(R)_2$, $O(CH_2)_n$-heteroaryl-$NR(CH_2)_n$—PO$(OR)_2$, $NR(CH_2)_n$-heteroaryl$(CH_2)_mCO_2R$, $NR(CH_2)_n$-heteroaryl-$C_{2-4}$ alkenyl-$CO_2R$, $NR(CH_2)_n$-heteroaryl$(CH_2)_m$-tetrazole, $NR(CH_2)_n$-heteroaryl$(CH_2)_mCN$, $NR(CH_2)_n$-heteroaryl$(CH_2)_mCON(R)_2$, $NR(CH_2)_n$-heteroaryl$(CH_2)_m$—PO$(OR)_2$, $NR(CH_2)_n$-heteroaryl-$NR(CH_2)_nCO_2R$, $NR(CH_2)_n$-heteroaryl-NR—$C_{2-4}$alkenyl-$CO_2R$, $NR(CH_2)_n$-heteroaryl-$NR(CH_2)_n$tetrazole, $NR(CH_2)_n$ heteroaryl-NR$(CH_2)_nCN$, $NR(CH_2)_n$-heteroaryl-$NR(CH_2)_nCON(R)_2$, $NR(CH_2)_n$-heteroaryl-$NR(CH_2)_nPO(OR)_2$, $NR(CH_2)_n$-heteroaryl-O$(CH_2)_nCO_2R$, $NR(CH_2)_n$-heteroaryl-O—$C_{2-4}$ alkenyl-$CO_2R$, $NR(CH_2)_n$-heteroaryl-O$(CH_2)_n$-tetrazole, $NR(CH_2)_n$-heteroaryl-O$(CH_2)_nCN$, $NR(CH_2)_n$-heteroaryl-O$(CH_2)_nCON(R)_2$, $NR(CH_2)_n$-heteroarylO$(CH_2)_nPO(OR)_2$, where heteroaryl is a 5-10 membered ring system consisting of carbon atoms and from 1-4 heteroatoms selected from N, O, and S, and wherein aryl and heteroaryl are substituted with 1-2 $X^4$ and tetrazole is substituted with 0-1 R;

$X^4$ is selected from H, OR, $C_{1-4}$ alkoxy, $C_{1-4}$ alkyl, $C_{2-4}$ alkenyl, $C_{2-4}$ alkynyl, halogen, $CF_3$, nitro, —CN, C(O)$NR_2$, $NRSO_2CH_3$, and, $SO_2N(R)C_{1-6}$alkyl;

$A^-$ is selected from Cl and Br;

M is independently selected from H, $C_{1-4}$ alkyl, $C_{3-6}$ cycloalkyl, $C_{2-4}$ alkenyl, $C_{2-4}$ alkynyl, aryl, $(CH_2)_n$-aryl, heteroaryl, and $(CH_2)_n$-heteroaryl, where heteroaryl is a 5-12 membered ring system consisting of carbon atoms and from 1-4 heteroatoms selected from N, O, and S; and, m is independently selected from 0, 1, and 2; and, n is independently selected from 1, 2, and 3;

provided that at least one of X, $X^1$, $X^2$, and $X^3$ is other than H, alkyl, alkoxy, hydroxyl, and halo.

[7a] In another embodiment, the present invention provides a novel compound of formula Ic, or a stereoisomer or pharmaceutically acceptable salt thereof, wherein:

three of X, $X^1$, $X^2$, and $X^3$ are H and the fourth is selected from OH, $C_{1-4}$ alkyl, $C_{2-4}$ alkenyl, $C_{2-4}$ alkynyl, halogen, $CF_3$, nitro, $C_{1-4}$ alkoxy, —CN, $N(R)_2$, $(CH_2)_m$-tetrazole, $(CH_2)_nCO_2R$, $(CH_2)_nCONR_2$, $(CH_2)_nCN$, $O(CH_2)_nCN$, $O(CH_2)_n$-tetrazole, $O(CH_2)_n(CO_2R$, $O(CH_2)_nCON(R)_2$, O—$C_{2-4}$ alkenyl-$CO_2R$, $O(CH_2)_nPO(OR)_2$, NR—$C_{2-4}$ alkenyl, $NRSO_2CH_3$, $NR(CH_2)_nCO_2R$, $NR(CH_2)_nCON(R)_2$, NR—$C_{2-4}$ alkenyl-$CO_2R$, $NR(CH_2)_nPO(OR)_2$, $NR(CH_2)_nSO_2OR$, $NR(CH_2)_n$-tetrazole, $SO_2NRCH_3$, $OCH_2CHMCONRCH_2CO_2R$, $CH_2$-aryl, $O(CH_2)_nPO(OR)_2$, $O(CH_2)_nSO_2OR$, $OCH_2(CH_2)_nN^+(CH_3)_3A^-$, $O(CH_2)_n$-biphenyl, $O(CH_2)_n$-biphenyl-$(CH_2)_nCO_2R$, $O(CH_2)_n$-biphenyl-$(CH_2)_m$tetrazole, $O(CH_2)_n$-biphenyl-$(CH_2)_mCN$, $O(CH_2)_n$-biphenyl-$(CH_2)_mCON(R)_2$, $NR(CH_2)_n$-biphenyl, $NR(CH_2)_n$-biphenyl-$(CH_2)_mCO_2R$, $NR(CH_2)_n$-biphenyl-$(CH_2)_m$tetrazole, $NR(CH_2)_n$-biphenyl-$(CH_2)_mCN$, $NR(CH_2)_n$-biphenyl-$(CH_2)_mCON(R)_2$, $O(CH_2)_n$-aryl, $O(CH_2)_n$-heteroaryl, $NR(CH_2)_n$-aryl, $NR(CH_2)_n$-heteroaryl, $O(CH_2)_n$-aryl$(CH_2)_mCO_2R$, $O(CH_2)_n$-aryl-$C_{2-4}$ alkenyl-$CO_2R$, $O(CH_2)_n$-aryl$(CH_2)_m$-tetrazole, $O(CH_2)_n$-aryl$(CH_2)_mCN$, $O(CH_2)_n$-aryl$(CH_2)_mCON(R)_2$, $O(CH_2)_n$-aryl$(CH_2)_m$—PO$(OR)_2$, $O(CH_2)_n$-aryl-O$(CH_2)_nCO_2R$, $O(CH_2)_n$-aryl-O—$C_{2-4}$ alkenyl-$CO_2R$, $O(CH_2)_n$-arylO$(CH_2)_n$-tetrazole, $O(CH_2)_n$-arylO$(CH_2)_nCN$, $O(CH_2)_n$-arylO$(CH_2)_nCON(R)_2$, $O(CH_2)_n$-arylO$(CH_2)_n$—PO$(OR)_2$, $O(CH_2)_n$-aryl-$NR(CH_2)_nCO_2R$, $O(CH_2)_n$-aryl-NR$C_{2-4}$ alkenyl-$CO_2R$, $O(CH_2)_n$-aryl-$NR(CH_2)_n$-tetrazole, $O(CH_2)_n$-aryl-$NR(CH_2)_nCN$, $O(CH_2)_n$-aryl-$NR(CH_2)_nCON(R)_2$, $O(CH_2)_n$-aryl-$NR(CH_2)_n$—PO$(OR)_2$, $NR(CH_2)_n$-aryl$(CH_2)_mCO_2R$, $NR(CH_2)_n$-aryl-$C_{2-4}$ alkenyl-$CO_2R$, $NR(CH_2)_n$-aryl$(CH_2)_m$-tetrazole, $NR(CH_2)_m$-aryl$(CH_2)_mCN$, $NR(CH_2)_n$-aryl$(CH_2)_mCON(R)_2$, $NR(CH_2)_n$-aryl$(CH_2)_m$—PO$(OR)_2$, $NR(CH_2)_n$-aryl-NR$(CH_2)_nCO_2R$, $NR(CH_2)_n$-aryl-NR—$C_{2-4}$ alkenyl-$CO_2R$, $NR(CH_2)_n$-aryl-$NR(CH_2)_n$-tetrazole, $NR(CH_2)_n$-aryl-NR$(CH_2)_nCN$, $NR(CH_2)_n$-aryl-$NR(CH_2)_nCON(R)_2$, $NR(CH_2)_n$-aryl-$NR(CH_2)_nPO(OR)_2$, $NR(CH_2)_n$-arylO$(CH_2)_nCO_2R$, $NR(CH_2)_n$-aryl-O—$C_{2-4}$ alkenyl-$CO_2R$, $NR(CH_2)_n$-aryl-O$(CH_2)_n$-tetrazole, $NR(CH_2)_n$-arylO$(CH_2)_nCN$, $NR(CH_2)_n$-aryl-O$(CH_2)_nCON(R)_2$, $NR(CH_2)_n$-arylO$(CH_2)_nPO(OR)_2$, $O(CH_2)_n$-heteroaryl$(CH_2)_mCO_2R$, $O(CH_2)_n$-heteroaryl-$C_{2-4}$ alkenyl-$CO_2R$, $O(CH_2)_n$-heteroaryl$(CH_2)_m$-tetrazole, $O(CH_2)_n$-heteroaryl-$(CH_2)_mCN$, $O(CH_2)_n$-heteroaryl$(CH_2)_mCON(R)_2$, $O(CH_2)_n$-heteroaryl$(CH_2)_m$—PO$(OR)_2$, $O(CH_2)_n$-heteroaryl-O$(CH_2)_nCO_2R$, $O(CH_2)_n$-heteroaryl-O—$C_{2-4}$ alkenyl-$CO_2R$, $O(CH_2)_n$-heteroarylO$(CH_2)_n$-tetrazole, $O(CH_2)_n$-heteroaryl O$(CH_2)_nCN$, $O(CH_2)_n$-heteroarylO$(CH_2)_nCON(R)_2$, $O(CH_2)_n$-heteroaryl$O(CH_2)_n$—$PO(OR)_2$, $O(CH_2)_n$-heteroaryl-$NR(CH_2)_n CO_2 R$, $O(CH_2)_n$-heteroaryl-$NR$—$C_{2-4}$ alkenyl-$CO_2 R$, $O(CH_2)_n$-heteroaryl-$NR(CH_1)_n$-tetrazole, $O(CH_2)_n$-heteroaryl-$NR(CH_2)_n CN$, $O(CH_2)_n$-heteroaryl-$NR(CH_2)_n CON(R)_2$, $O(CH_2)_n$-heteroaryl-$NR(CH_2)_n$—$PO(OR)_2$, $NR(CH_2)_n$-heteroaryl$(CH_2)_m CO_2 R$, $NR(CH_2)_n$-heteroaryl-$C_{2-4}$ alkenyl-$CO_2 R$, $NR(CH_2)_n$-heteroaryl$(CH_2)_m$-tetrazole, $NR(CH_2)_n$-heteroaryl$(CH_2)_m CN$, $NR(CH_2)_n$-heteroaryl$(CH_2)_m CON(R)_2$, $NR(CH_2)_n$-heteroaryl$(CH_2)_m$—$PO(OR)_2$, $NR(CH_2)_n$-heteroaryl-$NR(CH_2)_n CO_2 R$, $NR(CH_2)_n$-heteroaryl-$NR$—$C_{2-4}$ alkenyl-$CO_2 R$, $NR(CH_2)_n$-heteroaryl-$NR(CH_2)_n$-tetrazole, $NR(CH_2)_n$ heteroaryl-$NR(CH_2)_n CN$, $NR(CH_2)_n$-heteroaryl-$NR(CH_2)_n CON(R)_2$, $NR(CH_2)_n$-heteroaryl-$NR(CH_2)_n PO(OR)_2$, $NR(CH_2)_n$-heteroaryl-$O(CH_2)_n CO_2 R$, $NR(CH_2)_n$-heteroaryl-$O$—$C_{2-4}$ alkenyl-$CO_2 R$, $NR(CH_2)_n$-heteroaryl-$O(CH_2)_n$-tetrazole, $NR(CH_2)_n$-heteroaryl-$O(CH_2)_n CN$, $NR(CH_2)_n$-heteroaryl-$O(CH_2)_n CON(R)_2$, $NR(CH_2)_n$-heteroaryl$O(CH_2)_n PO(OR)_2$, where heteroaryl is a 5-10 membered ring system consisting of carbon atoms and from 1-4 heteroatoms selected from N, O, and S, and wherein aryl and heteroaryl are substituted with 1-2 $X^4$ and tetrazole is substituted with 0-1 R;

provided that at least one of X, $X^1$, $X^2$, and $X^3$ is other than H, alkyl, alkoxy, hydroxyl, and halo.

[8] In another embodiment, the present invention provides a novel compound of formula $Ic_1$ or a pharmaceutically acceptable salt thereof:

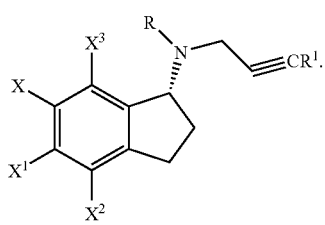

$Ic_1$

[9] In another embodiment, the present invention provides a novel compound of formula Id, or a stereoisomer or pharmaceutically acceptable salt thereof:

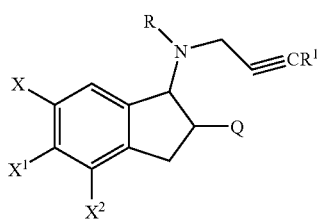

Id wherein:

R, at each occurrence, is independently selected from H, $C_{1-4}$ alkyl, $C_{2-4}$ alkenyl, and $C_{2-4}$ alkynyl;

$R^1$ is selected from H, $C_{1-4}$ alkyl, $(CH_2)_m CO_2 R$, $(CH_2)_n PO(OR)_2$, $C_{2-4}$ alkenyl, and $C_{2-4}$ alkynyl;

X, $X^1$, and $X^2$ are independently selected from H, OR, $C_{1-4}$ alkyl, $C_{2-4}$ alkenyl, $C_{2-4}$ alkynyl, halogen, $CF_3$, nitro, $O(CH_2)_n CON(R)_2$, O—$C_{2-4}$ alkenyl, $N(R)_2$, $NRSO_2 CH_3$, $SO_2 NRCH_3$, $CH_2 N(C_{1-4}$ alkyl$)_2$, $CH_2$-aryl, $CH_2$-heteroaryl, $O(CH_2)_n$-aryl, $O(CH_2)_n$-heteroaryl, $O(CH_2)_n$-aryl$(CH_2)_m CN$, $O(CH_2)_n$-aryl$(CH_2)_m CON(R)_2$, $O(CH_2)_n$-aryl$O(CH_2)_n CN$, $O(CH_2)_n$-aryl$O(CH_2)_n CON(R)_2$, $NR(CH_2)_n$-aryl$(CH_2)_m CN$, $NR(CH_2)_n$-aryl$(CH_2)_m CON(R)_2$, $NR(CH_2)_n$-aryl$O(CH_2)_n CN$, $NR(CH_2)_n$-aryl-$O(CH_2)_n CON(R)_2$, $NR(CH_2)_n$-aryl-$NR(CH_2)_n CN$, $NR(CH_2)_n$-aryl-$NR(CH_2)_n CON(R)_2$, $O(CH_2)_n$-biphenyl, $O(CH_2)_n$-biphenyl-CN, $O(CH_2)_n$-biphenyl-$CONH_2$, $NR(CH_2)_n$-biphenyl, $NR(CH_2)_n$-biphenyl-CN, $NR(CH_2)_n$-biphenyl-$CONH_2$, $O(CH_2)_n$-heteroaryl, $O(CH_2)_n$-heteroaryl-$(CH_2)_m CON(R)_2$, and $NR(CH_2)_n$-heteroaryl-$(CH_2)_m CON(R)_2$; where heteroaryl is a 5-12 membered ring system consisting of carbon atoms and from 1-4 heteroatoms selected from N, O, and S, and wherein aryl and heteroaryl are substituted with 1-2 $X^4$;

$X^4$ is selected from H, OH, $C_{1-6}$ alkoxy $C_{1-6}$ alkyl, $C_{2-6}$ alkenyl, $C_{2-6}$ alkynyl, halogen, $CF_3$, nitro, —CN, $C(O)NR_2$, $NRSO_2 CH_3$, and, $SO_2 N(R)C_{1-6}$alkyl;

Q is selected from OH, $C_{1-4}$ alkoxy, $O(CH_2)_n CO_2 R$, $O(CH_2)_n CON(R)_2$, O—$C_{2-4}$ alkenyl, O—$C_{2-4}$ alkenyl-$CO_2 R$, $OCH_2 CH_2 CONRCH_2 CO_2 R$, $OCH_2 CHMCONRCH_2 CO_2 R$, $O(CH_2)_n PO(OR)_2$, $O(CH_2)_n SO_2 OR$, $OCH_2 CH(NHAc)CO_2 R$, $OCH_2 CH(NHR)CO_2 R$, $O(CH_2)_n$-aryl, and $O(CH_2)_n$-5-10 membered heteroaryl consisting of carbon atoms and from 1-4 heteroatoms selected from N, O, and S;

M is independently selected from H, $C_{1-4}$ alkyl, $C_{3-6}$ cycloalkyl, $C_{2-4}$ alkenyl, $C_{2-4}$ alkynyl, aryl, $(CH_2)_n$-aryl, heteroaryl, and $(CH_2)_n$-heteroaryl, where heteroaryl is a 5-12 membered ring system consisting of carbon atoms and from 1-4 heteroatoms selected from N, O, and S; and, m is independently selected from 0, 1, and 2; and, n is independently selected from 1, 2, and 3;

provided that at least one of X, $X^1$, and $X^2$ is other than H, alkyl, alkoxy, hydroxyl, and halo.

[9a] In another embodiment, the present invention provides a novel compound of formula Id, or a stereoisomer or pharmaceutically acceptable salt thereof, wherein:

two of X, $X^1$, and $X^2$ are H and the third is selected from OH, $C_{1-4}$ alkyl, $C_{2-4}$ alkenyl, $C_{2-4}$ alkynyl, halogen, $CF_3$, nitro, $C_{1-4}$ alkoxy, $O(CH_2)_n CON(R)_2$, O—$C_{2-4}$ alkenyl, $N(R)_2$, $NRSO_2 CH_3$, $SO_2 NRCH_3$, $CH_2 N(C_{1-4}$ alkyl$)_2$, $CH_2$-aryl, $CH_2$-heteroaryl, $O(CH_2)_n$-aryl, $O(CH_2)_n$-heteroaryl, $O(CH_2)_n$-aryl$(CH_2)_m CN$, $O(CH_2)_n$-aryl$(CH_2)_m CON(R)_2$, $O(CH_2)_n$-aryl$O(CH_2)_n CN$, $O(CH_2)_n$-aryl$O(CH_2)_n CON(R)_2$, $NR(CH_2)_n$-aryl$(CH_2)_m CN$, $NR(CH_2)_n$-aryl$(CH_2)_m CON(R)_2$, $NR(CH_2)_n$-aryl$O(CH_2)_n CN$, $NR(CH_2)_n$-aryl-$O(CH_2)_n CON(R)_2$, $NR(CH_2)_n$-aryl-$NR(CH_2)_n CN$, $NR(CH_2)_n$-aryl-$NR(CH_2)_2 CON(R)_2$, $O(CH_2)_n$-biphenyl, $O(CH_2)_n$-biphenyl-CN, $O(CH_2)_n$-biphenyl-$CONH_2$, $NR(CH_2)_n$-biphenyl, $NR(CH_2)_n$-biphenyl-CN, $NR(CH_2)_n$-biphenyl-$CONH_2$, $O(CH_2)_n$-heteroaryl, $O(CH_2)_n$-heteroaryl-$(CH_2)_m CON(R)_2$, and $NR(CH_2)_n$-heteroaryl-$(CH_2)_m CON(R)_2$; where heteroaryl is a 5-12 membered ring system consisting of carbon atoms and from 1-4 heteroatoms selected from N, O, and S, and wherein aryl and heteroaryl are substituted with 1-2 $X^4$;

provided that at least one of X, $X^1$, and $X^2$ is other than H, alkyl, alkoxy, hydroxyl, and halo.

[10] In another embodiment, the present invention provides a novel compound of formula $Id_1$, or a stereoisomer or pharmaceutically acceptable salt thereof:

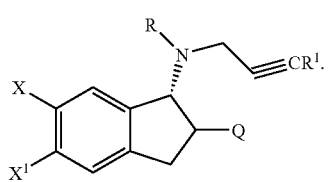

$Id_1$

[11] In another embodiment, the present invention provides a novel compound of formula IIa or a stereoisomer thereof:

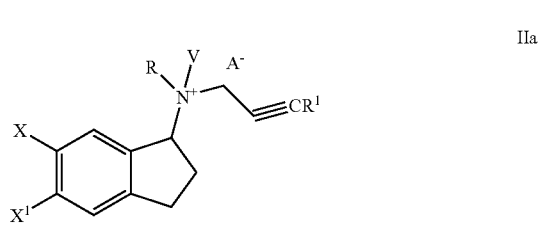

wherein:

R, at each occurrence, is independently selected from H, $C_{1-4}$ alkyl, $C_{2-4}$ alkenyl, and $C_{2-4}$ alkynyl;

$R^1$ is selected from H and $C_{1-4}$ alkyl;

$A^-$ is selected from $Cl^-$ and $Br^-$;

V is selected from $O^-$, $C_{1-4}$ alkyl, $C_{2-4}$ alkenyl, and $C_{2-4}$ alkynyl;

X and $X^1$ are independently selected from H, OR, $C_{1-4}$ alkyl, $C_{2-4}$ alkenyl, $C_{2-4}$ alkynyl, halogen, $CF_3$, nitro, $O(CH_2)_nCON(R)_2$, $O-C_{2-4}$ alkenyl, $NRSO_2CH_3$, $SO_2NRCH_3$, $CH_2$-aryl, $CH_2$-heteroaryl, $O(CH_2)_n$-aryl, $O(CH_2)_n$-heteroaryl, $O(CH_2)_n$-aryl$(CH_2)_m$CN, $O(CH_2)_n$-aryl$(CH_2)_n$CON(R)_2$, $O(CH_2)_n$-arylO$(CH_2)_n$CN, $O(CH_2)_n$-arylO$(CH_2)_n$CON(R)_2$, NR$(CH_2)_n$-aryl$(CH_2)_m$CN, NR$(CH_2)_n$-aryl$(CH_2)_m$CON(R)_2$, NR$(CH_2)_n$-arylO$(CH_2)_n$CN, NR$(CH_2)_n$-aryl-O$(CH_2)_n$CON(R)_2$, NR$(CH_2)_n$-aryl-NR$(CH_2)_n$CN, NR$(CH_2)_n$-aryl-NR$(CH_2)_n$CON(R)_2$, O$(CH_2)_n$-biphenyl, O$(CH_2)_n$-biphenyl-CN, O$(CH_2)_n$-biphenyl-CONH$_2$, NR$(CH_2)_n$-biphenyl, NR$(CH_2)_n$-biphenyl-CN, NR$(CH_2)_n$-biphenyl-CONH$_2$, O$(CH_2)_n$-heteroaryl, O$(CH_2)_n$-heteroaryl-$(CH_2)_m$CON(R)_2$, and NR$(CH_2)_n$-heteroaryl-$(CH_2)_m$CON(R)_2$; where heteroaryl is a 5-12 membered ring system consisting of carbon atoms and from 1-4 heteroatoms selected from N, O, and S, and wherein aryl and heteroaryl are substituted with 1-2 $X^4$;

$X^4$ is selected from H, OR, $C_{1-6}$ alkoxy $C_{1-6}$ alkyl, $C_{2-6}$ alkenyl, $C_{2-6}$ alkynyl, halogen, $CF_3$, nitro, —CN, C(O)NR$_2$, NRSO$_2$CH$_3$, and, SO$_2$N(R)C$_{1-6}$alkyl;

n is independently selected from 1, 2, and 3;

provided that at least one of X and $X^1$ is other than H, alkyl, alkoxy, hydroxyl, and halo.

[11a] In another embodiment, the present invention provides a novel compound of formula IIa or a stereoisomer thereof, wherein:

one of X and $X^1$ is H and the other is selected from OH, $C_{1-4}$ alkyl, $C_{2-4}$ alkenyl, $C_{2-4}$ alkynyl, halogen, $CF_3$, nitro, $C_{1-4}$ alkoxy, $O(CH_2)_nCON(R)_2$, $O-C_{2-4}$ alkenyl, $NRSO_2CH_3$, $SO_2NRCH_3$, $CH_2$-aryl, $CH_2$-heteroaryl, $O(CH_2)_n$-aryl, $O(CH_2)_n$-heteroaryl, $O(CH_2)_n$-aryl$(CH_2)_m$CN, $O(CH_2)_n$-aryl$(CH_2)_m$CON(R)_2$, $O(CH_2)_n$-arylO$(CH_2)_n$CN, $O(CH_2)_n$-arylO$(CH_2)_n$CON(R)_2$, NR$(CH_2)_n$-aryl$(CH_2)_m$CN, NR$(CH_2)_n$-aryl$(CH_2)_m$CON(R)_2$, NR$(CH_2)_n$-arylO$(CH_2)_n$CN, NR$(CH_2)_n$-aryl-O$(CH_2)_n$CON(R)_2$, NR$(CH_2)_n$-aryl-NR$(CH_2)_n$CN, NR$(CH_2)_n$-aryl-NR$(CH_2)_n$CON(R)_2$, O$(CH_2)_n$-biphenyl, O$(CH_2)_n$-biphenyl-CN, O$(CH_2)_n$-biphenyl-CONH$_2$, NR$(CH_2)_n$-biphenyl, NR$(CH_2)_n$-biphenyl-CN, NR$(CH_2)_n$-biphenyl-CONH$_2$, O$(CH_2)_n$-heteroaryl, O$(CH_2)_n$-heteroaryl-$(CH_2)_m$CON(R)_2$, and NR$(CH_2)_n$-heteroaryl-$(CH_2)_m$CON(R)_2$; where heteroaryl is a 5-12 membered ring system consisting of carbon atoms and from 1-4 heteroatoms selected from N, O, and S, and wherein aryl and heteroaryl are substituted with 1-2 $X^4$;

provided that at least one of X and $X^1$ is other than H, alkyl, alkoxy, hydroxyl, and halo.

[12] In another embodiment, the present invention provides a novel compound of formula IIa$_1$:

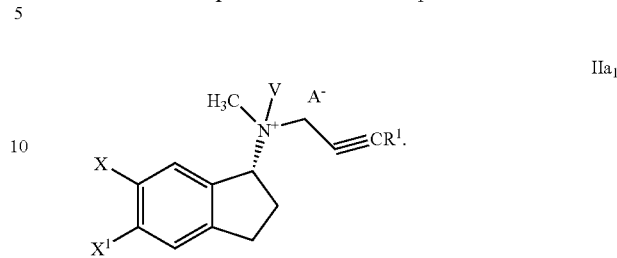

In another embodiment, the present invention provides novel pharmaceutical compositions, comprising: a pharmaceutically acceptable carrier and a therapeutically effective amount of a compound of the present invention or a stereoisomer or pharmaceutically acceptable salt form thereof.

In another embodiment, the present invention provides a novel method for treating a disease, comprising: administering to a patient in need thereof a therapeutically effective amount of a compound of the present invention or a pharmaceutically acceptable salt form thereof, wherein the disease is selected from obesity, diabetes, cardiometabolic disorders, and a combination thereof.

In another embodiment, the cardiometabolic disorder is selected from hypertension, dyslipidemias (e.g., undesirable blood lipid levels, elevated cholesterol levels, and lowered LDL levels), high blood pressure, and insulin resistance.

In another embodiment, the present invention provides a novel method for treating a co-morbidity of obesity, comprising: administering to a patient in need thereof a therapeutically effective amount of a compound of the present invention or a pharmaceutically acceptable salt form thereof.

In another embodiment, the present invention provides a novel method for treating a co-morbidity of obesity, comprising: administering to a patient in need thereof a therapeutically effective amount of a compound of the present invention or a pharmaceutically acceptable salt form thereof.

In another embodiment, the co-morbidity is selected from diabetes, Metabolic Syndrome, dementia, and heart disease.

In another embodiment, the co-morbidity is selected from hypertension; gallbladder disease; gastrointestinal disorders; menstrual irregularities; degenerative arthritis; venous statis ulcers; pulmonary hypoventilation syndrome; sleep apnea; snoring; coronary artery disease; arterial sclerotic disease; pseudotumor cerebri; accident proneness; increased risks with surgeries; osteoarthritis; high cholesterol; and, increased incidence of malignancies of the ovaries, cervix, uterus, breasts, prostrate, and gallbladder.

In another embodiment, the present invention provides a novel method for treating a CNS disorder, comprising: administering to a patient in need thereof a therapeutically effective amount of a compound of the present invention or a pharmaceutically acceptable salt form thereof.

In another embodiment, the CNS disorder is selected from acute and chronic neurological disorders, cognitive disorders, and memory deficits. Examples of these disorders include chronic or traumatic degenerative processes of the nervous system, which include Alzheimer's disease, other types of dementia, minimal cognitive impairment, and Parkinson's disease. Other examples of CNS disorders include psychiatric diseases, which include depression, anxiety, panic attack, social phobia, schizophrenia, and anorexia. Further examples of CNS disorders include withdrawal syndromes induced by alcohol, nicotine and other addictive drugs. Additional examples of CNS disorders include neuropathic pain and neuroinflamatory diseases (e.g., multiple sclerosis).

In another embodiment, the present invention also provides a method of preventing or reversing the deposition of adipose tissue in a mammal by the administration of a MAO-B inhibitor. By preventing or reversing the deposition of adipose tissue, MAO-B inhibitors are expected to reduce the incidence or severity of obesity, thereby reducing the incidence or severity of associated co-morbidities.

In another embodiment, the present invention provides a compound of the present invention for use in therapy.

In another embodiment, the present invention provides the use of the present invention for the manufacture of a medicament for the treatment of obesity, diabetes, cardiometabolic disorders, and a combination thereof.

The present invention may be embodied in other specific forms without departing from the spirit or essential attributes thereof. This invention encompasses all combinations of aspects of the invention noted herein. It is understood that any and all embodiments of the present invention may be taken in conjunction with any other embodiment or embodiments to describe additional embodiments. It is also to be understood that each individual element of the preferred embodiments is intended to be taken individually as its own independent embodiment. Furthermore, any element of an embodiment is meant to be combined with any and all other elements from any embodiment to describe an additional embodiment.

Definitions

The examples provided in the definitions present in this application are non-inclusive unless otherwise stated. They include but are not limited to the recited examples.

The compounds herein described may have asymmetric centers, geometric centers (e.g., double bond), or both. All chiral, diastereomeric, racemic forms and all geometric isomeric forms of a structure are intended, unless the specific stereochemistry or isomeric form is specifically indicated. Compounds of the present invention containing an asymmetrically substituted atom may be isolated in optically active or racemic forms. It is well known in the art how to prepare optically active forms, such as by resolution of racemic forms, by synthesis from optically active starting materials, or through use of chiral auxiliaries. Geometric isomers of olefins, C=N double bonds, or other types of double bonds may be present in the compounds described herein, and all such stable isomers are included in the present invention. Specifically, cis and trans geometric isomers of the compounds of the present invention may also exist and may be isolated as a mixture of isomers or as separated isomeric forms. All processes used to prepare compounds of the present invention and intermediates made therein are considered to be part of the present invention. All tautomers of shown or described compounds are also considered to be part of the present invention.

"Alkyl" includes both branched and straight-chain saturated aliphatic hydrocarbon groups having the specified number of carbon atoms. $C_{1-6}$ alkyl, for example, includes $C_1$, $C_2$, $C_3$, $C_4$, $C_5$, and $C_6$ alkyl groups. Examples of alkyl include methyl, ethyl, n-propyl, i-propyl, n-butyl, s-butyl, t-butyl, n-pentyl, and s-pentyl.

"Alkenyl" includes the specified number of hydrocarbon atoms in either straight or branched configuration with one or more unsaturated carbon-carbon bonds that may occur in any stable point along the chain, such as ethenyl and propenyl. $C_{2-6}$ alkenyl includes $C_2$, $C_3$, $C_4$, $C_5$, and $C_6$ alkenyl groups.

"Alkynyl" includes the specified number of hydrocarbon atoms in either straight or branched configuration with one or more triple carbon-carbon bonds that may occur in any stable point along the chain, such as ethynyl and propynyl. $C_{2-6}$ Alkynyl includes $C_2$, $C_3$, $C_4$, $C_5$, and $C_6$ alkynyl groups.

"Cycloalkyl" includes the specified number of hydrocarbon atoms in a saturated ring, such as cyclopropyl, cyclobutyl, cyclopentyl, cyclohexyl, cycloheptyl, and cyclooctyl. $C_{3-8}$ cycloalkyl includes $C_3$, $C_4$, $C_5$, $C_6$, $C_7$, and $C_8$ cycloalkyl groups.

"Alkoxy" represents an alkyl group as defined above with the indicated number of hydrocarbon atoms attached through an oxygen bridge. $C_{1-6}$ alkoxy, includes $C_1$, $C_2$, $C_3$, $C_4$, $C_5$, and $C_6$ alkoxy groups. Examples of alkoxy include methoxy, ethoxy, n-propoxy, i-propoxy, n-butoxy, s-butoxy, t-butoxy, n-pentoxy, and s-pentoxy.

"Halo" or "halogen" refers to fluoro, chloro, bromo, and iodo.

"Counterion" is used to represent a small, negatively charged species, such as chloride, bromide, hydroxide, acetate, and sulfate.

"Aryl" refers to any stable 6, 7, 8, 9, 10, 11, 12, or 13 membered monocyclic, bicyclic, or tricyclic ring, wherein at least one ring, if more than one is present, is aromatic. Examples of aryl include fluorenyl, phenyl, naphthyl, indanyl, adamantyl, and tetrahydronaphthyl.

"Heteroaryl" refers to any stable 5, 6, 7, 8, 9, 10, 11, or 12 membered monocyclic, bicyclic, or tricyclic heterocyclic ring that is aromatic, and which consists of carbon atoms and 1, 2, 3, or 4 heteroatoms independently selected from the group consisting of N, O, and S. If the heteroaryl group is bicyclic or tricyclic, then at least one of the two or three rings must contain a heteroatom, though both or all three may each contain one or more heteroatoms. If the heteroaryl group is bicyclic or tricyclic, then only one of the rings must be aromatic. The N group may be N, NH, or N-substituent, depending on the chosen ring and if substituents are recited. The nitrogen and sulfur heteroatoms may optionally be oxidized (e.g., S, S(O), S(O)$_2$, and N—O). The heteroaryl ring may be attached to its pendant group at any heteroatom or carbon atom that results in a stable structure. The heteroaryl rings described herein may be substituted on carbon or on a nitrogen atom if the resulting compound is stable.

Examples of heteroaryl includes acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, naphthyridinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, pteridinyl, pyranyl, pyrazinyl, pyrazolyl, pyridazinyl, pyridooxazole, pyridoimidazole, pyridothiazole, pyridinyl, pyridyl, pyrimidinyl, 2H-pyrrolyl, pyrrolyl, quinazolinyl, quinolinyl, 4H-quinolizinyl, quinoxalinyl, quinuclidinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Preventing the deposition of adipose tissue covers methods of treating wherein the levels of adipose tissue of a subject remain about the same as prior to being treated in accordance with the present invention (i.e., its pre-administration level) or not more than about 1, 2, 3, 4, 5, 6, 7, 8, 9, or 10% greater than pre-administration level (particularly when the subject is pre-disposed to increasing adipose tissue levels).

Reversing the deposition of adipose tissue covers methods of treating wherein the levels of adipose tissue of a subject are lower than those prior to being treated in accordance with the present invention (i.e., its pre-administration level). Examples of lower include 1, 2, 3, 4, 5, 6, 7, 8, 9, 10, 11, 12, 13, 14, 15, 16, 17, 18, 19, 20% or more lower than pre-administration level.

Mammal and patient covers warm blooded mammals that are typically under medical care (e.g., humans and domesticated animals). Examples of mammals include (a) feline, canine, equine, bovine, and human and (b) human.

"Treating" or "treatment" covers the treatment of a disease-state in a mammal, and includes: (a) inhibiting the disease-state, e.g., arresting it development; and/or (b) relieving the disease-state, e.g., causing regression of the disease state until a desired endpoint is reached. Treating also includes the amelioration of a symptom of a disease (e.g., lessen the pain or discomfort), wherein such amelioration may or may not be directly affecting the disease (e.g., cause, transmission, expression, etc.).

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 1,2-ethanedisulfonic, 2-acetoxybenzoic, 2-hydroxyethanesulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methanesulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluenesulfonic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 18th ed., Mack Publishing Company, Easton, Pa., 1990, p 1445, the disclosure of which is hereby incorporated by reference.

"Therapeutically effective amount" includes an amount of a compound of the present invention that is effective when administered alone or in combination to treat obesity or another indication listed herein. "Therapeutically effective amount" also includes an amount of the combination of compounds claimed that is effective to treat the desired indication. The combination of compounds is preferably a synergistic combination. Synergy, as described, for example, by Chou and Talalay, *Adv. Enzyme Regul.* 1984, 22:27-55, occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased effect, or some other beneficial effect of the combination compared with the individual components.

Utility

Obesity is defined as having a body mass index (BMI) of 30 or above. The index is a measure of an individual's body weight relative to height. BMI is calculated by dividing body weight (in kilograms) by height (in meters) squared. Normal and healthy body weight is defined as having a BMI between 20 and 24.9. Overweight is defined as having a BMI of 25 or above. Obesity has reached epidemic proportions in the U.S., with 44 million obese Americans, and an additional eighty million deemed medically overweight.

Obesity is a disease characterized as a condition resulting from the excess accumulation of adipose tissue, especially adipose tissue localized in the abdominal area. It is desirable to treat overweight or obese patients by reducing their amount of adipose tissue, and thereby reducing their overall body weight to within the normal range for their sex and height. In this way, their risk for co-morbidities such as diabetes and cardiovascular disease will be reduced. It is also desirable to prevent normal weight individuals from accumulating additional, excess adipose tissue, effectively maintaining their body weights at a BMI<25, and preventing the development of co-morbidities. It is also desirable to control obesity, effectively preventing overweight and obese individuals from accumulating additional, excess adipose tissue, reducing the risk of further exacerbating their co-morbidities.

There exist two forms of MAO, designated MAO-A and MAO-B. The two forms differ with respect to substrate and inhibitor specificities and amino acid number and sequence. A preferred substrate for MAO-B is beta-phenylethylamine. In contrast, a preferred substrate for MAO-A is serotonin. Some MAO inhibitors show selectivity for MAO-A or for MAO-B, whereas other MAO inhibitors show little, if any selectivity. For example, the MAO inhibitor clorgyline preferentially inhibits MAO-A; the MAO inhibitor L-selegiline preferentially inhibits MAO-B; and, the MAO inhibitor iproniazid is non-selective (i.e., has a similar affinity for both). Examples of selectivity include a compound having about 2, 3, 4, 5, 6, 7, 8, 9, 10, 20, 30, 40, 50, 100, 200, 300, 400, 500, 600, 700, 800, 900, 1000, or more fold higher affinity for one form of MAO than for the other form. One of ordinary skill in the art recognizes that there can be some difficulty in classifying MAO inhibitors. Some compounds may selectively inhibit one form of MAO in vitro and then lose their selectivity in vivo. Also, selectivity of a compound may vary from species to species or from tissue to tissue. In the context of the present invention, it is desirable to inhibit MAO-B activity in vivo in a mammal. Thus, selectivity and affinity are based on the in vivo activity of the MAO inhibitor and the mammalian species to which it is being or to be administered. Examples of the selectivity of a MAO-B inhibitor of the present invention include (a) at least a 2, 3, 4, 5, 6, 7, 8, 9, 10, 20, 30, 40, 50, to 100-fold greater affinity for MAO-B than MAO-A in the mammalian species (e.g., human) to be treated and (b) at least 100-fold greater affinity for MAO-B than MAO-A in the mammalian species (e.g., human) to be treated.

Some of the compounds of the present invention have been designed to have reduced CNS exposure by virtue of their inability or limited ability to penetrate the blood-brain barrier (e.g., quaternary salts or acid substituents) or by their participation in active transport systems, thus reducing centrally mediated side-effects, a potential problem with many anti-obesity agents.

Other compounds of the present invention are expected to penetrate the blood-brain barrier and therefore be useful to treat CNS disorders (e.g., Parkinson's disease, depression, and Alzheimer's disease).

MAO enzymes are also located in a number of peripheral (non-CNS) tissues, including adipocytes; the cells that comprise body fat. In order to treat non-CNS disorders (e.g., obesity, diabetes, and/or cardiometabolic disorders), it is necessary to administer enough of a drug sufficient to inhibit MAO in peripheral tissues. MAO inhibitors in use today to treat various psychiatric and neurological diseases, regardless of route of administration, enter the CNS from the systemic circulation. While present in the systemic circulation, such drugs have access to peripheral tissues, including adipose tissue, liver, and muscle. One of skill in the art recognizes that MAO inhibitors intended to enter the CNS from the systemic circulation in order to treat psychiatric and neurological diseases also have access to MAO in peripheral tissues, including adipose tissue, liver, and muscle. Thus, an MAO inhibitor useful for treating non-CNS disorders may have some access to the CNS from the systemic circulation.

Drugs enter the CNS from the systemic circulation by crossing the blood-brain barrier (BBB). The BBB is a highly specialized 'gate-keeper' that protects the brain by preventing the entry of many potentially harmful substances into the CNS from the systemic circulation. Much is known about the BBB, and of the physical-chemical properties required for compounds transported across it.

Drugs that do not cross the BBB into the CNS or that are readily eliminated through transport mechanisms (J Clin Invest. 97, 2517(1996)) are known in the literature and have low CNS activity due to their inability to develop brain levels necessary for pharmacological action. The BBB has at least one mechanism to remove drugs prior to their accumulation in the CNS. P-Glycoproteins (P-gp) localized in plasma membrane of the BBB can influence the brain penetration and pharmacological activity of many drugs through translocation across membranes. The lack of accumulation into the brain by some drugs can be explained by their active removal from the brain by P-gp residing in the BBB. For example, the typical opioid drug loperamide, clinically used as an antidiarrheal, is actively removed from the brain by P-gp, thus explaining its lack of opiate-like CNS effects. Another example is domperidone, a dopamine receptor blocker that participates in the P-gp transport (J Clin Invest. 97, 2517 (1996)). Whereas dopamine receptor blockers that cross the BBB can be used to treat schizophrenia, the readily-eliminated domperidone can be used to prevent emesis, without the likelihood of producing adverse CNS effects.

In addition to the above compounds, agents possessing structural characteristics that retard or prevent BBB penetration or contribute to participation in active elimination processes have been identified in various classes of therapeutics. These include antihistamines (Drug Metab. Dispos. 31, 312 (2003)), beta-adrenergic receptor antagonists (B-blockers) (Eur. J. Clin. Pharmacol. 28, Suppl: 21-3 (1985); Br. J. Clin. Pharmacol., 11 (6), 549-553 (1981)), non-nucleoside reverse transcriptase inhibitors (NNRTIs)(J. Pharm Sci., 88(10) 950-954 (1999)), and opioid antagonists. This latter group has been tested in relation to their activity in the GI tract. These peripherally selective opioid antagonists are described in various US patents as being useful in the treatment of non-CNS pathologies in mammals, in particular those of the GI tract (see U.S. Pat. Nos. 5,260,542; 5,434,171; 5,159,081; and 5,270,238).

Other types of non-brain penetrant compounds can be prepared through the creation of a charge within the molecule. Thus, the addition of a methyl group to the tertiary amine functionality of the drugs scopolamine or atropine, unlike the parent molecules, prevents their passage across the BBB through the presence of a positive charge. However, the new molecules (methyl-scopolamine and methyl-atropine) retain their full anticholinergic pharmacological properties. As such, these drugs can also be used to treat peripheral diseases, without the concern of adverse CNS effects. The quaternary ammonium compound methylnaltrexone is also used for the prevention and/or treatment of opioid and non-opioid induced side effects associated with opioid administration.

MAO-B inhibitors such as selegiline have been useful in the treatment of CNS disorders. The unexpected discovery that the anti-obesity activity mediated by these agents is mediated by a non-CNS mechanism may make it desirable that the compounds of the present invention be peripherally restricted, i.e., have an inability or limited ability to cross the BBB or be readily eliminated from the brain through active transport systems, when a non-CNS disorder is to be treated. It may be desirable for the compounds of the present invention to be peripherally restricted, which in turn will result in no or very limited CNS effects. Compounds that provide peripherally mediated anti-obesity properties should result in therapeutic agents with greater safety, as previously demonstrated in earlier classes of peripherally restricted agents. It can be desirable that the compounds of the present invention, when administered in a therapeutically effective amount, have no or very limited CNS effects. It can also be desirable that the lack of CNS effects is a result of the compounds of the present invention having minimal brain concentrations when administered in therapeutically effective amounts. In this context, minimal brain concentrations means levels that are too low to be therapeutically effective for the treatment of a CNS indication or too low to cause significant or measurable deleterious or undesired side effects. It is noted that CNS activity is desirable when seeking to treat a CNS disorder.

Compound A is Rasagiline when Q, R, $R^1$, W, X, $X^1$, $X^2$, and $X^3$ are all H. Rasagiline is a drug that crosses the BBB and is indicated for Parkinson's disease. In compound A, one of R, $R^1$, $R^2$, X, $X^1$, Y, and Z is a group capable of reducing or limiting the CNS activity of compound A. This reducing or limiting occurs via at least one of R, $R^1$, $R^2$, X, $X^1$, Y, and Z being a group the either limits compound A's ability to cross the BBB relative to that of Rasagiline or enables it to be actively removed at a level that is higher than Rasagiline's. Examples of brain levels of compound A include levels that are (a) from 50, 55, 60, 65, 70, 75, 80, 85, 90, 91, 92, 93, 94, 95, 96, 97, 98, 99, to 100% lower than Rasagiline, when administered at the same dosage; (b) from 90, 91, 92, 93, 94, 95, 96, 97, 98, 99, to 100% lower than Rasagiline, when administered at the same dosage; and, (c) from 98, 99, to 100% lower than Rasagiline, when administered at the same dosage.

Most methods of treating obesity are dependent on a significant reduction in energy intake, either by a decrease in food intake (e.g., sibutramine) or by inhibition of fat absorption (e.g., orlistat). In the present invention, it can be desirable for adipose tissue to be significantly reduced in the absence of a significant reduction in food intake. The weight loss, as a result of the present invention, comes from the treatment with an MAO-B inhibitor, largely independent of appetite and food intake. Examples of the level of food intake during adipose tissue loss include (a) food intake is maintained, increased or about 0, 1, 2, 3, 4, 5, 6, 7, 8, 9, 10, 11, 12, 13, 14, 15, 16, 17, 18, 19, or 20% below the normal range of the subject prior to being treated in accordance with the present invention (i.e., its pre-administration level); (b) food intake is maintained, increased, or about 0, 1, 2, 3, 4, 5, 6, 7, 8, 9, 10, 11, 12, 13, 14, or 15% below its pre-administration level; (c) food intake is maintained, increased or about 0, 1, 2, 3, 4, 5, 6, 7, 8, 9, or 10% below its pre-administration level; and (d) food intake level is maintained, increased or about 0, 1, 2, 3, 4, or 5% below its pre-administration level.

In some cases, loss of adipose tissue can be accompanied by a concomitant loss of lean muscle mass. This is particularly evident in cancer patients who show a wasting of all body tissue components, including adipose tissue and lean muscle mass. In the present invention, however, it can be desirable for body fat to be significantly reduced in the absence of a significant reduction in lean body mass. Adipose tissue loss comes from treatment with an MAO-B inhibitor, independent of a significant change in lean body mass. Examples of the level of lean body mass during adipose tissue loss include (a) lean body mass is maintained, increased, or is no more than about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30% below the normal range of the subject prior to being treated in accordance with the present invention (i.e., its pre-administration level); (b) lean body mass is maintained, increased, or is no more than about 1, 2, 3, 4, 5, 6, 7, 8, 9, 10, 11, 12, 13, 14, or 15% below pre-administration levels; (c) lean body mass is maintained, increased, or is no more than about 1, 2, 3, 4, 5, 6, 7, 8, 9, or 10% below pre-administration levels; and (d) lean body mass is maintained, increased, or is no more than about 1, 2, 3, 4, or 5% below pre-administration levels.

In some cases, loss of adipose tissue can be accompanied by a concomitant loss of water mass. This is particularly evident with diet regimens that promote dehydration. In the present invention, it can be desirable for body fat to be significantly reduced in the absence of a significant reduction in water mass. In other words, adipose tissue loss comes from treatment with an MAO-B inhibitor, independent of a significant change in water mass. Examples of the level of water mass during adipose tissue loss include (a) water mass is maintained, increased, or is no more than about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30% below the normal range of the subject prior to being treated in accordance with the present invention (i.e., its pre-administration level); (b) water mass is maintained, increased, or is no more than about 1, 2, 3, 4, 5, 6, 7, 8, 9, 10, 11, 12, 13, 14, or 15% below pre-administration levels; (c) water mass is maintained, increased, or is no more than about 1, 2, 3, 4, 5, 6, 7, 8, 9, or 10% below pre-administration levels; and (d) water mass is maintained, increased, or is no more than about 1, 2, 3, 4, or 5% below pre-administration levels.

Sibutramine and orlistat are currently marketed for use in the treatment of obesity. These two compounds achieve weight loss through entirely different mechanisms. Sibutramine, a CNS appetite suppressant, inhibits the neuronal reuptake of serotonin and noradrenaline. Orlistat inhibits gut lipase enzymes that are responsible for breaking down ingested fat.

The mechanism of action of MAO-B inhibitors is believed to be entirely different from appetite suppressants, gut lipase inhibitors, and other agents with similar indications (e.g., serotonin agonists, leptin, fatty acid synthase inhibitors, monoamine oxidase (MAO) inhibitors). Co-administration of a MAO-B inhibitor together with one or more other agents that are useful for treating the indications described above (e.g., obesity, diabetes, cardiometabolic disorders, and a combination thereof) is expected to be beneficial, by producing, for example, either additive or synergistic effects. Examples of additional agents include an appetite suppressant and a lipase inhibitor. Therefore, the present invention provides a method of treating obesity, diabetes, and/or cardiometabolic disorders, comprising administering a therapeutically effective amount of a compound of the present invention and a second component selected from an appetite suppressant (e.g., sibutramine, phentermine, fenfluramine) and a gut lipase inhibitor (e.g., orlistat).

MAO-B inhibitors are expected to promote weight loss without appreciably reducing caloric intake. Co-administration of an MAO-B inhibitor together with an appetite suppressant is expected to produce either additive or synergistic effects on weight loss. Similarly, co-administration of an MAO-B inhibitor together with a lipase inhibitor is expected to produce either additive or synergistic effects on weight loss.

The ability of compounds to inhibit MAOs can be determined using the method of R. Uebelhack et al., Pharmacopsychiatry 31, 1988, p187-192 (as described below).

Preparation of platelet-rich plasma and platelets. Venous blood from healthy subjects was collected between 8 and 8.30 a.m. after an overnight fast into EDTA-containing vacutainer tubes (11.6 mg EDTA/ml blood). After centrifugation of the blood at 250×g for 15 minutes at 20° C., the supernatant platelet-rich plasma (PRP) was collected and the number of platelets in PRP counted with a cell counter (MOIAB, Hilden, Germany). 2 ml of PRP was spun at 1500×g for 10 min to yield a platelet pellet. The pellet was washed three times with ice-cold saline, resuspended in 2 ml Soerensen phoshate buffer, pH 7.4 and stored at −18° C. for one day.

MAO assay. Fresh PRP or frozen platelet suspension (100 μL) was generally preincubated for 10 min in the absence or presence of drugs at 37° C. in 100 uL of 0.9% NaCl solution or phosphate buffer pH 7.4, respectively, at 37° C. 50 μL of 2-phenylethylamine-[ethyl-1-14C]hydrochloride (P EA) solution (specific activity 56 Ci/mol, Amersham) was then added in a final concentration of 5 μM, and the incubation was continued for 30 min. The reaction was terminated by the addition of 50 μL of 4M $HClO_4$. The reaction product of MAO, phenylacetaldehyde, was extracted into 2 mL of n-hexane. An aliquot of the organic phase was added to scintillator cocktail and the radioactivity was determined using a liquid scintillation counter. Product formation was linear with time for at least 60 min with appropriate platelet numbers. Blank values were obtained by including 2mM pargyline in the incubation mixtures. All assays were performed in duplicate.

The ability of compounds to inhibit MAO activity can also be determined using the following method. cDNA's encoding human MAO-B can be transiently transfected into EBNA cells using the procedure described by E.-J. Schlaeger and K. Christensen (Transient Gene Expression in Mammalian Cells Grown in Serum-free Suspension Culture; Cytotechnology, 15: 1-13, 1998). After transfection, cells are homogeneized by means of a Polytron homogeneiser in 20 mM Tris HCl buffer, pH 8.0, containing 0.5 mM EGTA and 0.5 mM phenylmethanesulfonyl fluoride. Cell membranes are obtained by centrifugation at 45,000×g and, after two rinsing steps with 20 mM Tris HCl buffer, pH 8.0, containing 0.5 mM EGTA, membranes are eventually re-suspended in buffer and aliquots stored at −80° C. until use.

MAO-B enzymatic activity can be assayed using a spectrophotometric assay adapted from the method described by M. Zhou and N. Panchuk-Voloshina (A One-Step Fluorometric Method for the Continuous Measurement of Monoamine Oxidase Activity, Analytical Biochemistry, 253: 169-174, 1997). Briefly, membrane aliquots are incubated in 0.1 M potassium phosphate buffer, pH 7.4, for 30 min at 37° C. with or without various concentrations of the compounds. After incubation, the enzymatic reaction is started by the addition of the MAO substrate tyramine together with 1 U/ml horseradish peroxidase (Roche Biochemicals) and 80 μM N-acetyl-3,7,-dihydroxyphenoxazine (Amplex Red, Molecular Probes). The samples are further incubated for 30 min at 37° C. in a final volume of 200 μl and absorbance is determined at a wavelength of 570 nm using a SpectraMax plate reader (Molecular Devices). Background (non-specific) absorbance is determined in the presence of 10 μM L-deprenyl for MAO-B. $IC_{50}$ values are determined from inhibition curves obtained using nine inhibitor concentrations in duplicate, by fitting data to a four parameter logistic equation.

Compounds of the present invention are expected to be MAO-B inhibitors. Representative compounds have been tested, as measured in the assay described herein, and have been shown to be active as their $IC_{50}$ values were found to be in the range of ≦10 μM. Compounds of the present invention are considered to be MAO-B inhibitors if they have an $IC_{50}$ value less than or equal to 10 μM. Additional examples of desirable activity levels of MAO-B inhibitors useful in the present invention include (a) an $IC_{50}$ value of 1 μM or lower, (b) an $IC_{50}$ value of 0.1 μM or lower, (c) an $IC_{50}$ value of 0.01 μM or lower, (d) an $IC_{50}$ value of 0.001 μM or lower, and (e) an $IC_{50}$ value of 0.0001 μM or lower.

In the present invention, MAO-B inhibitor(s) can be administered enterally, parenterally, orally, and transdermally. One skilled in this art is aware that the routes of administering the compounds of the present invention may vary significantly. In addition to other oral administrations, sustained release compositions may be favored. Other examples of routes include injections (e.g., intravenous, intramuscular, and intraperitoneal); subcutaneous; subdermal implants; buccal, sublingual, topical, rectal, vaginal, and intranasal administrations. Bioerodible, non-bioerodible, biodegradable, and non-biodegradable systems of administration may also be used.

If a solid composition in the form of tablets is prepared, the main active ingredient can be mixed with a pharmaceutical vehicle, examples of which include silica, starch, lactose, magnesium stearate, and talc. The tablets can be coated with sucrose or another appropriate substance or they can be treated so as to have a sustained or delayed activity and so as to release a predetermined amount of active ingredient continuously. Gelatin capsules can be obtained by mixing the active ingredient with a diluent and incorporating the resulting mixture into soft or hard gelatin capsules. A syrup or elixir can contain the active ingredient in conjunction with a sweetener, which is preferably calorie-free, an antiseptic (e.g., methylparaben and/or propylparaben), a flavoring, and an appropriate color. Water-dispersible powders or granules can contain the active ingredient mixed with dispersants or wetting agents or with suspending agents such as polyvinylpyrrolidone, as well as with sweeteners or taste correctors. Rectal administration can be effected using suppositories, which are prepared with binders melting at the rectal temperature (e.g., cocoa butter and/or polyethylene glycols). Parenteral administration can be effected using aqueous suspensions, isotonic saline solutions, or injectable sterile solutions, which contain pharmacologically compatible dispersants and/or wetting agents (e.g., propylene glycol and/or polyethylene glycol). The active ingredient can also be formulated as microcapsules or microspheres, optionally with one or more carriers or additives. The active ingredient can also be presented in the form of a complex with a cyclodextrin, for example α-, β-, or γ-cyclodextrin, 2-hydroxypropyl-β-cyclodextrin, and/or methyl-β-cyclodextrin.

The dose of the MAO-B inhibitor administered daily will vary on an individual basis and to some extent may be determined by the severity of the disease being treated (e.g., obesity). The dose of the MAO-B inhibitor will also vary depending on the MAO-B inhibitor administered. A example of a range of dosages of an MAO-B inhibitor is about from 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 2, 3, 4, 5, 6, 7, 8, 9, 10, 15, 20, 25, 30, 35, 40, 45, 50, 55, 60, 65, 70, 76, 80, 85, 90, 95, to 100 mg/kg of mammal body weight. The MAO-B inhibitor can be administered in a single dose or in a number of smaller doses over a period of time. The length of time during which the MAO-B inhibitor is administered varies on an individual basis, and can continue until the desired results are achieved (i.e., reduction of body fat, or prevention of a gain in body fat). Therapy could, therefore, last from 1 day to weeks, months, or even years depending upon the subject being treated, the desired results, and how quickly the subject responds to treatment in accordance with the present invention.

A possible example of a tablet of the present invention is as follows.

| Ingredient | mg/Tablet |
|---|---|
| Active ingredient | 100 |
| Powdered lactose | 95 |
| White corn starch | 35 |
| Polyvinylpyrrolidone | 8 |
| Na carboxymethylstarch | 10 |
| Magnesium stearate | 2 |
| Tablet weight | 250 |

A possible example of a capsule of the present invention is as follows.

| Ingredient | mg/Tablet |
|---|---|
| Active ingredient | 50 |
| Crystalline lactose | 60 |
| Microcrystalline cellulose | 34 |
| Talc | 5 |
| Magnesium stearate | 1 |
| Capsule fill weight | 150 |

In the above capsule, the active ingredient has a suitable particle size. The crystalline lactose and the microcrystalline cellulose are homogeneously mixed with one another, sieved, and thereafter the talc and magnesium stearate are admixed. The final mixture is filled into hard gelatin capsules of suitable size.

A possible example of an injection solution of the present invention is as follows.

| Ingredient | mg/Tablet |
|---|---|
| Active substance | 1.0 mg |
| 1 N HCl | 20.0 μl |
| acetic acid | 0.5 mg |
| NaCl | 8.0 mg |
| Phenol | 10.0 mg |
| 1 N NaOH | q.s. ad pH 5 |
| $H_2O$ | q.s. ad 1 mL |

Synthesis

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley and Sons, 1991). All references cited herein are hereby incorporated in their entirety herein by reference.

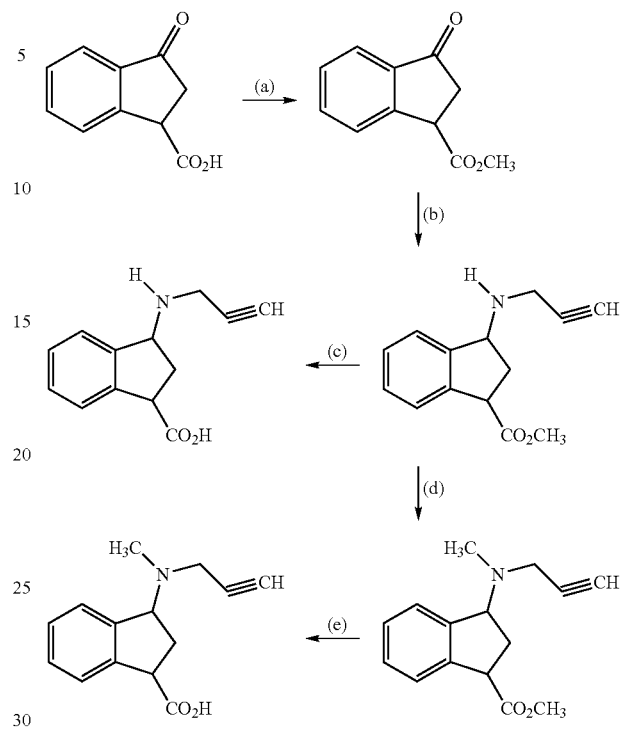

Scheme 1

In Scheme 1, the keto acid can be esterified using methanol and sulfuric acid (step a), and subsequent treatment with propargylamine and sodium cyanoborohydride in slightly acidic media should provide the propargylamino ester (step b). The corresponding acid can be produced by treatment with lithium hydroxide in aqueous solution containing a co-solvent (step c). Alternatively, the amino ester can be further alkylated with methyl bromide to give the tertary-amino ester (step d), and subsequent lithium hydroxide treatment should give tertiary amino acid (step e).

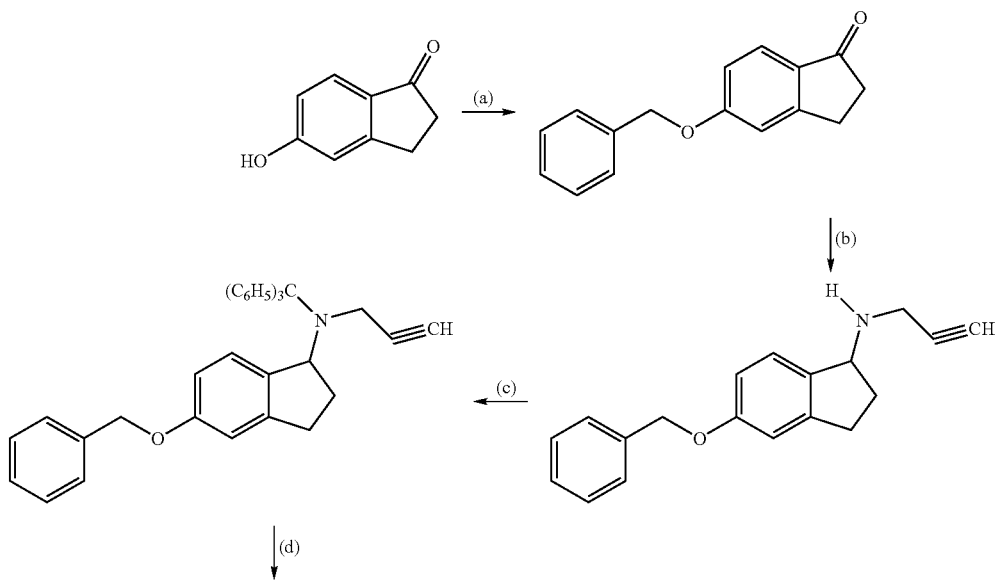

Scheme 2

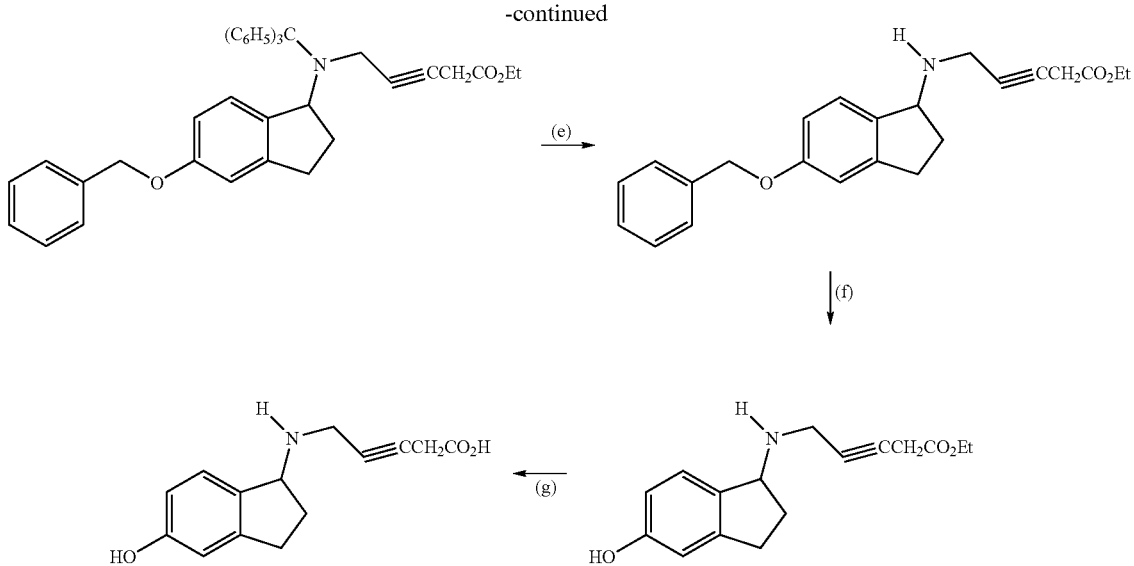

As shown in Scheme 2, hydroxyindanone can be benzylated using one equivalent of sodium hydride and benzyl bromide at low temperature in a solvent such as DMF or THF to give the benzyloxyindanone (step a). Treatment of the ketone with propargylamine and sodium cyanoborohydride in the presence of acetic acid in dichloroethane should provide the secondary amine (step b). Protection of the secondary amine with trityl chloride in pyridine solution should give the tritylated secondary amine (step c). Deprotonation of the protected propargylamine using n-butyl lithium followed by treatment with ethyl bromoacetate should produce the ester (step d). Treatment with dry hydrogen bromide in acetic acid should cause a loss of the trityl protecting group to give benzyloxy aminoester (step e), and subsequent exposure to trifluoroacetic acid should provide hydroxyindanylamino ester (step f). Lithium hydroxide treatment should give the secondary amino acid (step g). Alternatively, the benzyloxyindane amino ester of step e can also be hydrolyzed, as above, to give the benzyloxy-indane amino acid which may optionally have halogen, $CF_3$, alkyl or alkoxy substituents on the phenyl ring.

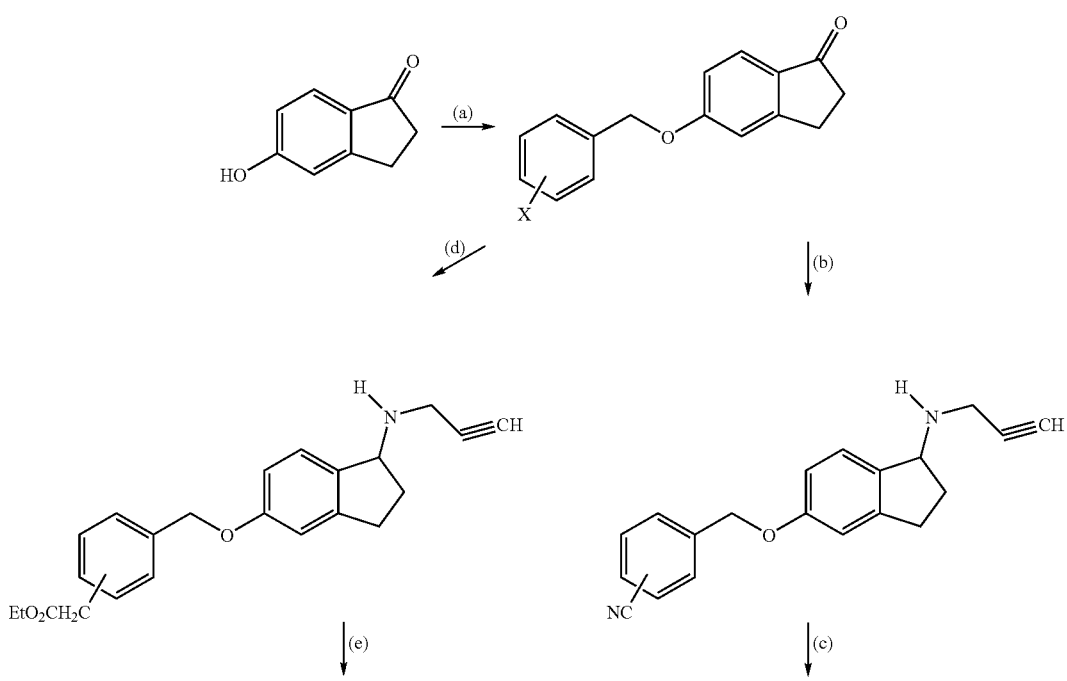

Scheme 2'

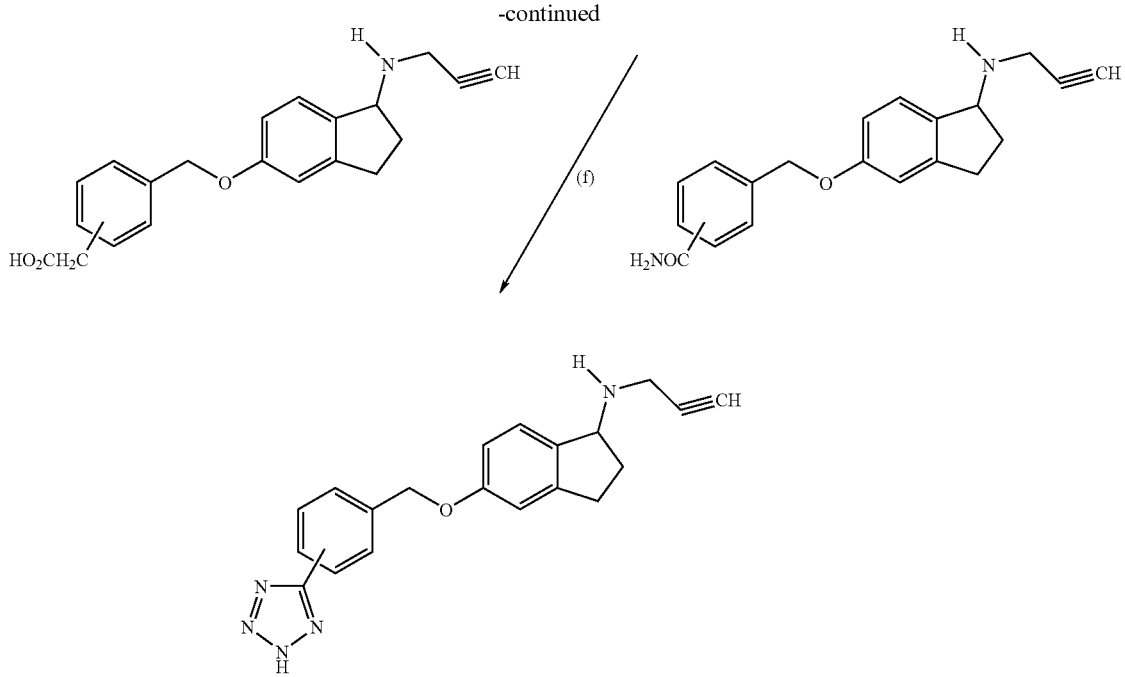

As shown in Scheme 2', hydroxyindanone can be benzylated with a variety of benzyl bromides that are optionally substituted with various groups (e.g., ester, alkylester, oxyalkylester nitrile, alkylnitrile, oxyalkylnitrile, halogen, $CF_3$, etc.) in acetone at about 60° C. in the presence of potassium carbonate to give the substituted benzyloxyindanones (step a). In the case of substituents on the phenyl group that are nitriles, treatment of these ketones with propargylamine and sodium cyanoborohydride in acetonitrile and acetic acid at about 30° C. should provide the secondary amine (step b). Hydration of these nitriles using 30% hydrogen peroxide in DMSO in the presence of potassium carbonate at about room temperature should yield the carboxamides (step c). Alternatively, the nitriles can be converted to tetrazoles by treatment with sodium azide and trioctyltin chloride in xylenes at reflux, followed by cleavage of the trialkylstannyl adduct with anhydrous HCl in toluene/THF solution (step f). In the case of indanones having benzyl groups with ester substituents, reductive amination with propargyl amine in acetonitrile and acetic acid at 30-50° C. can afford the amino esters (step d). Hydrolysis of the esters using lithium hydroxide in aqueous THF can produce the acids (step e). Halogen, alkyl, alkoxy and CF3-substituted benzyloxy indanes can be produced from the indanones via reductive amination as described above.

Scheme 3

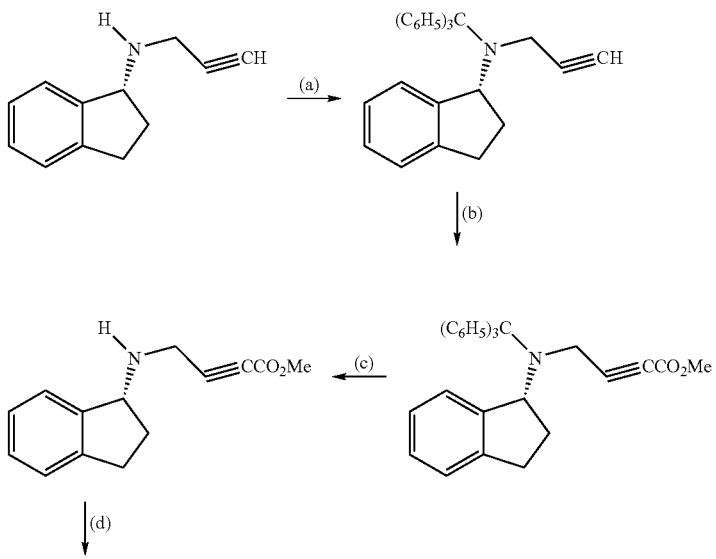

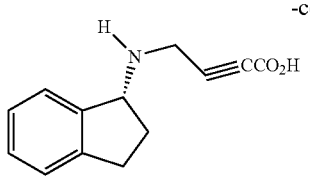

Scheme 3 describes how indanylpropargylamine (rasagiline) can be protected with trityl chloride to give the tritylated secondary amine (step a). Treatment with n-butyl lithium followed by methyl chloroformate should give the trityl-protected amino ester (step b), which can be de-protected with hydrogen bromide in acetic acid (step c). The corresponding acid can be produced by treatment with aqueous lithium hydroxide solution (step d).

lamino ester (step b). The secondary amine can be protected with trityl chloride or other suitable protecting groups to give the protected ester (step c). The ester can then be reduced with lithium aluminum hydride to give the primary alcohol (step d), which upon deprotonation with sodium hydride and alkylation with ethyl bromopropionate should provide the ester (step e). Removal of the protecting group using hydrogen

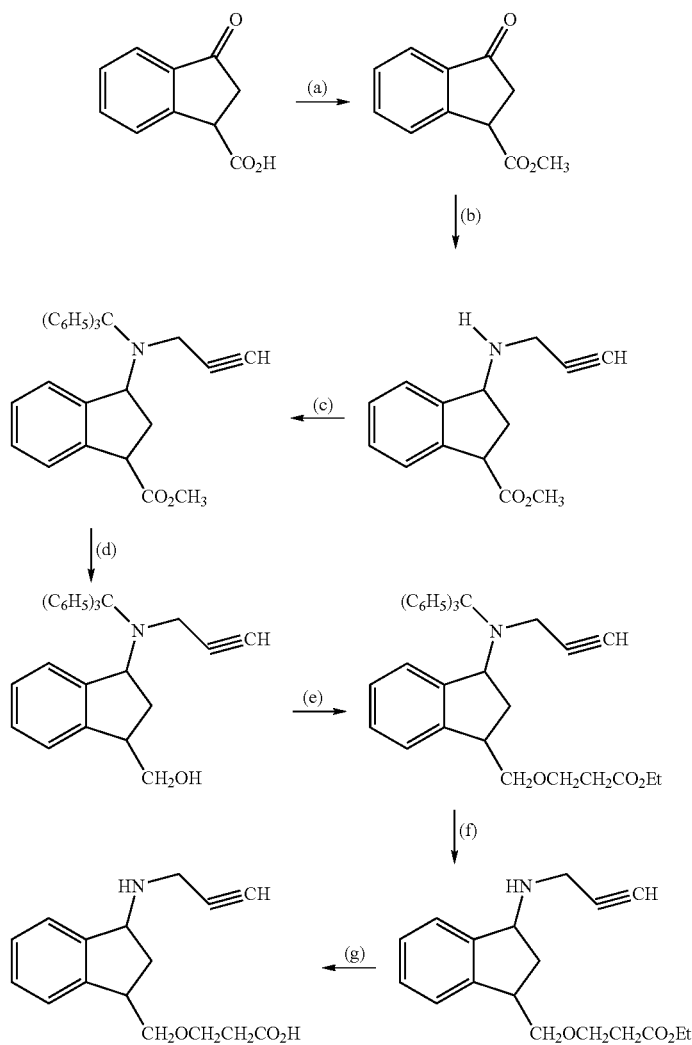

As illustrated in Scheme 4, a keto acid can be esterified using methanol and sulfuric acid (step a), and subsequent treatment with propargylamine and sodium cyanoborohydride in slightly acidic media should provide the propargybromide in acetic acid or other suitable deprotecting reagents should afford the secondary amino ester (step f), and hydrolysis of the ester with lithium hydroxide in aqueous solution should yield the amino acid (step g).

Scheme 5

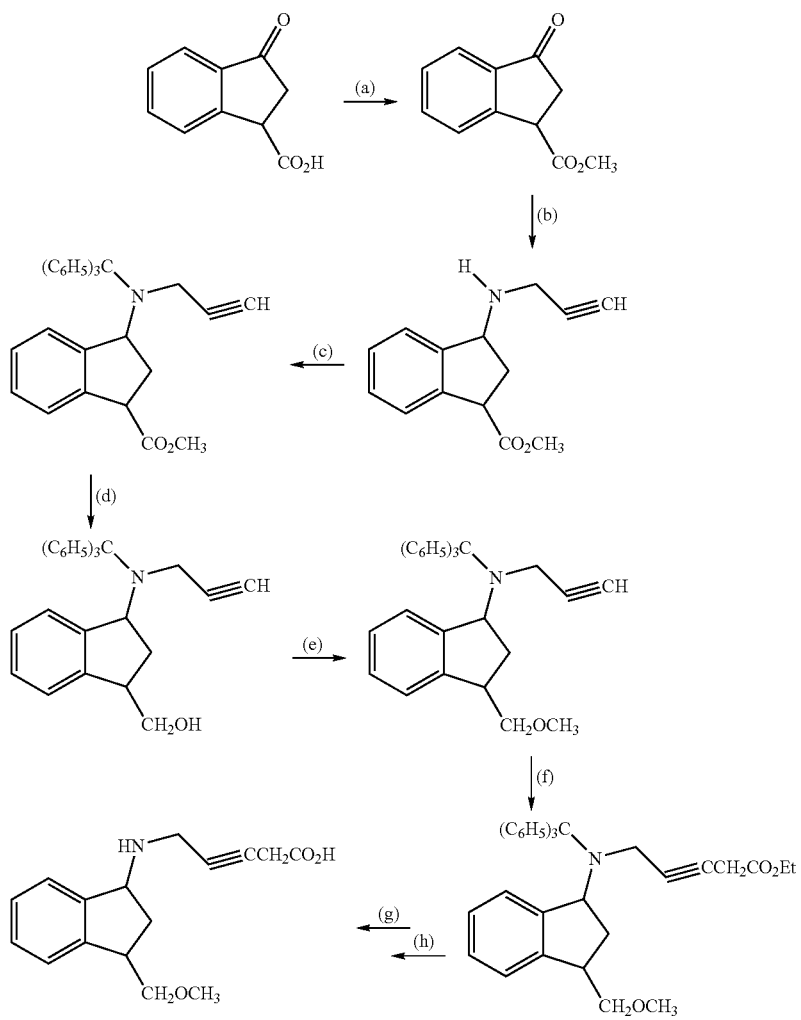

As depicted in Scheme 5, a keto acid can be esterified using methanol and sulfuric acid (step a), and subsequent treatment with propargylamine and sodium cyanoborohydride in slightly acidic media should provide the propargylamino ester (step b). The secondary amine can be protected with trityl chloride or other suitable protecting groups to give the protected ester (step c). The ester can then be reduced with lithium aluminum hydride to give the primary alcohol (step d) which upon deprotonation with sodium hydride and alkylation with methyl bromide should provide the ether (step e). Treatment of the methyl ether with n-butyl lithium followed by alkylation with ethyl iodoacetaate should provide the ester (step f). Subsequent deprotection of the amine using hydrogen bromide in acetic acid or other suitable deprotecting reagents (step g), and subsequent hydrolysis of the ester with lithium hydroxide in aqueous solution will produce the amino acid ether (step h).

Scheme 6

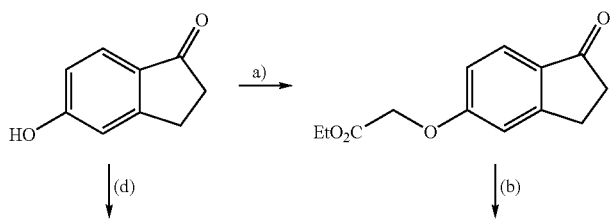

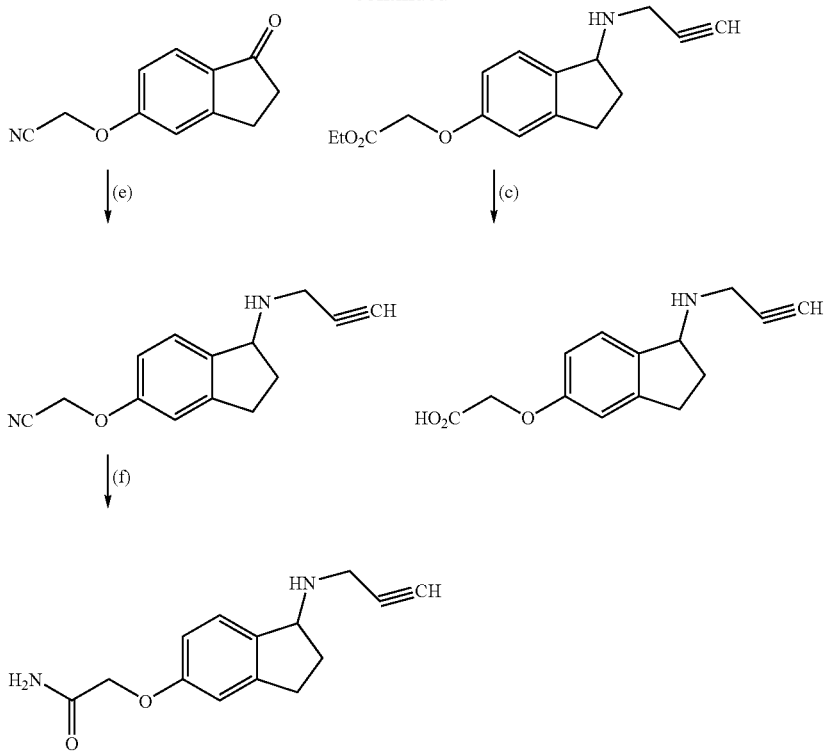

Scheme 6 shows alkylation of the hydroxyindanone using potassium carbonate in acetone using ethyl bromoacetate at about room temperature or above can give the indanone ester (step a). Treatment of the keto-ester with propargylamine and sodium cyanoborohydride in acetonitrile in the presence of acetic acid at about 30° C. can provide the secondary amine (step b). Hydrolysis of the ester using lithium hydroxide in aqueous solution should afford the amino acid (step c). Alternatively, the ester can be alkylated with formalin and sodium triacetoxyborohydride in dichloroethane in the presence of acetic acid to give the N-methyl analog which can be hydrolyzed to the acid as described above. Alkylation of the indanone with bromoacetonitrile in acetone in the presence of potassium carbonate at about room temperature or above can produce the keto-nitrile (step d). Treatment of the keto-nitrile with propargylamine and sodium cyanoborohydride in acetonitrile in the presence of acetic acid at about 30° C. should afford the secondary amine (step e). Subsequent hydration of the nitrile with 30% hydrogen peroxide in DMSO in the presence of potassium carbonate can provide the carboxamide (step f).

Scheme 7

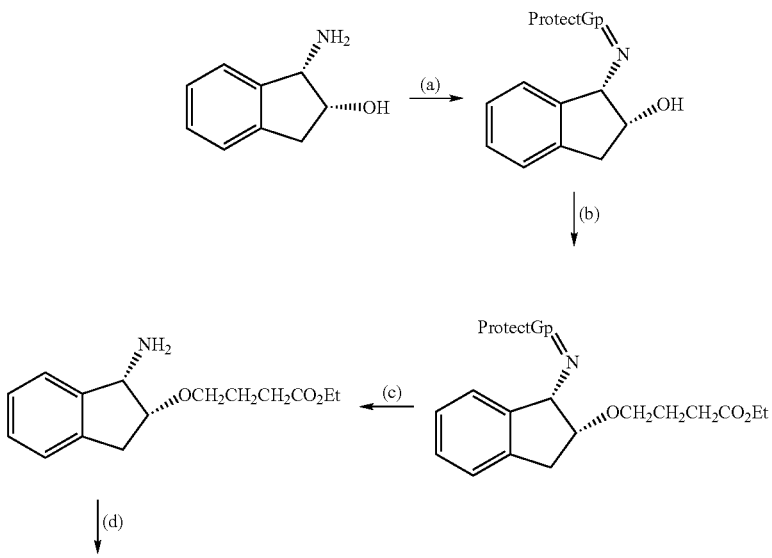

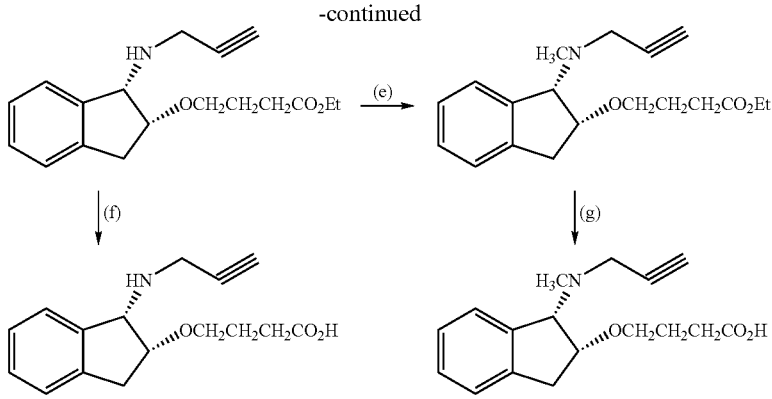

As shown in Scheme 7, an aminoalcohol can be treated with STABASE (1,1,4,4-tetramethydisilylaza-yclopentane), aryl aldehydes, or other suitable protecting agents to give a protected amino alcohol (step a). The alcohol can then be deprotonated with sodium hydride and alkylated with ethyl bromobutyrate to give the ester (step b). Removal of the protecting group using tosyl acid in methanol (STABASE) or other suitable conditions for other protecting groups should afford the primary amino ester after neutralization (step c). Treatment of this amine with propioaldehyde diethyl acetal and sodium cyanoborohydride under slightly acidic moist conditions should produce the propargyl aminoester (step d). Further alkylation of this amine using formalin and sodium cyanoborohydride can provide the methylated teriaryamino ester (step e). Subsequent treatment of the secondary (step f) or the tertiary (step g) amino esters with lithium hydroxide in aqueous solution should yield the secondary and tertiary amino acids, respectively.

Scheme 8

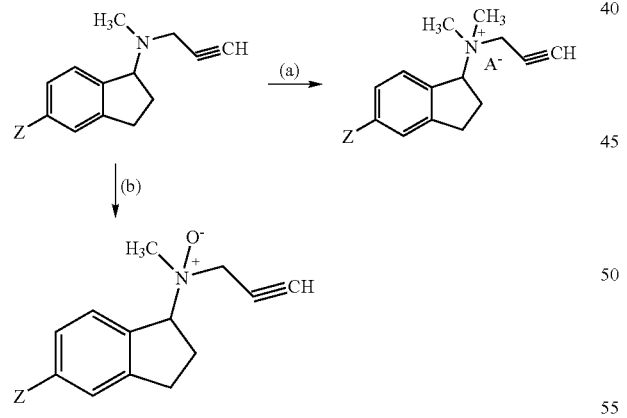

Scheme 8 shows how tertiary-amino indanes, where Z can be H or $O(CH_2)_n$-phenyl and the phenyl can be optionally substituted with halogen or $CF_3$, when treated with an alkyl halides, such as methyl bromide or methyl iodide, in a solvent such as toluene, ethanol or ether can give the corresponding quaternary ammonium salts (step a). Treatment of these tertiary amines with Davis reagent (phenyloxaziridinebenezene-sulfonamide) in methylene chloride at room temperature can give the corresponding amine N-oxides (step b).

One stereoisomer of a compound of the present invention may be a more potent MAO-B inhibitor than its counterpart(s). Thus, stereoisomers are included in the present invention. Some of these stereoisomers are shown below in Schemes 9-13. When required, separation of the racemic material can be achieved by HPLC using a chiral column or by a resolution using a resolving agent such as described in Wilen, S. H. *Tables of Resolving Agents and Optical Resolutions* 1972, 308 or using enantiomerically pure acids and bases. A chiral compound of the present invention may also be directly synthesized using a chiral catalyst or a chiral ligand, e.g., Jacobsen, E. *Acc. Chem. Res.* 2000, 33, 421-431 or using other enantio- and diastereo-selective reactions and reagents known to one skilled in the art of asymmetric synthesis.

Scheme 9

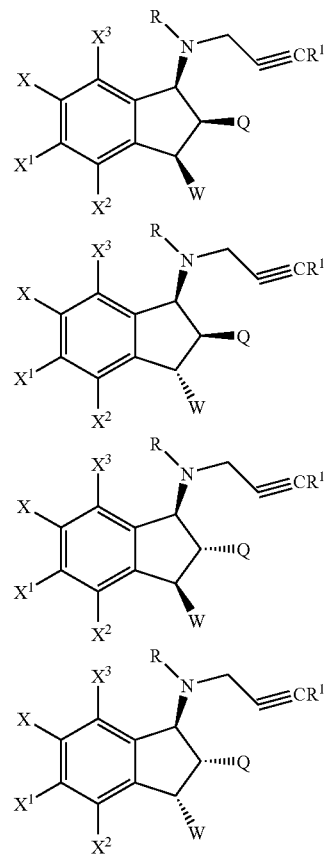

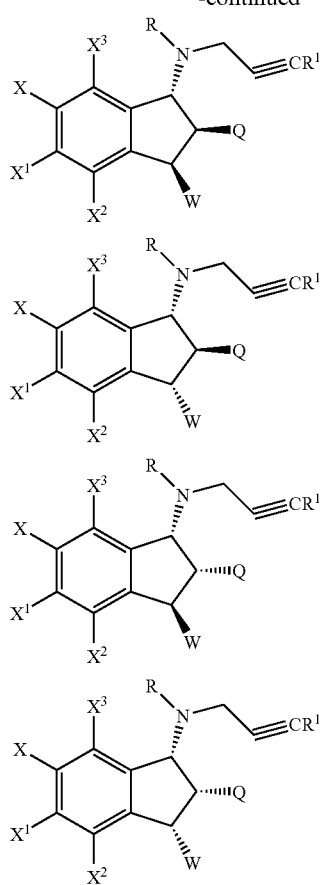
Scheme 10
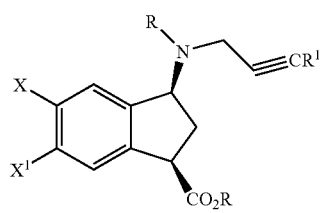
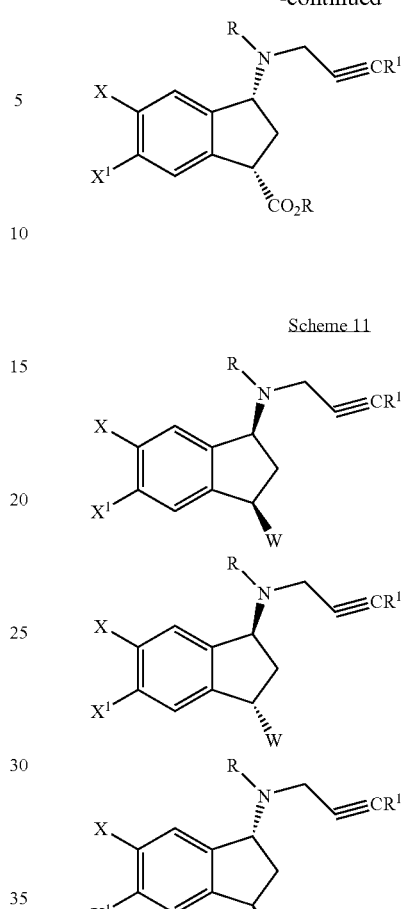
Scheme 11
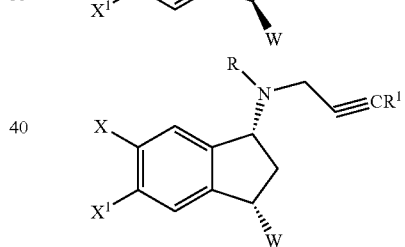
Scheme 12
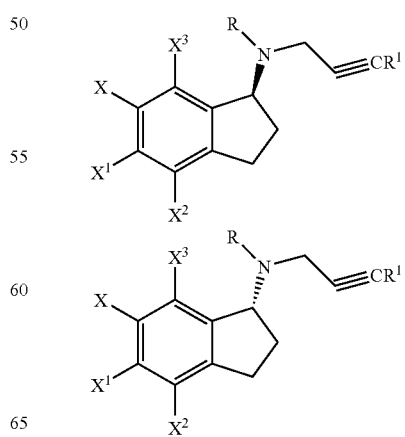

Scheme 13

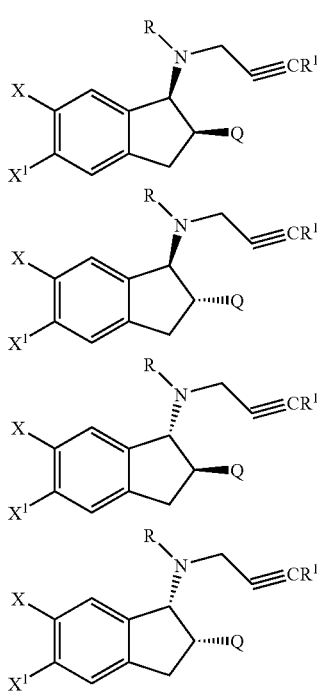

Other features of the invention will become apparent in the course of the following descriptions of exemplary embodiments that are given for illustration of the invention and are not intended to be limiting thereof.

EXAMPLES

Tables A-C below describe examples of the present invention that have been synthesized and tested. The activities of the compounds are as follows:

+=an IC50 of ≦10 μM;

++=IC50 of ≦1 μM; and,

+++=an IC50≦100 nM.

The examples can be prepared according to the methods of the scheme numbers provided for each example.

TABLE A

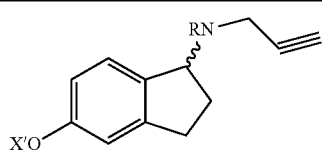

All compounds racemic

| Number | X | R | Results | NMR (CDCl$_3$-ppm) | Synthesis Route |
|---|---|---|---|---|---|
| 1 | CH$_2$C$_6$H$_5$ | H | + | ring-CH: 1.93 (m)<br>C≡CH: 2.27 (m)<br>ring-CH: 2.41 (m)<br>ring-CH: 2.85 (m)<br>ring-CH: 3.05 (m)<br>N—CH$_2$: 3.53 (m)<br>N—CH: 4.48 (t)<br>PhCH$_2$O: 5.09<br>aromatic H's 6.70-7.35 | Scheme 2 |
| 2 | CH$_2$CH$_2$C$_6$H$_5$ | H | +++ | ring-CH: 1.93 (m)<br>C≡CH: 2.26 (m)<br>ring-CH: 2.38 (m)<br>ring-CH: 2.78 (m)<br>ring-CH: 2.98 (m)<br>PhOCH$_2$: 3.09 (t)<br>N—CH$_2$: 3.51 (q)<br>PhOCH$_2$: 4.18 (t)<br>N—CH: 4.44 (t)<br>aromatic H's 6.78-7.50 | Scheme 2 |
| 3 | CH$_2$CO$_2$Et | CH$_3$ | + | ester-CH$_3$: 1.30 (t)<br>ring-CH$_2$: 2.17 (m)<br>C≡CH: 2.26 (m)<br>ring-CH: 2.87 (m)<br>ring-CH: 3.00 (m)<br>N—CH$_2$: 3.35 (dq)<br>ester-CH$_2$: 4.26 (q)<br>N—CH: 4.52 (t)<br>PhOCH$_2$: 4.64<br>aromatic H's 6.61-7.26 | Scheme 6 |
| 4 | CH$_2$CO$_2$Et | H | + | ester-CH$_3$: 1.29 (t)<br>ring-CH: 1.88 (m)<br>C≡CH: 2.26 (m)<br>ring-CH: 2.41 (m)<br>ring-CH: 2.86 (m)<br>ring-CH: 3.05 (m)<br>N—CH$_2$: 3.52 (q)<br>ester-CH$_2$: 4.26 (q)<br>N—CH: 4.43 (t)<br>PhOCH$_2$: 4.63<br>aromatic H's 6.61-7.18 | Scheme 6 |

TABLE B

All compounds racemic

| Number | X | R | Results (B) | NMR (CDCl$_3$) ppm | Synthesis Route |
|---|---|---|---|---|---|
| 5 | CH$_2$C$_6$H$_5$ | H | +++ | ring-CH: 2.03 (m)<br>C≡CH: 2.30 (m)<br>ring-CH: 2.39 (m)<br>ring-CH: 2.80 (m)<br>ring-CH: 3.08 (m) | Scheme 2 |

TABLE B-continued

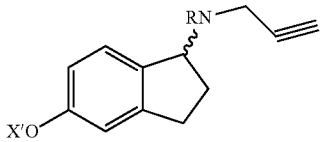

All compounds racemic

| Number | X | R | Results (B) | NMR (CDCl$_3$) ppm | Synthesis Route |
|---|---|---|---|---|---|
| 6 | CH$_2$CH$_2$C$_6$H$_5$ | H | +++ | N—CH$_2$: 3.52 (m)<br>N—CH: 4.43 (m)<br>PhCH$_2$O: 5.04<br>aromatic H's 6.82-7.42<br>ring-CH: 2.04 (m)<br>C≡CH: 2.32 (m)<br>ring-CH: 2.37 (m)<br>ring-CH: 2.79 (m)<br>ring-CH: 3.09 (m)<br>PhCH2: 3.10 (t)<br>N—CH$_2$: 3.52 (m)<br>N—CH: 4.47 (m)<br>PhOCH$_2$: 4.15 (t)<br>aromatic H's 6.73-7.26 | Scheme 2 |
| 7 | CH$_2$C$_6$H$_5$ | CH$_3$ | +++ | ring-CH$_2$: 2.18 (m)<br>C≡CH: 2.30 (m)<br>N—CH$_3$: 2.38 (s)<br>ring-CH: 2.80 (m)<br>ring-CH: 2.99 (m)<br>N—CH$_2$: 3.39 (q)<br>N—CH: 4.44 (m)<br>PhCH$_2$O: 5.05 (s)<br>aromatic H's 6.84-7.50 | Scheme 2 |
| 8 | CH$_2$CO$_2$Et | H | + | (CDCl$_3$)<br>ester-CH$_3$: 1.27 (t)<br>ring-CH: 1.89 (m)<br>C≡CH: 2.25 (m)<br>ring-CH: 2.38 (m)<br>ring-CH: 2.80 (m)<br>ring-CH: 3.00 (m)<br>N—CH$_2$: 3.49 (m)<br>ester-CH$_2$: 4.27 (q)<br>N—CH: 4.38 (m)<br>EtO$_2$CCH$_2$O: 4.60 (s)<br>aromatic H's 6.73-7.26 | Scheme 6 |
| 9 | CH$_2$CO$_2$Et | CH$_3$ | ++ | (CDCl$_3$)<br>ester-CH$_3$: 1.29 (t)<br>ring-CH$_2$: 2.12 (m)<br>C≡CH: 2.24 (m)<br>N—CH$_3$: 2.32 (s)<br>ring-CH: 2.78 (m)<br>ring-CH: 2.95 (m)<br>N—CH$_2$: 3.32 (q)<br>ester-CH$_2$: 4.27 (q)<br>N—CH: 4.38 (t)<br>EtO$_2$CCH$_2$O: 4.60 (s)<br>aromatic H's 6.76-7.31 | Scheme 6 |
| 10 | CH$_2$CO$_2$H | CH$_3$ | + | (CD$_3$OD)<br>ring-CH$_2$: 2.50 (m)<br>N—CH$_3$: 2.77 (s)<br>ring-CH: 3.00 (m)<br>ring-CH: 3.17 (m)<br>C≡CH: 3.38 (m)<br>N—CH$_2$: 4.05 (dq)<br>HO$_2$CCH$_2$O: 4.70 (s)<br>N—CH: 5.09 (dd)<br>aromatic H's 6.92-7.51 | Scheme 6 |

TABLE B-continued

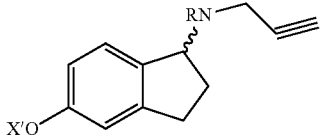

All compounds racemic

| Number | X | R | Results (B) | NMR (CDCl$_3$) ppm | Synthesis Route |
|---|---|---|---|---|---|
| 11 | (CH$_2$)$_4$CO$_2$Et | H | + | (CDCl$_3$)<br>ester-CH$_3$: 1.26 (t)<br>ring-CH$_2$: 1.92 (m)<br>C≡CH: 2.27 m<br>N—CH$_3$: 2.36 (s)<br>ring-CH: 2.81 (m)<br>ring-CH: 3.05 (m)<br>N—CH$_2$: 3.50 (s)<br>OCH$_2$: 3.95 (q)<br>ester-CH$_2$: 4.13 (q)<br>N—CH: 4.38 (t)<br>aromatic H's 6.72-7.26 | Scheme 6 |
| 12 | CH$_2$CH=CHCO$_2$Et | CH$_3$ | +++ | (CDCl$_3$)<br>ester-CH$_3$: 1.29 (t)<br>ring-CH$_2$: 2.24 (m)<br>C≡CH: 2.36 m<br>N—CH$_3$: 2.44 (s)<br>ring-CH: 2.83 (m)<br>ring-CH: 3.06 (m)<br>N—CH$_2$: 3.46 (br m)<br>ester-CH$_2$: 4.22 (q)<br>N—CH: 4.52 (m)<br>OCH$_2$-vinyl: 4.69 (q)<br>CH=: 6.19 (2 t)<br>CH=: 7.06 (2 t)<br>aromatic H's 6.78-7.45 | Scheme 6 |
| 13 | CH$_2$CH=CHCO$_2$Et | H | ++ | (CDCl$_3$)<br>ester-CH$_3$: 1.30 (t)<br>ring-CH: 1.93 (m)<br>C≡CH: 2.29 (m)<br>ring-CH: 2.40 (m)<br>ring-CH: 2.82 (m)<br>ring-CH: 3.09 (m)<br>N—CH$_2$: 3.51 (q)<br>ester-CH$_2$: 4.21 (q)<br>N—CH: 4.41 (t)<br>OCH$_2$-vinyl: 4.68 (q)<br>CH=: 6.19 (dt)<br>CH=: 7.07 (dt)<br>aromatic H's 6.74-7.3 | Scheme 6 |
| 14 | CH$_2$C$_6$H$_5$CO$_2$Me(4) | CH$_3$ | ++ | (CDCl$_3$)<br>ring-CH$_2$: 2.14 (m)<br>C≡CH: 2.25 (m)<br>N—CH$_3$: 2.33 (s)<br>ring-CH 2.78 (m)<br>ring-CH: 2.96 (m)<br>N—CH$_2$: 3.33 (dq)<br>OCH$_3$: 3.92 (s)<br>N—CH: 4.39 (t)<br>PhCH$_2$O: 5.11 (q)<br>aromatic H's 6.8-8.1 | Scheme 2' |
| 15 | CH$_2$C$_6$H$_5$CO$_2$Me(4) | H | + | (CDCl$_3$)<br>ring-CH: 1.94 (m)<br>ring-CH: 2.39 (m)<br>C≡CH: 2.28 (m)<br>ring-CH: 2.80 (m)<br>ring-CH: 3.06 (m)<br>N—CH$_2$: 3.50 (s)<br>OCH$_3$: 3.92 (s)<br>N—CH: 4.40 (t)<br>PhCH$_2$O: 5.10 (s)<br>aromatic H's 6.8-8.1 | Scheme 2' |

TABLE B-continued

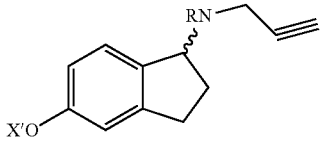

All compounds racemic

| Number | X | R | Results (B) | NMR (CDCl$_3$) ppm | Synthesis Route |
|---|---|---|---|---|---|
| 16 | CH$_2$C$_6$H$_5$CONH$_2$(4) | H | ++ | (CD$_3$OD)<br>ring-CH: 1.92 (m)<br>ring-CH: 2.35 (m)<br>C≡CH: 2.67 (m)<br>ring-CH: 2.81 (m)<br>ring-CH: 3.02 (m)<br>N—CH$_2$: 3.46 (q)<br>N—CH: 4.38 (t)<br>PhCH$_2$O: 5.15 (s)<br>aromatic H's 6.8-7.9 | Scheme 2' |
| 17 | CH$_2$C$_6$H$_5$CO$_2$Me(3) | CH$_3$ | ++ | (CDCl$_3$)<br>ring-CH$_2$: 2.14 (m)<br>C≡CH: 2.25 (m)<br>ring-CH: 2.78 (m)<br>ring-CH: 2.94 (m)<br>N—CH$_2$: 3.33 (q)<br>OCH$_3$: 3.93 (s)<br>N—CH: 4.39 (t)<br>PhCH$_2$O: 5.09 (s)<br>aromatic H's 6.8-8.15 | Scheme 2' |
| 18 | CH$_2$C$_6$H$_5$CO$_2$Me(3) | H | +++ | (CDCl$_3$)<br>ring-CH: 1.89 (m)<br>C≡CH: 2.26 (m)<br>ring-CH: 2.38 (m)<br>ring-CH: 2.80 (m)<br>ring-CH: 3.01 (m)<br>N—CH$_2$: 3.50 (q)<br>OCH$_3$: 3.93 (s)<br>N—CH: 4.37 (t)<br>PhCH$_2$O: 5.09 (s)<br>aromatic H's 6.8-8.13 | Scheme 2' |
| 19 | CH$_2$C$_6$H$_5$CO$_2$H(3) | H | + | (CD$_3$OD)<br>ring-CH: 2.08 (m)<br>ring-CH: 2.45 (m)<br>ring-CH: 2.90 (m)<br>C≡CH: 2.94 (m)<br>ring-CH: 3.10 (m)<br>N—CH$_2$: 3.69 (s)<br>N—CH: 4.59 (q)<br>PhCH$_2$O: 5.14 (s)<br>aromatic H's 6.9-8.10 | Scheme 2' |
| 20 | CH$_2$C$_6$H$_5$CONH$_2$(3) | H | +++ | (CD$_3$OD)<br>ring-CH$_2$: 2.15 (m)<br>C≡CH: 2.69 (m)<br>N—CH$_3$: 2.33 (s)<br>ring-CH: 2.78 (m)<br>ring-CH: 2.95 (m)<br>N—CH$_2$: 3.31 (s)<br>OCH$_3$: 3.92 (s)<br>N—CH: 4.39 (t)<br>PhCH$_2$O: 5.12 (s)<br>aromatic H's 6.85-8.0 | Scheme 2' |
| 21 | CH$_2$C$_6$H$_5$CH$_2$CO$_2$Me(4) | H | ++ | (CDCl$_3$)<br>ring-CH: 1.89 (m)<br>ring-CH: 2.37 (m)<br>ring-CH: 2.79 (m)<br>C≡CH: 2.27 (m)<br>ring-CH: 3.02 (m)<br>N—CH$_2$: 3.50 (q)<br>PhCH$_2$CO: 3.65 (s)<br>OCH$_3$: 3.70 (s)<br>N—CH: 4.37 (q)<br>PhCH$_2$O: 5.13 (s)<br>aromatic H's 6.8-7.45 | Scheme 2' |

TABLE B-continued

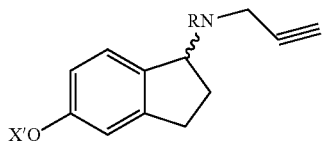

All compounds racemic

| Number | X | R | Results (B) | NMR (CDCl₃) ppm | Synthesis Route |
|---|---|---|---|---|---|
| 22 | CH₂C₆H₅CH₂CO₂H(4) | H | ~+ | (CD₃OD)<br>ring-CH: 1.90 (m)<br>ring-CH: 2.37 (m)<br>ring-CH: 2.80 (m)<br>C≡CH: 2.27 (m)<br>ring-CH: 3.02 (m)<br>N—CH₂: 3.48 (q)<br>PhCH₂CO: 3.31 (s)<br>N—CH: 4.37 (q)<br>PhCH₂O: 5.03 (s)<br>aromatic H's 6.8-7.35 | Scheme 2' |
| 23 | CH₂C₆H₅OCH₂CO₂Et(4) | H | + | (CDCl₃)<br>ester-CH₃: 1.30 (t)<br>ring-CH: 1.89 (m)<br>C≡CH: 2.26 (m)<br>ring-CH: 2.38 (m)<br>ring-CH: 2.78 (m)<br>ring-CH: 3.02 (m)<br>N—CH₂: 3.51 (q)<br>ester-CH₂: 4.28 (q)<br>N—CH: 4.37 (t)<br>OCH₂CO: 4.63 (s)<br>PhCH₂O: 4.97 (s)<br>aromatic H's 6.80-7.37 | Scheme 2' |
| 24 | CH₂C₆H₅OCH₂CONH₂(4) | H | ++ | (CD₃OD)<br>ring-CH: 1.90 (m)<br>ring-CH: 2.36 (m)<br>C≡CH: 2.68 (m)<br>ring-CH: 2.78 (m)<br>ring-CH: 3.05 (m)<br>N—CH₂: 3.45 (q)<br>OCH₂CO: 4.50 (s)<br>N—CH: 4.37 (q)<br>PhCH₂O: 4.99 (s)<br>aromatic H's 6.8-7.45 | Scheme 2' |
| 25 | CH₂C₄H₂O—CO₂Me(2,5) (furan) | H | + | (CDCl₃)<br>ring-CH: 1.89 (m)<br>C≡CH: 2.26 (m)<br>ring-CH: 2.39 (m)<br>ring-CH: 2.80 (m)<br>ring-CH: 3.00 (m)<br>N—CH₂: 3.50 (q)<br>O—CH₃: 3.90 (s)<br>N—CH: 4.37 (t)<br>OCH₂CO: 4.63 (s)<br>furan-CH₂O: 5.05 (s)<br>furan H's 6.51 (d), 6.80 (d)<br>phenyl H's 6.78-7.26 | Scheme 2' |
| 26 | CH₂CH₂CH₂PO(OEt)₂ | H | + | (CD₃OD)<br>ester-CH₃: 1.32 (t)<br>ring-CH: 1.98 (m)<br>chain-CH₂'s: 2.00 (m)<br>ring-CH: 2.38 (m)<br>C≡CH: 2.75 (m)<br>ring-CH: 2.83 (m)<br>ring-CH: 3.05 (m)<br>N—CH₂: 3.52 (q)<br>ester-CH₂ 4.10 (m)<br>O—CH₂ 4.02 (t)<br>N—CH: 4.43 (q)<br>aromatic H's 6.8-7.45 | Scheme 6 |

TABLE C

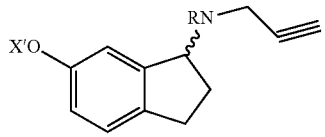

All compounds racemic

| Number | X | R | Results | NMR (CDCl₃-ppm) | Synthesis Route |
|---|---|---|---|---|---|
| 27 | CH₂C₆H₅ | H | + | ring-CH: 1.90 (m)<br>C≡CH: 2.24 (m)<br>ring-CH: 2.41 (m)<br>ring-CH: 2.76 (m)<br>ring-CH: 2.97 (m)<br>N—CH₂: 3.51 (s)<br>N—CH: 4.40 (m)<br>PhCH₂O: 5.06<br>aromatic H's 6.85-7.45 | Scheme 2 |
| 28 | CH₂C₆H₅ | CH₃ | + | ring-CH₂: 2.13 (m)<br>C≡CH: 2.26 (m)<br>N—CH₃: 2.34 (s)<br>ring-CH: 2.41 (m)<br>ring-CH: 2.76 (m)<br>ring-CH: 2.97 (m)<br>N—CH₂: 3.51 (s)<br>N—CH: 4.46 (m)<br>PhCH₂O: 5.06<br>aromatic H's 6.86-7.50 | Scheme 2 |
| 29 | CH₂CH₂C₆H₅ | H | + | ring-CH: 1.92 (m)<br>C≡CH: 2.27 (m)<br>ring-CH: 2.41 (m)<br>ring-CH: 2.75 (m)<br>ring-CH: 3.00 (m)<br>PhOCH₂: 3.10 (t)<br>N—CH₂: 3.52 (q)<br>PhOCH₂: 4.19 (t)<br>N—CH: 4.41 (t)<br>aromatic H's 6.77-7.37 | Scheme 2 |
| 30 | CH₂CO₂Et | CH₃ | + | ester-CH₃: 1.30 (t)<br>ring-CH₂: 2.13 (m)<br>C≡CH: 2.26 (m)<br>N—CH₃: 2.32 (s)<br>ring-CH: 2.74 (m)<br>ring-CH: 2.89 (m)<br>N—CH₂: 3.51 (s)<br>ester-CH₂: 4.27 (q)<br>N—CH: 4.43 (m)<br>aromatic H's 6.81-7.28 | Scheme 6 |
| 31 | CH₂CH=CHCO₂Et | CH₃ | ++ | ester-CH₃: 1.30 (t)<br>ring-CH₂: 2.16 (m)<br>C≡CH: 2.29 (m)<br>N—CH₃: 2.37 (s)<br>ring-CH: 2.77 (m)<br>ring-CH: 2.90 (m)<br>N—CH₂: 3.37 (m)<br>ester-CH₂: 4.20 (q)<br>N—CH: 4.48 (m)<br>OCH₂-vinyl: 4.70 (m)<br>CH=: 6.19 (dt)<br>CH=: 7.07 (dt)<br>aromatic H's 6.80-7.15 | Scheme 6 |
| 32 | CH₂CH=CHCO₂Et | H | + | ester-CH₃: 1.30 (t)<br>ring-CH: 1.95 (m)<br>C≡CH: 2.32 (m)<br>ring-CH: 2.44 (m)<br>ring-CH: 2.78 (m)<br>ring-CH: 3.00 (m)<br>N—CH₂: 3.54 (m)<br>ester-CH₂: 4.21 (q)<br>N—CH: 4.45 (m)<br>OCH₂-vinyl: 4.70 (m)<br>CH=: 6.19 (dt)<br>CH=: 7.07 (dt)<br>aromatic H's 6.80-7.2 | Scheme 6 |

TABLE C-continued

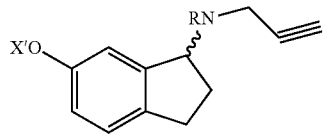

All compounds racemic

| Number | X | R | Results | NMR (CDCl$_3$-ppm) | Synthesis Route |
|---|---|---|---|---|---|
| 33 | CH$_2$C$_6$H$_5$CO$_2$Me(4) | CH$_3$ | + | ring-CH$_2$: 2.15 (m)<br>C≡CH: 2.27 (m)<br>N—CH$_3$: 2.35 (s)<br>ring-CH: 2.75 (m)<br>ring-CH: 2.89 (m)<br>N—CH$_2$: 3.35 (m)<br>OCH$_3$: 3.92 (s)<br>N—CH: 4.45 (m)<br>PhOCH$_2$: 5.13 (q)<br>aromatic H's 6.86-8.05 | Scheme 2' |
| 34 | CH$_2$C$_6$H$_5$CO$_2$Me(4) | H | + | ring-CH: 1.95 (m)<br>C≡CH: 2.26 (m)<br>ring-CH: 2.43 (m)<br>ring-CH: 2.77 (m)<br>ring-CH: 2.95 (m)<br>N—CH$_2$: 3.51 (q)<br>OCH$_3$: 3.92 (s)<br>N—CH: 4.38 (m)<br>PhOCH$_2$: 5.12 (s)<br>aromatic H's 6.83-8.10 | Scheme 2' |
| 35 | CH$_2$C$_6$H$_5$CO$_2$Me(3) | H | + | ring-CH: 1.93 (m)<br>C≡CH: 2.29 (m)<br>ring-CH: 2.42 (m)<br>ring-CH: 2.77 (m)<br>ring-CH: 2.97 (m)<br>N—CH$_2$: 3.51 (q)<br>OCH$_3$: 3.93 (s)<br>N—CH: 4.42 (t)<br>PhOCH$_2$: 5.10 (s)<br>aromatic H's 6.85-8.15 | Scheme 2' |
| 36 | CH$_2$C$_6$H$_5$OCH$_2$CN(3) | H | ++ | (CDCl$_3$)<br>ring-CH: 1.87 (m)<br>C≡CH: 2.27 (m)<br>ring-CH: 2.43 (m)<br>ring-CH: 2.77 (m)<br>ring-CH: 2.95 (m)<br>N—CH$_2$: 3.50 (q)<br>N—CH: 4.37 (t)<br>O—CH$_2$CN: 4.78 (s)<br>PhCH$_2$O: 5.06 (s)<br>aromatic H's 6.83-7.38 | Scheme 2' |
| 37 | CH$_2$C$_6$H$_5$CN(3) | H | + | (CDCl$_3$)<br>ring-CH: 1.87 (m)<br>C≡CH: 2.28 (m)<br>ring-CH: 2.44 (m)<br>ring-CH: 2.78 (m)<br>ring-CH: 2.95 (m)<br>N—CH$_2$: 3.51 (q)<br>N—CH: 4.38 (t)<br>PhCH$_2$O: 5.08 (s)<br>aromatic H's 6.82-7.73 | Scheme 2' |
| 38 | CH$_2$C$_6$H$_5$CONH$_2$(3) | H | + | (CD$_3$OD)<br>ring-CH: 1.88 (m)<br>ring-CH: 2.37 (m)<br>C≡CH: 2.67 (m)<br>ring-CH: 2.75 (m)<br>ring-CH: 2.94 (m)<br>N—CH$_2$: 3.43 (q)<br>N—CH: 4.38 (t)<br>PhCH$_2$O: 5.13 (s)<br>aromatic H's 6.86-7.97 | Scheme 2' |

Tables I-VI show representative examples of the compounds of the present invention. Each example in each table represents an individual species of the present invention.

TABLE I

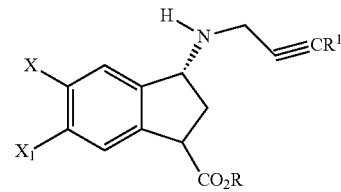

| Ex. # | X | X$^1$ | R | R$^1$ |
|---|---|---|---|---|
| 1 | H | H | CH$_3$ | H |
| 2 | H | H | H | H |
| 3 | H | H | CH$_3$ | CH$_3$ |
| 4 | H | H | H | CH$_3$ |
| 5 | OH | H | CH$_3$ | H |
| 6 | OH | H | H | H |
| 7 | OH | H | CH$_3$ | CH$_3$ |
| 8 | OH | H | H | CH$_3$ |
| 9 | H | OH | CH$_3$ | H |
| 10 | H | OH | H | H |
| 11 | H | OH | CH$_3$ | CH$_3$ |
| 12 | H | OH | H | CH$_3$ |
| 13 | OCH$_3$ | H | CH$_3$ | H |
| 14 | OCH$_3$ | H | H | H |
| 15 | OCH$_3$ | H | CH$_3$ | CH$_3$ |
| 16 | OCH$_3$ | H | H | CH$_3$ |
| 17 | H | OCH$_3$ | CH$_3$ | H |
| 18 | H | OCH$_3$ | H | H |
| 19 | H | OCH$_3$ | CH$_3$ | CH$_3$ |
| 20 | H | OCH$_3$ | H | CH$_3$ |
| 21 | OCH$_2$C$_6$H$_5$ | H | CH$_3$ | H |
| 22 | OCH$_2$C$_6$H$_5$ | H | H | H |
| 23 | OCH$_2$C$_6$H$_5$ | H | CH$_3$ | CH$_3$ |
| 24 | OCH$_2$C$_6$H$_5$ | H | H | CH$_3$ |
| 25 | H | OCH$_2$C$_6$H$_5$ | CH$_3$ | H |
| 26 | H | OCH$_2$C$_6$H$_5$ | H | H |
| 27 | H | OCH$_2$C$_6$H$_5$ | CH$_3$ | CH$_3$ |
| 28 | H | OCH$_2$C$_6$H$_5$ | H | CH$_3$ |
| 29 | OCH$_2$CH$_2$C$_6$H$_5$ | H | CH$_3$ | H |
| 30 | OCH$_2$CH$_2$C$_6$H$_5$ | H | H | H |
| 31 | OCH$_2$CH$_2$C$_6$H$_5$ | H | CH$_3$ | CH$_3$ |
| 32 | OCH$_2$CH$_2$C$_6$H$_5$ | H | H | CH$_3$ |
| 33 | OCH$_2$CH$_2$C$_6$H$_5$ | H | CH$_3$ | H |
| 34 | OCH$_2$CH$_2$C$_6$H$_5$ | H | H | H |
| 35 | OCH$_2$CH$_2$C$_6$H$_5$ | H | CH$_3$ | CH$_3$ |
| 36 | OCH$_2$CH$_2$C$_6$H$_5$ | H | H | CH$_3$ |
| 37 | H | OCH$_2$CH$_2$C$_6$H$_5$ | CH$_3$ | H |
| 38 | H | OCH$_2$CH$_2$C$_6$H$_5$ | H | H |
| 39 | H | OCH$_2$CH$_2$C$_6$H$_5$ | CH$_3$ | CH$_3$ |
| 40 | H | OCH$_2$CH$_2$C$_6$H$_5$ | H | CH$_3$ |
| 41 | OCH$_2$CH=CH$_2$ | H | CH$_3$ | H |
| 42 | OCH$_2$CH=CH$_2$ | H | H | H |
| 43 | OCH$_2$CH=CH$_2$ | H | CH$_3$ | CH$_3$ |
| 44 | OCH$_2$CH=CH$_2$ | H | H | CH$_3$ |
| 45 | H | OCH$_2$CH=CH$_2$ | CH$_3$ | H |
| 46 | H | OCH$_2$CH=CH$_2$ | H | H |
| 47 | H | OCH$_2$CH=CH$_2$ | CH$_3$ | CH$_3$ |
| 48 | H | OCH$_2$CH=CH$_2$ | H | CH$_3$ |
| 49 | OCH$_2$CONH$_2$ | H | CH$_3$ | H |
| 50 | OCH$_2$CONH$_2$ | H | H | H |
| 51 | OCH$_2$CONH$_2$ | H | CH$_3$ | CH$_3$ |
| 52 | OCH$_2$CONH$_2$ | H | H | CH$_3$ |
| 53 | H | OCH$_2$CONH$_2$ | CH$_3$ | H |
| 54 | H | OCH$_2$CONH$_2$ | H | H |
| 55 | H | OCH$_2$CONH$_2$ | CH$_3$ | CH$_3$ |
| 56 | H | OCH$_2$CONH$_2$ | H | CH$_3$ |
| 57 | Br | H | CH$_3$ | H |
| 58 | Br | H | H | H |
| 59 | Br | H | CH$_3$ | CH$_3$ |
| 60 | Br | H | H | CH$_3$ |
| 61 | H | Cl | CH$_3$ | H |
| 62 | H | Cl | H | H |
| 63 | H | Cl | CH$_3$ | CH$_3$ |
| 64 | H | Cl | H | CH$_3$ |
| 65 | NO$_2$ | H | CH$_3$ | H |
| 66 | NO$_2$ | H | H | H |
| 67 | NO$_2$ | H | CH$_3$ | CH$_3$ |
| 68 | NO$_2$ | H | H | CH$_3$ |
| 69 | NH$_2$ | H | CH$_3$ | H |
| 70 | NH$_2$ | H | H | H |
| 71 | NH$_2$ | H | CH$_3$ | CH$_3$ |
| 72 | NH$_2$ | H | H | CH$_3$ |
| 73 | NHSO$_2$CH$_3$ | H | CH$_3$ | H |
| 74 | NHSO$_2$CH$_3$ | H | H | H |
| 75 | NHSO$_2$CH$_3$ | H | CH$_3$ | CH$_3$ |
| 76 | NHSO$_2$CH$_3$ | H | H | CH$_3$ |
| 77 | H | CH$_3$ | CH$_3$ | H |
| 78 | H | CH$_3$ | H | H |
| 79 | H | CH$_3$ | CH$_3$ | CH$_3$ |
| 80 | H | CH$_3$ | H | CH$_3$ |

TABLE IIa

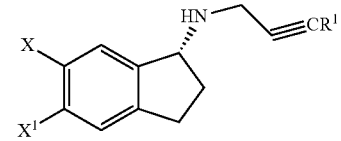

| Ex. # | X | X$^1$ | R$^1$ |
|---|---|---|---|
| 1. | H | H | CO$_2$CH$_2$CH$_3$ |
| 2. | H | H | CO$_2$H |
| 3. | OH | H | CO$_2$CH$_2$CH$_3$ |
| 4. | OH | H | CO$_2$H |
| 5. | OCH$_3$ | H | CO$_2$CH$_2$CH$_3$ |
| 6. | OCH$_3$ | H | CO$_2$H |
| 7. | OCH$_2$CH=CH$_2$ | H | CO$_2$CH$_2$CH$_3$ |
| 8. | OCH$_2$CH=CH$_2$ | H | CO$_2$H |
| 9. | OCH$_2$C$_6$H$_5$ | H | CO$_2$CH$_2$CH$_3$ |
| 10. | OCH$_2$C$_6$H$_5$ | H | CO$_2$H |
| 11. | OCH$_2$CH$_2$C$_6$H$_5$ | H | CO$_2$CH$_2$CH$_3$ |
| 12. | OCH$_2$CH$_2$C$_6$H$_5$ | H | CO$_2$H |
| 13. | OCH$_2$CONH$_2$ | H | CO$_2$CH$_2$CH$_3$ |
| 14. | OCH$_2$CONH$_2$ | H | CO$_2$H |
| 15. | H | Cl | CO$_2$CH$_2$CH$_3$ |
| 16. | H | Cl | CO$_2$H |
| 17. | Br | H | CO$_2$CH$_2$CH$_3$ |
| 18. | Br | H | CO$_2$H |
| 19. | H | CH$_3$ | CO$_2$CH$_2$CH$_3$ |
| 20. | H | CH$_3$ | CO$_2$H |
| 21. | NO$_2$ | H | CO$_2$CH$_2$CH$_3$ |
| 22. | NO$_2$ | H | CO$_2$H |
| 23. | NH$_2$ | H | CO$_2$CH$_2$CH$_3$ |
| 24. | NH$_2$ | H | CO$_2$H |
| 25. | NHSO$_2$CH$_3$ | H | CO$_2$CH$_2$CH$_3$ |
| 26. | NHSO$_2$CH$_3$ | H | CO$_2$H |
| 27. | H | OH | CO$_2$CH$_2$CH$_3$ |
| 28. | H | OH | CO$_2$H |
| 29. | H | OCH$_3$ | CO$_2$CH$_2$CH$_3$ |
| 30. | H | OCH$_3$ | CO$_2$H |
| 31. | H | OCH$_2$CH=CH$_2$ | CO$_2$CH$_2$CH$_3$ |
| 32. | H | OCH$_2$CH=CH$_2$ | CO$_2$H |
| 33. | H | OCH$_2$C$_6$H$_5$ | CO$_2$CH$_2$CH$_3$ |
| 34. | H | OCH$_2$C$_6$H$_5$ | CO$_2$H |
| 35. | H | OCH$_2$CH$_2$C$_6$H$_5$ | CO$_2$CH$_2$CH$_3$ |
| 36. | H | OCH$_2$CH$_2$C$_6$H$_5$ | CO$_2$H |

TABLE IIa-continued

| Ex. # | X | X¹ | R¹ |
|---|---|---|---|
| 37. | H | OCH₂CONH₂ | CO₂CH₂CH₃ |
| 38. | H | OCH₂CONH₂ | CO₂H |
| 39. | H | H | CH₂CO₂CH₂CH₃ |
| 40. | H | H | CH₂CO₂H |
| 41. | OH | H | CH₂CO₂CH₂CH₃ |
| 42. | OH | H | CH₂CO₂H |
| 43. | OCH₃ | H | CH₂CO₂CH₂CH₃ |
| 44. | OCH₃ | H | CH₂CO₂H |
| 45. | OCH₂CH=CH₂ | H | CH₂CO₂CH₂CH₃ |
| 46. | OCH₂CH=CH₂ | H | CH₂CO₂H |
| 47. | OCH₂C₆H₅ | H | CH₂CO₂CH₂CH₃ |
| 48. | OCH₂C₆H₅ | H | CH₂CO₂H |
| 49. | OCH₂CH₂C₆H₅ | H | CH₂CO₂CH₂CH₃ |
| 50. | OCH₂CH₂C₆H₅ | H | CH₂CO₂H |
| 51. | OCH₂CONH₂ | H | CH₂CO₂CH₂CH₃ |
| 52. | OCH₂CONH₂ | H | CH₂CO₂H |
| 53. | H | Cl | CH₂CO₂CH₂CH₃ |
| 54. | H | Cl | CH₂CO₂H |
| 55. | Br | H | CH₂CO₂CH₂CH₃ |
| 56. | Br | H | CH₂CO₂H |
| 57. | H | CH₃ | CH₂CO₂CH₂CH₃ |
| 58. | H | CH₃ | CH₂CO₂H |
| 59. | NO₂ | H | CH₂CO₂CH₂CH₃ |
| 60. | NO₂ | H | CH₂CO₂H |
| 61. | NH₂ | H | CH₂CO₂CH₂CH₃ |
| 62. | NH₂ | H | CH₂CO₂H |
| 63. | NHSO₂CH₃ | H | CH₂CO₂CH₂CH₃ |
| 64. | NHSO₂CH₃ | H | CH₂CO₂H |
| 65. | H | OH | CH₂CO₂CH₂CH₃ |
| 66. | H | OH | CH₂CO₂H |
| 67. | H | OCH₃ | CH₂CO₂CH₂CH₃ |
| 68. | H | OCH₃ | CH₂CO₂H |
| 69. | H | OCH₂CH=CH₂ | CH₂CO₂CH₂CH₃ |
| 70. | H | OCH₂CH=CH₂ | CH₂CO₂H |
| 71. | H | OCH₂C₆H₅ | CH₂CO₂CH₂CH₃ |
| 72. | H | OCH₂C₆H₅ | CH₂CO₂H |
| 73. | H | OCH₂CH₂C₆H₅ | CH₂CO₂CH₂CH₃ |
| 74. | H | OCH₂CH₂C₆H₅ | CH₂CO₂H |
| 75. | H | OCH₂CONH₂ | CH₂CO₂CH₂CH₃ |
| 76. | H | OCH₂CONH₂ | CH₂CO₂H |
| 77. | H | H | CH₂CH₂CO₂CH₂CH₃ |
| 78. | H | H | CH₂CH₂CO₂H |
| 79. | OH | H | CH₂CH₂CO₂CH₂CH₃ |
| 80. | OH | H | CH₂CH₂CO₂H |
| 81. | OCH₃ | H | CH₂CH₂CO₂CH₂CH₃ |
| 82. | OCH₃ | H | CH₂CH₂CO₂H |
| 83. | OCH₂CH=CH₂ | H | CH₂CH₂CO₂CH₂CH₃ |
| 84. | OCH₂CH=CH₂ | H | CH₂CH₂CO₂H |
| 85. | OCH₂C₆H₅ | H | CH₂CH₂CO₂CH₂CH₃ |
| 86. | OCH₂C₆H₅ | H | CH₂CH₂CO₂H |
| 87. | OCH₂CH₂C₆H₅ | H | CH₂CH₂CO₂CH₂CH₃ |
| 88. | OCH₂CH₂C₆H₅ | H | CH₂CH₂CO₂H |
| 89. | OCH₂CONH₂ | H | CH₂CH₂CO₂CH₂CH₃ |
| 90. | OCH₂CONH₂ | H | CH₂CH₂CO₂H |
| 91. | H | Cl | CH₂CH₂CO₂CH₂CH₃ |
| 92. | H | Cl | CH₂CH₂CO₂H |
| 93. | Br | H | CH₂CH₂CO₂CH₂CH₃ |
| 94. | Br | H | CH₂CH₂CO₂H |
| 95. | H | CH₃ | CH₂CO₂CH₂CH₂CH₃ |
| 96. | H | CH₃ | CH₂CH₂CO₂H |
| 97. | NO₂ | H | CH₂CH₂CO₂CH₂CH₃ |
| 98. | NO₂ | H | CH₂CH₂CO₂H |
| 99. | NH₂ | H | CH₂CO₂CH₂CH₂CH₃ |
| 100. | NH₂ | H | CH₂CH₂CO₂H |
| 101. | NHSO₂CH₃ | H | CH₂CH₂CO₂CH₂CH₃ |
| 102. | NHSO₂CH₃ | H | CH₂CH₂CO₂H |
| 103. | H | OH | CH₂CH₂CO₂CH₂CH₃ |
| 104. | H | OH | CH₂CH₂CO₂H |
| 105. | H | OCH₃ | CH₂CH₂CO₂CH₂CH₃ |
| 106. | H | OCH₃ | CH₂CH₂CO₂H |
| 107. | H | OCH₂CH=CH₂ | CH₂CO₂CH₂CH₂CH₃ |
| 108. | H | OCH₂CH=CH₂ | CH₂CH₂CO₂H |
| 109. | H | OCH₂C₆H₅ | CH₂CO₂CH₂CH₃ |
| 110. | H | OCH₂C₆H₅ | CH₂CH₂CO₂H |
| 111. | H | OCH₂CH₂C₆H₅ | CH₂CO₂CH₂CH₃ |
| 112. | H | OCH₂CH₂C₆H₅ | CH₂CH₂CO₂H |
| 113. | H | OCH₂CONH₂ | CH₂CO₂CH₂CH₃ |
| 114. | H | OCH₂CONH₂ | CH₂CH₂CO₂H |
| 115. | H | H | CH₂CH₂PO(OCH₂CH₃)₂ |
| 116. | H | H | CH₂CH₂PO(OH)₂ |
| 117. | OH | H | CH₂CH₂PO(OCH₂CH₃)₂ |
| 118. | OH | H | CH₂CH₂PO(OH)₂ |
| 119. | OCH₃ | H | CH₂CH₂PO(OCH₂CH₃)₂ |
| 120. | OCH₃ | H | CH₂CH₂PO(OH)₂ |
| 121. | OCH₂CH=CH₂ | H | CH₂CH₂PO(OCH₂CH₃)₂ |
| 122. | OCH₂CH=CH₂ | H | CH₂CH₂PO(OH)₂ |
| 123. | OCH₂C₆H₅ | H | CH₂CH₂PO(OCH₂CH₃)₂ |
| 124. | OCH₂C₆H₅ | H | CH₂CH₂PO(OH)₂ |
| 125. | OCH₂CH₂C₆H₅ | H | CH₂CH₂PO(OCH₂CH₃)₂ |
| 126. | OCH₂CH₂C₆H₅ | H | CH₂CH₂PO(OH)₂ |
| 127. | OCH₂CONH₂ | H | CH₂CH₂PO(OCH₂CH₃)₂ |
| 128. | OCH₂CONH₂ | H | CH₂CH₂PO(OH)₂ |
| 129. | H | Cl | CH₂CH₂PO(OCH₂CH₃)₂ |
| 130. | H | Cl | CH₂CH₂PO(OH)₂ |
| 131. | Br | H | CH₂CH₂PO(OCH₂CH₃)₂ |
| 132. | Br | H | CH₂CH₂PO(OH)₂ |
| 133. | H | CH₃ | CH₂CH₂PO(OCH₂CH₃)₂ |
| 134. | H | CH₃ | CH₂CH₂PO(OH)₂ |
| 135. | NO₂ | H | CH₂CH₂PO(OCH₂CH₃)₂ |
| 136. | NO₂ | H | CH₂CH₂PO(OH)₂ |
| 137. | NH₂ | H | CH₂CH₂PO(OCH₂CH₃)₂ |
| 138. | NH₂ | H | CH₂CH₂PO(OH)₂ |
| 139. | NHSO₂CH₃ | H | CH₂CH₂PO(OCH₂CH₃)₂ |
| 140. | NHSO₂CH₃ | H | CH₂CH₂PO(OH)₂ |
| 141. | H | OH | CH₂CH₂PO(OCH₂CH₃)₂ |
| 142. | H | OH | CH₂CH₂PO(OH)₂ |
| 143. | H | OCH₃ | CH₂CH₂PO(OCH₂CH₃)₂ |
| 144. | H | OCH₃ | CH₂CH₂PO(OH)₂ |
| 145. | H | OCH₂CH=CH₂ | CH₂CH₂PO(OCH₂CH₃)₂ |
| 146. | H | OCH₂CH=CH₂ | CH₂CH₂PO(OH)₂ |
| 147. | H | OCH₂C₆H₅ | CH₂CH₂PO(OCH₂CH₃)₂ |
| 148. | H | OCH₂C₆H₅ | CH₂CH₂PO(OH)₂ |
| 149. | H | OCH₂CH₂C₆H₅ | CH₂CH₂PO(OCH₂CH₃)₂ |
| 150. | H | OCH₂CH₂C₆H₅ | CH₂CH₂PO(OH)₂ |
| 151. | H | OCH₂CONH₂ | CH₂CH₂PO(OCH₂CH₃)₂ |
| 152. | H | OCH₂CONH₂ | CH₂CH₂PO(OH)₂ |
| 153. | H | H | CH₂CH=CHCO₂CH₂CH₃ |
| 154. | H | H | CH₂CH=CHCO₂H |
| 155. | OH | H | CH₂CH=CHCO₂CH₂CH₃ |
| 156. | OH | H | CH₂CH=CHCO₂H |
| 157. | OCH₃ | H | CH₂CH=CHCO₂CH₂CH₃ |
| 158. | OCH₃ | H | CH₂CH=CHCO₂H |
| 159. | OCH₂CH=CH₂ | H | CH₂CH=CHCO₂CH₂CH₃ |
| 160. | OCH₂CH=CH₂ | H | CH₂CH=CHCO₂H |
| 161. | OCH₂C₆H₅ | H | CH₂CH=CHCO₂CH₂CH₃ |
| 162. | OCH₂C₆H₅ | H | CH₂CH=CHCO₂H |
| 163. | OCH₂CH₂C₆H₅ | H | CH₂CH=CHCO₂CH₂CH₃ |
| 164. | OCH₂CH₂C₆H₅ | H | CH₂CH=CHCO₂H |
| 165. | OCH₂CONH₂ | H | CH₂CH=CHCO₂CH₂CH₃ |
| 166. | OCH₂CONH₂ | H | CH₂CH=CHCO₂H |
| 167. | H | Cl | CH₂CH=CHCO₂CH₂CH₃ |
| 168. | H | Cl | CH₂CH=CHCO₂H |
| 169. | Br | H | CH₂CH=CHCO₂CH₂CH₃ |
| 170. | Br | H | CH₂CH=CHCO₂H |
| 171. | H | CH₃ | CH₂CH=CHCO₂CH₂CH₃ |
| 172. | H | CH₃ | CH₂CH=CHCO₂H |
| 173. | NO₂ | H | CH₂CH=CHCO₂CH₂CH₃ |
| 174. | NO₂ | H | CH₂CH=CHCO₂H |
| 175. | NH₂ | H | CH₂CH=CHCO₂CH₂CH₃ |
| 176. | NH₂ | H | CH₂CH=CHCO₂H |

TABLE IIa-continued

| Ex. # | X | X¹ | R¹ |
|---|---|---|---|
| 177. | NHSO$_2$CH$_3$ | H | CH$_2$CH=CHCO$_2$CH$_2$CH$_3$ |
| 178. | NHSO$_2$CH$_3$ | H | CH$_2$CH=CHCO$_2$H |
| 179. | H | OH | CH$_2$CH=CHCO$_2$CH$_2$CH$_3$ |
| 180. | H | OH | CH$_2$CH=CHCO$_2$H |
| 181. | H | OCH$_3$ | CH$_2$CH=CHCO$_2$CH$_2$CH$_3$ |
| 182. | H | OCH$_3$ | CH$_2$CH=CHCO$_2$H |
| 183. | H | OCH$_2$CH=CH$_2$ | CH$_2$CH=CHCO$_2$CH$_2$CH$_3$ |
| 184. | H | OCH$_2$CH=CH$_2$ | CH$_2$CH=CHCO$_2$H |
| 185. | H | OCH$_2$C$_6$H$_5$ | CH$_2$CH=CHCO$_2$CH$_2$CH$_3$ |
| 186. | H | OCH$_2$C$_6$H$_5$ | CH$_2$CH=CHCO$_2$H |
| 187. | H | OCH$_2$CH$_2$C$_6$H$_5$ | CH$_2$CH=CHCO$_2$CH$_2$CH$_3$ |
| 188. | H | OCH$_2$CH$_2$C$_6$H$_5$ | CH$_2$CH=CHCO$_2$H |
| 189. | H | OCH$_2$CONH$_2$ | CH$_2$CH=CHCO$_2$CH$_2$CH$_3$ |
| 190. | H | OCH$_2$CONH$_2$ | CH$_2$CH=CHCO$_2$H |

TABLE IIb

| Ex. # | X | X¹ | R¹ |
|---|---|---|---|
| 1. | H | H | CO$_2$CH$_2$CH$_3$ |
| 2. | H | H | CO$_2$H |
| 3. | OH | H | CO$_2$CH$_2$CH$_3$ |
| 4. | OH | H | CO$_2$H |
| 5. | OCH$_3$ | H | CO$_2$CH$_2$CH$_3$ |
| 6. | OCH$_3$ | H | CO$_2$H |
| 7. | OCH$_2$CH=CH$_2$ | H | CO$_2$CH$_2$CH$_3$ |
| 8. | OCH$_2$CH=CH$_2$ | H | CO$_2$H |
| 9. | OCH$_2$C$_6$H$_5$ | H | CO$_2$CH$_2$CH$_3$ |
| 10. | OCH$_2$C$_6$H$_5$ | H | CO$_2$H |
| 11. | OCH$_2$CH$_2$C$_6$H$_5$ | H | CO$_2$CH$_2$CH$_3$ |
| 12. | OCH$_2$CH$_2$C$_6$H$_5$ | H | CO$_2$H |
| 13. | OCH$_2$CONH$_2$ | H | CO$_2$CH$_2$CH$_3$ |
| 14. | OCH$_2$CONH$_2$ | H | CO$_2$H |
| 15. | H | Cl | CO$_2$CH$_2$CH$_3$ |
| 16. | H | Cl | CO$_2$H |
| 17. | Br | H | CO$_2$CH$_2$CH$_3$ |
| 18. | Br | H | CO$_2$H |
| 19. | H | CH$_3$ | CO$_2$CH$_2$CH$_3$ |
| 20. | H | CH$_3$ | CO$_2$H |
| 21. | NO$_2$ | H | CO$_2$CH$_2$CH$_3$ |
| 22. | NO$_2$ | H | CO$_2$H |
| 23. | NH$_2$ | H | CO$_2$CH$_2$CH$_3$ |
| 24. | NH$_2$ | H | CO$_2$H |
| 25. | NHSO$_2$CH$_3$ | H | CO$_2$CH$_2$CH$_3$ |
| 26. | NHSO$_2$CH$_3$ | H | CO$_2$H |
| 27. | H | OH | CO$_2$CH$_2$CH$_3$ |
| 28. | H | OH | CO$_2$H |
| 29. | H | OCH$_3$ | CO$_2$CH$_2$CH$_3$ |
| 30. | H | OCH$_3$ | CO$_2$H |
| 31. | H | OCH$_2$CH=CH$_2$ | CO$_2$CH$_2$CH$_3$ |
| 32. | H | OCH$_2$CH=CH$_2$ | CO$_2$H |
| 33. | H | OCH$_2$C$_6$H$_5$ | CO$_2$CH$_2$CH$_3$ |
| 34. | H | OCH$_2$C$_6$H$_5$ | CO$_2$H |
| 35. | H | OCH$_2$CH$_2$C$_6$H$_5$ | CO$_2$CH$_2$CH$_3$ |
| 36. | H | OCH$_2$CH$_2$C$_6$H$_5$ | CO$_2$H |
| 37. | H | OCH$_2$CONH$_2$ | CO$_2$CH$_2$CH$_3$ |
| 38. | H | OCH$_2$CONH$_2$ | CO$_2$H |
| 39. | H | H | CH$_2$CO$_2$CH$_2$CH$_3$ |
| 40. | H | H | CH$_2$CO$_2$H |
| 41. | OH | H | CH$_2$CO$_2$CH$_2$CH$_3$ |
| 42. | OH | H | CH$_2$CO$_2$H |
| 43. | OCH$_3$ | H | CH$_2$CO$_2$CH$_2$CH$_3$ |
| 44. | OCH$_3$ | H | CH$_2$CO$_2$H |
| 45. | OCH$_2$CH=CH$_2$ | H | CH$_2$CO$_2$CH$_2$CH$_3$ |
| 46. | OCH$_2$CH=CH$_2$ | H | CH$_2$CO$_2$H |
| 47. | OCH$_2$C$_6$H$_5$ | H | CH$_2$CO$_2$CH$_2$CH$_3$ |

TABLE IIb-continued

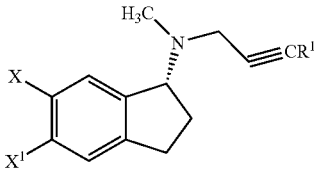

| Ex. # | X | X¹ | R¹ |
| --- | --- | --- | --- |
| 48. | OCH$_2$C$_6$H$_5$ | H | CH$_2$CO$_2$H |
| 49. | OCH$_2$CH$_2$C$_6$H$_5$ | H | CH$_2$CO$_2$CH$_2$CH$_3$ |
| 50. | OCH$_2$CH$_2$C$_6$H$_5$ | H | CH$_2$CO$_2$H |
| 51. | OCH$_2$CONH$_2$ | H | CH$_2$CO$_2$CH$_2$CH$_3$ |
| 52. | OCH$_2$CONH$_2$ | H | CH$_2$CO$_2$H |
| 53. | H | Cl | CH$_2$CO$_2$CH$_2$CH$_3$ |
| 54. | H | Cl | CH$_2$CO$_2$H |
| 55. | Br | H | CH$_2$CO$_2$CH$_2$CH$_3$ |
| 56. | Br | H | CH$_2$CO$_2$H |
| 57. | H | CH$_3$ | CH$_2$CO$_2$CH$_2$CH$_3$ |
| 58. | H | CH$_3$ | CH$_2$CO$_2$H |
| 59. | NO$_2$ | H | CH$_2$CO$_2$CH$_2$CH$_3$ |
| 60. | NO$_2$ | H | CH$_2$CO$_2$H |
| 61. | NH$_2$ | H | CH$_2$CO$_2$CH$_2$CH$_3$ |
| 62. | NH$_2$ | H | CH$_2$CO$_2$H |
| 63. | NHSO$_2$CH$_3$ | H | CH$_2$CO$_2$CH$_2$CH$_3$ |
| 64. | NHSO$_2$CH$_3$ | H | CH$_2$CO$_2$H |
| 65. | H | OH | CH$_2$CO$_2$CH$_2$CH$_3$ |
| 66. | H | OH | CH$_2$CO$_2$H |
| 67. | H | OCH$_3$ | CH$_2$CO$_2$CH$_2$CH$_3$ |
| 68. | H | OCH$_3$ | CH$_2$CO$_2$H |
| 69. | H | OCH$_2$CH=CH$_2$ | CH$_2$CO$_2$CH$_2$CH$_3$ |
| 70. | H | OCH$_2$CH=CH$_2$ | CH$_2$CO$_2$H |
| 71. | H | OCH$_2$C$_6$H$_5$ | CH$_2$CO$_2$CH$_2$CH$_3$ |
| 72. | H | OCH$_2$C$_6$H$_5$ | CH$_2$CO$_2$H |
| 73. | H | OCH$_2$CH$_2$C$_6$H$_5$ | CH$_2$CO$_2$CH$_2$CH$_3$ |
| 74. | H | OCH$_2$CH$_2$C$_6$H$_5$ | CH$_2$CO$_2$H |
| 75. | H | OCH$_2$CONH$_2$ | CH$_2$CO$_2$CH$_2$CH$_3$ |
| 76. | H | OCH$_2$CONH$_2$ | CH$_2$CO$_2$H |
| 77. | H | H | CH$_2$CH$_2$CO$_2$CH$_2$CH$_3$ |
| 78. | H | H | CH$_2$CH$_2$CO$_2$H |
| 79. | OH | H | CH$_2$CO$_2$CH$_2$CH$_2$CH$_3$ |
| 80. | OH | H | CH$_2$CH$_2$CO$_2$H |
| 81. | OCH$_3$ | H | CH$_2$CH$_2$CO$_2$CH$_2$CH$_3$ |
| 82. | OCH$_3$ | H | CH$_2$CH$_2$CO$_2$H |
| 83. | OCH$_2$CH=CH$_2$ | H | CH$_2$CO$_2$CH$_2$CH$_2$CH$_3$ |
| 84. | OCH$_2$CH=CH$_2$ | H | CH$_2$CH$_2$CO$_2$H |
| 85. | OCH$_2$C$_6$H$_5$ | H | CH$_2$CH$_2$CO$_2$CH$_2$CH$_3$ |
| 86. | OCH$_2$C$_6$H$_5$ | H | CH$_2$CH$_2$CO$_2$H |
| 87. | OCH$_2$CH$_2$C$_6$H$_5$ | H | CH$_2$CO$_2$CH$_2$CH$_2$CH$_3$ |
| 88. | OCH$_2$CH$_2$C$_6$H$_5$ | H | CH$_2$CH$_2$CO$_2$H |
| 89. | OCH$_2$CONH$_2$ | H | CH$_2$CH$_2$CO$_2$CH$_2$CH$_3$ |
| 90. | OCH$_2$CONH$_2$ | H | CH$_2$CH$_2$CO$_2$H |
| 91. | H | Cl | CH$_2$CO$_2$CH$_2$CH$_2$CH$_3$ |
| 92. | H | Cl | CH$_2$CH$_2$CO$_2$H |
| 93. | Br | H | CH$_2$CH$_2$CO$_2$CH$_2$CH$_3$ |
| 94. | Br | H | CH$_2$CH$_2$CO$_2$H |
| 95. | H | CH$_3$ | CH$_2$CO$_2$CH$_2$CH$_2$CH$_3$ |
| 96. | H | CH$_3$ | CH$_2$CH$_2$CO$_2$H |
| 97. | NO$_2$ | H | CH$_2$CH$_2$CO$_2$CH$_2$CH$_3$ |
| 98. | NO$_2$ | H | CH$_2$CH$_2$CO$_2$H |
| 99. | NH$_2$ | H | CH$_2$CO$_2$CH$_2$CH$_2$CH$_3$ |
| 100. | NH$_2$ | H | CH$_2$CH$_2$CO$_2$H |
| 101. | NHSO$_2$CH$_3$ | H | CH$_2$CH$_2$CO$_2$CH$_2$CH$_3$ |
| 102. | NHSO$_2$CH$_3$ | H | CH$_2$CH$_2$CO$_2$H |
| 103. | H | OH | CH$_2$CO$_2$CH$_2$CH$_2$CH$_3$ |
| 104. | H | OH | CH$_2$CH$_2$CO$_2$H |
| 105. | H | OCH$_3$ | CH$_2$CH$_2$CO$_2$CH$_2$CH$_3$ |
| 106. | H | OCH$_3$ | CH$_2$CH$_2$CO$_2$H |
| 107. | H | OCH$_2$CH=CH$_2$ | CH$_2$CO$_2$CH$_2$CH$_2$CH$_3$ |
| 108. | H | OCH$_2$CH=CH$_2$ | CH$_2$CH$_2$CO$_2$H |
| 109. | H | OCH$_2$C$_6$H$_5$ | CH$_2$CH$_2$CO$_2$CH$_2$CH$_3$ |
| 110. | H | OCH$_2$C$_6$H$_5$ | CH$_2$CH$_2$CO$_2$H |
| 111. | H | OCH$_2$CH$_2$C$_6$H$_5$ | CH$_2$CH$_2$CO$_2$CH$_2$CH$_3$ |
| 112. | H | OCH$_2$CH$_2$C$_6$H$_5$ | CH$_2$CH$_2$CO$_2$H |
| 113. | H | OCH$_2$CONH$_2$ | CH$_2$CO$_2$CH$_2$CH$_2$CH$_3$ |
| 114. | H | OCH$_2$CONH$_2$ | CH$_2$CH$_2$CO$_2$H |
| 115. | H | H | CH$_2$CH$_2$PO(OCH$_2$CH$_3$)$_2$ |
| 116. | H | H | CH$_2$CH$_2$PO(OH)$_2$ |

TABLE IIb-continued

[Structure: indane with N(CH3)(CH2C≡CR1) at position 1, X at position 5, X1 at position 6]

| Ex. # | X | X1 | R1 |
|---|---|---|---|
| 117. | OH | H | CH2CH2PO(OCH2CH3)2 |
| 118. | OH | H | CH2CH2PO(OH)2 |
| 119. | OCH3 | H | CH2CH2PO(OCH2CH3)2 |
| 120. | OCH3 | H | CH2CH2PO(OH)2 |
| 121. | OCH2CH=CH2 | H | CH2CH2PO(OCH2CH3)2 |
| 122. | OCH2CH=CH2 | H | CH2CH2PO(OH)2 |
| 123. | OCH2C6H5 | H | CH2CH2PO(OCH2CH3)2 |
| 124. | OCH2C6H5 | H | CH2CH2PO(OH)2 |
| 125. | OCH2CH2C6H5 | H | CH2CH2PO(OCH2CH3)2 |
| 126. | OCH2CH2C6H5 | H | CH2CH2PO(OH)2 |
| 127. | OCH2CONH2 | H | CH2CH2PO(OCH2CH3)2 |
| 128. | OCH2CONH2 | H | CH2CH2PO(OH)2 |
| 129. | H | Cl | CH2CH2PO(OCH2CH3)2 |
| 130. | H | Cl | CH2CH2PO(OH)2 |
| 131. | Br | H | CH2CH2PO(OCH2CH3)2 |
| 132. | Br | H | CH2CH2PO(OH)2 |
| 133. | H | CH3 | CH2CH2PO(OCH2CH3)2 |
| 134. | H | CH3 | CH2CH2PO(OH)2 |
| 135. | NO2 | H | CH2CH2PO(OCH2CH3)2 |
| 136. | NO2 | H | CH2CH2PO(OH)2 |
| 137. | NH2 | H | CH2CH2PO(OCH2CH3)2 |
| 138. | NH2 | H | CH2CH2PO(OH)2 |
| 139. | NHSO2CH3 | H | CH2CH2PO(OCH2CH3)2 |
| 140. | NHSO2CH3 | H | CH2CH2PO(OH)2 |
| 141. | H | OH | CH2CH2PO(OCH2CH3)2 |
| 142. | H | OH | CH2CH2PO(OH)2 |
| 143. | H | OCH3 | CH2CH2PO(OCH2CH3)2 |
| 144. | H | OCH3 | CH2CH2PO(OH)2 |
| 145. | H | OCH2CH=CH2 | CH2CH2PO(OCH2CH3)2 |
| 146. | H | OCH2CH=CH2 | CH2CH2PO(OH)2 |
| 147. | H | OCH2C6H5 | CH2CH2PO(OCH2CH3)2 |
| 148. | H | OCH2C6H5 | CH2CH2PO(OH)2 |
| 149. | H | OCH2CH2C6H5 | CH2CH2PO(OCH2CH3)2 |
| 150. | H | OCH2CH2C6H5 | CH2CH2PO(OH)2 |
| 151. | H | OCH2CONH2 | CH2CH2PO(OCH2CH3)2 |
| 152. | H | OCH2CONH2 | CH2CH2PO(OH)2 |
| 153. | H | H | CH2CH=CHCO2CH2CH3 |
| 154. | H | H | CH2CH=CHCO2H |
| 155. | OH | H | CH2CH=CHCO2CH2CH3 |
| 156. | OH | H | CH2CH=CHCO2H |
| 157. | OCH3 | H | CH2CH=CHCO2CH2CH3 |
| 158. | OCH3 | H | CH2CH=CHCO2H |
| 159. | OCH2CH=CH2 | H | CH2CH=CHCO2CH2CH3 |
| 160. | OCH2CH=CH2 | H | CH2CH=CHCO2H |
| 161. | OCH2C6H5 | H | CH2CH=CHCO2CH2CH3 |
| 162. | OCH2C6H5 | H | CH2CH=CHCO2H |
| 163. | OCH2CH2C6H5 | H | CH2CH=CHCO2CH2CH3 |
| 164. | OCH2CH2C6H5 | H | CH2CH=CHCO2H |
| 165. | OCH2CONH2 | H | CH2CH=CHCO2CH2CH3 |
| 166. | OCH2CONH2 | H | CH2CH=CHCO2H |
| 167. | H | Cl | CH2CH=CHCO2CH2CH3 |
| 168. | H | Cl | CH2CH=CHCO2H |
| 169. | Br | H | CH2CH=CHCO2CH2CH3 |
| 170. | Br | H | CH2CH=CHCO2H |
| 171. | H | CH3 | CH2CH=CHCO2CH2CH3 |
| 172. | H | CH3 | CH2CH=CHCO2H |
| 173. | NO2 | H | CH2CH=CHCO2CH2CH3 |
| 174. | NO2 | H | CH2CH=CHCO2H |
| 175. | NH2 | H | CH2CH=CHCO2CH2CH3 |
| 176. | NH2 | H | CH2CH=CHCO2H |
| 177. | NHSO2CH3 | H | CH2CH=CHCO2CH2CH3 |
| 178. | NHSO2CH3 | H | CH2CH=CHCO2H |
| 179. | H | OH | CH2CH=CHCO2CH2CH3 |
| 180. | H | OH | CH2CH=CHCO2H |
| 181. | H | OCH3 | CH2CH=CHCO2CH2CH3 |
| 182. | H | OCH3 | CH2CH=CHCO2H |
| 183. | H | OCH2CH=CH2 | CH2CH=CHCO2CH2CH3 |
| 184. | H | OCH2CH=CH2 | CH2CH=CHCO2H |
| 185. | H | OCH2C6H5 | CH2CH=CHCO2CH2CH3 |

TABLE IIb-continued

| Ex. # | X | X¹ | R¹ |
|---|---|---|---|
| 186. | H | OCH₂C₆H₅ | CH₂CH=CHCO₂H |
| 187. | H | OCH₂CH₂C₆H₅ | CH₂CH=CHCO₂CH₂CH₃ |
| 188. | H | OCH₂CH₂C₆H₅ | CH₂CH=CHCO₂H |
| 189. | H | OCH₂CONH₂ | CH₂CH=CHCO₂CH₂CH₃ |
| 190. | H | OCH₂CONH₂ | CH₂CH=CHCO₂H |

TABLE III

| Ex. # | X | X¹ | R¹ | R" |
|---|---|---|---|---|
| 1. | H | H | H | CH₂—CO₂CH₂CH₃ |
| 2. | H | H | CH₃ | CH₂—CO₂H |
| 3. | OH | H | H | CH₂—CO₂CH₂CH₃ |
| 4. | OH | H | CH₃ | CH₂—CO₂H |
| 5. | OCH₃ | H | H | CH₂—CO₂CH₂CH₃ |
| 6. | OCH₃ | H | CH₃ | CH₂—CO₂H |
| 7. | OCH₂CH=CH₂ | H | H | CH₂—CO₂CH₂CH₃ |
| 8. | OCH₂CH=CH₂ | H | CH₃ | CH₂—CO₂H |
| 9. | OCH₂C₆H₅ | H | H | CH₂—CO₂CH₂CH₃ |
| 10. | OCH₂C₆H₅ | H | CH₃ | CH₂—CO₂H |
| 11. | OCH₂CH₂C₆H₅ | H | H | CH₂—CO₂CH₂CH₃ |
| 12. | OCH₂CH₂C₆H₅ | H | CH₃ | CH₂—CO₂H |
| 13. | OCH₂—CONH₂ | H | H | CH₂—CO₂CH₂CH₃ |
| 14. | OCH₂—CONH₂ | H | CH₃ | CH₂—CO₂H |
| 15. | H | Cl | H | CH₂—CO₂CH₂CH₃ |
| 16. | H | Cl | CH₃ | CH₂—CO₂H |
| 17. | Br | H | H | CH₂—CO₂CH₂CH₃ |
| 18. | Br | H | CH₃ | CH₂—CO₂H |
| 19. | H | CH₃ | H | CH₂—CO₂CH₂CH₃ |
| 20. | H | CH₃ | CH₃ | CH₂—CO₂H |
| 21. | NO₂ | H | H | CH₂—CO₂CH₂CH₃ |
| 22. | NO₂ | H | CH₃ | CH₂—CO₂H |
| 23. | NH₂ | H | H | CH₂—CO₂CH₂CH₃ |
| 24. | NH₂ | H | CH₃ | CH₂—CO₂H |
| 25. | NHSO₂CH₃ | H | H | CH₂—CO₂CH₂CH₃ |
| 26. | NHSO₂CH₃ | H | CH₃ | CH₂—CO₂H |
| 27. | H | OH | H | CH₂—CO₂CH₂CH₃ |
| 28. | H | OH | CH₃ | CH₂—CO₂H |
| 29. | H | OCH₃ | H | CH₂—CO₂CH₂CH₃ |
| 30. | H | OCH₃ | CH₃ | CH₂—CO₂H |
| 31. | H | OCH₂CH=CH₂ | H | CH₂—CO₂CH₂CH₃ |
| 32. | H | OCH₂CH=CH₂ | CH₃ | CH₂—CO₂H |
| 33. | H | OCH₂C₆H₅ | H | CH₂—CO₂CH₂CH₃ |
| 34. | H | OCH₂C₆H₅ | CH₃ | CH₂—CO₂H |
| 35. | H | OCH₂CH₂C₆H₅ | H | CH₂—CO₂CH₂CH₃ |
| 36. | H | OCH₂CH₂C₆H₅ | CH₃ | CH₂—CO₂H |
| 37. | H | OCH₂—CONH₂ | H | CH₂—CO₂CH₂CH₃ |
| 38. | H | OCH₂—CONH₂ | CH₃ | CH₂—CO₂H |
| 39. | H | H | H | CH₂CH₂—CO₂CH₂CH₃ |
| 40. | H | H | CH₃ | CH₂CH₂—CO₂H |
| 41. | OH | H | H | CH₂CH₂—CO₂CH₂CH₃ |
| 42. | OH | H | CH₃ | CH₂CH₂—CO₂H |
| 43. | OCH₃ | H | H | CH₂CH₂—CO₂CH₂CH₃ |
| 44. | OCH₃ | H | CH₃ | CH₂CH₂—CO₂H |
| 45. | OCH₂CH=CH₂ | H | H | CH₂CH₂—CO₂CH₂CH₃ |
| 46. | OCH₂CH=CH₂ | H | CH₃ | CH₂CH₂—CO₂H |
| 47. | OCH₂C₆H₅ | H | H | CH₂CH₂—CO₂CH₂CH₃ |

TABLE III-continued

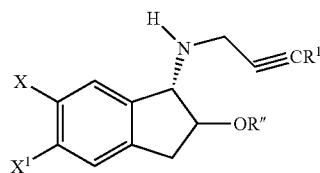

| Ex. # | X | X¹ | R¹ | R" |
|---|---|---|---|---|
| 48. | OCH$_2$C$_6$H$_5$ | H | CH$_3$ | CH$_2$CH$_2$—CO$_2$H |
| 49. | OCH$_2$CH$_2$C$_6$H$_5$ | H | H | CH$_2$CH$_2$—CO$_2$CH$_2$CH$_3$ |
| 50. | OCH$_2$CH$_2$C$_6$H$_5$ | H | CH$_3$ | CH$_2$CH$_2$—CO$_2$H |
| 51. | OCH$_2$—CONH$_2$ | H | H | CH$_2$CH$_2$—CO$_2$CH$_2$CH$_3$ |
| 52. | OCH$_2$—CONH$_2$ | H | CH$_3$ | CH$_2$CH$_2$—CO$_2$H |
| 53. | H | Cl | H | CH$_2$CH$_2$—CO$_2$CH$_2$CH$_3$ |
| 54. | H | Cl | CH$_3$ | CH$_2$CH$_2$—CO$_2$H |
| 55. | Br | H | H | CH$_2$CH$_2$—CO$_2$CH$_2$CH$_3$ |
| 56. | Br | H | CH$_3$ | CH$_2$CH$_2$—CO$_2$H |
| 57. | H | CH$_3$ | H | CH$_2$CH$_2$—CO$_2$CH$_2$CH$_3$ |
| 58. | H | CH$_3$ | CH$_3$ | CH$_2$CH$_2$—CO$_2$H |
| 59. | NO$_2$ | H | H | CH$_2$CH$_2$—CO$_2$CH$_2$CH$_3$ |
| 60. | NO$_2$ | H | CH$_3$ | CH$_2$CH$_2$—CO$_2$H |
| 61. | NH$_2$ | H | H | CH$_2$CH$_2$—CO$_2$CH$_2$CH$_3$ |
| 62. | NH$_2$ | H | CH$_3$ | CH$_2$CH$_2$—CO$_2$H |
| 63. | NHSO$_2$CH$_3$ | H | H | CH$_2$CH$_2$—CO$_2$CH$_2$CH$_3$ |
| 64. | NHSO$_2$CH$_3$ | H | CH$_3$ | CH$_2$CH$_2$—CO$_2$H |
| 65. | H | OH | H | CH$_2$CH$_2$—CO$_2$CH$_2$CH$_3$ |
| 66. | H | OH | CH$_3$ | CH$_2$CH$_2$—CO$_2$H |
| 67. | H | OCH$_3$ | H | CH$_2$CH$_2$—CO$_2$CH$_2$CH$_3$ |
| 68. | H | OCH$_3$ | CH$_3$ | CH$_2$CH$_2$—CO$_2$H |
| 69. | H | OCH$_2$CH=CH$_2$ | H | CH$_2$CH$_2$—CO$_2$CH$_2$CH$_3$ |
| 70. | H | OCH$_2$CH=CH$_2$ | CH$_3$ | CH$_2$CH$_2$—CO$_2$H |
| 71. | H | OCH$_2$C$_6$H$_5$ | H | CH$_2$CH$_2$—CO$_2$CH$_2$CH$_3$ |
| 72. | H | OCH$_2$C$_6$H$_5$ | CH$_3$ | CH$_2$CH$_2$—CO$_2$H |
| 73. | H | OCH$_2$CH$_2$C$_6$H$_5$ | H | CH$_2$CH$_2$—CO$_2$CH$_2$CH$_3$ |
| 74. | H | OCH$_2$CH$_2$C$_6$H$_5$ | CH$_3$ | CH$_2$CH$_2$—CO$_2$H |
| 75. | H | OCH$_2$—CONH$_2$ | H | CH$_2$CH$_2$—CO$_2$CH$_2$CH$_3$ |
| 76. | H | OCH$_2$—CONH$_2$ | CH$_3$ | CH$_2$CH$_2$—CO$_2$H |
| 77. | H | H | H | CH$_2$CH$_2$P—O(OCH$_2$CH$_3$)$_2$ |
| 78. | H | H | CH$_3$ | CH$_2$CH$_2$P—O(OH)$_2$ |
| 79. | OH | H | H | CH$_2$CH$_2$P—O(OCH$_2$CH$_3$)$_2$ |
| 80. | OH | H | CH$_3$ | CH$_2$CH$_2$P—O(OH)$_2$ |
| 81. | OCH$_3$ | H | H | CH$_2$CH$_2$P—O(OCH$_2$CH$_3$)$_2$ |
| 82. | OCH$_3$ | H | CH$_3$ | CH$_2$CH$_2$P—O(OH)$_2$ |
| 83. | OCH$_2$CH=CH$_2$ | H | H | CH$_2$CH$_2$P—O(OCH$_2$CH$_3$)$_2$ |
| 84. | OCH$_2$CH=CH$_2$ | H | CH$_3$ | CH$_2$CH$_2$P—O(OH)$_2$ |
| 85. | OCH$_2$C$_6$H$_5$ | H | H | CH$_2$CH$_2$P—O(OCH$_2$CH$_3$)$_2$ |
| 86. | OCH$_2$C$_6$H$_5$ | H | CH$_3$ | CH$_2$CH$_2$P—O(OH)$_2$ |
| 87. | OCH$_2$CH$_2$C$_6$H$_5$ | H | H | CH$_2$CH$_2$P—O(OCH$_2$CH$_3$)$_2$ |
| 88. | OCH$_2$CH$_2$C$_6$H$_5$ | H | CH$_3$ | CH$_2$CH$_2$P—O(OH)$_2$ |
| 89. | OCH$_2$—CONH$_2$ | H | H | CH$_2$CH$_2$P—O(OCH$_2$CH$_3$)$_2$ |
| 90. | OCH$_2$—CONH$_2$ | H | CH$_3$ | CH$_2$CH$_2$P—O(OH)$_2$ |
| 91. | H | Cl | H | CH$_2$CH$_2$P—O(OCH$_2$CH$_3$)$_2$ |
| 92. | H | Cl | CH$_3$ | CH$_2$CH$_2$P—O(OH)$_2$ |
| 93. | Br | H | H | CH$_2$CH$_2$P—O(OCH$_2$CH$_3$)$_2$ |
| 94. | Br | H | CH$_3$ | CH$_2$CH$_2$P—O(OH)$_2$ |
| 95. | H | CH$_3$ | H | CH$_2$CH$_2$P—O(OCH$_2$CH$_3$)$_2$ |
| 96. | H | CH$_3$ | CH$_3$ | CH$_2$CH$_2$P—O(OH)$_2$ |
| 97. | NO$_2$ | H | H | CH$_2$CH$_2$P—O(OCH$_2$CH$_3$)$_2$ |
| 98. | NO$_2$ | H | CH$_3$ | CH$_2$CH$_2$P—O(OH)$_2$ |
| 99. | NH$_2$ | H | H | CH$_2$CH$_2$P—O(OCH$_2$CH$_3$)$_2$ |
| 100. | NH$_2$ | H | CH$_3$ | CH$_2$CH$_2$P—O(OH)$_2$ |
| 101. | NHSO$_2$CH$_3$ | H | H | CH$_2$CH$_2$P—O(OCH$_2$CH$_3$)$_2$ |
| 102. | NHSO$_2$CH$_3$ | H | CH$_3$ | CH$_2$CH$_2$P—O(OH)$_2$ |
| 103. | H | OH | H | CH$_2$CH$_2$P—O(OCH$_2$CH$_3$)$_2$ |
| 104. | H | OH | CH$_3$ | CH$_2$CH$_2$P—O(OH)$_2$ |
| 105. | H | OCH$_3$ | H | CH$_2$CH$_2$P—O(OCH$_2$CH$_3$)$_2$ |
| 106. | H | OCH$_3$ | CH$_3$ | CH$_2$CH$_2$P—O(OH)$_2$ |
| 107. | H | OCH$_2$CH=CH$_2$ | H | CH$_2$CH$_2$P—O(OCH$_2$CH$_3$)$_2$ |
| 108. | H | OCH$_2$CH=CH$_2$ | CH$_3$ | CH$_2$CH$_2$P—O(OH)$_2$ |
| 109. | H | OCH$_2$C$_6$H$_5$ | H | CH$_2$CH$_2$P—O(OCH$_2$CH$_3$)$_2$ |
| 110. | H | OCH$_2$C$_6$H$_5$ | CH$_3$ | CH$_2$CH$_2$P—O(OH)$_2$ |
| 111. | H | OCH$_2$CH$_2$C$_6$H$_5$ | H | CH$_2$CH$_2$P—O(OCH$_2$CH$_3$)$_2$ |
| 112. | H | OCH$_2$CH$_2$C$_6$H$_5$ | CH$_3$ | CH$_2$CH$_2$P—O(OH)$_2$ |
| 113. | H | OCH$_2$—CONH$_2$ | H | CH$_2$CH$_2$P—O(OCH$_2$CH$_3$)$_2$ |
| 114. | H | OCH$_2$—CONH$_2$ | CH$_3$ | CH$_2$CH$_2$P—O(OH)$_2$ |
| 115. | H | H | H | CH$_2$CH=CH—CO$_2$CH$_2$CH$_3$ |
| 116. | H | H | CH$_3$ | CH$_2$CH=CH—CO$_2$H |

TABLE III-continued

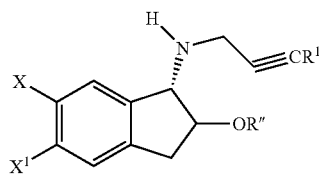

| Ex. # | X | X¹ | R¹ | R" |
|---|---|---|---|---|
| 117. | OH | H | H | $CH_2CH=CH-CO_2CH_2CH_3$ |
| 118. | OH | H | $CH_3$ | $CH_2CH=CH-CO_2H$ |
| 119. | $OCH_3$ | H | H | $CH_2CH=CH-CO_2CH_2CH_3$ |
| 120. | $OCH_3$ | H | $CH_3$ | $CH_2CH=CH-CO_2H$ |
| 121. | $OCH_2CH=CH_2$ | H | H | $CH_2CH=CH-CO_2CH_2CH_3$ |
| 122. | $OCH_2CH=CH_2$ | H | $CH_3$ | $CH_2CH=CH-CO_2H$ |
| 123. | $OCH_2C_6H_5$ | H | H | $CH_2CH=CH-CO_2CH_2CH_3$ |
| 124. | $OCH_2C_6H_5$ | H | $CH_3$ | $CH_2CH=CH-CO_2H$ |
| 125. | $OCH_2CH_2C_6H_5$ | H | H | $CH_2CH=CH-CO_2CH_2CH_3$ |
| 126. | $OCH_2CH_2C_6H_5$ | H | $CH_3$ | $CH_2CH=CH-CO_2H$ |
| 127. | $OCH_2-CONH_2$ | H | H | $CH_2CH=CH-CO_2CH_2CH_3$ |
| 128. | $OCH_2-CONH_2$ | H | $CH_3$ | $CH_2CH=CH-CO_2H$ |
| 129. | H | Cl | H | $CH_2CH=CH-CO_2CH_2CH_3$ |
| 130. | H | Cl | $CH_3$ | $CH_2CH=CH-CO_2H$ |
| 131. | Br | H | H | $CH_2CH=CH-CO_2CH_2CH_3$ |
| 132. | Br | H | $CH_3$ | $CH_2CH=CH-CO_2H$ |
| 133. | H | $CH_3$ | H | $CH_2CH=CH-CO_2CH_2CH_3$ |
| 134. | H | $CH_3$ | $CH_3$ | $CH_2CH=CH-CO_2H$ |
| 135. | $NO_2$ | H | H | $CH_2CH=CH-CO_2CH_2CH_3$ |
| 136. | $NO_2$ | H | $CH_3$ | $CH_2CH=CH-CO_2H$ |
| 137. | $NH_2$ | H | H | $CH_2CH=CH-CO_2CH_2CH_3$ |
| 138. | $NH_2$ | H | $CH_3$ | $CH_2CH=CH-CO_2H$ |
| 139. | $NHSO_2CH_3$ | H | H | $CH_2CH=CH-CO_2CH_2CH_3$ |
| 140. | $NHSO_2CH_3$ | H | $CH_3$ | $CH_2CH=CH-CO_2H$ |
| 141. | H | OH | H | $CH_2CH=CH-CO_2CH_2CH_3$ |
| 142. | H | OH | $CH_3$ | $CH_2CH=CH-CO_2H$ |
| 143. | H | $OCH_3$ | H | $CH_2CH=CH-CO_2CH_2CH_3$ |
| 144. | H | $OCH_3$ | $CH_3$ | $CH_2CH=CH-CO_2H$ |
| 145. | H | $OCH_2CH=CH_2$ | H | $CH_2CH=CH-CO_2CH_2CH_3$ |
| 146. | H | $OCH_2CH=CH_2$ | $CH_3$ | $CH_2CH=CH-CO_2H$ |
| 147. | H | $OCH_2C_6H_5$ | H | $CH_2CH=CH-CO_2CH_2CH_3$ |
| 148. | H | $OCH_2C_6H_5$ | $CH_3$ | $CH_2CH=CH-CO_2H$ |
| 149. | H | $OCH_2CH_2C_6H_5$ | H | $CH_2CH=CH-CO_2CH_2CH_3$ |
| 150. | H | $OCH_2CH_2C_6H_5$ | $CH_3$ | $CH_2CH=CH-CO_2H$ |
| 151. | H | $OCH_2-CONH_2$ | H | $CH_2CH=CH-CO_2CH_2CH_3$ |
| 152. | H | $OCH_2-CONH_2$ | $CH_3$ | $CH_2CH=CH-CO_2H$ |
| 153. | H | H | $CH_2-CO_2CH_2CH_3$ | $CH_3$ |
| 154. | H | H | $CH_2-CO_2H$ | $CH_3$ |
| 155. | OH | H | $CH_2-CO_2CH_2CH_3$ | $CH_3$ |
| 156. | OH | H | $CH_2-CO_2H$ | $CH_3$ |
| 157. | $OCH_3$ | H | $CH_2-CO_2CH_2CH_3$ | $CH_3$ |
| 158. | $OCH_3$ | H | $CH_2-CO_2H$ | $CH_3$ |
| 159. | $OCH_2CH=CH_2$ | H | $CH_2-CO_2CH_2CH_3$ | $CH_3$ |
| 160. | $OCH_2CH=CH_2$ | H | $CH_2-CO_2H$ | $CH_3$ |
| 161. | $OCH_2C_6H_5$ | H | $CH_2-CO_2CH_2CH_3$ | $CH_3$ |
| 162. | $OCH_2C_6H_5$ | H | $CH_2-CO_2H$ | $CH_3$ |
| 163. | $OCH_2CH_2C_6H_5$ | H | $CH_2-CO_2CH_2CH_3$ | $CH_3$ |
| 164. | $OCH_2CH_2C_6H_5$ | H | $CH_2-CO_2H$ | $CH_3$ |
| 165. | $OCH_2-CONH_2$ | H | $CH_2-CO_2CH_2CH_3$ | $CH_3$ |
| 166. | $OCH_2-CONH_2$ | H | $CH_2-CO_2H$ | $CH_3$ |
| 167. | H | Cl | $CH_2-CO_2CH_2CH_3$ | $CH_3$ |
| 168. | H | Cl | $CH_2-CO_2H$ | $CH_3$ |
| 169. | Br | H | $CH_2-CO_2CH_2CH_3$ | $CH_3$ |
| 170. | Br | H | $CH_2-CO_2H$ | $CH_3$ |
| 171. | H | $CH_3$ | $CH_2-CO_2CH_2CH_3$ | $CH_3$ |
| 172. | H | $CH_3$ | $CH_2-CO_2H$ | $CH_3$ |
| 173. | $NO_2$ | H | $CH_2-CO_2CH_2CH_3$ | $CH_3$ |
| 174. | $NO_2$ | H | $CH_2-CO_2H$ | $CH_3$ |
| 175. | $NH_2$ | H | $CH_2-CO_2CH_2CH_3$ | $CH_3$ |
| 176. | $NH_2$ | H | $CH_2-CO_2H$ | $CH_3$ |
| 177. | $NHSO_2CH_3$ | H | $CH_2-CO_2CH_2CH_3$ | $CH_3$ |
| 178. | $NHSO_2CH_3$ | H | $CH_2-CO_2H$ | $CH_3$ |
| 179. | H | OH | $CH_2-CO_2CH_2CH_3$ | $CH_3$ |
| 180. | H | OH | $CH_2-CO_2H$ | $CH_3$ |
| 181. | H | $OCH_3$ | $CH_2-CO_2CH_2CH_3$ | $CH_3$ |
| 182. | H | $OCH_3$ | $CH_2-CO_2H$ | $CH_3$ |
| 183. | H | $OCH_2CH=CH_2$ | $CH_2-CO_2CH_2CH_3$ | |
| 184. | H | $OCH_2CH=CH_2$ | $CH_2-CO_2H$ | $CH_3$ |
| 185. | H | $OCH_2C_6H_5$ | $CH_2-CO_2CH_2CH_3$ | |

TABLE III-continued

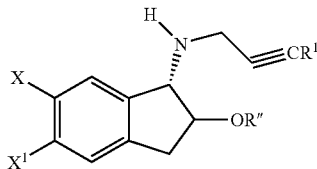

| Ex. # | X | X¹ | R¹ | R" |
|---|---|---|---|---|
| 186. | H | $OCH_2C_6H_5$ | $CH_2-CO_2H$ | $CH_3$ |
| 187. | H | $OCH_2CH_2C_6H_5$ | $CH_2-CO_2CH_2CH_3$ | |
| 188. | H | $OCH_2CH_2C_6H_5$ | $CH_2-CO_2H$ | $CH_3$ |
| 189. | H | $OCH_2-CONH_2$ | $CH_2-CO_2CH_2CH_3$ | |
| 190. | H | $OCH_2-CONH_2$ | $CH_2-CO_2H$ | $CH_3$ |
| 191. | H | H | $CH_2CH_2P-O(OCH_2CH_3)_2$ | $CH_3$ |
| 192. | H | H | $CH_2CH_2P-O(OH)_2$ | $CH_3$ |
| 193. | OH | H | $CH_2CH_2P-O(OCH_2CH_3)_2$ | $Ch_3$ |
| 194. | OH | H | $CH_2CH_2P-O(OH)_2$ | $CH_3$ |
| 195. | $OCH_3$ | H | $CH_2CH_2P-O(OCH_2CH_3)_2$ | $CH_3$ |
| 196. | $OCH_3$ | H | $CH_2CH_2P-O(OH)_2$ | $CH_3$ |
| 197. | $OCH_2CH=CH_2$ | H | $CH_2CH_2P-O(OCH_2CH_3)_2$ | $CH_3$ |
| 198. | $OCH_2CH=CH_2$ | H | $CH_2CH_2P-O(OH)_2$ | $CH_3$ |
| 199. | $OCH_2C_6H_5$ | H | $CH_2CH_2P-O(OCH_2CH_3)_2$ | $CH_3$ |
| 200. | $OCH_2C_6H_5$ | H | $CH_2CH_2P-O(OH)_2$ | $CH_3$ |
| 201. | $OCH_2CH_2C_6H_5$ | H | $CH_2CH_2P-O(OCH_2CH_3)_2$ | $CH_3$ |
| 202. | $OCH_2CH_2C_6H_5$ | H | $CH_2CH_2P-O(OH)_2$ | $CH_3$ |
| 203. | $OCH_2-CONH_2$ | H | $CH_2CH_2P-O(OCH_2CH_3)_2$ | $CH_3$ |
| 204. | $OCH_2-CONH_2$ | H | $CH_2CH_2P-O(OH)_2$ | $CH_3$ |
| 205. | H | Cl | $CH_2CH_2P-O(OCH_2CH_3)_2$ | $CH_3$ |
| 206. | H | Cl | $CH_2CH_2P-O(OH)_2$ | $CH_3$ |
| 207. | Br | H | $CH_2CH_2P-O(OCH_2CH_3)_2$ | $CH_3$ |
| 208. | Br | H | $CH_2CH_2P-O(OH)_2$ | $CH_3$ |
| 209. | H | $CH_3$ | $CH_2CH_2P-O(OCH_2CH_3)_2$ | $CH_3$ |
| 210. | H | $CH_3$ | $CH_2CH_2P-O(OH)_2$ | $CH_3$ |
| 211. | $NO_2$ | H | $CH_2CH_2P-O(OCH_2CH_3)_2$ | $CH_3$ |
| 212. | $NO_2$ | H | $CH_2CH_2P-O(OH)_2$ | $CH_3$ |
| 213. | $NH_2$ | H | $CH_2CH_2P-O(OCH_2CH_3)_2$ | $CH_3$ |
| 214. | $NH_2$ | H | $CH_2CH_2P-O(OH)_2$ | $CH_3$ |
| 215. | $NHSO_2CH_3$ | H | $CH_2CH_2P-O(OCH_2CH_3)_2$ | $CH_3$ |
| 216. | $NHSO_2CH_3$ | H | $CH_2CH_2P-O(OH)_2$ | $CH_3$ |
| 217. | H | OH | $CH_2CH_2P-O(OCH_2CH_3)_2$ | $CH_3$ |
| 218. | H | OH | $CH_2CH_2P-O(OH)_2$ | $CH_3$ |
| 219. | H | $OCH_3$ | $CH_2CH_2P-O(OCH_2CH_3)_2$ | $CH_3$ |
| 220. | H | $OCH_3$ | $CH_2CH_2P-O(OH)_2$ | $CH_3$ |
| 221. | H | $OCH_2CH=CH_2$ | $CH_2CH_2P-O(OCH_2CH_3)_2$ | $CH_3$ |
| 222. | H | $OCH_2CH=CH_2$ | $CH_2CH_2P-O(OH)_2$ | $CH_3$ |
| 223. | H | $OCH_2C_6H_5$ | $CH_2CH_2P-O(OCH_2CH_3)_2$ | $CH_3$ |
| 224. | H | $OCH_2C_6H_5$ | $CH_2CH_2P-O(OH)_2$ | $CH_3$ |
| 225. | H | $OCH_2CH_2C_6H_5$ | $CH_2CH_2P-O(OCH_2CH_3)_2$ | $CH_3$ |
| 226. | H | $OCH_2CH_2C_6H_5$ | $CH_2CH_2P-O(OH)_2$ | $CH_3$ |
| 227. | H | $OCH_2-CONH_2$ | $CH_2CH_2P-O(OCH_2CH_3)_2$ | $CH_3$ |
| 228. | H | $OCH_2-CONH_2$ | $CH_2CH_2P-O(OH)_2$ | $CH_3$ |
| 229. | H | H | $CH_2-CO_2CH_2CH_3$ | $CH_2CH=CH_2$ |
| 230. | H | H | $CH_2-CO_2H$ | $CH_2CH=CH_2$ |
| 231. | OH | H | $CH_2-CO_2CH_2CH_3$ | $CH_2CH=CH_2$ |
| 232. | OH | H | $CH_2-CO_2H$ | $CH_2CH=CH_2$ |
| 233. | $OCH_3$ | H | $CH_2-CO_2CH_2CH_3$ | $CH_2CH=CH_2$ |
| 234. | $OCH_3$ | H | $CH_2-CO_2H$ | $CH_2CH=CH_2$ |
| 235. | $OCH_2CH=CH_2$ | H | $CH_2-CO_2CH_2CH_3$ | $CH_2CH=CH_2$ |
| 236. | $OCH_2CH=CH_2$ | H | $CH_2-CO_2H$ | $CH_2CH=CH_2$ |
| 237. | $OCH_2C_6H_5$ | H | $CH_2-CO_2CH_2CH_3$ | $CH_2CH=CH_2$ |
| 238. | $OCH_2C_6H_5$ | H | $CH_2-CO_2H$ | $CH_2CH=CH_2$ |
| 239. | $OCH_2CH_2C_6H_5$ | H | $CH_2-CO_2CH_2CH_3$ | $CH_2CH=CH_2$ |
| 240. | $OCH_2CH_2C_6H_5$ | H | $CH_2-CO_2H$ | $CH_2CH=CH_2$ |
| 241. | $OCH_2-CONH_2$ | H | $CH_2-CO_2CH_2CH_3$ | $CH_2CH=CH_2$ |
| 242. | $OCH_2-CONH_2$ | H | $CH_2-CO_2H$ | $CH_2CH=CH_2$ |
| 243. | H | Cl | $CH_2-CH_2CH_2CH_3$ | $CH_2CH=CH_2$ |
| 244. | H | Cl | $CH_2-CO_2H$ | $CH_2CH=CH_2$ |
| 245. | Br | H | $CH_2-CO_2CH_2CH_3$ | $CH_2CH=CH_2$ |
| 246. | Br | H | $CH_2-CO_2H$ | $CH_2CH=CH_2$ |
| 247. | H | $CH_3$ | $CH_2-CO_2CH_2CH_3$ | $CH_2CH=CH_2$ |
| 248. | H | $CH_3$ | $CH_2-CO_2H$ | $CH_2CH=CH_2$ |
| 249. | $NO_2$ | H | $CH_2-CO_2CH_2CH_3$ | $CH_2CH=CH_2$ |
| 250. | $NO_2$ | H | $CH_2-CO_2H$ | $CH_2CH=CH_2$ |
| 251. | $NH_2$ | H | $CH_2-CO_2CH_2CH_3$ | $CH_2CH=CH_2$ |
| 252. | $NH_2$ | H | $CH_2-CO_2H$ | $CH_2CH=CH_2$ |
| 253. | $NHSO_2CH_3$ | H | $CH_2-CO_2CH_2CH_3$ | $CH_2CH=CH_2$ |
| 254. | $NHSO_2CH_3$ | H | $CH_2-CO_2H$ | $CH_2CH=CH_2$ |

TABLE III-continued

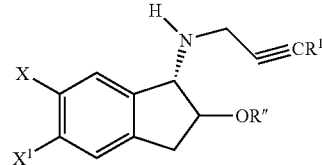

| Ex. # | X | X$^1$ | R$^1$ | R" |
|---|---|---|---|---|
| 255. | H | OH | CH$_2$—CO$_2$CH$_2$CH$_3$ | CH$_2$CH=CH$_2$ |
| 256. | H | OH | CH$_2$—CO$_2$H | CH$_2$CH=CH$_2$ |
| 257. | H | OCH$_3$ | CH$_2$—CO$_2$CH$_2$CH$_3$ | CH$_2$CH=CH$_2$ |
| 258. | H | OCH$_3$ | CH$_2$—CO$_2$H | CH$_2$CH=CH$_2$ |
| 259. | H | OCH$_2$CH=CH$_2$ | CH$_2$—CO$_2$CH$_2$CH$_3$ | CH$_2$CH=CH$_2$ |
| 260. | H | OCH$_2$CH=CH$_2$ | CH$_2$—CO$_2$H | CH$_2$CH=CH$_2$ |
| 261. | H | OCH$_2$C$_6$H$_5$ | CH$_2$—CO$_2$CH$_2$CH$_3$ | CH$_2$CH=CH$_2$ |
| 262. | H | OCH$_2$C$_6$H$_5$ | CH$_2$—CO$_2$H | CH$_2$CH=CH$_2$ |
| 263. | H | OCH$_2$CH$_2$C$_6$H$_5$ | CH$_2$—CO$_2$CH$_2$CH$_3$ | CH$_2$CH=CH$_2$ |
| 264. | H | OCH$_2$CH$_2$C$_6$H$_5$ | CH$_2$—CO$_2$H | CH$_2$CH=CH$_2$ |
| 265. | H | OCH$_2$—CONH$_2$ | CH$_2$—CO$_2$CH$_2$CH$_3$ | CH$_2$CH=CH$_2$ |
| 266. | H | OCH$_2$—CONH$_2$ | CH$_2$—CO$_2$H | CH$_2$CH=CH$_2$ |
| 267. | H | H | CH$_2$CH$_2$P—O(OCH$_2$CH$_3$)$_2$ | CH$_2$CH=CH$_2$ |
| 268. | H | H | CH$_2$CH$_2$P—O(OH)$_2$ | CH$_2$CH=CH$_2$ |
| 269. | OH | H | CH$_2$CH$_2$P—O(OCH$_2$CH$_3$)$_2$ | CH$_2$CH=CH$_2$ |
| 270. | OH | H | CH$_2$CH$_2$P—O(OH)$_2$ | CH$_2$CH=CH$_2$ |
| 271. | OCH$_3$ | H | CH$_2$CH$_2$P—O(OCH$_2$CH$_3$)$_2$ | CH$_2$CH=CH$_2$ |
| 272. | OCH$_3$ | H | CH$_2$CH$_2$P—O(OH)$_2$ | CH$_2$CH=CH$_2$ |
| 273. | OCH$_2$CH=CH$_2$ | H | CH$_2$CH$_2$P—O(OCH$_2$CH$_3$)$_2$ | CH$_2$CH=CH$_2$ |
| 274. | OCH$_2$CH=CH$_2$ | H | CH$_2$CH$_2$P—O(OH)$_2$ | CH$_2$CH=CH$_2$ |
| 275. | OCH$_2$C$_6$H$_5$ | H | CH$_2$CH$_2$P—O(OCH$_2$CH$_3$)$_2$ | CH$_2$CH=CH$_2$ |
| 276. | OCH$_2$C$_6$H$_5$ | H | CH$_2$CH$_2$P—O(OH)$_2$ | CH$_2$CH=CH$_2$ |
| 277. | OCH$_2$CH$_2$C$_6$H$_5$ | H | CH$_2$CH$_2$P—O(OCH$_2$CH$_3$)$_2$ | CH$_2$CH=CH$_2$ |
| 278. | OCH$_2$CH$_2$C$_6$H$_5$ | H | CH$_2$CH$_2$P—O(OH)$_2$ | CH$_2$CH=CH$_2$ |
| 279. | OCH$_2$—CONH$_2$ | H | CH$_2$CH$_2$P—O(OCH$_2$CH$_3$)$_2$ | CH$_2$CH=CH$_2$ |
| 280. | OCH$_2$—CONH$_2$ | H | CH$_2$CH$_2$P—O(OH)$_2$ | CH$_2$CH=CH$_2$ |
| 281. | H | Cl | CH$_2$CH$_2$P—O(OCH$_2$CH$_3$)$_2$ | CH$_2$CH=CH$_2$ |
| 282. | H | Cl | CH$_2$CH$_2$P—O(OH)$_2$ | CH$_2$CH=CH$_2$ |
| 283. | Br | H | CH$_2$CH$_2$P—O(OCH$_2$CH$_3$)$_2$ | CH$_2$CH=CH$_2$ |
| 284. | Br | H | CH$_2$CH$_2$P—O(OH)$_2$ | CH$_2$CH=CH$_2$ |
| 285. | H | CH$_3$ | CH$_2$CH$_2$P—O(OCH$_2$CH$_3$)$_2$ | CH$_2$CH=CH$_2$ |
| 286. | H | CH$_3$ | CH$_2$CH$_2$P—O(OH)$_2$ | CH$_2$CH=CH$_2$ |
| 287. | NO$_2$ | H | CH$_2$CH$_2$P—O(OCH$_2$CH$_3$)$_2$ | CH$_2$CH=CH$_2$ |
| 288. | NO$_2$ | H | CH$_2$CH$_2$P—O(OH)$_2$ | CH$_2$CH=CH$_2$ |
| 289. | NH$_2$ | H | CH$_2$CH$_2$P—O(OCH$_2$CH$_3$)$_2$ | CH$_2$CH=CH$_2$ |
| 290. | NH$_2$ | H | CH$_2$CH$_2$P—O(OH)$_2$ | CH$_2$CH=CH$_2$ |
| 291. | NHSO$_2$CH$_3$ | H | CH$_2$CH$_2$P—O(OCH$_2$CH$_3$)$_2$ | CH$_2$CH=CH$_2$ |
| 292. | NHSO$_2$CH$_3$ | H | CH$_2$CH$_2$P—O(OH)$_2$ | CH$_2$CH=CH$_2$ |
| 293. | H | OH | CH$_2$CH$_2$P—O(OCH$_2$CH$_3$)$_2$ | CH$_2$CH=CH$_2$ |
| 294. | H | OH | CH$_2$CH$_2$P—O(OH)$_2$ | CH$_2$CH=CH$_2$ |
| 295. | H | OCH$_3$ | CH$_2$CH$_2$P—O(OCH$_2$CH$_3$)$_2$ | CH$_2$CH=CH$_2$ |
| 296. | H | OCH$_3$ | CH$_2$CH$_2$P—O(OH)$_2$ | CH$_2$CH=CH$_2$ |
| 297. | H | OCH$_2$CH=CH$_2$ | CH$_2$CH$_2$P—O(OCH$_2$CH$_3$)$_2$ | CH$_2$CH=CH$_2$ |
| 298. | H | OCH$_2$CH=CH$_2$ | CH$_2$CH$_2$P—O(OH)$_2$ | CH$_2$CH=CH$_2$ |
| 299. | H | OCH$_2$C$_6$H$_5$ | CH$_2$CH$_2$P—O(OCH$_2$CH$_3$)$_2$ | CH$_2$CH=CH$_2$ |
| 300. | H | OCH$_2$C$_6$H$_5$ | CH$_2$CH$_2$P—O(OH)$_2$ | CH$_2$CH=CH$_2$ |
| 301. | H | OCH$_2$CH$_2$C$_6$H$_5$ | CH$_2$CH$_2$P—O(OCH$_2$CH$_3$)$_2$ | CH$_2$CH=CH$_2$ |
| 302. | H | OCH$_2$CH$_2$C$_6$H$_5$ | CH$_2$CH$_2$P—O(OH)$_2$ | CH$_2$CH=CH$_2$ |
| 303. | H | OCH$_2$—CONH$_2$ | CH$_2$CH$_2$P—O(OCH$_2$CH$_3$)$_2$ | CH$_2$CH=CH$_2$ |
| 304. | H | OCH$_2$—CONH$_2$ | CH$_2$CH$_2$P—O(OH)$_2$ | CH$_2$CH=CH$_2$ |
| 305. | H | H | CH$_2$—CO$_2$CH$_2$CH$_3$ | CH$_2$—CONH$_2$ |
| 306. | H | H | CH$_2$—CO$_2$H | CH$_2$—CONH$_2$ |
| 307. | OH | H | CH$_2$—CO$_2$CH$_2$CH$_3$ | CH$_2$—CONH$_2$ |
| 308. | OH | H | CH$_2$—CO$_2$H | CH$_2$—CONH$_2$ |
| 309. | OCH$_3$ | H | CH$_2$—CO$_2$CH$_2$CH$_3$ | CH$_2$—CONH$_2$ |
| 310. | OCH$_3$ | H | CH$_2$—CO$_2$H | CH$_2$—CONH$_2$ |
| 311. | OCH$_2$CH=CH$_2$ | H | CH$_2$—CO$_2$CH$_2$CH$_3$ | CH$_2$—CONH$_2$ |
| 312. | OCH$_2$CH=CH$_2$ | H | CH$_2$—CO$_2$H | CH$_2$—CONH$_2$ |
| 313. | OCH$_2$C$_6$H$_5$ | H | CH$_2$—CO$_2$CH$_2$CH$_3$ | CH$_2$—CONH$_2$ |
| 314. | OCH$_2$C$_6$H$_5$ | H | CH$_2$—CO$_2$H | CH$_2$—CONH$_2$ |
| 315. | OCH$_2$CH$_2$C$_6$H$_5$ | H | CH$_2$—CO$_2$CH$_2$CH$_3$ | CH$_2$—CONH$_2$ |
| 316. | OCH$_2$CH$_2$C$_6$H$_5$ | H | CH$_2$—CO$_2$H | CH$_2$—CONH$_2$ |
| 317. | OCH$_2$—CONH$_2$ | H | CH$_2$—CO$_2$CH$_2$CH$_3$ | CH$_2$—CONH$_2$ |
| 318. | OCH$_2$—CONH$_2$ | H | CH$_2$—CO$_2$H | CH$_2$—CONH$_2$ |
| 319. | H | Cl | CH$_2$—CO$_2$CH$_2$CH$_3$ | CH$_2$—CONH$_2$ |
| 320. | H | Cl | CH$_2$—CO$_2$H | CH$_2$—CONH$_2$ |
| 321. | Br | H | CH$_2$—CO$_2$CH$_2$CH$_3$ | CH$_2$—CONH$_2$ |
| 322. | Br | H | CH$_2$—CO$_2$H | CH$_2$—CONH$_2$ |
| 323. | H | CH$_3$ | CH$_2$—CO$_2$CH$_2$CH$_3$ | CH$_2$—CONH$_2$ |

TABLE III-continued

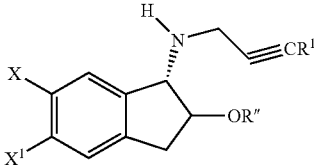

| Ex. # | X | X[1] | R[1] | R" |
|---|---|---|---|---|
| 324. | H | $CH_3$ | $CH_2$—$CO_2H$ | $CH_2$—$CONH_2$ |
| 325. | $NO_2$ | H | $CH_2$—$CO_2CH_2CH_3$ | $CH_2$—$CONH_2$ |
| 326. | $NO_2$ | H | $CH_2$—$CO_2H$ | $CH_2$—$CONH_2$ |
| 327. | $NH_2$ | H | $CH_2$—$CO_2CH_2CH_3$ | $CH_2$—$CONH_2$ |
| 328. | $NH_2$ | H | $CH_2$—$CO_2H$ | $CH_2$—$CONH_2$ |
| 329. | $NHSO_2CH_3$ | H | $CH_2$—$CO_2CH_2CH_3$ | $CH_2$—$CONH_2$ |
| 330. | $NHSO_2CH_3$ | H | $CH_2$—$CO_2H$ | $CH_2$—$CONH_2$ |
| 331. | H | OH | $CH_2$—$CO_2CH_2CH_3$ | $CH_2$—$CONH_2$ |
| 332. | H | OH | $CH_2$—$CO_2H$ | $CH_2$—$CONH_2$ |
| 333. | H | $OCH_3$ | $CH_2$—$CO_2CH_2CH_3$ | $CH_2$—$CONH_2$ |
| 334. | H | $OCH_3$ | $CH_2$—$CO_2H$ | $CH_2$—$CONH_2$ |
| 335. | H | $OCH_2CH$=$CH_2$ | $CH_2$—$CO_2CH_2CH_3$ | $CH_2$—$CONH_2$ |
| 336. | H | $OCH_2CH$=$CH_2$ | $CH_2$—$CO_2H$ | $CH_2$—$CONH_2$ |
| 337. | H | $OCH_2C_6H_5$ | $CH_2$—$CO_2CH_2CH_3$ | $CH_2$—$CONH_2$ |
| 338. | H | $OCH_2C_6H_5$ | $CH_2$—$CO_2H$ | $CH_2$—$CONH_2$ |
| 339. | H | $OCH_2CH_2C_6H_5$ | $CH_2$—$CO_2CH_2CH_3$ | $CH_2$—$CONH_2$ |
| 340. | H | $OCH_2CH_2C_6H_5$ | $CH_2$—$CO_2H$ | $CH_2$—$CONH_2$ |
| 341. | H | $OCH_2$—$CONH_2$ | $CH_2$—$CO_2CH_2CH_3$ | $CH_2$—$CONH_2$ |
| 342. | H | $OCH_2$—$CONH_2$ | $CH_2$—$CO_2H$ | $CH_2$—$CONH_2$ |
| 343. | H | H | $CH_2CH_2P$—$O(OCH_2CH_3)_2$ | $CH_2$—$CONH_2$ |
| 344. | H | H | $CH_2CH_2P$—$O(OH)_2$ | $CH_2$—$CONH_2$ |
| 345. | OH | H | $CH_2CH_2P$—$O(OCH_2CH_3)_2$ | $CH_2$—$CONH_2$ |
| 346. | OH | H | $CH_2CH_2P$—$O(OH)_2$ | $CH_2$—$CONH_2$ |
| 347. | $OCH_3$ | H | $CH_2CH_2P$—$O(OCH_2CH_3)_2$ | $CH_2$—$CONH_2$ |
| 348. | $OCH_3$ | H | $CH_2CH_2P$—$O(OH)_2$ | $CH_2$—$CONH_2$ |
| 349. | $OCH_2CH$=$CH_2$ | H | $CH_2CH_2P$—$O(OCH_2CH_3)_2$ | $CH_2$—$CONH_2$ |
| 350. | $OCH_2CH$=$CH_2$ | H | $CH_2CH_2P$—$O(OH)_2$ | $CH_2$—$CONH_2$ |
| 351. | $OCH_2C_6H_5$ | H | $CH_2CH_2P$—$O(OCH_2CH_3)_2$ | $CH_2$—$CONH_2$ |
| 352. | $OCH_2C_6H_5$ | H | $CH_2CH_2P$—$O(OH)_2$ | $CH_2$—$CONH_2$ |
| 353. | $OCH_2CH_2C_6H_5$ | H | $CH_2CH_2P$—$O(OCH_2CH_3)_2$ | $CH_2$—$CONH_2$ |
| 354. | $OCH_2CH_2C_6H_5$ | H | $CH_2CH_2P$—$O(OH)_2$ | $CH_2$—$CONH_2$ |
| 355. | $OCH_2$—$CONH_2$ | H | $CH_2CH_2P$—$O(OCH_2CH_3)_2$ | $CH_2$—$CONH_2$ |
| 356. | $OCH_2$—$CONH_2$ | H | $CH_2CH_2P$—$O(OH)_2$ | $CH_2$—$CONH_2$ |
| 357. | H | Cl | $CH_2CH_2P$—$O(OCH_2CH_3)_2$ | $CH_2$—$CONH_2$ |
| 358. | H | Cl | $CH_2CH_2P$—$O(OH)_2$ | $CH_2$—$CONH_2$ |
| 359. | Br | H | $CH_2CH_2P$—$O(OCH_2CH_3)_2$ | $CH_2$—$CONH_2$ |
| 360. | Br | H | $CH_2CH_2P$—$O(OH)_2$ | $CH_2$—$CONH_2$ |
| 361. | H | $CH_3$ | $CH_2CH_2P$—$O(OCH_2CH_3)_2$ | $CH_2$—$CONH_2$ |
| 362. | H | $CH_3$ | $CH_2CH_2P$—$O(OH)_2$ | $CH_2$—$CONH_2$ |
| 363. | $NO_2$ | H | $CH_2CH_2P$—$O(OCH_2CH_3)_2$ | $CH_2$—$CONH_2$ |
| 364. | $NO_2$ | H | $CH_2CH_2P$—$O(OH)_2$ | $CH_2$—$CONH_2$ |
| 365. | $NH_2$ | H | $CH_2CH_2P$—$O(OCH_2CH_3)_2$ | $CH_2$—$CONH_2$ |
| 366. | $NH_2$ | H | $CH_2CH_2P$—$O(OH)_2$ | $CH_2$—$CONH_2$ |
| 367. | $NHSO_2CH_3$ | H | $CH_2CH_2P$—$O(OCH_2CH_3)_2$ | $CH_2$—$CONH_2$ |
| 368. | $NHSO_2CH_3$ | H | $CH_2CH_2P$—$O(OH)_2$ | $CH_2$—$CONH_2$ |
| 369. | H | OH | $CH_2CH_2P$—$O(OCH_2CH_3)_2$ | $CH_2$—$CONH_2$ |
| 370. | H | OH | $CH_2CH_2P$—$O(OH)_2$ | $CH_2$—$CONH_2$ |
| 371. | H | $OCH_3$ | $CH_2CH_2P$—$O(OCH_2CH_3)_2$ | $CH_2$—$CONH_2$ |
| 372. | H | $OCH_3$ | $CH_2CH_2P$—$O(OH)_2$ | $CH_2$—$CONH_2$ |
| 373. | H | $OCH_2CH$=$CH_2$ | $CH_2CH_2P$—$O(OCH_2CH_3)_2$ | $CH_2$—$CONH_2$ |
| 374. | H | $OCH_2CH$=$CH_2$ | $CH_2CH_2P$—$O(OH)_2$ | $CH_2$—$CONH_2$ |
| 375. | H | $OCH_2C_6H_5$ | $CH_2CH_2P$—$O(OCH_2CH_3)_2$ | $CH_2$—$CONH_2$ |
| 376. | H | $OCH_2C_6H_5$ | $CH_2CH_2P$—$O(OH)_2$ | $CH_2$—$CONH_2$ |
| 377. | H | $OCH_2CH_2C_6H_5$ | $CH_2CH_2P$—$O(OCH_2CH_3)_2$ | $CH_2$—$CONH_2$ |
| 378. | H | $OCH_2CH_2C_6H_5$ | $CH_2CH_2P$—$O(OH)_2$ | $CH_2$—$CONH_2$ |
| 379. | H | $OCH_2$—$CONH_2$ | $CH_2CH_2P$—$O(OCH_2CH_3)_2$ | $CH_2$—$CONH_2$ |
| 380. | H | $OCH_2$—$CONH_2$ | $CH_2CH_2P$—$O(OH)_2$ | $CH_2$—$CONH_2$ |
| 381. | H | H | $CH_2$—$CO_2CH_2CH_3$ | $CH_2C_6H_5$ |
| 382. | H | H | $CH_2$—$CO_2H$ | $CH_2C_6H_5$ |
| 383. | OH | H | $CH_2$—$CO_2CH_2CH_3$ | $CH_2C_6H_5$ |
| 384. | OH | H | $CH_2$—$CO_2H$ | $CH_2C_6H_5$ |
| 385. | $OCH_3$ | H | $CH_2$—$CO_2CH_2CH_3$ | $CH_2C_6H_5$ |
| 386. | $OCH_3$ | H | $CH_2$—$CO_2H$ | $CH_2C_6H_5$ |
| 387. | $OCH_2CH$=$CH_2$ | H | $CH_2$—$CO_2CH_2CH_3$ | $CH_2C_6H_5$ |
| 388. | $OCH_2CH$=$CH_2$ | H | $CH_2$—$CO_2H$ | $CH_2C_6H_5$ |
| 389. | $OCH_2C_6H_5$ | H | $CH_2$—$CO_2CH_2CH_3$ | $CH_2C_6H_5$ |
| 390. | $OCH_2C_6H_5$ | H | $CH_2$—$CO_2H$ | $CH_2C_6H_5$ |
| 391. | $OCH_2CH_2C_6H_5$ | H | $CH_2$—$CO_2CH_2CH_3$ | $CH_2C_6H_5$ |
| 392. | $OCH_2CH_2C_6H_5$ | H | $CH_2$—$CO_2H$ | $CH_2C_6H_5$ |

TABLE III-continued

| Ex. # | X | X¹ | R¹ | R" |
|---|---|---|---|---|
| 393. | $OCH_2-CONH_2$ | H | $CH_2-CO_2CH_2CH_3$ | $CH_2C_6H_5$ |
| 394. | $OCH_2-CONH_2$ | H | $CH_2-CO_2H$ | $CH_2C_6H_5$ |
| 395. | H | Cl | $CH_2-CO_2CH_2CH_3$ | $CH_2C_6H_5$ |
| 396. | H | Cl | $CH_2-CO_2H$ | $CH_2C_6H_5$ |
| 397. | Br | H | $CH_2-CO_2CH_2CH_3$ | $CH_2C_6H_5$ |
| 398. | Br | H | $CH_2-CO_2H$ | $CH_2C_6H_5$ |
| 399. | H | $CH_3$ | $CH_2-CO_2CH_2CH_3$ | $CH_2C_6H_5$ |
| 400. | H | $CH_3$ | $CH_2-CO_2H$ | $CH_2C_6H_5$ |
| 401. | $NO_2$ | H | $CH_2-CO_2CH_2CH_3$ | $CH_2C_6H_5$ |
| 402. | $NO_2$ | H | $CH_2-CO_2H$ | $CH_2C_6H_5$ |
| 403. | $NH_2$ | H | $CH_2-CO_2CH_2CH_3$ | $CH_2C_6H_5$ |
| 404. | $NH_2$ | H | $CH_2-CO_2H$ | $CH_2C_6H_5$ |
| 405. | $NHSO_2CH_3$ | H | $CH_2-CO_2CH_2CH_3$ | $CH_2C_6H_5$ |
| 406. | $NHSO_2CH_3$ | H | $CH_2-CO_2H$ | $CH_2C_6H_5$ |
| 407. | H | OH | $CH_2-CO_2CH_2CH_3$ | $CH_2C_6H_5$ |
| 408. | H | OH | $CH_2-CO_2H$ | $CH_2C_6H_5$ |
| 409. | H | $OCH_3$ | $CH_2-CO_2CH_2CH_3$ | $CH_2C_6H_5$ |
| 410. | H | $OCH_3$ | $CH_2-CO_2H$ | $CH_2C_6H_5$ |
| 411. | H | $OCH_2CH=CH_2$ | $CH_2-CO_2CH_2CH_3$ | $CH_2C_6H_5$ |
| 412. | H | $OCH_2CH=CH_2$ | $CH_2-CO_2H$ | $CH_2C_6H_5$ |
| 413. | H | $OCH_2C_6H_5$ | $CH_2-CO_2CH_2CH_3$ | $CH_2C_6H_5$ |
| 414. | H | $OCH_2C_6H_5$ | $CH_2-CO_2H$ | $CH_2C_6H_5$ |
| 415. | H | $OCH_2CH_2C_6H_5$ | $CH_2-CO_2CH_2CH_3$ | $CH_2C_6H_5$ |
| 416. | H | $OCH_2CH_2C_6H_5$ | $CH_2-CO_2H$ | $CH_2C_6H_5$ |
| 417. | H | $OCH_2-CONH_2$ | $CH_2-CO_2CH_2CH_3$ | $CH_2C_6H_5$ |
| 418. | H | $OCH_2-CONH_2$ | $CH_2-CO_2H$ | $CH_2C_6H_5$ |
| 419. | H | H | $CH_2CH_2P-O(OCH_2CH_3)_2$ | $CH_2C_6H_5$ |
| 420. | H | H | $CH_2CH_2P-O(OH)_2$ | $CH_2C_6H_5$ |
| 421. | OH | H | $CH_2CH_2P-O(OCH_2CH_3)_2$ | $CH_2C_6H_5$ |
| 422. | OH | H | $CH_2CH_2P-O(OH)_2$ | $CH_2C_6H_5$ |
| 423. | $OCH_3$ | H | $CH_2CH_2P-O(OCH_2CH_3)_2$ | $CH_2C_6H_5$ |
| 424. | $OCH_3$ | H | $CH_2CH_2P-O(OH)_2$ | $CH_2C_6H_5$ |
| 425. | $OCH_2CH=CH_2$ | H | $CH_2CH_2P-O(OCH_2CH_3)_2$ | $CH_2C_6H_5$ |
| 426. | $OCH_2CH=CH_2$ | H | $CH_2CH_2P-O(OH)_2$ | $CH_2C_6H_5$ |
| 427. | $OCH_2C_6H_5$ | H | $CH_2CH_2P-O(OCH_2CH_3)_2$ | $CH_2C_6H_5$ |
| 428. | $OCH_2C_6H_5$ | H | $CH_2CH_2P-O(OH)_2$ | $CH_2C_6H_5$ |
| 429. | $OCH_2CH_2C_6H_5$ | H | $CH_2CH_2P-O(OCH_2CH_3)_2$ | $CH_2C_6H_5$ |
| 430. | $OCH_2CH_2C_6H_5$ | H | $CH_2CH_2P-O(OH)_2$ | $CH_2C_6H_5$ |
| 431. | $OCH_2-CONH_2$ | H | $CH_2CH_2P-O(OCH_2CH_3)_2$ | $CH_2C_6H_5$ |
| 432. | $OCH_2-CONH_2$ | H | $CH_2CH_2P-O(OH)_2$ | $CH_2C_6H_5$ |
| 433. | H | Cl | $CH_2CH_2P-O(OCH_2CH_3)_2$ | $CH_2C_6H_5$ |
| 434. | H | Cl | $CH_2CH_2P-O(OH)_2$ | $CH_2C_6H_5$ |
| 435. | Br | H | $CH_2CH_2P-O(OCH_2CH_3)_2$ | $CH_2C_6H_5$ |
| 436. | Br | H | $CH_2CH_2P-O(OH)_2$ | $CH_2C_6H_5$ |
| 437. | H | $CH_3$ | $CH_2CH_2P-O(OCH_2CH_3)_2$ | $CH_2C_6H_5$ |
| 438. | H | $CH_3$ | $CH_2CH_2P-O(OH)_2$ | $CH_2C_6H_5$ |
| 439. | $NO_2$ | H | $CH_2CH_2P-O(OCH_2CH_3)_2$ | $CH_2C_6H_5$ |
| 440. | $NO_2$ | H | $CH_2CH_2P-O(OH)_2$ | $CH_2C_6H_5$ |
| 441. | $NH_2$ | H | $CH_2CH_2P-O(OCH_2CH_3)_2$ | $CH_2C_6H_5$ |
| 442. | $NH_2$ | H | $CH_2CH_2P-O(OH)_2$ | $CH_2C_6H_5$ |
| 443. | $NHSO_2CH_3$ | H | $CH_2CH_2P-O(OCH_2CH_3)_2$ | $CH_2C_6H_5$ |
| 444. | $NHSO_2CH_3$ | H | $CH_2CH_2P-O(OH)_2$ | $CH_2C_6H_5$ |
| 445. | H | OH | $CH_2CH_2P-O(OCH_2CH_3)_2$ | $CH_2C_6H_5$ |
| 446. | H | OH | $CH_2CH_2P-O(OH)_2$ | $CH_2C_6H_5$ |
| 447. | H | $OCH_3$ | $CH_2CH_2P-O(OCH_2CH_3)_2$ | $CH_2C_6H_5$ |
| 448. | H | $OCH_3$ | $CH_2CH_2P-O(OH)_2$ | $CH_2-CONH_2$ |
| 449. | H | $OCH_2CH=CH_2$ | $CH_2CH_2P-O(OCH_2CH_3)_2$ | $CH_2-CONH_2$ |
| 450. | H | $OCH_2CH=CH_2$ | $CH_2CH_2P-O(OH)_2$ | $CH_2-CONH_2$ |
| 451. | H | $OCH_2C_6H_5$ | $CH_2CH_2P-O(OCH_2CH_3)_2$ | $CH_2-CONH_2$ |
| 452. | H | $OCH_2C_6H_5$ | $CH_2CH_2P-O(OH)_2$ | $CH_2-CONH_2$ |
| 453. | H | $OCH_2CH_2C_6H_5$ | $CH_2CH_2P-O(OCH_2CH_3)_2$ | $CH_2-CONH_2$ |
| 454. | H | $OCH_2CH_2C_6H_5$ | $CH_2CH_2P-O(OH)_2$ | $CH_2-CONH_2$ |
| 455. | H | $OCH_2-CONH_2$ | $CH_2CH_2P-O(OCH_2CH_3)_2$ | $CH_2-CONH_2$ |
| 456. | H | $OCH_2-CONH_2$ | $CH_2CH_2P-O(OH)_2$ | $CH_2-CONH_2$ |

TABLE IV

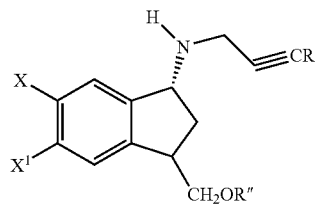

| Ex. # | X | X¹ | R¹ | R" |
|---|---|---|---|---|
| 1. | H | H | H | $CH_2-CO_2CH_2CH_3$ |
| 2. | H | H | $CH_3$ | $CH_2-CO_2H$ |
| 3. | OH | H | H | $CH_2-CO_2CH_2CH_3$ |
| 4. | OH | H | $CH_3$ | $CH_2-CO_2H$ |
| 5. | $OCH_3$ | H | H | $CH_2-CO_2CH_2CH_3$ |
| 6. | $OCH_3$ | H | $CH_3$ | $CH_2-CO_2H$ |
| 7. | $OCH_2CH=CH_2$ | H | H | $CH_2-CO_2CH_2CH_3$ |
| 8. | $OCH_2CH=CH_2$ | H | $CH_3$ | $CH_2-CO_2H$ |
| 9. | $OCH_2C_6H_5$ | H | H | $CH_2-CO_2CH_2CH_3$ |
| 10. | $OCH_2C_6H_5$ | H | $CH_3$ | $CH_2-CO_2H$ |
| 11. | $OCH_2CH_2C_6H_5$ | H | H | $CH_2-CO_2CH_2CH_3$ |
| 12. | $OCH_2CH_2C_6H_5$ | H | $CH_3$ | $CH_2-CO_2H$ |
| 13. | $OCH_2-CONH_2$ | H | H | $CH_2-CO_2CH_2CH_3$ |
| 14. | $OCH_2-CONH_2$ | H | $CH_3$ | $CH_2-CO_2H$ |
| 15. | H | CL | H | $CH_2-CO_2CH_2CH_3$ |
| 16. | H | Cl | $CH_3$ | $CH_2-CO_2H$ |
| 17. | Br | H | H | $CH_2-CO_2CH_2CH_3$ |
| 18. | Br | H | $CH_3$ | $CH_2-CO_2H$ |
| 19. | H | $CH_3$ | H | $CH_2-CO_2CH_2CH_3$ |
| 20. | H | $CH_3$ | $CH_3$ | $CH_2-CO_2H$ |
| 21. | $NO_2$ | H | H | $CH_2-CO_2CH_2CH_3$ |
| 22. | $NO_2$ | H | $CH_3$ | $CH_2-CO_2H$ |
| 23. | $NH_2$ | H | H | $CH_2-CO_2CH_2CH_3$ |
| 24. | $NH_2$ | H | $CH_3$ | $CH_2-CO_2H$ |
| 25. | $NHSO_2CH_3$ | H | H | $CH_2-CO_2CH_2CH_3$ |
| 26. | $NHSO_2CH_3$ | H | $CH_3$ | $CH_2-CO_2H$ |
| 27. | H | OH | H | $CH_2-CO_2CH_2CH_3$ |
| 28. | H | OH | $CH_3$ | $CH_2-CO_2H$ |
| 29. | H | $OCH_3$ | H | $CH_2-CO_2CH_2CH_3$ |
| 30. | H | $OCH_3$ | $CH_3$ | $CH_2-CO_2H$ |
| 31. | H | $OCH_2CH=CH_2$ | H | $CH_2-CO_2CH_2CH_3$ |
| 32. | H | $OCH_2CH=CH_2$ | $CH_3$ | $CH_2-CO_2H$ |
| 33. | H | $OCH_2C_6H_5$ | H | $CH_2-CO_2CH_2CH_3$ |
| 34. | H | $OCH_2C_6H_5$ | $CH_3$ | $CH_2-CO_2H$ |
| 35. | H | $OCH_2CH_2C_6H_5$ | H | $CH_2-CO_2CH_2CH_3$ |
| 36. | H | $OCH_2CH_2C_6H_5$ | $CH_3$ | $CH_2-CO_2H$ |
| 37. | H | $OCH_2-CONH_2$ | H | $CH_2-CO_2CH_2CH_3$ |
| 38. | H | $OCH_2-CONH_2$ | $CH_3$ | $CH_2-CO_2H$ |
| 39. | H | H | H | $CH_2CH_2-CO_2CH_2CH_3$ |
| 40. | H | H | $CH_3$ | $CH_2CH_2-CO_2H$ |
| 41. | OH | H | H | $CH_2CH_2-CO_2CH_2CH_3$ |
| 42. | OH | H | $CH_3$ | $CH_2CH_2-CO_2H$ |
| 43. | $OCH_3$ | H | H | $CH_2CH_2-CO_2CH_2CH_3$ |
| 44. | $OCH_3$ | H | $CH_3$ | $CH_2CH_2-CO_2H$ |
| 45. | $OCH_2CH=CH_2$ | H | H | $CH_2CH_2-CO_2CH_2CH_3$ |
| 46. | $OCH_2CH=CH_2$ | H | $CH_3$ | $CH_2CH_2-CO_2H$ |
| 47. | $OCH_2C_6H_5$ | H | H | $CH_2CH_2-CO_2CH_2CH_3$ |
| 48. | $OCH_2C_6H_5$ | H | $CH_3$ | $CH_2CH_2-CO_2H$ |
| 49. | $OCH_2CH_2C_6H_5$ | H | H | $CH_2CH_2-CO_2CH_2CH_3$ |
| 50. | $OCH_2CH_2C_6H_5$ | H | $CH_3$ | $CH_2CH_2-CO_2H$ |
| 51. | $OCH_2-CONH_2$ | H | H | $CH_2CH_2-CO_2CH_2CH_3$ |
| 52. | $OCH_2-CONH_2$ | H | $CH_3$ | $CH_2CH_2-CO_2H$ |
| 53. | H | Cl | H | $CH_2CH_2-CO_2CH_2CH_3$ |
| 54. | H | Cl | $CH_3$ | $CH_2CH_2-CO_2H$ |
| 55. | Br | H | H | $CH_2CH_2-CO_2CH_2CH_3$ |
| 56. | Br | H | $CH_3$ | $CH_2CH_2-CO_2H$ |
| 57. | H | $CH_3$ | H | $CH_2CH_2-CO_2CH_2CH_3$ |
| 58. | H | $CH_3$ | $CH_3$ | $CH_2CH_2-CO_2H$ |
| 59. | $NO_2$ | H | H | $CH_2CH_2-CO_2CH_2CH_3$ |
| 60. | $NO_2$ | H | $CH_3$ | $CH_2CH_2-CO_2H$ |
| 61. | $NH_2$ | H | H | $CH_2CH_2-CO_2CH_2CH_3$ |
| 62. | $NH_2$ | H | $CH_3$ | $CH_2CH_2-CO_2H$ |
| 63. | $NHSO_2CH_3$ | H | H | $CH_2CH_2-CO_2CH_2CH_3$ |
| 64. | $NHSO_2CH_3$ | H | $CH_3$ | $CH_2CH_2-CO_2H$ |
| 65. | H | OH | H | $CH_2CH_2-CO_2CH_2CH_3$ |
| 66. | H | OH | $CH_3$ | $CH_2CH_2-CO_2H$ |
| 67. | H | $OCH_3$ | H | $CH_2CH_2-CO_2CH_2CH_3$ |

TABLE IV-continued

[Structure: indane with X at 5-position, X¹ at 6-position, NH-CH₂-C≡C-R¹ substituent at 1-position, and CH₂OR'' substituent at 3-position]

| Ex. # | X | X¹ | R¹ | R" |
|---|---|---|---|---|
| 68. | H | OCH₃ | CH₃ | CH₂CH₂—CO₂H |
| 69. | H | OCH₂CH=CH₂ | H | CH₂CH₂—CO₂CH₂CH₃ |
| 70. | H | OCH₂CH=CH₂ | CH₃ | CH₂CH₂—CO₂H |
| 71. | H | OCH₂C₆H₅ | H | CH₂CH₂—CO₂CH₂CH₃ |
| 72. | H | OCH₂C₆H₅ | CH₃ | CH₂CH₂—CO₂H |
| 73. | H | OCH₂CH₂C₆H₅ | H | CH₂CH₂—CO₂CH₂CH₃ |
| 74. | H | OCH₂CH₂C₆H₅ | CH₃ | CH₂CH₂—CO₂H |
| 75. | H | OCH₂—CONH₂ | H | CH₂CH₂—CO₂CH₂CH₃ |
| 76. | H | OCH₂—CONH₂ | CH₃ | CH₂CH₂—CO₂H |
| 77. | H | H | H | CH₂CH₂P—O(OCH₂CH₃)₂ |
| 78. | H | H | CH₃ | CH₂CH₂P—O(OH)₂ |
| 79. | OH | H | H | CH₂CH₂P—O(OCH₂CH₃)₂ |
| 80. | OH | H | CH₃ | CH₂CH₂P—O(OH)₂ |
| 81. | OCH₃ | H | H | CH₂CH₂P—O(OCH₂CH₃)₂ |
| 82. | OCH₃ | H | CH₃ | CH₂CH₂P—O(OH)₂ |
| 83. | OCH₂CH=CH₂ | H | H | CH₂CH₂P—O(OCH₂CH₃)₂ |
| 84. | OCH₂CH=CH₂ | H | CH₃ | CH₂CH₂P—O(OH)₂ |
| 85. | OCH₂C₆H₅ | H | H | CH₂CH₂P—O(OCH₂CH₃)₂ |
| 86. | OCH₂C₆H₅ | H | CH₃ | CH₂CH₂P—O(OH)₂ |
| 87. | OCH₂CH₂C₆H₅ | H | H | CH₂CH₂P—O(OCH₂CH₃)₂ |
| 88. | OCH₂CH₂C₆H₅ | H | CH₃ | CH₂CH₂P—O(OH)₂ |
| 89. | OCH₂—CONH₂ | H | H | CH₂CH₂P—O(OCH₂CH₃)₂ |
| 90. | OCH₂—CONH₂ | H | CH₃ | CH₂CH₂P—O(OH)₂ |
| 91. | H | Cl | H | CH₂CH₂P—O(OCH₂CH₃)₂ |
| 92. | H | Cl | CH₃ | CH₂CH₂P—O(OH)₂ |
| 93. | Br | H | H | CH₂CH₂P—O(OCH₂CH₃)₂ |
| 94. | Br | H | CH₃ | CH₂CH₂P—O(OH)₂ |
| 95. | H | CH₃ | H | CH₂CH₂P—O(OCH₂CH₃)₂ |
| 96. | H | CH₃ | CH₃ | CH₂CH₂P—O(OH)₂ |
| 97. | NO₂ | H | H | CH₂CH₂P—O(OCH₂CH₃)₂ |
| 98. | NO₂ | H | CH₃ | CH₂CH₂P—O(OH)₂ |
| 99. | NH₂ | H | H | CH₂CH₂P—O(OCH₂CH₃)₂ |
| 100. | NH₂ | H | CH₃ | CH₂CH₂P—O(OH)₂ |
| 101. | NHSO₂CH₃ | H | H | CH₂CH₂P—O(OCH₂CH₃)₂ |
| 102. | NHSO₂CH₃ | H | CH₃ | CH₂CH₂P—O(OH)₂ |
| 103. | H | OH | H | CH₂CH₂P—O(OCH₂CH₃)₂ |
| 104. | H | OH | CH₃ | CH₂CH₂P—O(OH)₂ |
| 105. | H | OCH₃ | H | CH₂CH₂P—O(OCH₂CH₃)₂ |
| 106. | H | OCH₃ | CH₃ | CH₂CH₂P—O(OH)₂ |
| 107. | H | OCH₂CH=CH₂ | H | CH₂CH₂P—O(OCH₂CH₃)₂ |
| 108. | H | OCH₂CH=CH₂ | CH₃ | CH₂CH₂P—O(OH)₂ |
| 109. | H | OCH₂C₆H₅ | H | CH₂CH₂P—O(OCH₂CH₃)₂ |
| 110. | H | OCH₂C₆H₅ | CH₃ | CH₂CH₂P—O(OH)₂ |
| 111. | H | OCH₂CH₂C₆H₅ | H | CH₂CH₂P—O(OCH₂CH₃)₂ |
| 112. | H | OCH₂CH₂C₆H₅ | CH₃ | CH₂CH₂P—O(OH)₂ |
| 113. | H | OCH₂—CONH₂ | H | CH₂CH₂P—O(OCH₂CH₃)₂ |
| 114. | H | OCH₂—CONH₂ | CH₃ | CH₂CH₂P—O(OH)₂ |
| 115. | H | H | H | CH₂CH=CH—CO₂CH₂CH₃ |
| 116. | H | H | CH₃ | CH₂CH=CH—CO₂H |
| 117. | OH | H | H | CH₂CH=CH—CO₂CH₂CH₃ |
| 118. | OH | H | CH₃ | CH₂CH=CH—CO₂H |
| 119. | OCH₃ | H | H | CH₂CH=CH—CO₂CH₂CH₃ |
| 120. | OCH₃ | H | CH₃ | CH₂CH=CH—CO₂H |
| 121. | OCH₂CH=CH₂ | H | H | CH₂CH=CH—CO₂CH₂CH₃ |
| 122. | OCH₂CH=CH₂ | H | CH₃ | CH₂CH=CH—CO₂H |
| 123. | OCH₂C₆H₅ | H | H | CH₂CH=CH—CO₂CH₂CH₃ |
| 124. | OCH₂C₆H₅ | H | CH₃ | CH₂CH=CH—CO₂H |
| 125. | OCH₂CH₂C₆H₅ | H | H | CH₂CH=CH—CO₂CH₂CH₃ |
| 126. | OCH₂CH₂C₆H₅ | H | CH₃ | CH₂CH=CH—CO₂H |
| 127. | OCH₂—CONH₂ | H | H | CH₂CH=CH—CO₂CH₂CH₃ |
| 128. | OCH₂—CONH₂ | H | CH₃ | CH₂CH=CH—CO₂H |
| 129. | H | Cl | H | CH₂CH=CH—CO₂CH₂CH₃ |
| 130. | H | Cl | CH₃ | CH₂CH=CH—CO₂H |
| 131. | Br | H | H | CH₂CH=CH—CO₂CH₂CH₃ |
| 132. | Br | H | CH₃ | CH₂CH=CH—CO₂H |
| 133. | H | CH₃ | H | CH₂CH=CH—CO₂CH₂CH₃ |
| 134. | H | CH₃ | CH₃ | CH₂CH=CH—CO₂H |

TABLE IV-continued

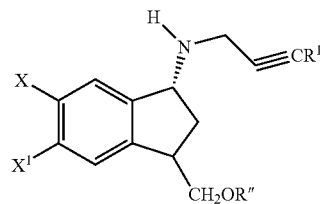

| Ex. # | X | $X^1$ | $R^1$ | R" |
|---|---|---|---|---|
| 135. | $NO_2$ | H | H | $CH_2CH=CH-CO_2CH_2CH_3$ |
| 136. | $NO_2$ | H | $CH_3$ | $CH_2CH=CH-CO_2H$ |
| 137. | $NH_2$ | H | H | $CH_2CH=CH-CO_2CH_2CH_3$ |
| 138. | $NH_2$ | H | $CH_3$ | $CH_2CH=CH-CO_2H$ |
| 139. | $NHSO_2CH_3$ | H | H | $CH_2CH=CH-CO_2CH_2CH_3$ |
| 140. | $NHSO_2CH_3$ | H | $CH_3$ | $CH_2CH=CH-CO_2H$ |
| 141. | H | OH | H | $CH_2CH=CH-CO_2CH_2CH_3$ |
| 142. | H | OH | $CH_3$ | $CH_2CH=CH-CO_2H$ |
| 143. | H | $OCH_3$ | H | $CH_2CH=CH-CO_2CH_2CH_3$ |
| 144. | H | $OCH_3$ | $CH_3$ | $CH_2CH=CH-CO_2H$ |
| 145. | H | $OCH_2CH=CH_2$ | H | $CH_2CH=CH-CO_2CH_2CH_3$ |
| 146. | H | $OCH_2CH=CH_2$ | $CH_3$ | $CH_2CH=CH-CO_2H$ |
| 147. | H | $OCH_2C_6H_5$ | H | $CH_2CH=CH-CO_2CH_2CH_3$ |
| 148. | H | $OCH_2C_6H_5$ | $CH_3$ | $CH_2CH=CH-CO_2H$ |
| 149. | H | $OCH_2CH_2C_6H_5$ | H | $CH_2CH=CH-CO_2CH_2CH_3$ |
| 150. | H | $OCH_2CH_2C_6H_5$ | $CH_3$ | $CH_2CH=CH-CO_2H$ |
| 151. | H | $OCH_2-CONH_2$ | H | $CH_2CH=CH-CO_2CH_2CH_3$ |
| 152. | H | $OCH_2-CONH_2$ | $CH_3$ | $CH_2CH=CH-CO_2H$ |
| 153. | H | H | $CH_2-CO_2CH_2CH_3$ | $CH_3$ |
| 154. | H | H | $CH_2-CO_2H$ | $CH_3$ |
| 155. | OH | H | $CH_2-CO_2CH_2CH_3$ | $CH_3$ |
| 156. | OH | H | $CH_2-CO_2H$ | $CH_3$ |
| 157. | $OCH_3$ | H | $CH_2-CO_2CH_2CH_3$ | $CH_3$ |
| 158. | $OCH_3$ | H | $CH_2-CO_2H$ | $CH_3$ |
| 159. | $OCH_2CH=CH_2$ | H | $CH_2-CO_2CH_2CH_3$ | $CH_3$ |
| 160. | $OCH_2CH=CH_2$ | H | $CH_2-CO_2H$ | $CH_3$ |
| 161. | $OCH_2C_6H_5$ | H | $CH_2-CO_2CH_2CH_3$ | $CH_3$ |
| 162. | $OCH_2C_6H_5$ | H | $CH_2-CO_2H$ | $CH_3$ |
| 163. | $OCH_2CH_2C_6H_5$ | H | $CH_2-CO_2CH_2CH_3$ | $CH_3$ |
| 164. | $OCH_2CH_2C_6H_5$ | H | $CH_2-CO_2H$ | $CH_3$ |
| 165. | $OCH_2-CONH_2$ | H | $CH_2-CO_2CH_2CH_3$ | $CH_3$ |
| 166. | $OCH_2-CONH_2$ | H | $CH_2-CO_2H$ | $CH_3$ |
| 167. | H | Cl | $CH_2-CO_2CH_2CH_3$ | $CH_3$ |
| 168. | H | Cl | $CH_2-CO_2H$ | $CH_3$ |
| 169. | Br | H | $CH_2-CO_2CH_2CH_3$ | $CH_3$ |
| 170. | Br | H | $CH_2-CO_2H$ | $CH_3$ |
| 171. | H | $CH_3$ | $CH_2-CO_2CH_2CH_3$ | $CH_3$ |
| 172. | H | $CH_3$ | $CH_2-CO_2H$ | $CH_3$ |
| 173. | $NO_2$ | H | $CH_2-CO_2CH_2CH_3$ | $CH_3$ |
| 174. | $NO_2$ | H | $CH_2-CO_2H$ | $CH_3$ |
| 175. | $NH_2$ | H | $CH_2-CO_2CH_2CH_3$ | $CH_3$ |
| 176. | $NH_2$ | H | $CH_2-CO_2H$ | $CH_3$ |
| 177. | $NHSO_2CH_3$ | H | $CH_2-CO_2CH_2CH_3$ | $CH_3$ |
| 178. | $NHSO_2CH_3$ | H | $CH_2-CO_2H$ | $CH_3$ |
| 179. | H | OH | $CH_2-CO_2CH_2CH_3$ | $CH_3$ |
| 180. | H | OH | $CH_2-CO_2H$ | $CH_3$ |
| 181. | H | $OCH_3$ | $CH_2-CO_2CH_2CH_3$ | $CH_3$ |
| 182. | H | $OCH_3$ | $CH_2CO_2H$ | $CH_3$ |
| 183. | H | $OCH_2CH=CH_2$ | $CH_2-CO_2CH_2CH_3$ | $CH_3$ |
| 184. | H | $OCH_2CH=CH_2$ | $CH_2-CO_2H$ | $CH_3$ |
| 185. | H | $OCH_2C_6H_5$ | $CH_2-CO_2CH_2CH_3$ | $CH_3$ |
| 186. | H | $OCH_2C_6H_5$ | $CH_2-CO_2H$ | $CH_3$ |
| 187. | H | $OCH_2CH_2C_6H_5$ | $CH_2-CO_2CH_2CH_3$ | $CH_3$ |
| 188. | H | $OCH_2CH_2C_6H_5$ | $CH_2-CO_2H$ | $CH_3$ |
| 189. | H | $OCH_2-CONH_2$ | $CH_2-CO_2CH_2CH_3$ | $CH_3$ |
| 190. | H | $OCH_2-CONH_2$ | $CH_2-CO_2H$ | $CH_3$ |
| 191. | H | H | $CH_2CH_2P=O(OCH_2CH_3)_2$ | $CH_3$ |
| 192. | H | H | $CH_2CH_2P=O(OH)_2$ | $CH_3$ |
| 193. | OH | H | $CH_2CH_2P=O(OCH_2CH_3)_2$ | $CH_3$ |
| 194. | OH | H | $CH_2CH_2P=O(OH)_2$ | $CH_3$ |
| 195. | $OCH_3$ | H | $CH_2CH_2P=O(OCH_2CH_3)_2$ | $CH_3$ |
| 196. | $OCH_3$ | H | $CH_2CH_2P=O(OH)_2$ | $CH_3$ |
| 197. | $OCH_2CH=CH_2$ | H | $CH_2CH_2P=O(OCH_2CH_3)_2$ | $CH_3$ |
| 198. | $OCH_2CH=CH_2$ | H | $CH_2CH_2P=O(OH)_2$ | $CH_3$ |
| 199. | $OCH_2C_6H_5$ | H | $CH_2CH_2P=O(OCH_2CH_3)_2$ | $CH_3$ |
| 200. | $OCH_2C_6H_5$ | H | $CH_2CH_2P=O(OH)_2$ | $CH_3$ |
| 201. | $OCH_2CH_2C_6H_5$ | H | $CH_2CH_2P=O(OCH_2CH_3)_2$ | $CH_3$ |

TABLE IV-continued

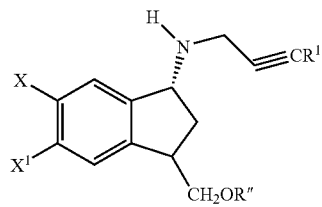

| Ex. # | X | X¹ | R¹ | R" |
|---|---|---|---|---|
| 202. | $OCH_2CH_2C_6H_5$ | H | $CH_2CH_2P-O(OH)_2$ | $CH_3$ |
| 203. | $OCH_2-CONH_2$ | H | $CH_2CH_2P-O(OCH_2CH_3)_2$ | $CH_3$ |
| 204. | $OCH_2-CONH_2$ | H | $CH_2CH_2P-O(OH)_2$ | $CH_3$ |
| 205. | H | Cl | $CH_2CH_2P-O(OCH_2CH_3)_2$ | $CH_3$ |
| 206. | H | Cl | $CH_2CH_2P-O(OH)_2$ | $CH_3$ |
| 207. | Br | H | $CH_2CH_2P-O(OCH_2CH_3)_2$ | $CH_3$ |
| 208. | Br | H | $CH_2CH_2P-O(OH)_2$ | $CH_3$ |
| 209. | H | $CH_3$ | $CH_2CH_2P-O(OCH_2CH_3)_2$ | $CH_3$ |
| 210. | H | $CH_3$ | $CH_2CH_2P-O(OH)_2$ | $CH_3$ |
| 211. | $NO_2$ | H | $CH_2CH_2P-O(OCH_2CH_3)_2$ | $CH_3$ |
| 212. | $NO_2$ | H | $CH_2CH_2P-O(OH)_2$ | $CH_3$ |
| 213. | $NH_2$ | H | $CH_2CH_2P-O(OCH_2CH_3)_2$ | $CH_3$ |
| 214. | $NH_2$ | H | $CH_2CH_2P-O(OH)_2$ | $CH_3$ |
| 215. | $NHSO_2CH_3$ | H | $CH_2CH_2P-O(OCH_2CH_3)_2$ | $CH_3$ |
| 216. | $NHSO_2CH_3$ | H | $CH_2CH_2P-O(OH)_2$ | $CH_3$ |
| 217. | H | OH | $CH_2CH_2P-O(OCH_2CH_3)_2$ | $CH_3$ |
| 218. | H | OH | $CH_2CH_2P-O(OH)_2$ | $CH_3$ |
| 219. | H | $OCH_3$ | $CH_2CH_2P-O(OCH_2CH_3)_2$ | $CH_3$ |
| 220. | H | $OCH_3$ | $CH_2CH_2P-O(OH)_2$ | $CH_3$ |
| 221. | H | $OCH_2CH=CH_2$ | $CH_2CH_2P-O(OCH_2CH_3)_2$ | $CH_3$ |
| 222. | H | $OCH_2CH=CH_2$ | $CH_2CH_2P-O(OH)_2$ | $CH_3$ |
| 223. | H | $OCH_2C_6H_5$ | $CH_2CH_2P-O(OCH_2CH_3)_2$ | $CH_3$ |
| 224. | H | $OCH_2C_6H_5$ | $CH_2CH_2P-O(OH)_2$ | $CH_3$ |
| 225. | H | $OCH_2CH_2C_6H_5$ | $CH_2CH_2P-O(OCH_2CH_3)_2$ | $CH_3$ |
| 226. | H | $OCH_2CH_2C_6H_5$ | $CH_2CH_2P-O(OH)_2$ | $CH_3$ |
| 227. | H | $OCH_2-CONH_2$ | $CH_2CH_2P-O(OCH_2CH_3)_2$ | $CH_3$ |
| 228. | H | $OCH_2-CONH_2$ | $CH_2CH_2P-O(OH)_2$ | $CH_3$ |
| 229. | H | H | $CH_2-CO_2CH_2CH_3$ | $CH_2CH=CH_2$ |
| 230. | H | H | $CH_2-CO_2H$ | $CH_2CH=CH_2$ |
| 231. | OH | H | $CH_2-CO_2CH_2CH_3$ | $CH_2CH=CH_2$ |
| 232. | OH | H | $CH_2-CO_2H$ | $CH_2CH=CH_2$ |
| 233. | $OCH_3$ | H | $CH_2-CO_2CH_2CH_3$ | $CH_2CH=CH_2$ |
| 234. | $OCH_3$ | H | $CH_2-CO_2H$ | $CH_2CH=CH_2$ |
| 235. | $OCH_2CH=CH_2$ | H | $CH_2-CO_2CH_2CH_3$ | $CH_2CH=CH_2$ |
| 236. | $OCH_2CH=CH_2$ | H | $CH_2-CO_2H$ | $CH_2CH=CH_2$ |
| 237. | $OCH_2C_6H_5$ | H | $CH_2-CO_2CH_2CH_3$ | $CH_2CH=CH_2$ |
| 238. | $OCH_2C_6H_5$ | H | $CH_2-CO_2H$ | $CH_2CH=CH_2$ |
| 239. | $OCH_2CH_2C_6H_5$ | H | $CH_2-CO_2CH_2CH_3$ | $CH_2CH=CH_2$ |
| 240. | $OCH_2CH_2C_6H_5$ | H | $CH_2-CO_2H$ | $CH_2CH=CH_2$ |
| 241. | $OCH_2-CONH_2$ | H | $CH_2-CO_2CH_2CH_3$ | $CH_2CH=CH_2$ |
| 242. | $OCH_2-CONH_2$ | H | $CH_2-CO_2H$ | $CH_2CH=CH_2$ |
| 243. | H | Cl | $CH_2-CO_2CH_2CH_3$ | $CH_2CH=CH_2$ |
| 244. | H | Cl | $CH_2-CO_2H$ | $CH_2CH=CH_2$ |
| 245. | Br | H | $CH_2-CO_2CH_2CH_3$ | $CH_2CH=CH_2$ |
| 246. | Br | H | $CH_2-CO_2H$ | $CH_2CH=CH_2$ |
| 247. | H | $CH_3$ | $CH_2-CO_2CH_2CH_3$ | $CH_2CH=CH_2$ |
| 248. | H | $CH_3$ | $CH_2-CO_2H$ | $CH_2CH=CH_2$ |
| 249. | $NO_2$ | H | $CH_2-CO_2CH_2CH_3$ | $CH_2CH=CH_2$ |
| 250. | $NO_2$ | H | $CH_2-CO_2H$ | $CH_2CH=CH_2$ |
| 251. | $NH_2$ | H | $CH_2-CO_2CH_2CH_3$ | $CH_2CH=CH_2$ |
| 252. | $NH_2$ | H | $CH_2-CO_2H$ | $CH_2CH=CH_2$ |
| 253. | $NHSO_2CH_3$ | H | $CH_2-CO_2CH_2CH_3$ | $CH_2CH=CH_2$ |
| 254. | $NHSO_2CH_3$ | H | $CH_2-CO_2H$ | $CH_2CH=CH_2$ |
| 255. | H | OH | $CH_2-CO_2CH_2CH_3$ | $CH_2CH=CH_2$ |
| 256. | H | OH | $CH_2-CO_2H$ | $CH_2CH=CH_2$ |
| 257. | H | $OCH_3$ | $CH_2-CO_2CH_2CH_3$ | $CH_2CH=CH_2$ |
| 258. | H | $OCH_3$ | $CH_2-CO_2H$ | $CH_2CH=CH_2$ |
| 259. | H | $OCH_2CH=CH_2$ | $CH_2-CO_2CH_2CH_3$ | $CH_2CH=CH_2$ |
| 260. | H | $OCH_2CH=CH_2$ | $CH_2-CO_2H$ | $CH_2CH=CH_2$ |
| 261. | H | $OCH_2C_6H_5$ | $CH_2-CO_2CH_2CH_3$ | $CH_2CH=CH_2$ |
| 262. | H | $OCH_2C_6H_5$ | $CH_2-CO_2H$ | $CH_2CH=CH_2$ |
| 263. | H | $OCH_2CH_2C_6H_5$ | $CH_2-CO_2CH_2CH_3$ | $CH_2CH=CH_2$ |
| 264. | H | $OCH_2CH_2C_6H_5$ | $CH_2-CO_2H$ | $CH_2CH=CH_2$ |
| 265. | H | $OCH_2-CONH_2$ | $CH_2-CO_2CH_2CH_3$ | $CH_2CH=CH_2$ |
| 266. | H | $OCH_2-CONH_2$ | $CH_2-CO_2H$ | $CH_2CH=CH_2$ |
| 267. | H | H | $CH_2CH_2P-O(OCH_2CH_3)_2$ | $CH_2CH=CH_2$ |
| 268. | H | H | $CH_2CH_2P-O(OH)_2$ | $CH_2CH=CH_2$ |

TABLE IV-continued

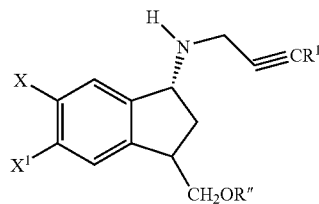

| Ex. # | X | X¹ | R¹ | R" |
|---|---|---|---|---|
| 269. | OH | H | $CH_2CH_2P-O(OCH_2CH_3)_2$ | $CH_2CH=CH_2$ |
| 270. | OH | H | $CH_2CH_2P-O(OH)_2$ | $CH_2CH=CH_2$ |
| 271. | $OCH_3$ | H | $CH_2CH_2P-O(OCH_2CH_3)_2$ | $CH_2CH=CH_2$ |
| 272. | $OCH_3$ | H | $CH_2CH_2P-O(OH)_2$ | $CH_2CH=CH_2$ |
| 273. | $OCH_2CH=CH_2$ | H | $CH_2CH_2P-O(OCH_2CH_3)_2$ | $CH_2CH=CH_2$ |
| 274. | $OCH_2CH=CH_2$ | H | $CH_2CH_2P-O(OH)_2$ | $CH_2CH=CH_2$ |
| 275. | $OCH_2C_6H_5$ | H | $CH_2CH_2P-O(OCH_2CH_3)_2$ | $CH_2CH=CH_2$ |
| 276. | $OCH_2C_6H_5$ | H | $CH_2CH_2P-O(OH)_2$ | $CH_2CH=CH_2$ |
| 277. | $OCH_2CH_2C_6H_5$ | H | $CH_2CH_2P-O(OCH_2CH_3)_2$ | $CH_2CH=CH_2$ |
| 278. | $OCH_2CH_2C_6H_5$ | H | $CH_2CH_2P-O(OH)_2$ | $CH_2CH=CH_2$ |
| 279. | $OCH_2-CONH_2$ | H | $CH_2CH_2P-O(OCH_2CH_3)_2$ | $CH_2CH=CH_2$ |
| 280. | $OCH_2-CONH_2$ | H | $CH_2CH_2P-O(OH)_2$ | $CH_2CH=CH_2$ |
| 281. | H | Cl | $CH_2CH_2P-O(OCH_2CH_3)_2$ | $CH_2CH=CH_2$ |
| 282. | H | Cl | $CH_2CH_2P-O(OH)_2$ | $CH_2CH=CH_2$ |
| 283. | Br | H | $CH_2CH_2P-O(OCH_2CH_3)_2$ | $CH_2CH=CH_2$ |
| 284. | Br | H | $CH_2CH_2P-O(OH)_2$ | $CH_2CH=CH_2$ |
| 285. | H | $CH_3$ | $CH_2CH_2P-O(OCH_2CH_3)_2$ | $CH_2CH=CH_2$ |
| 286. | H | $CH_3$ | $CH_2CH_2P-O(OH)_2$ | $CH_2CH=CH_2$ |
| 287. | $NO_2$ | H | $CH_2CH_2P-O(OCH_2CH_3)_2$ | $CH_2CH=CH_2$ |
| 288. | $NO_2$ | H | $CH_2CH_2P-O(OH)_2$ | $CH_2CH=CH_2$ |
| 289. | $NH_2$ | H | $CH_2CH_2P-O(OCH_2CH_3)_2$ | $CH_2CH=CH_2$ |
| 290. | $NH_2$ | H | $CH_2CH_2P-O(OH)_2$ | $CH_2CH=CH_2$ |
| 291. | $NHSO_2CH_3$ | H | $CH_2CH_2P-O(OCH_2CH_3)_2$ | $CH_2CH=CH_2$ |
| 292. | $NHSO_2CH_3$ | H | $CH_2CH_2P-O(OH)_2$ | $CH_2CH=CH_2$ |
| 293. | H | OH | $CH_2CH_2P-O(OCH_2CH_3)_2$ | $CH_2CH=CH_2$ |
| 294. | H | OH | $CH_2CH_2P-O(OH)_2$ | $CH_2CH=CH_2$ |
| 295. | H | $OCH_3$ | $CH_2CH_2P-O(OCH_2CH_3)_2$ | $CH_2CH=CH_2$ |
| 296. | H | $OCH_3$ | $CH_2CH_2P-O(OH)_2$ | $CH_2CH=CH_2$ |
| 297. | H | $OCH_2CH=CH_2$ | $CH_2CH_2P-O(OCH_2CH_3)_2$ | $CH_2CH=CH_2$ |
| 298. | H | $OCH_2CH=CH_2$ | $CH_2CH_2P-O(OH)_2$ | $CH_2CH=CH_2$ |
| 299. | H | $OCH_2C_6H_5$ | $CH_2CH_2P-O(OCH_2CH_3)_2$ | $CH_2CH=CH_2$ |
| 300. | H | $OCH_2C_6H_5$ | $CH_2CH_2P-O(OH)_2$ | $CH_2CH=CH_2$ |
| 301. | H | $OCH_2CH_2C_6H_5$ | $CH_2CH_2P-O(OCH_2CH_3)_2$ | $CH_2CH=CH_2$ |
| 302. | H | $OCH_2CH_2C_6H_5$ | $CH_2CH_2P-O(OH)_2$ | $CH_2CH=CH_2$ |
| 303. | H | $OCH_2-CONH_2$ | $CH_2CH_2P-O(OCH_2CH_3)_2$ | $CH_2CH=CH_2$ |
| 304. | H | $OCH_2-CONH_2$ | $CH_2CH_2P-O(OH)_2$ | $CH_2CH=CH_2$ |
| 305. | H | H | $CH_2-CO_2CH_2CH_3$ | $CH_2-CONH_2$ |
| 306. | H | H | $CH_2-CO_2H$ | $CH_2-CONH_2$ |
| 307. | OH | H | $CH_2-CO_2CH_2CH_3$ | $CH_2-CONH_2$ |
| 308. | OH | H | $CH_2-CO_2H$ | $CH_2-CONH_2$ |
| 309. | $OCH_3$ | H | $CH_2-CO_2CH_2CH_3$ | $CH_2-CONH_2$ |
| 310. | $OCH_3$ | H | $CH_2-CO_2H$ | $CH_2-CONH_2$ |
| 311. | $OCH_2CH=CH_2$ | H | $CH_2-CO_2CH_2CH_3$ | $CH_2-CONH_2$ |
| 312. | $OCH_2CH=CH_2$ | H | $CH_2-CO_2H$ | $CH_2-CONH_2$ |
| 313. | $OCH_2C_6H_5$ | H | $CH_2-CO_2CH_2CH_3$ | $CH_2-CONH_2$ |
| 314. | $OCH_2C_6H_5$ | H | $CH_2-CO_2H$ | $CH_2-CONH_2$ |
| 315. | $OCH_2CH_2C_6H_5$ | H | $CH_2-CO_2CH_2CH_3$ | $CH_2-CONH_2$ |
| 316. | $OCH_2CH_2C_6H_5$ | H | $CH_2-CO_2H$ | $CH_2-CONH_2$ |
| 317. | $OCH_2-CONH_2$ | H | $CH_2-CO_2CH_2CH_3$ | $CH_2-CONH_2$ |
| 318. | $OCH_2-CONH_2$ | H | $CH_2-CO_2H$ | $CH_2-CONH_2$ |
| 319. | H | Cl | $CH_2-CO_2CH_2CH_3$ | $CH_2-CONH_2$ |
| 320. | H | Cl | $CH_2-CO_2H$ | $CH_2-CONH_2$ |
| 321. | Br | H | $CH_2-CO_2CH_2CH_3$ | $CH_2-CONH_2$ |
| 322. | Br | H | $CH_2-CO_2H$ | $CH_2-CONH_2$ |
| 323. | H | $CH_3$ | $CH_2-CO_2CH_2CH_3$ | $CH_2-CONH_2$ |
| 324. | H | $CH_3$ | $CH_2-CO_2H$ | $CH_2-CONH_2$ |
| 325. | $NO_2$ | H | $CH_2-CO_2CH_2CH_3$ | $CH_2-CONH_2$ |
| 326. | $NO_2$ | H | $CH_2-CO_2H$ | $CH_2-CONH_2$ |
| 327. | $NH_2$ | H | $CH_2-CO_2CH_2CH_3$ | $CH_2-CONH_2$ |
| 328. | $NH_2$ | H | $CH_2-CO_2H$ | $CH_2-CONH_2$ |
| 329. | $NHSO_2CH_3$ | H | $CH_2-CO_2CH_2CH_3$ | $CH_2-CONH_2$ |
| 330. | $NHSO_2CH_3$ | H | $CH_2-CO_2H$ | $CH_2-CONH_2$ |
| 331. | H | OH | $CH_2-CO_2CH_2CH_3$ | $CH_2-CONH_2$ |
| 332. | H | OH | $CH_2-CO_2H$ | $CH_2-CONH_2$ |
| 333. | H | $OCH_3$ | $CH_2-CO_2CH_2CH_3$ | $CH_2-CONH_2$ |
| 334. | H | $OCH_3$ | $CH_2-CO_2H$ | $CH_2-CONH_2$ |
| 335. | H | $OCH_2CH=CH_2$ | $CH_2-CO_2CH_2CH_3$ | $CH_2-CONH_2$ |

TABLE IV-continued

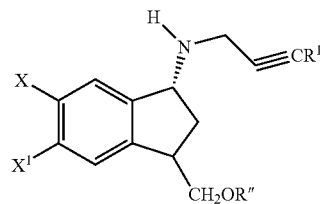

| Ex. # | X | X¹ | R¹ | R" |
|---|---|---|---|---|
| 336. | H | OCH₂CH=CH₂ | CH₂—CO₂H | CH₂—CONH₂ |
| 337. | H | OCH₂C₆H₅ | CH₂—CO₂CH₂CH₃ | CH₂—CONH₂ |
| 338. | H | OCH₂C₆H₅ | CH₂—CO₂H | CH₂—CONH₂ |
| 339. | H | OCH₂CH₂C₆H₅ | CH₂—CO₂CH₂CH₃ | CH₂—CONH₂ |
| 340. | H | OCH₂CH₂C₆H₅ | CH₂—CO₂H | CH₂—CONH₂ |
| 341. | H | OCH₂—CONH₂ | CH₂—CO₂CH₂CH₃ | CH₂—CONH₂ |
| 342. | H | OCH₂—CONH₂ | CH₂—CO₂H | CH₂—CONH₂ |
| 343. | H | H | CH₂CH₂P—O(OCH₂CH₃)₂ | CH₂—CONH₂ |
| 344. | H | H | CH₂CH₂P—O(OH)₂ | CH₂—CONH₂ |
| 345. | OH | H | CH₂CH₂P—O(OCH₂CH₃)₂ | CH₂—CONH₂ |
| 346. | OH | H | CH₂CH₂P—O(OH)₂ | CH₂—CONH₂ |
| 347. | OCH₃ | H | CH₂CH₂P—O(OCH₂CH₃)₂ | CH₂—CONH₂ |
| 348. | OCH₃ | H | CH₂CH₂P—O(OH)₂ | CH₂—CONH₂ |
| 349. | OCH₂CH=CH₂ | H | CH₂CH₂P—O(OCH₂CH₃)₂ | CH₂—CONH₂ |
| 350. | OCH₂CH=CH₂ | H | CH₂CH₂P—O(OH)₂ | CH₂—CONH₂ |
| 351. | OCH₂C₆H₅ | H | CH₂CH₂P—O(OCH₂CH₃)₂ | CH₂—CONH₂ |
| 352. | OCH₂C₆H₅ | H | CH₂CH₂P—O(OH)₂ | CH₂—CONH₂ |
| 353. | OCH₂CH₂C₆H₅ | H | CH₂CH₂P—O(OCH₂CH₃)₂ | CH₂—CONH₂ |
| 354. | OCH₂CH₂C₆H₅ | H | CH₂CH₂P—O(OH)₂ | CH₂—CONH₂ |
| 355. | OCH₂—CONH₂ | H | CH₂CH₂P—O(OCH₂CH₃)₂ | CH₂—CONH₂ |
| 356. | OCH₂—CONH₂ | H | CH₂CH₂P—O(OH)₂ | CH₂—CONH₂ |
| 357. | H | Cl | CH₂CH₂P—O(OCH₂CH₃)₂ | CH₂—CONH₂ |
| 358. | H | Cl | CH₂CH₂P—O(OH)₂ | CH₂—CONH₂ |
| 359. | Br | H | CH₂CH₂P—O(OCH₂CH₃)₂ | CH₂—CONH₂ |
| 360. | Br | H | CH₂CH₂P—O(OH)₂ | CH₂—CONH₂ |
| 361. | H | CH₃ | CH₂CH₂P—O(OCH₂CH₃)₂ | CH₂—CONH₂ |
| 362. | H | CH₃ | CH₂CH₂P—O(OH)₂ | CH₂—CONH₂ |
| 363. | NO₂ | H | CH₂CH₂P—O(OCH₂CH₃)₂ | CH₂—CONH₂ |
| 364. | NO₂ | H | CH₂CH₂P—O(OH)₂ | CH₂—CONH₂ |
| 365. | NH₂ | H | CH₂CH₂P—O(OCH₂CH₃)₂ | CH₂—CONH₂ |
| 366. | NH₂ | H | CH₂CH₂P—O(OH)₂ | CH₂—CONH₂ |
| 367. | NHSO₂CH₃ | H | CH₂CH₂P—O(OCH₂CH₃)₂ | CH₂—CONH₂ |
| 368. | NHSO₂CH₃ | H | CH₂CH₂P—O(OH)₂ | CH₂—CONH₂ |
| 369. | H | OH | CH₂CH₂P—O(OCH₂CH₃)₂ | CH₂—CONH₂ |
| 370. | H | OH | CH₂CH₂P—O(OH)₂ | CH₂—CONH₂ |
| 371. | H | OCH₃ | CH₂CH₂P—O(OCH₂CH₃)₂ | CH₂—CONH₂ |
| 372. | H | OCH₃ | CH₂CH₂P—O(OH)₂ | CH₂—CONH₂ |
| 373. | H | OCH₂CH=CH₂ | CH₂CH₂P—O(OCH₂CH₃)₂ | CH₂—CONH₂ |
| 374. | H | OCH₂CH=CH₂ | CH₂CH₂P—O(OH)₂ | CH₂—CONH₂ |
| 375. | H | OCH₂C₆H₅ | CH₂CH₂P—O(OCH₂CH₃)₂ | CH₂—CONH₂ |
| 376. | H | OCH₂C₆H₅ | CH₂CH₂P—O(OH)₂ | CH₂—CONH₂ |
| 377. | H | OCH₂CH₂C₆H₅ | CH₂CH₂P—O(OCH₂CH₃)₂ | CH₂—CONH₂ |
| 378. | H | OCH₂CH₂C₆H₅ | CH₂CH₂P—O(OH)₂ | CH₂—CONH₂ |
| 379. | H | OCH₂—CONH₂ | CH₂CH₂P—O(OCH₂CH₃)₂ | CH₂—CONH₂ |
| 380. | H | OCH₂—CONH₂ | CH₂CH₂P—O(OH)₂ | CH₂—CONH₂ |
| 381. | H | H | CH₂—CO₂CH₂CH₃ | CH₂C₆H₅ |
| 382. | H | H | CH₂—CO₂H | CH₂C₆H₅ |
| 383. | OH | H | CH₂—CO₂CH₂CH₃ | CH₂C₆H₅ |
| 384. | OH | H | CH₂—CO₂H | CH₂C₆H₅ |
| 385. | OCH₃ | H | CH₂—CO₂CH₂CH₃ | CH₂C₆H₅ |
| 386. | OCH₃ | H | CH₂—CO₂H | CH₂C₆H₅ |
| 387. | OCH₂CH=CH₂ | H | CH₂—CO₂CH₂CH₃ | CH₂C₆H₅ |
| 388. | OCH₂CH=CH₂ | H | CH₂—CO₂H | CH₂C₆H₅ |
| 389. | OCH₂C₆H₅ | H | CH₂—CO₂CH₂CH₃ | CH₂C₆H₅ |
| 390. | OCH₂C₆H₅ | H | CH₂—CO₂H | CH₂C₆H₅ |
| 391. | OCH₂CH₂C₆H₅ | H | CH₂—CO₂CH₂CH₃ | CH₂C₆H₅ |
| 392. | OCH₂CH₂C₆H₅ | H | CH₂—CO₂H | CH₂C₆H₅ |
| 393. | OCH₂—CONH₂ | H | CH₂—CO₂CH₂CH₃ | CH₂C₆H₅ |
| 394. | OCH₂—CONH₂ | H | CH₂—CO₂H | CH₂C₆H₅ |
| 395. | H | Cl | CH₂—CO₂CH₂CH₃ | CH₂C₆H₅ |
| 396. | H | Cl | CH₂—CO₂H | CH₂C₆H₅ |
| 397. | Br | H | CH₂—CO₂CH₂CH₃ | CH₂C₆H₅ |
| 398. | Br | H | CH₂—CO₂H | CH₂C₆H₅ |
| 399. | H | CH₃ | CH₂—CO₂CH₂CH₃ | CH₂C₆H₅ |
| 400. | H | CH₃ | CH₂—CO₂H | CH₂C₆H₅ |
| 401. | NO₂ | H | CH₂—CO₂CH₂CH₃ | CH₂C₆H₅ |
| 402. | NO₂ | H | CH₂—CO₂H | CH₂C₆H₅ |

TABLE IV-continued

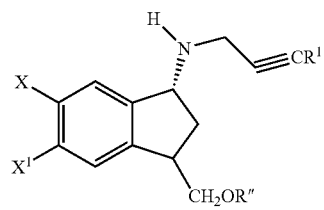

| Ex. # | X | X$^1$ | R$^1$ | R" |
|---|---|---|---|---|
| 403. | NH$_2$ | H | CH$_2$—CO$_2$CH$_2$CH$_3$ | CH$_2$C$_6$H$_5$ |
| 404. | NH$_2$ | H | CH$_2$—CO$_2$H | CH$_2$C$_6$H$_5$ |
| 405. | NHSO$_2$CH$_3$ | H | CH$_2$—CO$_2$CH$_2$CH$_3$ | CH$_2$C$_6$H$_5$ |
| 406. | NHSO$_2$CH$_3$ | H | CH$_2$—CO$_2$H | CH$_2$C$_6$H$_5$ |
| 407. | H | OH | CH$_2$—CO$_2$CH$_2$CH$_3$ | CH$_2$C$_6$H$_5$ |
| 408. | H | OH | CH$_2$—CO$_2$H | CH$_2$C$_6$H$_5$ |
| 409. | H | OCH$_3$ | CH$_2$—CO$_2$CH$_2$CH$_3$ | CH$_2$C$_6$H$_5$ |
| 410. | H | OCH$_3$ | CH$_2$—CO$_2$H | CH$_2$C$_6$H$_5$ |
| 411. | H | OCH$_2$CH=CH$_2$ | CH$_2$—CO$_2$CH$_2$CH$_3$ | CH$_2$C$_6$H$_5$ |
| 412. | H | OCH$_2$CH=CH$_2$ | CH$_2$—CO$_2$H | CH$_2$C$_6$H$_5$ |
| 413. | H | OCH$_2$C$_6$H$_5$ | CH$_2$—CO$_2$CH$_2$CH$_3$ | CH$_2$C$_6$H$_5$ |
| 414. | H | OCH$_2$C$_6$H$_5$ | CH$_2$—CO$_2$H | CH$_2$C$_6$H$_5$ |
| 415. | H | OCH$_2$CH$_2$C$_6$H$_5$ | CH$_2$—CO$_2$CH$_2$CH$_3$ | CH$_2$C$_6$H$_5$ |
| 416. | H | OCH$_2$CH$_2$C$_6$H$_5$ | CH$_2$—CO$_2$H | CH$_2$C$_6$H$_5$ |
| 417. | H | OCH$_2$—CONH$_2$ | CH$_2$—CO$_2$CH$_2$CH$_3$ | CH$_2$C$_6$H$_5$ |
| 418. | H | OCH$_2$—CONH$_2$ | CH$_2$—CO$_2$H | CH$_2$C$_6$H$_5$ |
| 419. | H | H | CH$_2$CH$_2$P—O(OCH$_2$CH$_3$)$_2$ | CH$_2$C$_6$H$_5$ |
| 420. | H | H | CH$_2$CH$_2$P—O(OH)$_2$ | CH$_2$C$_6$H$_5$ |
| 421. | OH | H | CH$_2$CH$_2$P—O(OCH$_2$CH$_3$)$_2$ | CH$_2$C$_6$H$_5$ |
| 422. | OH | H | CH$_2$CH$_2$P—O(OH)$_2$ | CH$_2$C$_6$H$_5$ |
| 423. | OCH$_3$ | H | CH$_2$CH$_2$P—O(OCH$_2$CH$_3$)$_2$ | CH$_2$C$_6$H$_5$ |
| 424. | OCH$_3$ | H | CH$_2$CH$_2$P—O(OH)$_2$ | CH$_2$C$_6$H$_5$ |
| 425. | OCH$_2$CH=CH$_2$ | H | CH$_2$CH$_2$P—O(OCH$_2$CH$_3$)$_2$ | CH$_2$C$_6$H$_5$ |
| 426. | OCH$_2$CH=CH$_2$ | H | CH$_2$CH$_2$P—O(OH)$_2$ | CH$_2$C$_6$H$_5$ |
| 427. | OCH$_2$C$_6$H$_5$ | H | CH$_2$CH$_2$P—O(OCH$_2$CH$_3$)$_2$ | CH$_2$C$_6$H$_5$ |
| 428. | OCH$_2$C$_6$H$_5$ | H | CH$_2$CH$_2$P—O(OH)$_2$ | CH$_2$C$_6$H$_5$ |
| 429. | OCH$_2$CH$_2$C$_6$H$_5$ | H | CH$_2$CH$_2$P—O(OCH$_2$CH$_3$)$_2$ | CH$_2$C$_6$H$_5$ |
| 430. | OCH$_2$CH$_2$C$_6$H$_5$ | H | CH$_2$CH$_2$P—O(OH)$_2$ | CH$_2$C$_6$H$_5$ |
| 431. | OCH$_2$—CONH$_2$ | H | CH$_2$CH$_2$P—O(OCH$_2$CH$_3$)$_2$ | CH$_2$C$_6$H$_5$ |
| 432. | OCH$_2$—CONH$_2$ | H | CH$_2$CH$_2$P—O(OH)$_2$ | CH$_2$C$_6$H$_5$ |
| 433. | H | Cl | CH$_2$CH$_2$P—O(OCH$_2$CH$_3$)$_2$ | CH$_2$C$_6$H$_5$ |
| 434. | H | Cl | CH$_2$CH$_2$P—O(OH)$_2$ | CH$_2$C$_6$H$_5$ |
| 435. | Br | H | CH$_2$CH$_2$P—O(OCH$_2$CH$_3$)$_2$ | CH$_2$C$_6$H$_5$ |
| 436. | Br | H | CH$_2$CH$_2$P—O(OH)$_2$ | CH$_2$C$_6$H$_5$ |
| 437. | H | CH$_3$ | CH$_2$CH$_2$P—O(OCH$_2$CH$_3$)$_2$ | CH$_2$C$_6$H$_5$ |
| 438. | H | CH$_3$ | CH$_2$CH$_2$P—O(OH)$_2$ | CH$_2$C$_6$H$_5$ |
| 439. | NO$_2$ | H | CH$_2$CH$_2$P—O(OCH$_2$CH$_3$)$_2$ | CH$_2$C$_6$H$_5$ |
| 440. | NO$_2$ | H | CH$_2$CH$_2$P—O(OH)$_2$ | CH$_2$C$_6$H$_5$ |
| 441. | NH$_2$ | H | CH$_2$CH$_2$P—O(OCH$_2$CH$_3$)$_2$ | CH$_2$C$_6$H$_5$ |
| 442. | NH$_2$ | H | CH$_2$CH$_2$P—O(OH)$_2$ | CH$_2$C$_6$H$_5$ |
| 443. | NHSO$_2$CH$_3$ | H | CH$_2$CH$_2$P—O(OCH$_2$CH$_3$)$_2$ | CH$_2$C$_6$H$_5$ |
| 444. | NHSO$_2$CH$_3$ | H | CH$_2$CH$_2$P—O(OH)$_2$ | CH$_2$C$_6$H$_5$ |
| 445. | H | OH | CH$_2$CH$_2$P—O(OCH$_2$CH$_3$)$_2$ | CH$_2$C$_6$H$_5$ |
| 446. | H | OH | CH$_2$CH$_2$P—O(OH)$_2$ | CH$_2$C$_6$H$_5$ |
| 447. | H | OCH$_3$ | CH$_2$CH$_2$P—O(OCH$_2$CH$_3$)$_2$ | CH$_2$C$_6$H$_5$ |
| 448. | H | OCH$_3$ | CH$_2$CH$_2$P—O(OH)$_2$ | CH$_2$—CONH$_2$ |
| 449. | H | OCH$_2$CH=CH$_2$ | CH$_2$CH$_2$P—O(OCH$_2$CH$_3$)$_2$ | CH$_2$—CONH$_2$ |
| 450. | H | OCH$_2$CH=CH$_2$ | CH$_2$CH$_2$P—O(OH)$_2$ | CH$_2$—CONH$_2$ |
| 451. | H | OCH$_2$C$_6$H$_5$ | CH$_2$CH$_2$P—O(OCH$_2$CH$_3$)$_2$ | CH$_2$—CONH$_2$ |
| 452. | H | OCH$_2$C$_6$H$_5$ | CH$_2$CH$_2$P—O(OH)$_2$ | CH$_2$—CONH$_2$ |
| 453. | H | OCH$_2$CH$_2$C$_6$H$_5$ | CH$_2$CH$_2$P—O(OCH$_2$CH$_3$)$_2$ | CH$_2$—CONH$_2$ |
| 454. | H | OCH$_2$CH$_2$C$_6$H$_5$ | CH$_2$CH$_2$P—O(OH)$_2$ | CH$_2$—CONH$_2$ |
| 455. | H | OCH$_2$—CONH$_2$ | CH$_2$CH$_2$P—O(OCH$_2$CH$_3$)$_2$ | CH$_2$—CONH$_2$ |
| 456. | H | OCH$_2$—CONH$_2$ | CH$_2$CH$_2$P—O(OH)$_2$ | CH$_2$—CONH$_2$ |

TABLE Va

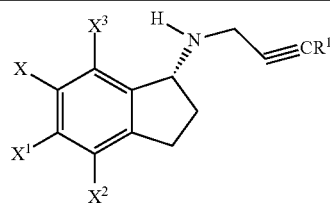

| Ex. # | X | X¹ | X² | X³ | R¹ |
|---|---|---|---|---|---|
| 1. | OCH$_2$CO$_2$—CH$_2$CH$_3$ | H | H | H | H |
| 2. | OCH$_2$CO$_2$—CH$_2$CH$_3$ | H | H | H | CH$_3$ |
| 3. | OCH$_2$CO$_2$H | H | H | H | H |
| 4. | OCH$_2$CO$_2$H | H | H | H | CH$_3$ |
| 5. | OCH$_2$CH$_2$—CO$_2$CH$_2$CH$_3$ | H | H | H | H |
| 6. | OCH$_2$CH$_2$—CO$_2$CH$_2$CH$_3$ | H | H | H | CH$_3$ |
| 7. | OCH$_2$CH$_2$—CO$_2$H | H | H | H | H |
| 8. | OCH$_2$CH$_2$—CO$_2$H | H | H | H | CH$_3$ |
| 9. | OCH$_2$CH=CH—CO$_2$CH$_2$CH$_3$ | H | H | H | H |
| 10. | OCH$_2$CH=CH—CO$_2$CH$_2$CH$_3$ | H | H | H | CH$_3$ |
| 11. | OCH$_2$CH=CH—CO$_2$H | H | H | H | H |
| 12. | OCH$_2$CH=CH—CO$_2$H | H | H | H | CH$_3$ |
| 13. | OCH$_2$CH$_2$—PO(OCH$_2$CH$_3$)$_2$ | H | H | H | H |
| 14. | OCH$_2$CH$_2$—PO(OCH$_2$CH$_3$)$_2$ | H | H | H | CH$_3$ |
| 15. | OCH$_2$CH$_2$—PO(OH)$_2$ | H | H | H | H |
| 16. | OCH$_2$CH$_2$—PO(OH)$_2$ | H | H | H | CH$_3$ |
| 17. | H | OCH$_2$CO$_2$—CH$_2$CH$_3$ | H | H | H |
| 18. | H | OCH$_2$CO$_2$—CH$_2$CH$_3$ | H | H | CH$_3$ |
| 19. | H | OCH$_2$CO$_2$H | H | H | H |
| 20. | H | OCH$_2$CO$_2$H | H | H | CH$_3$ |
| 21. | H | OCH$_2$CH$_2$CO$_2$—CH$_2$CH$_3$ | H | H | H |
| 22. | H | OCH$_2$CH$_2$CO$_2$—CH$_2$CH$_3$ | H | H | CH$_3$ |
| 23. | H | OCH$_2$CH$_2$CO$_2$H | H | H | H |
| 24. | H | OCH$_2$CH$_2$CO$_2$H | H | H | CH$_3$ |
| 25. | H | OCH$_2$CH=CH—CO$_2$CH$_2$CH$_3$ | H | H | H |
| 26. | H | OCH$_2$CH=CH—CO$_2$CH$_2$CH$_3$ | H | H | CH$_3$ |
| 27. | H | OCH$_2$CH=CH—CO$_2$H | H | H | H |
| 28. | H | OCH$_2$CH=CH—CO$_2$H | H | H | CH$_3$ |
| 29. | H | OCH$_2$CH$_2$—PO(OCH$_2$CH$_3$)$_2$ | H | H | H |
| 30. | H | OCH$_2$CH$_2$—PO(OCH$_2$CH$_3$)$_2$ | H | H | CH$_3$ |
| 31. | H | OCH$_2$CH$_2$—PO(OH)$_2$ | H | H | H |
| 32. | H | OCH$_2$CH$_2$—PO(OH)$_2$ | H | H | CH$_3$ |
| 33. | H | H | OCH$_2$CO$_2$—CH$_2$CH$_3$ | H | H |
| 34. | H | H | OCH$_2$CO$_2$—CH$_2$CH$_3$ | H | CH$_3$ |
| 35. | H | H | OCH$_2$CO$_2$H | H | H |
| 36. | H | H | OCH$_2$CO$_2$H | H | CH$_3$ |
| 37. | H | H | OCH$_2$CH$_2$—CO$_2$CH$_2$CH$_3$ | H | H |
| 38. | H | H | OCH$_2$CH$_2$—CO$_2$CH$_2$CH$_3$ | H | CH$_3$ |
| 39. | H | H | OCH$_2$CH$_2$—CO$_2$H | H | H |
| 40. | H | H | OCH$_2$CH$_2$—CO$_2$H | H | CH$_3$ |
| 41. | H | H | OCH$_2$—CH=CH—CO$_2$CH$_2$CH$_3$ | H | H |
| 42. | H | H | OCH$_2$—CH=CH—CO$_2$CH$_2$CH$_3$ | H | CH$_3$ |
| 43. | H | H | OCH$_2$—CH=CHCO$_2$H | H | H |
| 44. | H | H | OCH$_2$—CH=CHCO$_2$H | H | CH$_3$ |
| 45. | H | H | OCH$_2$CH$_2$PO—(OCH$_2$CH$_3$)$_2$ | H | H |
| 46. | H | H | OCH$_2$CH$_2$PO—(OCH$_2$CH$_3$)$_2$ | H | CH$_3$ |
| 47. | H | H | OCH$_2$CH$_2$—PO(OH)$_2$ | H | H |
| 48. | H | H | OCH$_2$CH$_2$—PO(OH)$_2$ | H | CH$_3$ |
| 49. | H | H | H | OCH$_2$CO$_2$—CH$_2$CH$_3$ | H |
| 50. | H | H | H | OCH$_2$CO$_2$—CH$_2$CH$_3$ | CH$_3$ |
| 51. | H | H | H | OCH$_2$CO$_2$H | H |
| 52. | H | H | H | OCH$_2$CO$_2$H | CH$_3$ |
| 53. | H | H | H | OCH$_2$CH$_2$—CO$_2$CH$_2$CH$_3$ | H |
| 54. | H | H | H | OCH$_2$CH$_2$—CO$_2$CH$_2$CH$_3$ | CH$_3$ |
| 55. | H | H | H | OCH$_2$CH$_2$—CO$_2$H | H |
| 56. | H | H | H | OCH$_2$CH$_2$—CO$_2$H | CH$_3$ |
| 57. | H | H | H | OCH$_2$—CH=CH—CO$_2$CH$_2$CH$_3$ | H |
| 58. | H | H | H | OCH$_2$—CH=CH—CO$_2$CH$_2$CH$_3$ | CH$_3$ |
| 59. | H | H | H | OCH$_2$—CH=CHCO$_2$H | H |
| 60. | H | H | H | OCH$_2$—CH=CHCO$_2$H | CH$_3$ |
| 61. | H | H | H | OCH$_2$CH$_2$PO—(OCH$_2$CH$_3$)$_2$ | H |
| 62. | H | H | H | OCH$_2$CH$_2$PO—(OCH$_2$CH$_3$)$_2$ | CH$_3$ |
| 63. | H | H | H | OCH$_2$CH$_2$—PO(OH)$_2$ | H |
| 64. | H | H | H | OCH$_2$CH$_2$—PO(OH)$_2$ | CH$_3$ |

TABLE Vb

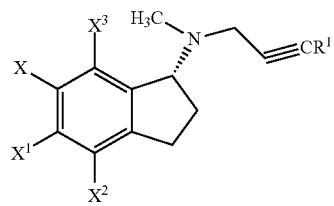

| Ex. # | X | X¹ | X² | X³ | R¹ |
|---|---|---|---|---|---|
| 1. | OCH₂CO₂—CH₂CH₃ | H | H | H | H |
| 2. | OCH₂CO₂—CH₂CH₃ | H | H | H | CH₃ |
| 3. | OCH₂CO₂H | H | H | H | H |
| 4. | OCH₂CO₂H | H | H | H | CH₃ |
| 5. | OCH₂CH₂—CO₂CH₂CH₃ | H | H | H | H |
| 6. | OCH₂CH₂—CO₂CH₂CH₃ | H | H | H | CH₃ |
| 7. | OCH₂CH₂—CO₂H | H | H | H | H |
| 8. | OCH₂CH₂—CO₂H | H | H | H | CH₃ |
| 9. | OCH₂CH=CH—CO₂CH₂CH₃ | H | H | H | H |
| 10. | OCH₂CH=CH—CO₂CH₂CH₃ | H | H | H | CH₃ |
| 11. | OCH₂CH=CH—CO₂H | H | H | H | H |
| 12. | OCH₂CH=CH—CO₂H | H | H | H | CH₃ |
| 13. | OCH₂CH₂—PO(OCH₂CH₃)₂ | H | H | H | H |
| 14. | OCH₂CH₂—PO(OCH₂CH₃)₂ | H | H | H | CH₃ |
| 15. | OCH₂CH₂—PO(OH)₂ | H | H | H | H |
| 16. | OCH₂CH₂—PO(OH)₂ | H | H | H | CH₃ |
| 17. | H | OCH₂CO₂—CH₂CH₃ | H | H | H |
| 18. | H | OCH₂CO₂—CH₂CH₃ | H | H | CH₃ |
| 19. | H | OCH₂CO₂H | H | H | H |
| 20. | H | OCH₂CO₂H | H | H | CH₃ |
| 21. | H | OCH₂CH₂CO₂—CH₂CH₃ | H | H | H |
| 22. | H | OCH₂CH₂CO₂—CH₂CH₃ | H | H | CH₃ |
| 23. | H | OCH₂CH₂CO₂H | H | H | H |
| 24. | H | OCH₂CH₂CO₂H | H | H | CH₃ |
| 25. | H | OCH₂CH=CH—CO₂CH₂CH₃ | H | H | H |
| 26. | H | OCH₂CH=CH—CO₂CH₂CH₃ | H | H | CH₃ |
| 27. | H | OCH₂CH=CH—CO₂H | H | H | H |
| 28. | H | OCH₂CH=CH—CO₂H | H | H | CH₃ |
| 29. | H | OCH₂CH₂—PO(OCH₂CH₃)₂ | H | H | H |
| 30. | H | OCH₂CH₂—PO(OCH₂CH₃)₂ | H | H | CH₃ |
| 31. | H | OCH₂CH₂—PO(OH)₂ | H | H | H |
| 32. | H | OCH₂CH₂—PO(OH)₂ | H | H | CH₃ |
| 33. | H | H | OCH₂CO₂—CH₂CH₃ | H | H |
| 34. | H | H | OCH₂CO₂—CH₂CH₃ | H | CH₃ |
| 35. | H | H | OCH₂CO₂H | H | H |
| 36. | H | H | OCH₂CO₂H | H | CH₃ |
| 37. | H | H | OCH₂CH₂—CO₂CH₂CH₃ | H | H |
| 38. | H | H | OCH₂CH₂—CO₂CH₂CH₃ | H | CH₃ |
| 39. | H | H | OCH₂CH₂—CO₂H | H | H |
| 40. | H | H | OCH₂CH₂—CO₂H | H | CH₃ |
| 41. | H | H | OCH₂—CH=CH—CO₂CH₂CH₃ | H | H |
| 42. | H | H | OCH₂—CH=CH—CO₂CH₂CH₃ | H | CH₃ |
| 43. | H | H | OCH₂—CH=CHCO₂H | H | H |
| 44. | H | H | OCH₂—CH=CHCO₂H | H | CH₃ |
| 45. | H | H | OCH₂CH₂PO—(OCH₂CH₃)₂ | H | H |
| 46. | H | H | OCH₂CH₂PO—(OCH₂CH₃)₂ | H | CH₃ |
| 47. | H | H | OCH₂CH₂—PO(OH)₂ | H | H |
| 48. | H | H | OCH₂CH₂—PO(OH)₂ | H | CH₃ |
| 49. | H | H | H | OCH₂CO₂—CH₂CH₃ | H |
| 50. | H | H | H | OCH₂CO₂—CH₂CH₃ | CH₃ |
| 51. | H | H | H | OCH₂CO₂H | H |
| 52. | H | H | H | OCH₂CO₂H | CH₃ |
| 53. | H | H | H | OCH₂CH₂—CO₂CH₂CH₃ | H |
| 54. | H | H | H | OCH₂CH₂—CO₂CH₂CH₃ | CH₃ |
| 55. | H | H | H | OCH₂CH₂—CO₂H | H |
| 56. | H | H | H | OCH₂CH₂—CO₂H | CH₃ |
| 57. | H | H | H | OCH₂—CH=CH—CO₂CH₂CH₃ | H |
| 58. | H | H | H | OCH₂—CH=CH—CO₂CH₂CH₃ | CH₃ |
| 59. | H | H | H | OCH₂—CH=CHCO₂H | H |
| 60. | H | H | H | OCH₂—CH=CHCO₂H | CH₃ |
| 61. | H | H | H | OCH₂CH₂PO—(OCH₂CH₃)₂ | H |
| 62. | H | H | H | OCH₂CH₂PO—(OCH₂CH₃)₂ | CH₃ |
| 63. | H | H | H | OCH₂CH₂—PO(OH)₂ | H |
| 64. | H | H | H | OCH₂CH₂—PO(OH)₂ | CH₃ |

TABLE VIa

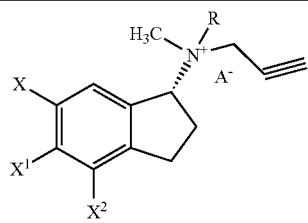

| Ex. # | X | X¹ | X² | R | A⁻ |
|---|---|---|---|---|---|
| 1. | H | H | H | CH₃ | Cl⁻ |
| 2. | H | H | H | CH₂C≡CH | Cl⁻ |
| 3. | H | OCH₃ | H | CH₃ | Cl⁻ |
| 4. | H | OCH₃ | H | CH₂C≡CH | Cl⁻ |
| 5. | H | H | OCH₃ | CH₃ | Cl⁻ |
| 6. | H | H | OCH₃ | CH₂C≡CH | Cl⁻ |
| 7. | OCH₃ | H | H | CH₃ | Cl⁻ |
| 8. | OCH₃ | H | H | CH₂C≡CH | Cl⁻ |
| 9. | H | OCH₂C₆H₅ | H | CH₃ | Cl⁻ |
| 10. | H | OCH₂C₆H₅ | H | CH₂C≡CH | Cl⁻ |
| 11. | H | H | OCH₂C₆H₅ | CH₃ | Cl⁻ |
| 12. | H | H | OCH₂C₆H₅ | CH₂C≡CH | Cl⁻ |
| 13. | OCH₂C₆H₅ | H | H | CH₃ | Cl⁻ |
| 14. | OCH₂C₆H₅ | H | H | CH₂C≡CH | Cl⁻ |
| 15. | H | Cl | H | CH₃ | Cl⁻ |
| 16. | H | Cl | H | CH₂C≡CH | Cl⁻ |
| 17. | H | H | Cl | CH₃ | Cl⁻ |
| 18. | H | H | Cl | CH₂C≡CH | Cl⁻ |
| 19. | Cl | H | H | CH₃ | Cl⁻ |
| 20. | Cl | H | H | CH₂C≡CH | Cl⁻ |
| 21. | H | OH | H | CH₃ | Cl⁻ |
| 22. | H | OH | H | CH₂C≡CH | Cl⁻ |
| 23. | H | H | OH | CH₃ | Cl⁻ |
| 24. | H | H | OH | CH₂C≡CH | Cl⁻ |
| 25. | OH | H | H | CH₃ | Cl⁻ |
| 26. | OH | H | H | CH₂C≡CH | Cl⁻ |
| 27. | H | OCH₂CH=CH₂ | H | CH₃ | Cl⁻ |
| 28. | H | OCH₂CH=CH₂ | H | CH₂C≡CH | Cl⁻ |
| 29. | H | H | OCH₂CH=CH₂ | CH₃ | Cl⁻ |
| 30. | H | H | OCH₂CH=CH₂ | CH₂C≡CH | Cl⁻ |
| 31. | OCH₂CH=CH₂ | H | H | CH₃ | Cl⁻ |
| 32. | OCH₂CH=CH₂ | H | H | CH₂C≡CH | Cl⁻ |
| 33. | H | NO₂ | H | CH₃ | Cl⁻ |
| 34. | H | NO₂ | H | CH₂C≡CH | Cl⁻ |
| 35. | H | H | NO₂ | CH₃ | Cl⁻ |
| 36. | H | H | NO₂ | CH₂C≡CH | Cl⁻ |
| 37. | NO₂ | H | H | CH₃ | Cl⁻ |
| 38. | NO₂ | H | H | CH₂C≡CH | Cl⁻ |
| 39. | H | NHSO₂CH₃ | H | CH₃ | Cl⁻ |
| 40. | H | NHSO₂CH₃ | H | CH₂C≡CH | Cl⁻ |
| 41. | H | H | NHSO₂CH₃ | CH₃ | Cl⁻ |
| 42. | H | H | NHSO₂CH₃ | CH₂C≡CH | Cl⁻ |
| 43. | NHSO₂CH₃ | H | H | CH₃ | Cl⁻ |
| 44. | NHSO₂CH₃ | H | H | CH₂C≡CH | Cl⁻ |
| 45. | H | H | OCH₂CONH₂ | CH₃ | Cl⁻ |
| 46. | H | H | OCH₂CONH₂ | CH₂C≡CH | Cl⁻ |
| 47. | H | OCH₂CONH₂ | H | CH₃ | Cl⁻ |
| 48. | H | OCH₂CONH₂ | H | CH₂C≡CH | Cl⁻ |
| 49. | OCH₂CONH₂ | H | H | CH₃ | Cl⁻ |
| 50. | OCH₂CONH₂ | H | H | CH₂C≡CH | Cl⁻ |
| 51. | H | OCH₂CH₂C₆H₅ | H | CH₃ | Cl⁻ |
| 52. | H | OCH₂CH₂C₆H₅ | H | CH₂C≡CH | Cl⁻ |
| 53. | H | H | OCH₂CH₂C₆H₅ | CH₃ | Cl⁻ |
| 54. | H | H | OCH₂CH₂C₆H₅ | CH₂C≡CH | Cl |
| 55. | OCH₂CH₂C₆H₅ | H | H | CH₃ | Cl |
| 56. | OCH₂CH₂C₆H₅ | H | H | CH₂C≡CH | Cl |
| 57. | H | OCH₂C₆H₄—Cl(3) | H | CH₃ | Cl |
| 58. | H | OCH₂C₆H₄—Cl(3) | H | CH₂C≡CH | Cl |
| 59. | H | H | OCH₂C₆H₄—Cl(3) | CH₃ | Cl |
| 60. | H | H | OCH₂C₆H₄—Cl(3) | CH₂C≡CH | Cl |
| 61. | OCH₂C₆H₄—Cl(3) | H | H | CH₃ | Cl |
| 62. | OCH₂C₆H₄—Cl(3) | H | H | CH₂C≡CH | Cl |
| 63. | H | OCH₂C₆H₄—Cl(4) | H | CH₃ | Cl |
| 64. | H | OCH₂C₆H₄—Cl(4) | H | CH₂C≡CH | Cl |
| 65. | H | H | OCH₂C₆H₄—Cl(4) | CH₃ | Cl |
| 66. | H | H | OCH₂C₆H₄—Cl(4) | CH₂C≡CH | Cl |
| 67. | OCH₂C₆H₄—Cl(4) | H | H | CH₃ | Cl |

TABLE VIa-continued

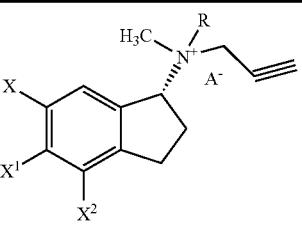

| Ex. # | X | X¹ | X² | R | A⁻ |
|---|---|---|---|---|---|
| 68. | OCH₂C₆H₄—Cl(4) | H | H | CH₂C≡CH | Cl |
| 69. | H | OCH₂C₆H₄CF₃(3) | H | CH₃ | Cl |
| 70. | H | OCH₂C₆H₄CF₃(3) | H | CH₂C≡CH | Cl |
| 71. | OCH₂C₆H₄CF₃(3) | H | H | CH₃ | Cl |
| 72. | OCH₂C₆H₄CF₃(3) | H | H | CH₂C≡CH | Cl |
| 73. | H | H | OCH₂C₆H₄CF₃(3) | CH₃ | Cl |
| 74. | H | H | OCH₂C₆H₄CF₃(3) | CH₂C≡CH | Cl |
| 75. | H | OCH₂C₆H₄CF₃(4) | H | CH₃ | Cl |
| 76. | H | OCH₂C₆H₄CF₃(4) | H | CH₂C≡CH | Cl |
| 77. | OCH₂C₆H₄CF₃(4) | H | H | CH₃ | Cl |
| 78. | OCH₂C₆H₄CF₃(4) | H | H | CH₂C≡CH | Cl |
| 79. | H | H | OCH₂C₆H₄CF₃(4) | CH₃ | Cl |
| 80. | H | H | OCH₂C₆H₄CF₃(4) | CH₂C≡CH | Cl |

TABLE VIb

| Ex. # | X | X¹ | X² | R¹ |
|---|---|---|---|---|
| 1. | H | H | H | H |
| 2. | H | H | H | CH₃ |
| 3. | H | OCH₃ | H | H |
| 4. | H | OCH₃ | H | CH₃ |
| 5. | H | H | OCH₃ | H |
| 6. | H | H | OCH₃ | CH₃ |
| 7. | OCH₃ | H | H | H |
| 8. | OCH₃ | H | H | CH₃ |
| 9. | H | OCH₂C₆H₅ | H | H |
| 10. | H | OCH₂C₆H₅ | H | CH₃ |
| 11. | H | H | OCH₂C₆H₅ | H |
| 12. | H | H | OCH₂C₆H₅ | CH₃ |
| 13. | OCH₂C₆H₅ | H | H | H |
| 14. | OCH₂C₆H₅ | H | H | CH₃ |
| 15. | H | Cl | H | H |
| 16. | H | Cl | H | CH₃ |
| 17. | H | H | Cl | H |
| 18. | H | H | Cl | CH₃ |
| 19. | Cl | H | H | H |
| 20. | Cl | H | H | CH₃ |
| 21. | H | OH | H | H |
| 22. | H | OH | H | CH₃ |
| 23. | H | H | OH | H |
| 24. | H | H | OH | CH₃ |
| 25. | OH | H | H | H |
| 26. | OH | H | H | CH₃ |
| 27. | H | OCH₂CH=CH₂ | H | H |
| 28. | H | OCH₂CH=CH₂ | H | CH₃ |
| 29. | H | H | OCH₂CH=CH₂ | H |
| 30. | H | H | OCH₂CH=CH₂ | CH₃ |
| 31. | OCH₂CH=CH₂ | H | H | H |
| 32. | OCH₂CH=CH₂ | H | H | CH₃ |
| 33. | H | NO₂ | H | H |
| 34. | H | NO₂ | H | CH₃ |
| 35. | H | H | NO₂ | H |

TABLE VIb-continued

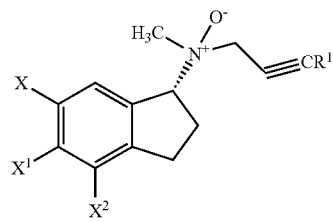

| Ex. # | X | $X^1$ | $X^2$ | $R^1$ |
|---|---|---|---|---|
| 36. | H | H | $NO_2$ | $CH_3$ |
| 37. | $NO_2$ | H | H | H |
| 38. | $NO_2$ | H | H | $CH_3$ |
| 39. | H | $NHSO_2CH_3$ | H | H |
| 40. | H | $NHSO_2CH_3$ | H | $CH_3$ |
| 41. | H | H | $NHSO_2CH_3$ | H |
| 42. | H | H | $NHSO_2CH_3$ | $CH_3$ |
| 43. | $NHSO_2CH_3$ | H | H | H |
| 44. | $NHSO_2CH_3$ | H | H | $CH_3$ |
| 45. | H | H | $OCH_2CONH_2$ | H |
| 46. | H | H | $OCH_2CONH_2$ | $CH_3$ |
| 47. | H | $OCH_2CONH_2$ | H | H |
| 48. | H | $OCH_2CONH_2$ | H | $CH_3$ |
| 49. | $OCH_2CONH_2$ | H | H | H |
| 50. | $OCH_2CONH_2$ | H | H | $CH_3$ |
| 51. | H | $OCH_2CH_2C_6H_5$ | H | H |
| 52. | H | $OCH_2CH_2C_6H_5$ | H | $CH_3$ |
| 53. | H | H | $OCH_2CH_2C_6H_5$ | H |
| 54. | H | H | $OCH_2CH_2C_6H_5$ | $CH_3$ |
| 55. | $OCH_2CH_2C_6H_5$ | H | H | H |
| 56. | $OCH_2CH_2C_6H_5$ | H | H | $CH_3$ |
| 57. | H | $OCH_2C_6H_4—Cl(3)$ | H | H |
| 58. | H | $OCH_2C_6H_4—Cl(3)$ | H | $CH_3$ |
| 59. | H | H | $OCH_2C_6H_4—Cl(3)$ | H |
| 60. | H | H | $OCH_2C_6H_4—Cl(3)$ | $CH_3$ |
| 61. | $OCH_2C_6H_4—Cl(3)$ | H | H | H |
| 62. | $OCH_2C_6H_4—Cl(3)$ | H | H | $CH_3$ |
| 63. | H | $OCH_2C_6H_4—Cl(4)$ | H | H |
| 64. | H | $OCH_2C_6H_4—Cl(4)$ | H | $CH_3$ |
| 65. | H | H | $OCH_2C_6H_4—Cl(4)$ | $CH_3$ |
| 66. | H | H | $OCH_2C_6H_4—Cl(4)$ | H |
| 67. | $OCH_2C_6H_4—Cl(4)$ | H | H | $CH_3$ |
| 68. | $OCH_2C_6H_4—Cl(4)$ | H | H | H |
| 69. | H | $OCH_2C_6H_4CF_3(3)$ | H | H |
| 70. | H | $OCH_2C_6H_4CF_3(3)$ | H | $CH_3$ |
| 71. | $OCH_2C_6H_4CF_3(3)$ | H | H | H |
| 72. | $OCH_2C_6H_4CF_3(3)$ | H | H | $CH_3$ |
| 73. | H | H | $OCH_2C_6H_4CF_3(3)$ | H |
| 74. | H | H | $OCH_2C_6H_4CF_3(3)$ | $CH_3$ |
| 75. | H | $OCH_2C_6H_4CF_3(4)$ | H | H |
| 76. | H | $OCH_2C_6H_4CF_3(4)$ | H | $CH_3$ |
| 77. | $OCH_2C_6H_4CF_3(4)$ | H | H | H |
| 78. | $OCH_2C_6H_4CF_3(4)$ | H | H | $CH_3$ |
| 79. | H | H | $OCH_2C_6H_4CF_3(4)$ | H |
| 80. | H | H | $OCH_2C_6H_4CF_3(4)$ | $CH_3$ |

TABLE VIIa

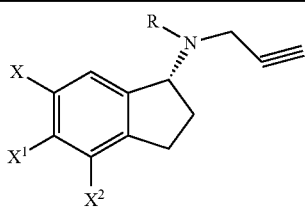

| Ex. # | X | $X^1$ | $X^2$ | R |
|---|---|---|---|---|
| 1. | $OCH_2CH=CH_2$ | H | H | H |
| 2. | $OCH_2CH=CH_2$ | H | H | $CH_3$ |
| 3. | $CF_3$ | H | H | H |
| 4. | $CF_3$ | H | H | $CH_3$ |

TABLE VIIa-continued

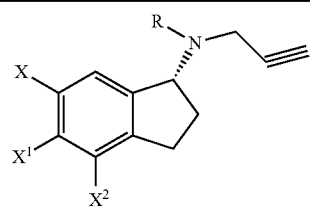

| Ex. # | X | $X^1$ | $X^2$ | R |
|---|---|---|---|---|
| 5. | $NO_2$ | H | H | H |
| 6. | $NO_2$ | H | H | $CH_3$ |
| 7. | $CH_3$ | H | H | H |
| 8. | $CH_3$ | H | H | $CH_3$ |

TABLE VIIa-continued

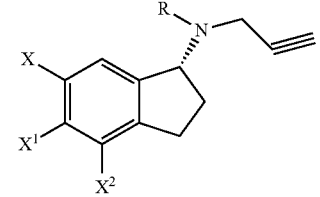

| Ex. # | X | X¹ | X² | R |
|---|---|---|---|---|
| 9. | NHSO$_2$CH$_3$ | H | H | H |
| 10. | NHSO$_2$CH$_3$ | H | H | CH$_3$ |
| 11. | OCH$_2$C$_6$H$_5$ | H | H | H |
| 12. | OCH$_2$C$_6$H$_5$ | H | H | CH$_3$ |
| 13. | OCH$_2$C$_6$H$_4$—Cl(3) | H | H | H |
| 14. | OCH$_2$C$_6$H$_4$—Cl(3) | H | H | CH$_3$ |
| 15. | OCH$_2$C$_6$H$_4$—Cl(4) | H | H | H |
| 16. | OCH$_2$C$_6$H$_4$—Cl(4) | H | H | CH$_3$ |
| 17. | OCH$_2$C$_6$H$_4$—F(3) | H | H | H |
| 18. | OCH$_2$C$_6$H$_4$—F(3) | H | H | CH$_3$ |
| 19. | OCH$_2$C$_6$H$_4$—F(4) | H | H | H |
| 20. | OCH$_2$C$_6$H$_4$—F(4) | H | H | CH$_3$ |
| 21. | OCH$_2$C$_6$H$_4$—CF$_3$(3) | H | H | H |
| 22. | OCH$_2$C$_6$H$_4$—CF$_3$(3) | H | H | CH$_3$ |
| 23. | OCH$_2$C$_6$H$_4$—CF$_3$(4) | H | H | H |
| 24. | OCH$_2$C$_6$H$_4$—CF$_3$(4) | H | H | CH$_3$ |
| 25. | OCH$_2$C$_6$H$_4$—NO$_2$(3) | H | H | H |
| 26. | OCH$_2$C$_6$H$_4$—NO$_2$(3) | H | H | CH$_3$ |
| 27. | OCH$_2$C$_6$H$_4$—NO$_2$(4) | H | H | H |
| 28. | OCH$_2$C$_6$H$_4$—NO$_2$(4) | H | H | CH$_3$ |
| 29. | OCH$_2$C$_6$H$_4$—NHSO$_2$CH$_3$(3) | H | H | H |
| 30. | OCH$_2$C$_6$H$_4$—NHSO$_2$CH$_3$(3) | H | H | CH$_3$ |
| 31. | OCH$_2$C$_6$H$_4$—NHSO$_2$CH$_3$(4) | H | H | H |
| 32. | OCH$_2$C$_6$H$_4$—NHSO$_2$CH$_3$(4) | H | H | CH$_3$ |
| 33. | OCH$_2$C$_6$H$_4$—CN(3) | H | H | H |
| 34. | OCH$_2$C$_6$H$_4$—CN(3) | H | H | CH$_3$ |
| 35. | OCH$_2$C$_6$H$_4$—CN(4) | H | H | H |
| 36. | OCH$_2$C$_6$H$_4$—CN(4) | H | H | CH$_3$ |
| 37. | OCH$_2$C$_6$H$_4$—CONH$_2$(3) | H | H | H |
| 38. | OCH$_2$C$_6$H$_4$—CONH$_2$(3) | H | H | CH$_3$ |
| 39. | OCH$_2$C$_6$H$_4$—CONH$_2$(4) | H | H | H |
| 40. | OCH$_2$C$_6$H$_4$—CONH$_2$(4) | H | H | CH$_3$ |
| 41. | OCH$_2$C$_6$H$_4$—CH$_2$CN(3) | H | H | H |
| 42. | OCH$_2$C$_6$H$_4$—CH$_2$CN(3) | H | H | CH$_3$ |
| 43. | OCH$_2$C$_6$H$_4$—CH$_2$CN(4) | H | H | H |
| 44. | OCH$_2$C$_6$H$_4$—CH$_2$CN(4) | H | H | CH$_3$ |
| 45. | OCH$_2$C$_6$H$_4$—CH$_2$CONH$_2$(3) | H | H | H |
| 46. | OCH$_2$C$_6$H$_4$—CH$_2$CONH$_2$(3) | H | H | CH$_3$ |
| 47. | OCH$_2$C$_6$H$_4$—CH$_2$CONH$_2$(4) | H | H | H |
| 48. | OCH$_2$C$_6$H$_4$—CH$_2$CONH$_2$(4) | H | H | CH$_3$ |
| 49. | OCH$_2$C$_6$H$_4$—OCH$_2$CN(3) | H | H | H |
| 50. | OCH$_2$C$_6$H$_4$—OCH$_2$CN(3) | H | H | CH$_3$ |
| 51. | OCH$_2$C$_6$H$_4$—OCH$_2$CN(4) | H | H | H |
| 52. | OCH$_2$C$_6$H$_4$—OCH$_2$CN(4) | H | H | CH$_3$ |
| 53. | OCH$_2$C$_6$H$_4$—OCH$_2$CONH$_2$(3) | H | H | H |
| 54. | OCH$_2$C$_6$H$_4$—OCH$_2$CONH$_2$(3) | H | H | CH$_3$ |
| 55. | OCH$_2$C$_6$H$_4$—OCH$_2$CONH$_2$(4) | H | H | H |
| 56. | OCH$_2$C$_6$H$_4$—OCH$_2$CONH$_2$(4) | H | H | CH$_3$ |
| 57. | OCH$_2$C$_6$H$_3$—(CN)$_2$(3,5) | H | H | H |
| 58. | OCH$_2$C$_6$H$_3$—(CN)$_2$(3,5) | H | H | CH$_3$ |
| 59. | OCH$_2$C$_6$H$_3$—(CN)$_2$(3,5) | H | H | H |
| 60. | OCH$_2$C$_6$H$_3$—(CN)$_2$(3,5) | H | H | CH$_3$ |
| 61. | OCH$_2$C$_6$H$_3$—(CONH$_2$)$_2$(3,5) | H | H | H |
| 62. | OCH$_2$C$_6$H$_3$—(CONH$_2$)$_2$(3,5) | H | H | CH$_3$ |
| 63. | OCH$_2$C$_6$H$_3$—(CONH$_2$)$_2$(3,5) | H | H | H |
| 64. | OCH$_2$C$_6$H$_3$—(CONH$_2$)$_2$(3,5) | H | H | CH$_3$ |
| 65. | OCH$_2$CH$_2$C$_6$H$_5$ | H | H | H |
| 66. | OCH$_2$CH$_2$C$_6$H$_5$ | H | H | CH$_3$ |
| 67. | OCH$_2$C$_6$H$_4$C$_6$H$_4$CN(2) | H | H | H |
| 68. | OCH$_2$C$_6$H$_4$C$_6$H$_4$CN(2) | H | H | CH$_3$ |
| 69. | OCH$_2$C$_6$H$_4$C$_6$H$_4$CONH$_2$(2) | H | H | H |
| 70. | OCH$_2$C$_6$H$_4$C$_6$H$_4$CONH$_2$(2) | H | H | CH$_3$ |

TABLE VIIb

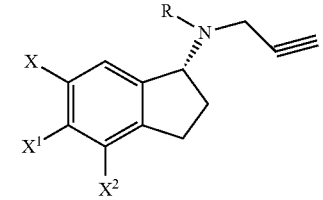

| Ex. # | X¹ | X | X² | R |
|---|---|---|---|---|
| 1. | OCH$_2$CH=CH$_2$ | H | H | H |
| 2. | OCH$_2$CH=CH$_2$ | H | H | CH$_3$ |
| 3. | CF$_3$ | H | H | H |
| 4. | CF$_3$ | H | H | CH$_3$ |
| 5. | NO$_2$ | H | H | H |
| 6. | NO$_2$ | H | H | CH$_3$ |
| 7. | CH$_3$ | H | H | H |
| 8. | CH$_3$ | H | H | CH$_3$ |
| 9. | NHSO$_2$CH$_3$ | H | H | H |
| 10. | NHSO$_2$CH$_3$ | H | H | CH$_3$ |
| 11. | OCH$_2$C$_6$H$_5$ | H | H | H |
| 12. | OCH$_2$C$_6$H$_5$ | H | H | CH$_3$ |
| 13. | OCH$_2$C$_6$H$_4$—Cl(3) | H | H | H |
| 14. | OCH$_2$C$_6$H$_4$—Cl(3) | H | H | CH$_3$ |
| 15. | OCH$_2$C$_6$H$_4$—Cl(4) | H | H | H |
| 16. | OCH$_2$C$_6$H$_4$—Cl(4) | H | H | CH$_3$ |
| 17. | OCH$_2$C$_6$H$_4$—F(3) | H | H | H |
| 18. | OCH$_2$C$_6$H$_4$—F(3) | H | H | CH$_3$ |
| 19. | OCH$_2$C$_6$H$_4$—F(4) | H | H | H |
| 20. | OCH$_2$C$_6$H$_4$—F(4) | H | H | CH$_3$ |
| 21. | OCH$_2$C$_6$H$_4$—CF$_3$(3) | H | H | H |
| 22. | OCH$_2$C$_6$H$_4$—CF$_3$(3) | H | H | CH$_3$ |
| 23. | OCH$_2$C$_6$H$_4$—CF$_3$(4) | H | H | H |
| 24. | OCH$_2$C$_6$H$_4$—CF$_3$(4) | H | H | CH$_3$ |
| 25. | OCH$_2$C$_6$H$_4$—NO$_2$(3) | H | H | H |
| 26. | OCH$_2$C$_6$H$_4$—NO$_2$(3) | H | H | CH$_3$ |
| 27. | OCH$_2$C$_6$H$_4$—NO$_2$(4) | H | H | H |
| 28. | OCH$_2$C$_6$H$_4$—NO$_2$(4) | H | H | CH$_3$ |
| 29. | OCH$_2$C$_6$H$_4$—NHSO$_2$CH$_3$(3) | H | H | H |
| 30. | OCH$_2$C$_6$H$_4$—NHSO$_2$CH$_3$(3) | H | H | CH$_3$ |
| 31. | OCH$_2$C$_6$H$_4$—NHSO$_2$CH$_3$(4) | H | H | H |
| 32. | OCH$_2$C$_6$H$_4$—NHSO$_2$CH$_3$(4) | H | H | CH$_3$ |
| 33. | OCH$_2$C$_6$H$_4$—CN(3) | H | H | H |
| 34. | OCH$_2$C$_6$H$_4$—CN(3) | H | H | CH$_3$ |
| 35. | OCH$_2$C$_6$H$_4$—CN(4) | H | H | H |
| 36. | OCH$_2$C$_6$H$_4$—CN(4) | H | H | CH$_3$ |
| 37. | OCH$_2$C$_6$H$_4$—CONH$_2$(3) | H | H | H |
| 38. | OCH$_2$C$_6$H$_4$—CONH$_2$(3) | H | H | CH$_3$ |
| 39. | OCH$_2$C$_6$H$_4$—CONH$_2$(4) | H | H | H |
| 40. | OCH$_2$C$_6$H$_4$—CONH$_2$(4) | H | H | CH$_3$ |
| 41. | OCH$_2$C$_6$H$_4$—CH$_2$CN(3) | H | H | H |
| 42. | OCH$_2$C$_6$H$_4$—CH$_2$CN(3) | H | H | CH$_3$ |
| 43. | OCH$_2$C$_6$H$_4$—CH$_2$CN(4) | H | H | H |
| 44. | OCH$_2$C$_6$H$_4$—CH$_2$CN(4) | H | H | CH$_3$ |
| 45. | OCH$_2$C$_6$H$_4$—CH$_2$CONH$_2$(3) | H | H | H |
| 46. | OCH$_2$C$_6$H$_4$—CH$_2$CONH$_2$(3) | H | H | CH$_3$ |
| 47. | OCH$_2$C$_6$H$_4$—CH$_2$CONH$_2$(4) | H | H | H |
| 48. | OCH$_2$C$_6$H$_4$—CH$_2$CONH$_2$(4) | H | H | CH$_3$ |
| 49. | OCH$_2$C$_6$H$_4$—OCH$_2$CN(3) | H | H | H |
| 50. | OCH$_2$C$_6$H$_4$—OCH$_2$CN(3) | H | H | CH$_3$ |
| 51. | OCH$_2$C$_6$H$_4$—OCH$_2$CN(4) | H | H | H |
| 52. | OCH$_2$C$_6$H$_4$—OCH$_2$CN(4) | H | H | CH$_3$ |
| 53. | OCH$_2$C$_6$H$_4$—OCH$_2$CONH$_2$(3) | H | H | H |
| 54. | OCH$_2$C$_6$H$_4$—OCH$_2$CONH$_2$(3) | H | H | CH$_3$ |
| 55. | OCH$_2$C$_6$H$_4$—OCH$_2$CONH$_2$(4) | H | H | H |
| 56. | OCH$_2$C$_6$H$_4$—OCH$_2$CONH$_2$(4) | H | H | CH$_3$ |
| 57. | OCH$_2$C$_6$H$_3$—(CN)$_2$(3,5) | H | H | H |
| 58. | OCH$_2$C$_6$H$_3$—(CN)$_2$(3,5) | H | H | CH$_3$ |
| 59. | OCH$_2$C$_6$H$_3$—(CN)$_2$(3,5) | H | H | H |
| 60. | OCH$_2$C$_6$H$_3$—(CN)$_2$(3,5) | H | H | CH$_3$ |
| 61. | OCH$_2$C$_6$H$_3$—(CONH$_2$)$_2$(3,5) | H | H | H |
| 62. | OCH$_2$C$_6$H$_3$—(CONH$_2$)$_2$(3,5) | H | H | CH$_3$ |
| 63. | OCH$_2$C$_6$H$_3$—(CONH$_2$)$_2$(3,5) | H | H | H |
| 64. | OCH$_2$C$_6$H$_3$—(CONH$_2$)$_2$(3,5) | H | H | CH$_3$ |
| 65. | OCH$_2$CH$_2$C$_6$H$_5$ | H | H | H |
| 66. | OCH$_2$CH$_2$C$_6$H$_5$ | H | H | CH$_3$ |
| 67. | OCH$_2$C$_6$H$_4$C$_6$H$_4$CN(2) | H | H | H |

TABLE VIIb-continued

| Ex. # | X¹ | X | X² | R |
|---|---|---|---|---|
| 68. | OCH₂C₆H₄C₆H₄CN(2) | H | H | CH₃ |
| 69. | OCH₂C₆H₄C₆H₄CONH₂(2) | H | H | H |
| 70. | OCH₂C₆H₄C₆H₄CONH₂(2) | H | H | CH₃ |

TABLE VIIc

| Ex. # | X² | X | X¹ | R |
|---|---|---|---|---|
| 1. | OCH₂CH=CH₂ | H | H | H |
| 2. | OCH₂CH=CH₂ | H | H | CH₃ |
| 3. | CF₃ | H | H | H |
| 4. | CF₃ | H | H | CH₃ |
| 5. | NO₂ | H | H | H |
| 6. | NO₂ | H | H | CH₃ |
| 7. | CH₃ | H | H | H |
| 8. | CH₃ | H | H | CH₃ |
| 9. | NHSO₂CH₃ | H | H | H |
| 10. | NHSO₂CH₃ | H | H | CH₃ |
| 11. | OCH₂C₆H₅ | H | H | H |
| 12. | OCH₂C₆H₅ | H | H | CH₃ |
| 13. | OCH₂C₆H₄—Cl(3) | H | H | H |
| 14. | OCH₂C₆H₄—Cl(3) | H | H | CH₃ |
| 15. | OCH₂C₆H₄—Cl(4) | H | H | H |
| 16. | OCH₂C₆H₄—Cl(4) | H | H | CH₃ |
| 17. | OCH₂C₆H₄—F(3) | H | H | H |
| 18. | OCH₂C₆H₄—F(3) | H | H | CH₃ |
| 19. | OCH₂C₆H₄—F(4) | H | H | H |
| 20. | OCH₂C₆H₄—F(4) | H | H | CH₃ |
| 21. | OCH₂C₆H₄—CF₃(3) | H | H | H |
| 22. | OCH₂C₆H₄—CF₃(3) | H | H | CH₃ |
| 23. | OCH₂C₆H₄—CF₃(4) | H | H | H |
| 24. | OCH₂C₆H₄—CF₃(4) | H | H | CH₃ |
| 25. | OCH₂C₆H₄—NO₂(3) | H | H | H |
| 26. | OCH₂C₆H₄—NO₂(3) | H | H | CH₃ |
| 27. | OCH₂C₆H₄—NO₂(4) | H | H | H |
| 28. | OCH₂C₆H₄—NO₂(4) | H | H | CH₃ |
| 29. | OCH₂C₆H₄—NHSO₂CH₃(3) | H | H | H |
| 30. | OCH₂C₆H₄—NHSO₂CH₃(3) | H | H | CH₃ |
| 31. | OCH₂C₆H₄—NHSO₂CH₃(4) | H | H | H |
| 32. | OCH₂C₆H₄—NHSO₂CH₃(4) | H | H | CH₃ |
| 33. | OCH₂C₆H₄—CN(3) | H | H | H |
| 34. | OCH₂C₆H₄—CN(3) | H | H | CH₃ |
| 35. | OCH₂C₆H₄—CN(4) | H | H | H |
| 36. | OCH₂C₆H₄—CN(4) | H | H | CH₃ |
| 37. | OCH₂C₆H₄—CONH₂(3) | H | H | H |
| 38. | OCH₂C₆H₄—CONH₂(3) | H | H | CH₃ |
| 39. | OCH₂C₆H₄—CONH₂(4) | H | H | H |
| 40. | OCH₂C₆H₄—CONH₂(4) | H | H | CH₃ |
| 41. | OCH₂C₆H₄—CH₂CN(3) | H | H | H |
| 42. | OCH₂C₆H₄—CH₂CN(3) | H | H | CH₃ |
| 43. | OCH₂C₆H₄—CH₂CN(4) | H | H | H |
| 44. | OCH₂C₆H₄—CH₂CN(4) | H | H | CH₃ |
| 45. | OCH₂C₆H₄—CH₂CONH₂(3) | H | H | H |
| 46. | OCH₂C₆H₄—CH₂CONH₂(3) | H | H | CH₃ |
| 47. | OCH₂C₆H₄—CH₂CONH₂(4) | H | H | H |

TABLE VIIc-continued

| Ex. # | X² | X | X¹ | R |
|---|---|---|---|---|
| 48. | OCH₂C₆H₄—CH₂CONH₂(4) | H | H | CH₃ |
| 49. | OCH₂C₆H₄—OCH₂CN(3) | H | H | H |
| 50. | OCH₂C₆H₄—OCH₂CN(3) | H | H | CH₃ |
| 51. | OCH₂C₆H₄—OCH₂CN(4) | H | H | H |
| 52. | OCH₂C₆H₄—OCH₂CN(4) | H | H | CH₃ |
| 53. | OCH₂C₆H₄—OCH₂CONH₂(3) | H | H | H |
| 54. | OCH₂C₆H₄—OCH₂CONH₂(3) | H | H | CH₃ |
| 55. | OCH₂C₆H₄—OCH₂CONH₂(4) | H | H | H |
| 56. | OCH₂C₆H₄—OCH₂CONH₂(4) | H | H | CH₃ |
| 57. | OCH₂C₆H₃—(CN)₂(3,5) | H | H | H |
| 58. | OCH₂C₆H₃—(CN)₂(3,5) | H | H | CH₃ |
| 59. | OCH₂C₆H₃—(CN)₂(3,5) | H | H | H |
| 60. | OCH₂C₆H₃—(CN)₂(3,5) | H | H | CH₃ |
| 61. | OCH₂C₆H₃—(CONH₂)₂(3,5) | H | H | H |
| 62. | OCH₂C₆H₃—(CONH₂)₂(3,5) | H | H | CH₃ |
| 63. | OCH₂C₆H₃—(CONH₂)₂(3,5) | H | H | H |
| 64. | OCH₂C₆H₃—(CONH₂)₂(3,5) | H | H | CH₃ |
| 65. | OCH₂CH₂C₆H₅ | H | H | H |
| 66. | OCH₂CH₂C₆H₅ | H | H | CH₃ |
| 67. | OCH₂C₆H₄C₆H₄CN(2) | H | H | H |
| 68. | OCH₂C₆H₄C₆H₄CN(2) | H | H | CH₃ |
| 69. | OCH₂C₆H₄C₆H₄CONH₂(2) | H | H | H |
| 70. | OCH₂C₆H₄C₆H₄CONH₂(2) | H | H | CH₃ |

Numerous modifications and variations of the present invention are possible in light of the above teachings. It is therefore to be understood that within the scope of the appended claims, the invention may be practiced otherwise that as specifically described herein.

What is claimed is:

1. A method of treating a disease, comprising: administering to a mammal in need thereof a therapeutically effective amount of a compound of formula I or II, or a stereoisomer or pharmaceutically acceptable salt thereof, wherein the disease is selected from obesity, Type 2 diabetes, hypertension, dyslipidemia, high blood pressure, insulin resistance, and a combination thereof:

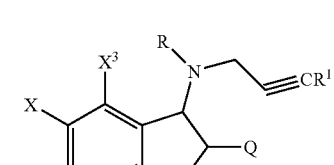

I

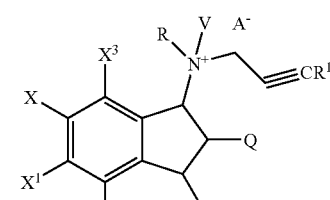

II wherein:
R, at each occurrence, is independently selected from H, $C_{1-6}$ alkyl, $C_{2-6}$ alkenyl, and $C_{2-6}$ alkynyl;
$R^1$ is selected from H, $C_{1-6}$ alkyl, $C_{2-6}$ alkenyl, $C_{2-6}$ alkynyl, $(CH_2)_mCO_2R$, $C_{2-6}$ alkenyl-$CO_2R$, $CH_2CH(NHAc)CO_2R$, $CH_2CH(NHR)CO_2R$, and, $(CH_2)_nPO(OR)_2$;
$A^-$ is a counter ion;
V is selected from $O^-$, $C_{1-4}$ alkyl, $C_{2-4}$ alkenyl, and $C_{2-4}$ alkynyl;
X, $X^1$, $X^2$, and $X^3$ are independently selected from H, OR, $C_{1-6}$ alkyl, $C_{2-6}$ alkenyl, $C_{2-6}$ alkynyl, halogen, $CF_3$, —CN, $(CH_2)_nCO_2R$, $(CH_2)_nCONR_2$, $(CH_2)_nCN$, $O(CH_2)_nCN$, $O(CH_2)_nCO_2R$, $O(CH_2)_nCON(R)_2$, $O$—$C_{2-6}$ alkenyl-$CO_2R$, $O(CH_2)_nPO(OR)_2$, NR—$C_{2-6}$ alkenyl, $NRSO_2CH_3$, $NR(CH_2)_nCO_2R$, $NR(CH_2)_nCON(R)_2$, NR—$C_{2-4}$ alkenyl-$CO_2R$, $NR(CH_2)_nPO(OR)_2$, $NR(CH_2)_nSO_2OR$, $SO_2NRCH_3$, $OCH_2CHMCONRCH_2CO_2R$, $CH_2$-aryl, $O(CH_2)_nPO(OR)_2$, $O(CH_2)_nSO_2OR$, $OCH_2(CH_2)_nN^+(CH_3)_3A^-$, $O(CH_2)_n$-biphenyl, $O(CH_2)_n$-biphenyl-$(CH_2)_mCO_2R$, $O(CH_2)_n$-biphenyl-$(CH_2)_mCN$, $O(CH_2)_n$-biphenyl-$(CH_2)_mCON(R)_2$, $NR(CH_2)_n$-biphenyl, $NR(CH_2)_n$-biphenyl-$(CH_2)_mCO_2R$, $NR(CH_2)_n$-biphenyl-$(CH_2)_mCN$, $NR(CH_2)_n$-biphenyl-$(CH_2)_mCON(R)_2$, $O(CH_2)_n$-aryl, $NR(CH_2)_n$-aryl, $O(CH_2)_n$-aryl$(CH_2)_mCO_2R$, $O(CH_2)_n$-aryl-$C_{2-6}$ alkenyl-$CO_2R$, $O(CH_2)_n$-aryl$(CH_2)_mCN$, $O(CH_2)_n$-aryl$(CH_2)_mCON(R)_2$, $O(CH_2)_n$-aryl$(CH_2)_m$-$PO(OR)_2$, $O(CH_2)_n$-aryl-$O(CH_2)_nCO_2R$, $O(CH_2)_n$-aryl-O—$C_{2-6}$ alkenyl-$CO_2R$, $O(CH_2)_n$-arylO$(CH_2)_nCN$, $O(CH_2)_n$-arylO$(CH_2)_nCON(R)_2$, $O(CH_2)_n$-arylO$(CH_2)_n$-$PO(OR)_2$, $O(CH_2)_n$-aryl-$NR(CH_2)_nCO_2R$, $O(CH_2)_n$-aryl-$NRC_{2-6}$ alkenyl-$CO_2R$, $O(CH_2)_n$-aryl-$NR(CH_2)_nCN$, $O(CH_2)_n$-aryl-$NR(CH_2)_nCON(R)_2$, $O(CH_2)_n$-aryl-$NR(CH_2)_n$-$PO(OR)_2$, $NR(CH_2)_n$-aryl$(CH_2)_mCO_2R$, $NR(CH_2)_n$-aryl-$C_{2-6}$ alkenyl-$CO_2R$, $NR(CH_2)_n$-aryl$(CH_2)_mCN$, $NR(CH_2)_n$-aryl$(CH_2)_mCON(R)_2$, $NR(CH_2)_n$-aryl$(CH_2)_m$-$PO(OR)_2$, $NR(CH_2)_n$-aryl-$NR(CH_2)_nCO_2R$, $NR(CH_2)_n$-aryl-NR—$C_{2-6}$ alkenyl-$CO_2R$, $NR(CH_2)_n$-aryl-$NR(CH_2)_nCN$, $NR(CH_2)_n$-aryl-$NR(CH_2)_nCON(R)_2$, $NR(CH_2)_n$-aryl-$NR(CH_2)_nPO(OR)_2$, $NR(CH_2)_n$-arylO$(CH_2)_nCO_2R$, $NR(CH_2)_n$-aryl-O—$C_{2-6}$ alkenyl-$CO_2R$, $NR(CH_2)_n$-arylO$(CH_2)_nCN$, $NR(CH_2)_n$-aryl-O$(CH_2)_nCON(R)_2$, and $NR(CH_2)_n$-arylO$(CH_2)_nPO(OR)_2$, wherein aryl is substituted with 1-2 $X^4$;
$X^4$ is selected from H, OR, O—$C_{2-6}$ alkenyl, $C_{1-6}$ alkyl, $C_{2-6}$ alkenyl, $C_{2-6}$ alkynyl, halogen, $CF_3$, nitro, —CN, $C(O)NR_2$, $NRSO_2CH_3$, and, $SO_2N(R)C_{1-6}$alkyl;
Q is selected from H, OH, $C_{1-6}$ alkoxy, $O(CH_2)_nCO_2R$, $O(CH_2)_nCON(R)_2$, O—$C_{2-6}$ alkenyl, O—$C_{2-6}$ alkenyl-$CO_2R$, $OCH_2CH_2CONRCH_2CO_2R$, $OCH_2CHMCONRCH_2CO_2R$, $O(CH_2)_nPO(OR)_2$, $O(CH_2)_nSO_2OR$, $OCH_2CH(NHAc)CO_2R$, $OCH_2CH(NHR)CO_2R$, and $O(CH_2)_n$-aryl;
W is selected from H, $CO_2R$, $CON(R)_2$, $CH_2OH$, $CH_2OC_{1-6}$ alkyl, $CH_2OC_{2-6}$ alkenyl, $CH_2O(CH_2)_nCO_2R$, $CH_2O(CH_2)_nCON(R)_2$, $CH_2O$—$C_{2-6}$ alkenyl-$CO_2R$, $CH_2OCH_2CH_2CONRCH_2CO_2R$, $CH_2OCH_2CHMCONRCH_2CO_2R$, $CH_2O(CH_2)_nPO(OR)_2$, $CH_2O(CH_2)_nSO_2OR$, $CH_2OCH_2CH(NHAc)CO_2R$, $CH_2OCH_2CH(NHR)CO_2R$, $CH_2O$—$C_{2-6}$ alkenyl, and $CH_2O(CH_2)_nCONH_2$, and $CH_2O(CH_2)_n$-aryl;
M is independently selected from H, $C_{1-6}$ alkyl, $C_{3-8}$ cycloalkyl, $C_{2-6}$ alkenyl, $C_{2-6}$ alkynyl, aryl, and $(CH_2)_n$-aryl, wherein aryl is substituted with 1-2 $X^4$;
m is independently selected from 0, 1, 2, 3, and 4; and,
n is independently selected from 1, 2, 3, and 4;

provided that at least one of X, $X^1$, $X^2$, and $X^3$ is other than H, alkyl, alkoxy, hydroxyl, $CF_3$, and halo.

2. A method of treating of claim 1, wherein the compound is of formula $I_1$ or $II_1$, or a stereoisomer or pharmaceutically acceptable salt thereof:

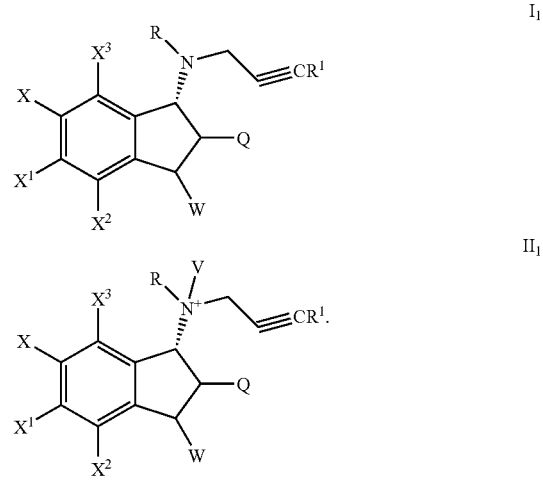

3. A method of treating of claim 1, wherein the compound is of formula Ia, or a stereoisomer or pharmaceutically acceptable salt thereof:

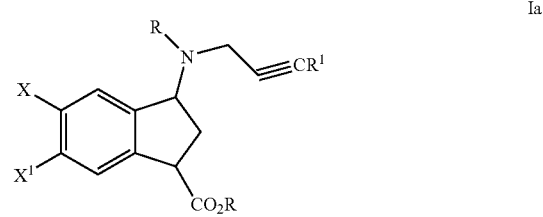

wherein:
R, at each occurrence, is independently selected from H and $C_{1-4}$ alkyl;
$R^1$ is selected from H and $C_{1-4}$ alkyl;
X and $X^1$ are independently selected from H, OR, $C_{1-4}$ alkyl, $C_{2-4}$ alkenyl, $C_{2-4}$ alkynyl, halogen, $CF_3$, —CN, $O(CH_2)_nCON(R)_2$, O—$C_{2-4}$ alkenyl, $NRSO_2CH_3$, $SO_2NRCH_3$, $CH_2N(C_{1-4}$ alkyl$)_2$, $CH_2$-aryl, $O(CH_2)_n$-aryl, $NR(CH_2)_n$-aryl, $O(CH_2)_n$-aryl-$(CH_2)_mCON(R)_2$, $O(CH_2)_n$-aryl-$O(CH_2)_nCON(R)_2$, $O(CH_2)_n$-aryl-$NR(CH_2)_nCON(R)_2$, $NR(CH_2)_n$-aryl-$(CH_2)_mCON(R)_2$, $NR(CH_2)_n$-aryl-$O(CH_2)_nCON(R)_2$, $NR(CH_2)_n$-aryl-$NR(CH_2)_nCON(R)_2$, $O(CH_2)_n$-biphenyl, $O(CH_2)_n$-biphenyl-CN, $O(CH_2)_n$-biphenyl-$CONH_2$, $NR(CH_2)_n$-biphenyl, $NR(CH_2)_n$-biphenyl-CN, and $NR(CH_2)_n$-biphenyl-$CONH_2$, wherein aryl is substituted with 1-2 $X^4$;
$X^4$ is selected from H, OH, $C_{1-4}$ alkoxy, $C_{1-4}$ alkyl, $C_{2-4}$ alkenyl, $C_{2-4}$ alkynyl, halogen, $CF_3$, nitro, —CN, $C(O)NR_2$, $NRSO_2CH_3$, and, $SO_2N(R)C_{1-6}$alkyl;
n is independently selected from 1, 2, and 3;
provided that at least one of X and $X^1$ is other than H, alkyl, alkoxy, hydroxyl, $CF_3$, and halo.

4. A method of of claim 3, wherein:
one of X and $X^1$ is H and the other is selected from OH, $C_{1-4}$ alkyl, $C_{2-4}$ alkenyl, $C_{2-4}$ alkynyl, halogen, $CF_3$, —CN, $C_{1-4}$ alkoxy, $O(CH_2)_nCON(R)_2$, $O—C_{2-4}$ alkenyl, $NRSO_2CH_3$, $SO_2NRCH_3$, $CH_2N(C_{1-4}$ alkyl$)_2$, $CH_2$-aryl, $O(CH_2)_n$-aryl, $NR(CH_2)_n$-aryl, $O(CH_2)_n$-aryl-$(CH_2)_mCON(R)_2$, $O(CH_2)_n$-aryl-$O(CH_2)_nCON(R)_2$, $O(CH_2)_n$-aryl-$NR(CH_2)_nCON(R)_2$, $NR(CH_2)_n$-aryl-$(CH_2)_mCON(R)_2$, $NR(CH_2)_n$-aryl-$O(CH_2)_nCON(R)_2$, $NR(CH_2)_n$-aryl-$NR(CH_2)_nCON(R)_2$, $O(CH_2)_n$-biphenyl, $O(CH_2)_n$-biphenyl-CN, $O(CH_2)_n$-biphenyl-$CONH_2$, $NR(CH_2)_n$-biphenyl, $NR(CH_2)_n$-biphenyl-CN, and $NR(CH_2)_n$-biphenyl-$CONH_2$, wherein aryl is substituted with 1-2 $X^4$;

provided that at least one of X and $X^1$ is other than H, alkyl, alkoxy, hydroxyl, $CF_3$, and halo.

5. A method of treating of claim 3, wherein the compound is of formula $Ia_1$, or a stereoisomer or pharmaceutically acceptable salt thereof:

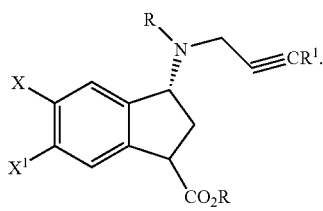

$Ia_1$

6. A method of of claim 1, wherein the compound is of formula Ib, or a stereoisomer or pharmaceutically acceptable salt thereof:

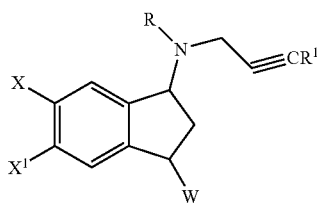

Ib wherein:
R, at each occurrence, is independently selected from H and $C_{1-4}$ alkyl;
$R^1$ is selected from H, $C_{1-4}$ alkyl, $(CH_2)_mCO_2R$, $C_{2-4}$ alkenyl-$CO_2R$, $CH_2CH(NHAc)CO_2R$, $CH_2CH(NHR)CO_2R$, and, $(CH_2)_nPO(OR)_2$;
X and $X^1$ are independently selected from H, OR, $C_{1-4}$ alkyl, $C_{2-4}$ alkenyl, $C_{2-4}$ alkynyl, halogen, $CF_3$, —CN, $O(CH_2)_nCON(R)_2$, $O—C_{2-4}$ alkenyl, $NRSO_2CH_3$, $SO_2NRCH_3$, $CH_2N(C_{1-4}$ alkyl$)_2$, $CH_2$-aryl, $O(CH_2)_n$-aryl, $NR(CH_2)_n$-aryl, $O(CH_2)_n$-aryl-$(CH_2)_mCON(R)_2$, $O(CH_2)_n$-aryl-$O(CH_2)_nCON(R)_2$, $O(CH_2)_n$-aryl-$NR(CH_2)_nCON(R)_2$, $NR(CH_2)_n$-aryl-$(CH_2)_mCON(R)_2$, $NR(CH_2)_n$-aryl-$O(CH_2)_nCON(R)_2$, $NR(CH_2)_n$-aryl-$NR(CH_2)_nCON(R)_2$, $O(CH_2)_n$-biphenyl, $O(CH_2)_n$-biphenyl-CN, $O(CH_2)_n$-biphenyl-$CONH_2$, $NR(CH_2)_n$-biphenyl, $NR(CH_2)_n$-biphenyl-CN, $NR(CH_2)_n$-biphenyl-$CONH_2$, wherein aryl is substituted with 1-2 $X^4$;
$X^4$ is selected from H, OH, $C_{1-4}$ alkoxy, $C_{1-4}$ alkyl, $C_{2-4}$ alkenyl, $C_{2-4}$ alkynyl, halogen, $CF_3$, nitro, —CN, $C(O)NR_2$, $NRSO_2CH_3$, and, $SO_2N(R)C_{1-6}$alkyl;
W is selected from H, $CH_2OH$, $CH_2OC_{1-4}$ alkyl, $CH_2OC_{2-4}$ alkenyl, $CH_2O(CH_2)_nCO_2R$, $CH_2O—C_{2-4}$ alkenyl-$CO_2R$, $CH_2O(CH_2)_nCON(R)_2$, $CH_2O(CH_2)_nPO(OR)_2$, and $CH_2O(CH_2)_n$-aryl;

m is independently selected from 0, 1, and 2; and,
n is independently selected from 1, 2, and 3;
provided that at least one of X and $X^1$ is other than H, alkyl, alkoxy, hydroxyl, $CF_3$, and halo.

7. A method of treating of claim 6, wherein:
one of X and $X^1$ is H and the other is selected from OH, $C_{1-4}$ alkyl, $C_{2-4}$ alkenyl, $C_{2-4}$ alkynyl, halogen, $CF_3$, —CN, $C_{1-4}$ alkoxy, $O(CH_2)_nCON(R)_2$, $O—C_{2-4}$ alkenyl, $NRSO_2CH_3$, $SO_2NRCH_3$, $CH_2N(C_{1-4}$ alkyl$)_2$, $CH_2$-aryl, $O(CH_2)_n$-aryl, $NR(CH_2)_n$-aryl, $O(CH_2)_n$-aryl-$(CH_2)_mCON(R)_2$, $O(CH_2)_n$-aryl-$O(CH_2)_nCON(R)_2$, $O(CH_2)_n$-aryl-$NR(CH_2)_nCON(R)_2$, $NR(CH_2)_n$-aryl-$(CH_2)_mCON(R)_2$, $NR(CH_2)_n$-aryl-$O(CH_2)_nCON(R)_2$, $NR(CH_2)_n$-aryl-$NR(CH_2)_nCON(R)_2$, $O(CH_2)_n$-biphenyl, $O(CH_2)_n$-biphenyl-CN, $O(CH_2)_n$-biphenyl-$CONH_2$, $NR(CH_2)_n$-biphenyl, $NR(CH_2)_n$-biphenyl-CN, $NR(CH_2)_n$-biphenyl-$CONH_2$, wherein aryl is substituted with 1-2 $X^4$;
provided that at least one of X and $X^1$ is other than H, alkyl, alkoxy, hydroxyl, $CF_3$, and halo.

8. A method of treating of claim 6, wherein the compound is of formula $Ib_1$, or a stereoisomer or pharmaceutically acceptable salt thereof:

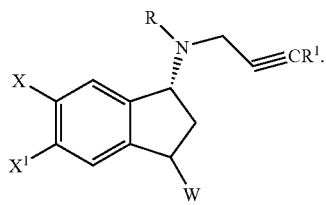

$Ib_1$

9. A method of treating of claim 1, wherein the compound is of formula Ic, or a stereoisomer or pharmaceutically acceptable salt thereof:

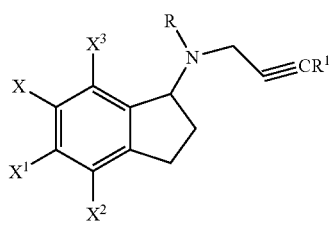

Ic wherein:
R, at each occurrence, is independently selected from H, $C_{1-4}$ alkyl, $C_{2-4}$ alkenyl, and $C_{2-4}$ alkynyl;
$R^1$ is selected from H and $C_{1-4}$ alkyl;
X, $X^1$, $X^2$, and $X^3$ are independently selected from H, OR, $C_{1-4}$ alkyl, $C_{2-4}$ alkenyl, $C_{2-4}$ alkynyl, halogen, $CF_3$, —CN, $(CH_2)_nCO_2R$, $(CH_2)_nCONR_2$, $(CH_2)_nCN$, $O(CH_2)_nCN$, $O(CH_2)_nCO_2R$, $O(CH_2)_nCON(R)_2$, $O—C_{2-4}$ alkenyl-$CO_2R$, $O(CH_2)_nPO(OR)_2$, $NR—C_{2-4}$ alkenyl, $NRSO_2CH_3$, $NR(CH_2)_nCO_2R$, $NR(CH_2)_nCON(R)_2$, $NR—C_{2-4}$ alkenyl-$CO_2R$, $NR(CH_2)_nPO(OR)_2$, $NR(CH_2)_nSO_2OR$, $SO_2NRCH_3$, $OCH_2CHMCONRCH_2CO_2R$, $CH_2$-aryl, $O(CH_2)_nPO(OR)_2$, $O(CH_2)_nSO_2OR$, $OCH_2(CH_2)_nN^+(CH_3)_3A^-$, $O(CH_2)_n$-biphenyl, $O(CH_2)_n$-biphenyl-$(CH_2)_mCO_2R$, O(CH$_2$)$_n$-biphenyl-(CH$_2$)$_m$CN, O(CH$_2$)$_n$-biphenyl-(CH$_2$)$_m$CON(R)$_2$, NR(CH$_2$)$_n$-biphenyl, NR(CH$_2$)$_n$-biphenyl-(CH$_2$)$_m$CO$_2$R, NR(CH$_2$)$_n$-biphenyl-(CH$_2$)$_m$CN, NR(CH$_2$)$_n$-biphenyl-(CH$_2$)$_m$CON(R)$_2$, O(CH$_2$)$_n$-aryl, O(CH$_2$)$_n$-aryl(CH$_2$)$_m$CO$_2$R, O(CH$_2$)$_n$-aryl-C$_{2-4}$ alkenyl-CO$_2$R, O(CH$_2$)$_n$-aryl(CH$_2$)$_m$CN, O(CH$_2$)$_n$-aryl(CH$_2$)$_m$CON(R)$_2$, O(CH$_2$)$_n$-aryl(CH$_2$)$_m$-PO(OR)$_2$, O(CH$_2$)$_n$-aryl-O(CH$_2$)$_n$CO$_2$R, O(CH$_2$)$_n$-aryl-O—C$_{2-4}$ alkenyl-CO$_2$R, O(CH$_2$)$_n$-arylO(CH$_2$)$_n$CN, O(CH$_2$)$_n$-arylO(CH$_2$)$_n$CON(R)$_2$, O(CH$_2$)$_n$-arylO(CH$_2$)$_n$-PO(OR)$_2$, O(CH$_2$)$_n$-aryl-NR(CH$_2$)$_n$CO$_2$R, O(CH$_2$)$_n$-aryl-NRC$_{2-4}$alkenyl-CO$_2$R, O(CH$_2$)$_n$-aryl-NR(CH$_2$)$_n$CN, O(CH$_2$)$_n$-aryl-NR(CH$_2$)$_n$CON(R)$_2$, O(CH$_2$)$_n$-aryl-NR(CH$_2$)$_n$-PO(OR)$_2$, NR(CH$_2$)$_n$-aryl(CH$_2$)$_m$CO$_2$R, NR(CH$_2$)$_n$-aryl-C$_{2-4}$ alkenyl-CO$_2$R, NR(CH$_2$)$_n$-aryl(CH$_2$)$_m$CN, NR(CH$_2$)$_n$-aryl(CH$_2$)$_m$CON(R)$_2$, NR(CH$_2$)$_n$-aryl(CH$_2$)$_m$-PO(OR)$_2$, NR(CH$_2$)$_n$-aryl-NR(CH$_2$)$_n$CO$_2$R, NR(CH$_2$)$_n$-aryl-NR—C$_{2-4}$ alkenyl-CO$_2$R, NR(CH$_2$)$_n$-aryl-NR(CH$_2$)$_n$CN, NR(CH$_2$)$_n$-aryl-NR(CH$_2$)$_n$CON(R)$_2$, NR(CH$_2$)$_n$-aryl-NR(CH$_2$)$_n$PO(OR)$_2$, NR(CH$_2$)$_n$-arylO(CH$_2$)$_n$CO$_2$R, NR(CH$_2$)$_n$-aryl-O—C$_{2-4}$ alkenyl-CO$_2$R, NR(CH$_2$)$_n$-arylO(CH$_2$)$_n$CN, NR(CH$_2$)$_n$-aryl-O(CH$_2$)$_n$CON(R)$_2$, and NR(CH$_2$)$_n$-arylO(CH$_2$)$_n$PO(OR)$_2$, wherein is substituted with 1-2 X$^4$;

X$^4$ is selected from H, OR, C$_{1-4}$ alkoxy, C$_{1-4}$ alkyl, C$_{2-4}$ alkenyl, C$_{2-4}$ alkynyl, halogen, CF$_3$, nitro, —CN, C(O)NR$_2$, NRSO$_2$CH$_3$, and, SO$_2$N(R)C$_{1-6}$alkyl;

A$^-$ is selected from Cl and Br;

M is independently selected from H, C$_{1-4}$ alkyl, C$_{3-6}$ cycloalkyl, C$_{2-4}$ alkenyl, C$_{2-4}$ alkynyl, aryl, and (CH$_2$)$_n$-aryl; and, m is independently selected from 0, 1, and 2; and, n is independently selected from 1, 2, and 3;

provided that at least one of X, X$^1$, X$^2$, and X$^3$ is other than H, alkyl, alkoxy, hydroxyl, CF$_3$, and halo.

10. A method of treating of claim 9, wherein:

three of X, X$^1$, X$^2$, and X$^3$ are H and the fourth is selected from OH, C$_{1-4}$ alkyl, C$_{2-4}$ alkenyl, C$_{2-4}$ alkynyl, halogen, CF$_3$, C$_{1-4}$ alkoxy, —CN, (CH$_2$)$_n$CO$_2$R, (CH$_2$)$_n$CONR$_2$, (CH$_2$)$_n$CN, O(CH$_2$)$_n$CN, O(CH$_2$)$_n$CO$_2$R, O(CH$_2$)$_n$CON(R)$_2$, O—C$_{2-4}$ alkenyl-CO$_2$R, O(CH$_2$)$_n$PO(OR)$_2$, NR—C$_{2-4}$ alkenyl, NRSO$_2$CH$_3$, NR(CH$_2$)$_n$CO$_2$R, NR(CH$_2$)$_n$CON(R)$_2$, NR—C$_{2-4}$ alkenyl-CO$_2$R, NR(CH$_3$)$_n$PO(OR)$_2$, NR(CH$_2$)$_n$SO$_2$OR, SO$_2$NRCH$_3$, OCH$_2$CHMCONRCH$_2$CO$_2$R, CH$_2$-aryl, O(CH$_2$)$_n$PO(OR)$_2$, O(CH$_2$)$_n$SO$_2$OR, OCH$_2$(CH$_2$)$_n$N$^+$(CH$_3$)$_3$A$^-$, O(CH$_2$)$_n$-biphenyl, O(CH$_2$)$_n$-biphenyl-(CH$_2$)$_m$CO$_2$R, O(CH$_2$)$_n$-biphenyl-(CH$_2$)$_m$CN, O(CH$_2$)$_n$-biphenyl-(CH$_2$)$_m$CON(R)$_2$, NR(CH$_2$)$_n$-biphenyl, NR(CH$_2$)$_n$-biphenyl-(CH$_2$)$_m$CO$_2$R, NR(CH$_2$)$_n$-biphenyl-(CH$_2$)$_m$CN, NR(CH$_2$)$_n$-biphenyl-(CH$_2$)$_m$CON(R)$_2$, O(CH$_2$)$_n$-aryl, O(CH$_2$)$_n$-aryl(CH$_2$)$_m$CO$_2$R, O(CH$_2$)$_n$-aryl-C$_{2-4}$ alkenyl-CO$_2$R, O(CH$_2$)$_n$-aryl(CH$_2$)$_m$CN, O(CH$_2$)$_n$-aryl(CH$_2$)$_m$CON(R)$_2$, O(CH$_2$)$_n$-aryl(CH$_2$)$_m$-PO(OR)$_2$, O(CH$_2$)$_n$-aryl-O(CH$_2$)$_n$CO$_2$R, O(CH$_2$)$_n$-aryl-O—C$_{2-4}$ alkenyl-CO$_2$R, O(CH$_2$)$_n$-arylO(CH$_2$)$_n$CN, O(CH$_2$)$_n$-arylO(CH$_2$)$_n$CON(R)$_2$, O(CH$_2$)$_n$-arylO(CH$_2$)$_n$-PO(OR)$_2$, O(CH$_2$)$_n$-aryl-NR(CH$_2$)$_n$CO$_2$R, O(CH$_2$)$_n$-aryl-NRC$_{2-4}$ alkenyl-CO$_2$R, O(CH$_2$)$_n$-aryl-NR(CH$_2$)$_n$CN, O(CH$_2$)$_n$-aryl-NR(CH$_2$)$_n$CON(R)$_2$, O(CH$_2$)$_n$-aryl-NR(CH$_2$)$_n$-PO(OR)$_2$, NR(CH$_2$)$_n$-aryl(CH$_2$)$_m$CO$_2$R, NR(CH$_2$)$_n$-aryl-C$_{2-4}$ alkenyl-CO$_2$R, NR(CH$_2$)$_n$-aryl(CH$_2$)$_m$CN, NR(CH$_2$)$_n$-aryl(CH$_2$)$_n$CON(R)$_2$, NR(CH$_2$)$_n$-aryl(CH$_2$)$_m$-PO(OR)$_2$, NR(CH$_2$)$_n$-aryl-NR(CH$_2$)$_n$CO$_2$R, NR(CH$_2$)$_n$-aryl-NR—C$_{2-4}$ alkenyl-CO$_2$R, NR(CH$_2$)$_n$-aryl-NR(CH$_2$)$_n$CN, NR(CH$_2$)$_n$-aryl-NR(CH$_2$)$_n$CON(R)$_2$, NR(CH$_2$)$_n$-aryl-NR(CH$_2$)$_n$PO(OR)$_2$, NR(CH$_2$)$_n$-arylO(CH$_2$)$_n$CO$_2$R, NR(CH$_2$)$_n$-aryl-O—C$_{2-4}$ alkenyl-CO$_2$R, NR(CH$_2$)$_n$-arylO(CH$_2$)$_n$CN, NR(CH$_2$)$_n$-aryl-O(CH$_2$)$_n$CON(R)$_2$, and NR(CH$_2$)$_n$-arylO(CH$_2$)$_n$PO(OR)$_2$, O(CH$_2$)$_n$— wherein aryl is substituted with 1-2 X$^4$;

provided that at least one of X, X$^1$, X$^2$, and X$^3$ is other than H, alkyl, alkoxy, hydroxyl, CF$_3$, and halo.

11. A method of treating of claim 9, wherein the compound is of formula Ic$_1$, or a stereoisomer or pharmaceutically acceptable salt thereof:

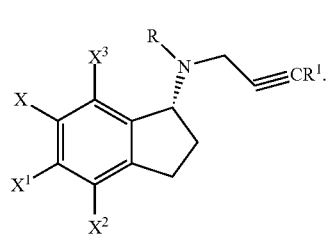

Ic$_1$

12. A method of treating of claim 1, wherein the compound is of formula Id, or a stereoisomer or pharmaceutically acceptable salt thereof:

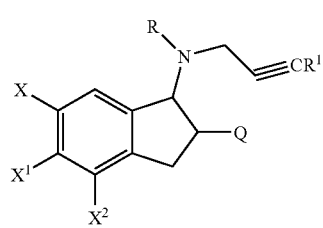

Id wherein:

R, at each occurrence, is independently selected from H, C$_{1-4}$ alkyl, C$_{2-4}$ alkenyl, and C$_{2-4}$ alkynyl;

R$^1$ is selected from H, C$_{1-4}$ alkyl, (CH$_2$)$_m$CO$_2$R, (CH$_2$)$_n$PO(OR)$_2$, C$_{2-4}$ alkenyl, and C$_{2-4}$ alkynyl;

X, X$^1$, and X$^2$ are independently selected from H, OR, C$_{1-4}$ alkyl, C$_{2-4}$ alkenyl, C$_{2-4}$ alkynyl, halogen, CF$_3$, O(CH$_2$)$_n$CON(R)$_2$, O—C$_{2-4}$ alkenyl, NRSO$_2$CH$_3$, SO$_2$NRCH$_3$, CH$_2$N(C$_{1-4}$ alkyl)$_2$, CH$_2$-aryl, O(CH$_2$)$_n$-aryl, O(CH$_2$)$_n$-aryl(CH$_2$)$_m$CN, O(CH$_2$)$_n$-aryl(CH$_2$)$_m$CON(R)$_2$, O(CH$_2$)$_n$-arylO(CH$_2$)$_n$CN, O(CH$_2$)$_n$-arylO(CH$_2$)$_n$CON(R)$_2$, NR(CH$_2$)$_n$-aryl(CH$_2$)$_m$CN, NR(CH$_2$)$_n$-aryl(CH$_2$)$_m$CON(R)$_2$, NR(CH$_2$)$_n$-arylO(CH$_2$)$_n$CN, NR(CH$_2$)$_n$-arylO(CH$_2$)$_n$CON(R)$_2$, NR(CH$_2$)$_n$-aryl-NR(CH$_2$)$_n$CN, NR(CH$_2$)$_n$-aryl-NR(CH$_2$)$_n$CON(R)$_2$, O(CH$_2$)$_n$-biphenyl, O(CH$_2$)$_n$-biphenyl-CN, O(CH$_2$)$_n$-biphenyl-CONH$_2$, NR(CH$_2$)$_n$-biphenyl, NR(CH$_2$)$_n$-biphenyl-CN, and NR(CH$_2$)$_n$-biphenyl-CONH$_2$, wherein aryl is substituted with 1-2 X$^4$;

X$^4$ is selected from H, OH, C$_{1-6}$ alkoxy C$_{1-6}$ alkyl, C$_{2-6}$ alkenyl, C$_{2-6}$ alkynyl, halogen, CF$_3$, nitro, —CN, C(O)NR$_2$, NRSO$_2$CH$_3$, and, SO$_2$N(R)C$_{1-6}$alkyl;

Q is selected from OH, C$_{1-4}$ alkoxy, O(CH$_2$)$_n$CO$_2$R, O(CH$_2$)$_n$CON(R)$_2$, O—C$_{2-4}$ alkenyl, O—C$_{2-4}$ alkenyl-CO$_2$R, OCH$_2$CH$_2$CONRCH$_2$CO$_2$R, OCH$_2$CHMCONRCH$_2$CO$_2$R, O(CH$_2$)$_n$PO(OR)$_2$, O(CH$_2$)$_n$SO$_2$OR, OCH$_2$CH(NHAc)CO$_2$R, OCH$_2$CH(NHR)CO$_2$R, and O(CH$_2$)$_n$-aryl;

M is independently selected from H, $C_{1-4}$ alkyl, $C_{3-6}$ cycloalkyl, $C_{2-4}$ alkenyl, $C_{2-4}$ alkynyl, aryl, and $(CH_2)_n$-aryl; and, m is independently selected from 0, 1, and 2; and, n is independently selected from 1, 2, and 3;

provided that at least one of X, $X^1$, and $X^2$ is other than H, alkyl, alkoxy, hydroxyl, $CF_3$, and halo.

13. A method of treating of claim 12, wherein:

two of X, $X^1$, and $X^2$ are H and the third is selected from OH, $C_{1-4}$ alkyl, $C_{2-4}$ alkenyl, $C_{2-4}$ alkynyl, halogen, $CF_3$, $C_{1-4}$ alkoxy, $O(CH_2)_nCON(R)_2$, $O-C_{2-4}$ alkenyl, $NRSO_2CH_3$, $SO_2NRCH_3$, $CH_2N(C_{1-4}$ alkyl$)_2$, $CH_2$-aryl, $O(CH_2)_n$-aryl, $O(CH_2)_n$-aryl$(CH_2)_mCN$, $O(CH_2)_n$-aryl$(CH_2)_mCON(R)_2$, $O(CH_2)_n$-arylO$(CH_2)_nCN$, $O(CH_2)_n$-arylO$(CH_2)_nCON(R)_2$, $NR(CH_2)_n$-aryl$(CH_2)_mCN$, $NR(CH_2)_n$-aryl$(CH_2)_mCON(R)_2$, $NR(CH_2)_n$-arylO$(CH_2)_nCN$, $NR(CH_2)_n$-aryl-O$(CH_2)_nCON(R)_2$, $NR(CH_2)_n$-aryl-NR$(CH_2)_nCN$, $NR(CH_2)_n$-aryl-NR$(CH_2)_nCON(R)_2$, $O(CH_2)_n$-biphenyl, $O(CH_2)_n$-biphenyl-CN, $O(CH_2)_n$-biphenyl-$CONH_2$, $NR(CH_2)_n$-biphenyl, $NR(CH_2)_n$-biphenyl-CN, and $NR(CH_2)_n$-biphenyl-$CONH_2$, wherein aryl is substituted with 1-2 $X^4$;

provided that at least one of X, $X^1$, and $X^2$ is other than H, alkyl, alkoxy, hydroxyl, $CF_3$, and halo.

14. A method of treating of claim 12, wherein the compound is of formula $Id_1$, or a stereoisomer or pharmaceutically acceptable salt thereof:

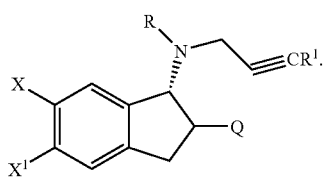

$Id_1$

15. A method of treating of claim 1, wherein the compound is of formula IIa, or a stereoisomer or pharmaceutically acceptable salt thereof:

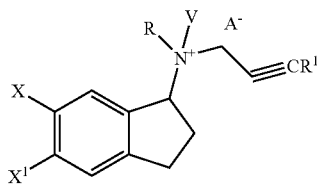

IIa wherein:

R, at each occurrence, is independently selected from H, $C_{1-4}$ alkyl, $C_{2-4}$ alkenyl, and $C_{2-4}$ alkynyl;

$R^1$ is selected from H and $C_{1-4}$ alkyl;

$A^-$ is selected from $Cl^-$ and $Br^-$;

V is selected from $O^-$, $C_{1-4}$ alkyl, $C_{2-4}$ alkenyl, and $C_{2-4}$ alkynyl;

X and $X^1$ are independently selected from H, OR, $C_{1-4}$ alkyl, $C_{2-4}$ alkenyl, $C_{2-4}$ alkynyl, halogen, $CF_3$, $O(CH_2)_nCON(R)_2$, $O-C_{2-4}$ alkenyl, $NRSO_2CH_3$, $SO_2NRCH_3$, $CH_2$-aryl, $O(CH_2)_n$-aryl, $O(CH_2)_n$-aryl$(CH_2)_mCN$, $O(CH_2)_n$-aryl$(CH_2)_mCON(R)_2$, $O(CH_2)_n$-arylO$(CH_2)_nCN$, $O(CH_2)_n$-arylO$(CH_2)_nCON(R)_2$, $NR(CH_2)_n$-aryl$(CH_2)_mCN$, $NR(CH_2)_n$-aryl$(CH_2)_mCON(R)_2$, $NR(CH_2)_n$-arylO$(CH_2)_nCN$, $NR(CH_2)_n$-aryl-O$(CH_2)_nCON(R)_2$, $NR(CH_2)_n$-aryl-NR$(CH_2)_nCN$, $NR(CH_2)_n$-aryl-NR$(CH_2)_nCON(R)_2$, $O(CH_2)_n$-biphenyl, $O(CH_2)_n$-biphenyl-CN, $O(CH_2)_n$-biphenyl-$CONH_2$, $NR(CH_2)_n$-biphenyl, $NR(CH_2)_n$-biphenyl-CN, and $NR(CH_2)_n$-biphenyl-$CONH_2$, wherein aryl is substituted with 1-2 $X^4$;

$X^4$ is selected from H, OR, $C_{1-6}$ alkoxy $C_{1-6}$ alkyl, $C_{2-6}$ alkenyl, $C_{2-6}$ alkynyl, halogen, $CF_3$, nitro, $-CN$, $C(O)NR_2$, $NRSO_2CH_3$, and, $SO_2N(R)C_{1-6}$alkyl;

n is independently selected from 1, 2, and 3;

provided that at least one of X and $X^1$ is other than H, alkyl, alkoxy, hydroxyl, $CF_3$, and halo.

16. A method of treating of claim 15, wherein:

one of X and $X^1$ is H and the other is selected from OH, $C_{1-4}$ alkyl, $C_{2-4}$ alkenyl, $C_{2-4}$ alkynyl, halogen, $CF_3$, $C_{1-4}$ alkoxy, $O(CH_2)_nCON(R)_2$, $O-C_{2-4}$ alkenyl, $NRSO_2CH_3$, $SO_2NRCH_3$, $CH_2$-aryl, $O(CH_2)_n$-aryl, $O(CH_2)_n$-aryl$(CH_2)_mCN$, $O(CH_2)_n$-aryl$(CH_2)_mCON(R)_2$, $O(CH_2)_n$-arylO$(CH_2)_nCN$, $O(CH_2)_n$-arylO$(CH_2)_nCON(R)_2$, $NR(CH_2)_n$-aryl$(CH_2)_mCN$, $NR(CH_2)_n$-aryl$(CH_2)_mCON(R)_2$, $NR(CH_2)_n$-arylO$(CH_2)_nCN$, $NR(CH_2)_n$-aryl-O$(CH_2)_nCON(R)_2$, $NR(CH_2)_n$-aryl-NR$(CH_2)_nCN$, $NR(CH_2)_n$-aryl-NR$(CH_2)_nCON(R)_2$, $O(CH_2)_n$-biphenyl, $O(CH_2)_n$-biphenyl-CN, $O(CH_2)_n$-biphenyl-$CONH_2$, $NR(CH_2)_n$-biphenyl, $NR(CH_2)_n$-biphenyl-CN, and $NR(CH_2)_n$-biphenyl-$CONH_2$, wherein aryl is substituted with 1-2 $X^4$;

provided that at least one of X and $X^1$ is other than H, alkyl, alkoxy, hydroxyl, $CF_3$, and halo.

17. A method of treating of claim 15, wherein the compound is of formula $IIa_1$, or a stereoisomer or pharmaceutically acceptable salt thereof:

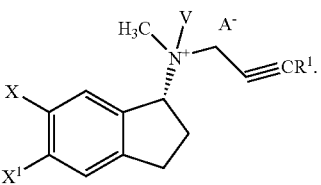

$IIa_1$

18. A method of treating a disease, comprising: administering to a mammal in need thereof a therapeutically effective amount of a compound of formula I or II or a pharmaceutically acceptable salt form thereof, wherein the disease is a co-morbidty of obesity selected from Type 2 diabetes, Metabolic Syndrome, dementia, hypertension, pulmonary hypoventilation syndrome, coronary artery disease, arterial sclerotic disease, and high cholesterol:

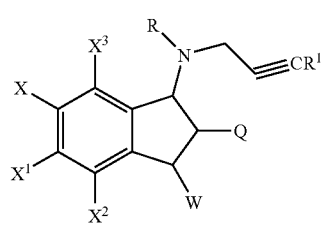

I

-continued

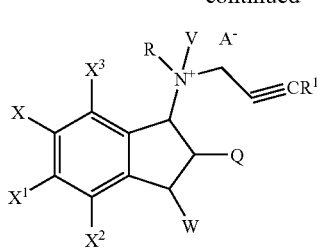

wherein:
R, at each occurrence, is independently selected from H, $C_{1-6}$ alkyl, $C_{2-6}$ alkenyl, and $C_{2-6}$ alkynyl;
$R^1$ is selected from H, $C_{1-6}$ alkyl, $C_{2-6}$ alkenyl, $C_{2-6}$ alkynyl, $(CH_2)_mCO_2R$, $C_{2-6}$ alkenyl-$CO_2R$, $CH_2CH(NHAc)CO_2R$, $CH_2CH(NHR)CO_2R$, and, $(CH_2)_nPO(OR)_2$;
$A^-$ is a counter ion;
V is selected from $O^-$, $C_{1-4}$ alkyl, $C_{2-4}$ alkenyl, and $C_{2-4}$ alkynyl;
X, $X^1$, $X^2$, and $X^3$ are independently selected from H, OR, $C_{1-6}$ alkyl, $C_{2-6}$ alkenyl, $C_{2-6}$ alkynyl, halogen, $CF_3$, —CN, $(CH_2)_nCO_2R$, $(CH_2)_nCONR_2$, $(CH_2)_nCN$, $O(CH_2)_nCN$, $O(CH_2)_nCO_2R$, $O(CH_2)_nCON(R)_2$, O—$C_{2-6}$ alkenyl-$CO_2R$, $O(CH_2)_nPO(OR)_2$, NR—$C_{2-4}$ alkenyl, $NRSO_2CH_3$, $NR(CH_2)_nCO_2R$, $NR(CH_2)_nCON(R)_2$, NR—$C_{2-4}$ alkenyl-$CO_2R$, $NR(CH_2)_nPO(OR)_2$, $NR(CH_2)_nSO_2OR$, $SO_2NRCH_3$, $OCH_2CHMCONRCH_2CO_2R$, $CH_2$-aryl, $O(CH_2)_nPO(OR)_2$, $O(CH_2)_nSO_2OR$, $OCH_2(CH_2)_nN^+(CH_3)_3A^-$, $O(CH_2)_n$-biphenyl, $O(CH_2)_n$-biphenyl-$(CH_2)_mCO_2R$, $O(CH_2)_n$-biphenyl-$(CH_2)_mCN$, $O(CH_2)_n$-biphenyl-$(CH_2)_mCON(R)_2$, $NR(CH_2)_n$-biphenyl, $NR(CH_2)_n$-biphenyl-$(CH_2)_mCO_2R$, $NR(CH_2)_n$-biphenyl-$(CH_2)_mCN$, $NR(CH_2)_n$-biphenyl-$(CH_2)_mCON(R)_2$, $O(CH_2)_n$-aryl, $NR(CH_2)_n$-aryl, $O(CH_2)_n$-aryl$(CH_2)_mCO_2R$, $O(CH_2)_n$-aryl-$C_{2-6}$ alkenyl-$CO_2R$, $O(CH_2)_n$-aryl$(CH_2)_mCN$, $O(CH_2)_n$-aryl$(CH_2)_mCON(R)_2$, $O(CH_2)_n$-aryl$(CH_2)_m$-$PO(OR)_2$, $O(CH_2)_n$-aryl-$O(CH_2)_nCO_2R$, $O(CH_2)_n$-aryl-O—$C_{2-6}$ alkenyl-$CO_2R$, $O(CH_2)_n$-arylO$(CH_2)_nCN$, $O(CH_2)_n$-arylO$(CH_2)_nCON(R)_2$, $O(CH_2)_n$-arylO$(CH_2)_n$-$PO(OR)_2$, $O(CH_2)_n$-aryl-NR$(CH_2)_nCO_2R$, $O(CH_2)_n$-aryl-NR$C_{2-6}$ alkenyl-$CO_2R$, $O(CH_2)_n$-aryl-NR$(CH_2)_nCN$, $O(CH_2)_n$-aryl-NR$(CH_2)_nCON(R)_2$, $O(CH_2)_n$-aryl-NR$(CH_2)_n$-$PO(OR)_2$, $NR(CH_2)_n$-aryl$(CH_2)_mCO_2R$, $NR(CH_2)_n$-aryl-$C_{2-6}$ alkenyl-$CO_2R$, $NR(CH_2)_n$-aryl$(CH_2)_mCN$, $NR(CH_2)_n$-aryl$(CH_2)_mCON(R)_2$, $NR(CH_2)_n$-aryl$(CH_2)_m$-$PO(OR)_2$, $NR(CH_2)_n$-aryl-$NR(CH_2)_nCO_2R$, $NR(CH_2)_n$-aryl-NR—$C_{2-6}$ alkenyl-$CO_2R$, $NR(CH_2)_n$-aryl-NR$(CH_2)_nCN$, $NR(CH_2)_n$-aryl-$NR(CH_2)_nCON(R)_2$, $NR(CH_2)_n$-aryl-NR$(CH_2)_nPO(OR)_2$, $NR(CH_2)_n$-arylO$(CH_2)_nCO_2R$, $NR(CH_2)_n$-aryl-O—$C_{2-6}$ alkenyl-$CO_2R$, $NR(CH_2)_n$-arylO$(CH_2)_nCN$, $NR(CH_2)_n$-aryl-O$(CH_2)_nCON(R)_2$, and $NR(CH_2)_n$-arylO$(CH_2)_nPO(OR)_2$, wherein aryl is substituted with 1-2 $X^4$;
$X^4$ is selected from H, OR, O—$C_{2-6}$ alkenyl, $C_{1-6}$ alkyl, $C_{2-6}$ alkenyl, $C_{2-6}$ alkynyl, halogen, $CF_3$, nitro, —CN, $C(O)NR_2$, $NRSO_2CH_3$, and, $SO_2N(R)C_{1-6}$alkyl;
Q is selected from H, OH, $C_{1-6}$ alkoxy, $O(CH_2)_nCO_2R$, $O(CH_2)_nCON(R)_2$, O—$C_{2-6}$ alkenyl, O—$C_{2-6}$ alkenyl-$CO_2R$, $OCH_2CH_2CONRCH_2CO_2R$, $OCH_2CHMCONRCH_2CO_2R$, $O(CH_2)_nPO(OR)_2$, $O(CH_2)_nSO_2OR$, $OCH_2CH(NHAc)CO_2R$, $OCH_2CH(NHR)CO_2R$, and $O(CH_2)_n$-aryl;
W is selected from H, $CO_2R$, $CON(R)_2$, $CH_2OH$, $CH_2OC_{1-6}$ alkyl, $CH_2OC_{2-6}$ alkenyl, $CH_2O(CH_2)_nCO_2R$, $CH_2O(CH_2)_nCON(R)_2$, $CH_2O$—$C_{2-6}$ alkenyl-$CO_2R$, $CH_2OCH_2CH_2CONRCH_2CO_2R$, $CH_2OCH_2CHMCONRCH_2CO_2R$, $CH_2O(CH_2)_nPO(OR)_2$, $CH_2O(CH_2)_nSO_2OR$, $CH_2OCH_2CH(NHAc)CO_2R$, $CH_2OCH_2CH(NHR)CO_2R$, $CH_2O$—$C_{2-6}$ alkenyl, and $CH_2O(CH_2)_nCONH_2$, and $CH_2O(CH_2)_n$-aryl;
M is independently selected from H, $C_{1-6}$ alkyl, $C_{3-8}$ cycloalkyl, $C_{2-6}$ alkenyl, $C_{2-6}$ alkynyl, aryl, and $(CH_2)_n$-aryl, wherein aryl is substituted with 1-2 $X^4$;
m is independently selected from 0, 1, 2, 3, and 4; and,
n is independently selected from 1, 2, 3, and 4;
provided that at least one of X, $X^1$, $X^2$, and $X^3$ is other than H, alkyl, alkoxy, hydroxyl, $CF_3$, and halo.

19. A method of treating a disease, comprising: administering to a mammal in need thereof a therapeutically effective amount of a compound of formula I or II or a pharmaceutically acceptable salt form thereof, wherein the disease is a CNS disorder selected from Parkinson's disease, depression, anxiety, panic attack, social phobia, schizophrenia, anorexia, and neuropathic pain:

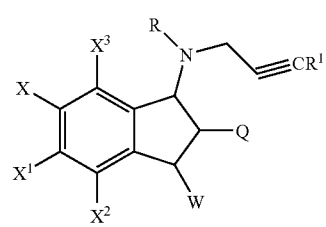

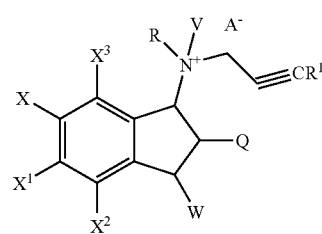

wherein:
R, at each occurrence, is independently selected from H, $C_{1-6}$ alkyl, $C_{2-6}$ alkenyl, and $C_{2-6}$ alkynyl;
$R^1$ is selected from H, $C_{1-6}$ alkyl, $C_{2-6}$ alkenyl, $C_{2-6}$ alkynyl, $(CH_2)_mCO_2R$, $C_{2-6}$ alkenyl-$CO_2R$, $CH_2CH(NHAc)CO_2R$, $CH_2CH(NHR)CO_2R$, and, $(CH_2)_nPO(OR)_2$;
$A^-$ is a counter ion;
V is selected from $O^-$, $C_{1-4}$ alkyl, $C_{2-4}$ alkenyl, and $C_{2-4}$ alkynyl;
X, $X^1$, $X^2$, and $X^3$ are independently selected from H, OR, $C_{1-6}$ alkyl, $C_{2-6}$ alkenyl, $C_{2-6}$ alkynyl, halogen, $CF_3$, —CN, $(CH_2)_nCO_2R$, $(CH_2)_nCONR_2$, $(CH_2)_nCN$, $O(CH_2)_nCN$, $O(CH_2)_nCO_2R$, $O(CH_2)_nCON(R)_2$, O—$C_{2-6}$ alkenyl-$CO_2R$, $O(CH_2)_nPO(OR)_2$, NR—$C_{2-4}$ alkenyl, $NRSO_2CH_3$, $NR(CH_2)_nCO_2R$, $NR(CH_2)_nCON(R)_2$, NR—$C_{2-4}$ alkenyl-$CO_2R$, $NR(CH_2)_nPO(OR)_2$, $NR(CH_2)_nSO_2OR$, $SO_2NRCH_3$, $OCH_2CHMCONRCH_2CO_2R$, $CH_2$-aryl, $O(CH_2)_nPO(OR)_2$, $O(CH_2)_nSO_2OR$, $OCH_2(CH_2)_nN^+(CH_3)_3A^-$, $O(CH_2)_n$-biphenyl, $O(CH_2)_n$-biphenyl-$(CH_2)_mCO_2R$, $O(CH_2)_n$-biphenyl-$(CH_2)_mCN$, $O(CH_2)_n$-biphenyl-$(CH_2)_mCON(R)_2$, $NR(CH_2)_n$-biphenyl, $NR(CH_2)_n$-biphenyl-$(CH_2)_mCO_2R$, $NR(CH_2)_n$-biphenyl-$(CH_2)_mCN$, NR(CH$_2$)$_n$-biphenyl-(CH$_2$)$_m$CON(R)$_2$, O(CH$_2$)$_n$-aryl, NR(CH$_2$)$_n$-aryl, O(CH$_2$)$_n$-aryl(CH$_2$)$_m$CO$_2$R, O(CH$_2$)$_n$-aryl-C$_{2-6}$ alkenyl-CO$_2$R, O(CH$_2$)$_n$-aryl(CH$_2$)$_m$CN, O(CH$_2$)$_n$-aryl(CH$_2$)$_m$CON(R)$_2$, O(CH$_2$)$_n$-aryl(CH$_2$)$_m$PO(OR)$_2$, O(CH$_2$)$_n$-aryl-O(CH$_2$)$_n$CO$_2$R, O(CH$_2$)$_n$-aryl-O—C$_{2-6}$ alkenyl-CO$_2$R, O(CH$_2$)$_n$-arylO(CH$_2$)$_n$CN, O(CH$_2$)$_n$-arylO(CH$_2$)$_n$CON(R)$_2$, O(CH$_2$)$_n$-arylO(CH$_2$)$_n$-PO(OR)$_2$, O(CH$_2$)$_n$-aryl-NR(CH$_2$)$_n$CO$_2$R, O(CH$_2$)$_n$-aryl-NRC$_{2-6}$ alkenyl-CO$_2$R, O(CH$_2$)$_n$-aryl-NR(CH$_2$)$_n$CN, O(CH$_2$)$_n$-aryl-NR(CH$_2$)$_n$CON(R)$_2$, O(CH$_2$)$_n$-aryl-NR(CH$_2$)$_n$-PO(OR)$_2$, NR(CH$_2$)$_n$-aryl(CH$_2$)$_m$CO$_2$R, NR(CH$_2$)$_n$-aryl-C$_{2-6}$ alkenyl-CO$_2$R, NR(CH$_2$)$_n$-aryl(CH$_2$)$_m$CN, NR(CH$_2$)$_n$-aryl(CH$_2$)$_m$CON(R)$_2$, NR(CH$_2$)$_n$-aryl(CH$_2$)$_m$-PO(OR)$_2$, NR(CH$_2$)$_n$-aryl-NR(CH$_2$)$_n$CO$_2$R, NR(CH$_2$)$_n$-aryl-NR—C$_{2-6}$ alkenyl-CO$_2$R, NR(CH$_2$)$_n$-aryl-NR(CH$_2$)$_n$CN, NR(CH$_2$)$_n$-aryl-NR(CH$_2$)$_n$CON(R)$_2$, NR(CH$_2$)$_n$-aryl-NR(CH$_2$)$_n$PO(OR)$_2$, NR(CH$_2$)$_n$-arylO(CH$_2$)$_n$CO$_2$R, NR(CH$_2$)$_n$-aryl-O—C$_{2-6}$ alkenyl-CO$_2$R, NR(CH$_2$)$_n$-arylO(CH$_2$)$_n$CN, NR(CH$_2$)$_n$-aryl-O(CH$_2$)$_n$CON(R)$_2$, and NR(CH$_2$)$_n$-arylO(CH$_2$)$_n$PO(OR)$_2$, wherein aryl is substituted with 1-2 X$^4$;

X$^4$ is selected from H, OR, O—C$_{2-6}$ alkenyl, C$_{1-6}$ alkyl, C$_{2-6}$ alkenyl, C$_{2-6}$ alkynyl, halogen, CF$_3$, nitro, —CN, C(O)NR$_2$, NRSO$_2$CH$_3$, and, SO$_2$N(R)C$_{1-6}$alkyl;

Q is selected from H, OH, C$_{1-6}$ alkoxy, O(CH$_2$)$_n$CO$_2$R, O(CH$_2$)$_n$CON(R)$_2$, O—C$_{2-6}$ alkenyl, O-C$_{2-6}$ alkenyl-CO$_2$R, OCH$_2$CH$_2$CONRCH$_2$CO$_2$R, OCH$_2$CHMCONRCH$_2$CO$_2$R, O(CH$_2$)$_n$PO(OR)$_2$, O(CH$_2$)$_n$SO$_2$OR, OCH$_2$CH(NHAc)CO$_2$R, OCH$_2$CH(NHR)CO$_2$R, and O(CH$_2$)$_n$-aryl;

W is selected from H, CO$_2$R, CON(R)$_2$, CH$_2$OH, CH$_2$OC$_{1-6}$ alkyl, CH$_2$OC$_{2-6}$ alkenyl, CH$_2$O(CH$_2$)$_n$CO$_2$R, CH$_2$O(CH$_2$)$_n$CON(R)$_2$, CH$_2$O—C$_{2-6}$ alkenyl-CO$_2$R, CH$_2$OCH$_2$CH$_2$CONRCH$_2$CO$_2$R, CH$_2$OCH$_2$CHMCONRCH$_2$CO$_2$R, CH$_2$O(CH$_2$)$_n$PO(OR)$_2$, CH$_2$O(CH$_2$)$_n$SO$_2$OR, CH$_2$OCH$_2$CH(NHAc)CO$_2$R, CH$_2$OCH$_2$CH(NHR)CO$_2$R, CH$_2$O—C$_{2-6}$ alkenyl, and CH$_2$O(CH$_2$)$_n$CONH$_2$, and CH$_2$O(CH$_2$)$_n$-aryl;

M is independently selected from H, C$_{1-6}$ alkyl, C$_{3-8}$ cycloalkyl, C$_{2-6}$ alkenyl, C$_{2-6}$ alkynyl, aryl, and (CH$_2$)$_n$-aryl, wherein aryl is substituted with 1-2 X$^4$;

m is independently selected from 0, 1, 2, 3, and 4; and, n is independently selected from 1, 2, 3, and 4;

provided that at least one of X, X$^1$, X$^2$, and X$^3$ is other than H, alkyl, alkoxy, hydroxyl, CF$_3$, and halo.

20. The method of claim 1, wherein the compound is a compound selected from Tables A-C or a stereoisomer or pharmaceutically acceptable salt thereof:

TABLE A

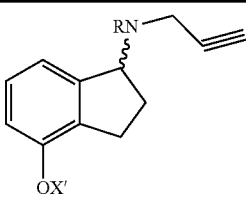

All compounds racemic

| Number | X | R |
|---|---|---|
| 1 | CH$_2$C$_6$H$_5$ | H |
| 2 | CH$_2$CH$_2$C$_6$H$_5$ | H |

TABLE A-continued

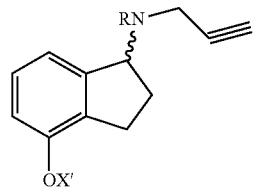

All compounds racemic

| Number | X | R |
|---|---|---|
| 3 | CH$_2$CO$_2$Et | CH$_3$ |
| 4 | CH$_2$CO$_2$Et | H |

TABLE B

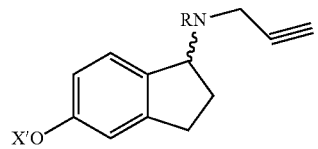

All compounds racemic

| Number | X | R |
|---|---|---|
| 5 | CH$_2$C$_6$H$_5$ | H |
| 6 | CH$_2$CH$_2$C$_6$H$_5$ | H |
| 7 | CH$_2$C$_6$H$_5$ | CH$_3$ |
| 8 | CH$_2$CO$_2$Et | H |
| 9 | CH$_2$CO$_2$Et | CH$_3$ |
| 10 | CH$_2$CO$_2$H | CH$_3$ |
| 11 | (CH$_2$)$_4$CO$_2$Et | H |
| 12 | CH$_2$CH=CHCO$_2$Et | CH$_3$ |
| 13 | CH$_2$CH=CHCO$_2$Et | H |
| 14 | CH$_2$C$_6$H$_5$CO$_2$Me(4) | CH$_3$ |
| 15 | CH$_2$C$_6$H$_5$CO$_2$Me(4) | H |
| 16 | CH$_2$C$_6$H$_5$CONH$_2$(4) | H |
| 17 | CH$_2$C$_6$H$_5$CO$_2$Me(3) | CH$_3$ |
| 18 | CH$_2$C$_6$H$_5$CO$_2$Me(3) | H |
| 19 | CH$_2$C$_6$H$_5$CO$_2$H(3) | H |
| 20 | CH$_2$C$_6$H$_5$CONH$_2$(3) | H |
| 21 | CH$_2$C$_6$H$_5$CH$_2$CO$_2$Me(4) | H |
| 22 | CH$_2$C$_6$H$_5$CH$_2$CO$_2$H(4) | H |
| 23 | CH$_2$C$_6$H$_5$OCH$_2$CO$_2$Et(4) | H |
| 24 | CH$_2$C$_6$H$_5$OCH$_2$CONH$_2$(4) | H |
| 26 | CH$_2$CH$_2$CH$_2$PO(OEt)$_2$ | H |

TABLE C

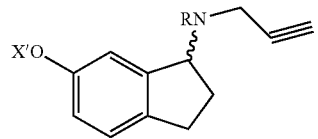

All compounds racemic

| Number | X | R |
|---|---|---|
| 27 | CH$_2$C$_6$H$_5$ | H |
| 28 | CH$_2$C$_6$H$_5$ | CH$_3$ |
| 29 | CH$_2$CH$_2$C$_6$H$_5$ | H |
| 30 | CH$_2$CO$_2$Et | CH$_3$ |
| 31 | CH$_2$CH=CHCO$_2$Et | CH$_3$ |
| 32 | CH$_2$CH=CHCO$_2$Et | H |
| 33 | CH$_2$C$_6$H$_5$CO$_2$Me(4) | CH$_3$ |
| 34 | CH$_2$C$_6$H$_5$CO$_2$Me(4) | H |
| 35 | CH$_2$C$_6$H$_5$CO$_2$Me(3) | H |

TABLE C-continued

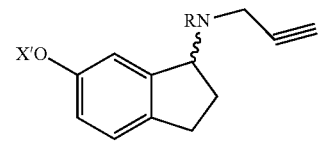

All compounds racemic

| Number | X | R |
|---|---|---|
| 36 | CH$_2$C$_6$H$_5$OCH$_2$CN(3) | H |
| 37 | CH$_2$C$_6$H$_5$CN(3) | H |
| 38 | CH$_2$C$_6$H$_5$CONH$_2$(3) | H |

21. The method of claim 1, wherein the compound is a compound selected from Tables I-Vb and VIIa-VIIc or a stereoisomer or a pharmaceutically acceptable salt thereof:

TABLE I

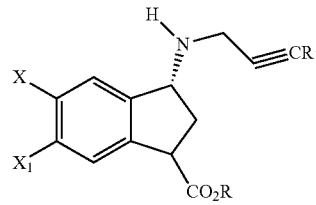

| Ex. # | X | X$^1$ | R | R$^1$ |
|---|---|---|---|---|
| 21 | OCH$_2$C$_6$H$_5$ | H | CH$_3$ | H |
| 22 | OCH$_2$C$_6$H$_5$ | H | H | H |
| 23 | OCH$_2$C$_6$H$_5$ | H | CH$_3$ | CH$_3$ |
| 24 | OCH$_2$C$_6$H$_5$ | H | H | CH$_3$ |
| 25 | H | OCH$_2$C$_6$H$_5$ | CH$_3$ | H |
| 26 | H | OCH$_2$C$_6$H$_5$ | H | H |
| 27 | H | OCH$_2$C$_6$H$_5$ | CH$_3$ | CH$_3$ |
| 28 | H | OCH$_2$C$_6$H$_5$ | H | CH$_3$ |
| 29 | OCH$_2$C$_6$H$_5$ | H | CH$_3$ | H |
| 30 | OCH$_2$C$_6$H$_5$ | H | H | H |
| 31 | OCH$_2$C$_6$H$_5$ | H | CH$_3$ | CH$_3$ |
| 32 | OCH$_2$C$_6$H$_5$ | H | H | CH$_3$ |
| 33 | OCH$_2$CH$_2$C$_6$H$_5$ | H | CH$_3$ | H |
| 34 | OCH$_2$CH$_2$C$_6$H$_5$ | H | H | H |
| 35 | OCH$_2$CH$_2$C$_6$H$_5$ | H | CH$_3$ | CH$_3$ |
| 36 | OCH$_2$CH$_2$C$_6$H$_5$ | H | H | CH$_3$ |
| 37 | H | OCH$_2$CH$_2$C$_6$H$_5$ | CH$_3$ | H |
| 38 | H | OCH$_2$CH$_2$C$_6$H$_5$ | H | H |
| 39 | H | OCH$_2$CH$_2$C$_6$H$_5$ | CH$_3$ | CH$_3$ |
| 40 | H | OCH$_2$CH$_2$C$_6$H$_5$ | H | CH$_3$ |
| 41 | OCH$_2$CH=CH$_2$ | H | CH$_3$ | H |
| 42 | OCH$_2$CH=CH$_2$ | H | H | H |
| 43 | OCH$_2$CH=CH$_2$ | H | CH$_3$ | CH$_3$ |
| 44 | OCH$_2$CH=CH$_2$ | H | H | CH$_3$ |
| 45 | H | OCH$_2$CH=CH$_2$ | CH$_3$ | H |
| 46 | H | OCH$_2$CH=CH$_2$ | H | H |
| 47 | H | OCH$_2$CH=CH$_2$ | CH$_3$ | CH$_3$ |
| 48 | H | OCH$_2$CH=CH$_2$ | H | CH$_3$ |
| 49 | OCH$_2$CONH$_2$ | H | CH$_3$ | H |
| 50 | OCH$_2$CONH$_2$ | H | H | H |
| 51 | OCH$_2$CONH$_2$ | H | CH$_3$ | CH$_3$ |
| 52 | OCH$_2$CONH$_2$ | H | H | CH$_3$ |
| 53 | H | OCH$_2$CONH$_2$ | CH$_3$ | H |
| 54 | H | OCH$_2$CONH$_2$ | H | H |
| 55 | H | OCH$_2$CONH$_2$ | CH$_3$ | CH$_3$ |
| 56 | H | OCH$_2$CONH$_2$ | H | CH$_3$ |
| 69 | NH$_2$ | H | CH$_3$ | H |
| 70 | NH$_2$ | H | H | H |
| 71 | NH$_2$ | H | CH$_3$ | CH$_3$ |
| 72 | NH$_2$ | H | H | CH$_3$ |
| 73 | NHSO$_2$CH$_3$ | H | CH$_3$ | H |

TABLE I-continued

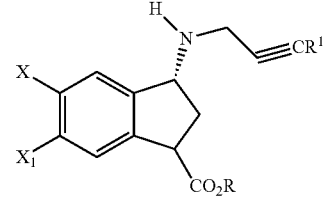

| Ex. # | X | X$^1$ | R | R$^1$ |
|---|---|---|---|---|
| 74 | NHSO$_2$CH$_3$ | H | H | H |
| 75 | NHSO$_2$CH$_3$ | H | CH$_3$ | CH$_3$ |
| 76 | NHSO$_2$CH$_3$ | H | H | CH$_3$ |

TABLE IIa

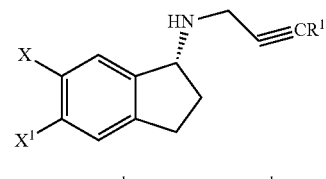

| Ex. # | X | X$^1$ | R$^1$ |
|---|---|---|---|
| 1. | OCH$_2$CH=CH$_2$ | H | CO$_2$CH$_2$CH$_3$ |
| 2. | OCH$_2$CH=CH$_2$ | H | CO$_2$H |
| 3. | OCH$_2$C$_6$H$_5$ | H | CO$_2$CH$_2$CH$_3$ |
| 4. | OCH$_2$C$_6$H$_5$ | H | CO$_2$H |
| 5. | OCH$_2$CH$_2$C$_6$H$_5$ | H | CO$_2$CH$_2$CH$_3$ |
| 6. | OCH$_2$CH$_2$C$_6$H$_5$ | H | CO$_2$H |
| 7. | OCH$_2$CONH$_2$ | H | CO$_2$CH$_2$CH$_3$ |
| 8. | OCH$_2$CONH$_2$ | H | CO$_2$H |
| 9. | NH$_2$ | H | CO$_2$CH$_2$CH$_3$ |
| 10. | NH$_2$ | H | CO$_2$H |
| 11. | NHSO$_2$CH$_3$ | H | CO$_2$CH$_2$CH$_3$ |
| 12. | NHSO$_2$CH$_3$ | H | CO$_2$H |
| 13. | H | OCH$_2$CH=CH$_2$ | CO$_2$CH$_2$CH$_3$ |
| 14. | H | OCH$_2$CH=CH$_2$ | CO$_2$H |
| 15. | H | OCH$_2$C$_6$H$_5$ | CO$_2$CH$_2$CH$_3$ |
| 16. | H | OCH$_2$C$_6$H$_5$ | CO$_2$H |
| 17. | H | OCH$_2$CH$_2$C$_6$H$_5$ | CO$_2$CH$_2$CH$_3$ |
| 18. | H | OCH$_2$CH$_2$C$_6$H$_5$ | CO$_2$H |
| 19. | H | OCH$_2$CONH$_2$ | CO$_2$CH$_2$CH$_3$ |
| 20. | H | OCH$_2$CONH$_2$ | CO$_2$H |
| 21. | OCH$_2$CH=CH$_2$ | H | CH$_2$CO$_2$CH$_2$CH$_3$ |
| 22. | OCH$_2$CH=CH$_2$ | H | CH$_2$CO$_2$H |
| 23. | OCH$_2$C$_6$H$_5$ | H | CH$_2$CO$_2$CH$_2$CH$_3$ |
| 24. | OCH$_2$C$_6$H$_5$ | H | CH$_2$CO$_2$H |
| 25. | OCH$_2$CH$_2$C$_6$H$_5$ | H | CH$_2$CO$_2$CH$_2$CH$_3$ |
| 26. | OCH$_2$CH$_2$C$_6$H$_5$ | H | CH$_2$CO$_2$H |
| 27. | OCH$_2$CONH$_2$ | H | CH$_2$CO$_2$CH$_2$CH$_3$ |
| 28. | OCH$_2$CONH$_2$ | H | CH$_2$CO$_2$H |
| 29. | NH$_2$ | H | CH$_2$CO$_2$CH$_2$CH$_3$ |
| 30. | NH$_2$ | H | CH$_2$CO$_2$H |
| 31. | NHSO$_2$CH$_3$ | H | CH$_2$CO$_2$CH$_2$CH$_3$ |
| 32. | NHSO$_2$CH$_3$ | H | CH$_2$CO$_2$H |
| 33. | H | OCH$_2$CH=CH$_2$ | CH$_2$CO$_2$CH$_2$CH$_3$ |
| 34. | H | OCH$_2$CH=CH$_2$ | CH$_2$CO$_2$H |
| 35. | H | OCH$_2$C$_6$H$_5$ | CH$_2$CO$_2$CH$_2$CH$_3$ |
| 36. | H | OCH$_2$C$_6$H$_5$ | CH$_2$CO$_2$H |
| 37. | H | OCH$_2$CH$_2$C$_6$H$_5$ | CH$_2$CO$_2$CH$_2$CH$_3$ |
| 38. | H | OCH$_2$CH$_2$C$_6$H$_5$ | CH$_2$CO$_2$H |
| 39. | H | OCH$_2$CONH$_2$ | CH$_2$CO$_2$CH$_2$CH$_3$ |
| 40. | H | OCH$_2$CONH$_2$ | CH$_2$CO$_2$H |
| 41. | OCH$_2$CH=CH$_2$ | H | CH$_2$CH$_2$CO$_2$CH$_2$CH$_3$ |
| 42. | OCH$_2$CH=CH$_2$ | H | CH$_2$CH$_2$CO$_2$H |
| 43. | OCH$_2$C$_6$H$_5$ | H | CH$_2$CH$_2$CO$_2$CH$_2$CH$_3$ |
| 44. | OCH$_2$C$_6$H$_5$ | H | CH$_2$CH$_2$CO$_2$H |
| 45. | OCH$_2$CH$_2$C$_6$H$_5$ | H | CH$_2$CH$_2$CO$_2$CH$_2$CH$_3$ |
| 46. | OCH$_2$CH$_2$C$_6$H$_5$ | H | CH$_2$CH$_2$CO$_2$H |
| 47. | OCH$_2$CONH$_2$ | H | CH$_2$CH$_2$CO$_2$CH$_2$CH$_3$ |
| 48. | OCH$_2$CONH$_2$ | H | CH$_2$CH$_2$CO$_2$H |
| 49. | NH$_2$ | H | CH$_2$CO$_2$CH$_2$CH$_2$CH$_3$ |

TABLE IIa-continued

Structure: indanyl with X and X¹ substituents on the benzene ring, and an HN-CH2-C≡C-CR¹ group at the 1-position.

| Ex. # | X | X¹ | R¹ |
|---|---|---|---|
| 50. | NH₂ | H | CH₂CH₂CO₂H |
| 51. | NHSO₂CH₃ | H | CH₂CH₂CO₂CH₂CH₃ |
| 52. | NHSO₂CH₃ | H | CH₂CH₂CO₂H |
| 53. | H | OCH₂CH=CH₂ | CH₂CO₂CH₂CH₃ |
| 54. | H | OCH₂CH=CH₂ | CH₂CH₂CO₂H |
| 55. | H | OCH₂C₆H₅ | CH₂CO₂CH₂CH₃ |
| 56. | H | OCH₂C₆H₅ | CH₂CH₂CO₂H |
| 57. | H | OCH₂CH₂C₆H₅ | CH₂CO₂CH₂CH₃ |
| 58. | H | OCH₂CH₂C₆H₅ | CH₂CH₂CO₂H |
| 59. | H | OCH₂CONH₂ | CH₂CO₂CH₂CH₃ |
| 60. | H | OCH₂CONH₂ | CH₂CH₂CO₂H |
| 61. | OCH₂CH=CH₂ | H | CH₂CH₂PO(OCH₂CH₃)₂ |
| 62. | OCH₂CH=CH₂ | H | CH₂CH₂PO(OH)₂ |
| 63. | OCH₂C₆H₅ | H | CH₂CH₂PO(OCH₂CH₃)₂ |
| 64. | OCH₂C₆H₅ | H | CH₂CH₂PO(OH)₂ |
| 65. | OCH₂CH₂C₆H₅ | H | CH₂CH₂PO(OCH₂CH₃)₂ |
| 66. | OCH₂CH₂C₆H₅ | H | CH₂CH₂PO(OH)₂ |
| 67. | OCH₂CONH₂ | H | CH₂CH₂PO(OCH₂CH₃)₂ |
| 68. | OCH₂CONH₂ | H | CH₂CH₂PO(OH)₂ |
| 69. | NH₂ | H | CH₂CH₂PO(OCH₂CH₃)₂ |
| 70. | NH₂ | H | CH₂CH₂PO(OH)₂ |
| 71. | NHSO₂CH₃ | H | CH₂CH₂PO(OCH₂CH₃)₂ |
| 72. | NHSO₂CH₃ | H | CH₂CH₂PO(OH)₂ |
| 73. | H | OCH₂CH=CH₂ | CH₂CH₂PO(OCH₂CH₃)₂ |
| 74. | H | OCH₂CH=CH₂ | CH₂CH₂PO(OH)₂ |
| 75. | H | OCH₂C₆H₅ | CH₂CH₂PO(OCH₂CH₃)₂ |
| 76. | H | OCH₂C₆H₅ | CH₂CH₂PO(OH)₂ |
| 77. | H | OCH₂CH₂C₆H₅ | CH₂CH₂PO(OCH₂CH₃)₂ |
| 78. | H | OCH₂CH₂C₆H₅ | CH₂CH₂PO(OH)₂ |
| 79. | H | OCH₂CONH₂ | CH₂CH₂PO(OCH₂CH₃)₂ |
| 80. | H | OCH₂CONH₂ | CH₂CH₂PO(OH)₂ |
| 81. | OCH₂CH=CH₂ | H | CH₂CH=CHCO₂CH₂CH₃ |
| 82. | OCH₂CH=CH₂ | H | CH₂CH=CHCO₂H |
| 83. | OCH₂C₆H₅ | H | CH₂CH=CHCO₂CH₂CH₃ |
| 84. | OCH₂C₆H₅ | H | CH₂CH=CHCO₂H |
| 85. | OCH₂CH₂C₆H₅ | H | CH₂CH=CHCO₂CH₂CH₃ |
| 86. | OCH₂CH₂C₆H₅ | H | CH₂CH=CHCO₂H |
| 87. | OCH₂CONH₂ | H | CH₂CH=CHCO₂CH₂CH₃ |
| 88. | OCH₂CONH₂ | H | CH₂CH=CHCO₂H |
| 89. | NH₂ | H | CH₂CH=CHCO₂CH₂CH₃ |
| 90. | NH₂ | H | CH₂CH=CHCO₂H |
| 91. | NHSO₂CH₃ | H | CH₂CH=CHCO₂CH₂CH₃ |
| 92. | NHSO₂CH₃ | H | CH₂CH=CHCO₂H |
| 93. | H | OCH₂CH=CH₂ | CH₂CH=CHCO₂CH₂CH₃ |
| 94. | H | OCH₂CH=CH₂ | CH₂CH=CHCO₂H |
| 95. | H | OCH₂C₆H₅ | CH₂CH=CHCO₂CH₂CH₃ |
| 96. | H | OCH₂C₆H₅ | CH₂CH=CHCO₂H |
| 97. | H | OCH₂CH₂C₆H₅ | CH₂CH=CHCO₂CH₂CH₃ |
| 98. | H | OCH₂CH₂C₆H₅ | CH₂CH=CHCO₂H |
| 99. | H | OCH₂CONH₂ | CH₂CH=CHCO₂CH₂CH₃ |
| 100. | H | OCH₂CONH₂ | CH₂CH=CHCO₂H |

TABLE IIb

Structure: indanyl with X and X¹ substituents on the benzene ring, and an H₃C-N-CH2-C≡C-CR¹ group at the 1-position.

| EX. # | X | X¹ | R¹ |
|---|---|---|---|
| 1. | OCH₂CH=CH₂ | H | CO₂CH₂CH₃ |
| 2. | OCH₂CH=CH₂ | H | CO₂H |
| 3. | OCH₂C₆H₅ | H | CO₂CH₂CH₃ |

TABLE IIb-continued

| EX. # | X | X¹ | R¹ |
|---|---|---|---|
| 4. | OCH₂C₆H₅ | H | CO₂H |
| 5. | OCH₂CH₂C₆H₅ | H | CO₂CH₂CH₃ |
| 6. | OCH₂CH₂C₆H₅ | H | CO₂H |
| 7. | OCH₂CONH₂ | H | CO₂CH₂CH₃ |
| 8. | OCH₂CONH₂ | H | CO₂H |
| 9. | NH₂ | H | CO₂CH₂CH₃ |
| 10. | NH₂ | H | CO₂H |
| 11. | NHSO₂CH₃ | H | CO₂CH₂CH₃ |
| 12. | NHSO₂CH₃ | H | CO₂H |
| 13. | H | OCH₂CH=CH₂ | CO₂CH₂CH₃ |
| 14. | H | OCH₂CH=CH₂ | CO₂H |
| 15. | H | OCH₂C₆H₅ | CO₂CH₂CH₃ |
| 16. | H | OCH₂C₆H₅ | CO₂H |
| 17. | H | OCH₂CH₂C₆H₅ | CO₂CH₂CH₃ |
| 18. | H | OCH₂CH₂C₆H₅ | CO₂H |
| 19. | H | OCH₂CONH₂ | CO₂CH₂CH₃ |
| 20. | H | OCH₂CONH₂ | CO₂H |
| 21. | OCH₂CH=CH₂ | H | CH₂CO₂CH₂CH₃ |
| 22. | OCH₂CH=CH₂ | H | CH₂CO₂H |
| 23. | OCH₂C₆H₅ | H | CH₂CO₂CH₂CH₃ |
| 24. | OCH₂C₆H₅ | H | CH₂CO₂H |
| 25. | OCH₂CH₂C₆H₅ | H | CH₂CO₂CH₂CH₃ |
| 26. | OCH₂CH₂C₆H₅ | H | CH₂CO₂H |
| 27. | OCH₂CONH₂ | H | CH₂CO₂CH₂CH₃ |
| 28. | OCH₂CONH₂ | H | CH₂CO₂H |
| 29. | NH₂ | H | CH₂CO₂CH₂CH₃ |
| 30. | NH₂ | H | CH₂CO₂H |
| 31. | NHSO₂CH₃ | H | CH₂CO₂CH₂CH₃ |
| 32. | NHSO₂CH₃ | H | CH₂CO₂H |
| 33. | H | OCH₂CH=CH₂ | CH₂CO₂CH₂CH₃ |
| 34. | H | OCH₂CH=CH₂ | CH₂CO₂H |
| 35. | H | OCH₂C₆H₅ | CH₂CO₂CH₂CH₃ |
| 36. | H | OCH₂C₆H₅ | CH₂CO₂H |
| 37. | H | OCH₂CH₂C₆H₅ | CH₂CO₂CH₂CH₃ |
| 38. | H | OCH₂CH₂C₆H₅ | CH₂CO₂H |
| 39. | H | OCH₂CONH₂ | CH₂CO₂CH₂CH₃ |
| 40. | H | OCH₂CONH₂ | CH₂CO₂H |
| 41. | OCH₂CH=CH₂ | H | CH₂CH₂CO₂CH₂CH₃ |
| 42. | OCH₂CH=CH₂ | H | CH₂CH₂CO₂H |
| 43. | OCH₂C₆H₅ | H | CH₂CH₂CO₂CH₂CH₃ |
| 44. | OCH₂C₆H₅ | H | CH₂CH₂CO₂H |
| 45. | OCH₂CH₂C₆H₅ | H | CH₂CH₂CO₂CH₂CH₃ |
| 46. | OCH₂CH₂C₆H₅ | H | CH₂CH₂CO₂H |
| 47. | OCH₂CONH₂ | H | CH₂CH₂CO₂CH₂CH₃ |
| 48. | OCH₂CONH₂ | H | CH₂CH₂CO₂H |
| 49. | NH₂ | H | CH₂CH₂CO₂CH₂CH₃ |
| 50. | NH₂ | H | CH₂CH₂CO₂H |
| 51. | NHSO₂CH₃ | H | CH₂CH₂CO₂CH₂CH₃ |
| 52. | NHSO₂CH₃ | H | CH₂CH₂CO₂H |
| 53. | H | OCH₂CH=CH₂ | CH₂CH₂CO₂CH₂CH₃ |
| 54. | H | OCH₂CH=CH₂ | CH₂CH₂CO₂H |
| 55. | H | OCH₂C₆H₅ | CH₂CH₂CO₂CH₂CH₃ |
| 56. | H | OCH₂C₆H₅ | CH₂CH₂CO₂H |
| 57. | H | OCH₂CH₂C₆H₅ | CH₂CH₂CO₂CH₂CH₃ |
| 58. | H | OCH₂CH₂C₆H₅ | CH₂CH₂CO₂H |
| 59. | H | OCH₂CONH₂ | CH₂CH₂CO₂CH₂CH₃ |
| 60. | H | OCH₂CONH₂ | CH₂CH₂CO₂H |
| 61. | OCH₂CH=CH₂ | H | CH₂CH₂PO(OCH₂CH₃)₂ |
| 62. | OCH₂CH=CH₂ | H | CH₂CH₂PO(OH)₂ |
| 63. | OCH₂C₆H₅ | H | CH₂CH₂PO(OCH₂CH₃)₂ |
| 64. | OCH₂C₆H₅ | H | CH₂CH₂PO(OH)₂ |
| 65. | OCH₂CH₂C₆H₅ | H | CH₂CH₂PO(OCH₂CH₃)₂ |
| 66. | OCH₂CH₂C₆H₅ | H | CH₂CH₂PO(OH)₂ |
| 67. | OCH₂CONH₂ | H | CH₂CH₂PO(OCH₂CH₃)₂ |
| 68. | OCH₂CONH₂ | H | CH₂CH₂PO(OH)₂ |
| 69. | NH₂ | H | CH₂CH₂PO(OCH₂CH₃)₂ |
| 70. | NH₂ | H | CH₂CH₂PO(OH)₂ |
| 71. | NHSO₂CH₃ | H | CH₂CH₂PO(OCH₂CH₃)₂ |
| 72. | NHSO₂CH₃ | H | CH₂CH₂PO(OH)₂ |

TABLE IIb-continued

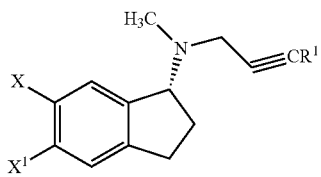

| EX. # | X | X¹ | R¹ |
|---|---|---|---|
| 73. | H | $OCH_2CH=CH_2$ | $CH_2CH_2PO(OCH_2CH_3)_2$ |
| 74. | H | $OCH_2CH=CH_2$ | $CH_2CH_2PO(OH)_2$ |
| 75. | H | $OCH_2C_6H_5$ | $CH_2CH_2PO(OCH_2CH_3)_2$ |
| 76. | H | $OCH_2C_6H_5$ | $CH_2CH_2PO(OH)_2$ |
| 77. | H | $OCH_2CH_2C_6H_5$ | $CH_2CH_2PO(OCH_2CH_3)_2$ |
| 78. | H | $OCH_2CH_2C_6H_5$ | $CH_2CH_2PO(OH)_2$ |
| 79. | H | $OCH_2CONH_2$ | $CH_2CH_2PO(OCH_2CH_3)_2$ |
| 80. | H | $OCH_2CONH_2$ | $CH_2CH_2PO(OH)_2$ |
| 81. | $OCH_2CH=CH_2$ | H | $CH_2CH=CHCO_2CH_2CH_3$ |
| 82. | $OCH_2CH=CH_2$ | H | $CH_2CH=CHCO_2H$ |
| 83. | $OCH_2C_6H_5$ | H | $CH_2CH=CHCO_2CH_2CH_3$ |
| 84. | $OCH_2C_6H_5$ | H | $CH_2CH=CHCO_2H$ |
| 85. | $OCH_2CH_2C_6H_5$ | H | $CH_2CH=CHCO_2CH_2CH_3$ |
| 86. | $OCH_2CH_2C_6H_5$ | H | $CH_2CH=CHCO_2H$ |
| 87. | $OCH_2CONH_2$ | H | $CH_2CH=CHCO_2CH_2CH_3$ |

TABLE IIb-continued

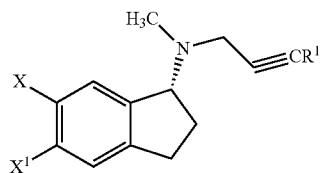

| EX. # | X | X¹ | R¹ |
|---|---|---|---|
| 88. | $OCH_2CONH_2$ | H | $CH_2CH=CHCO_2H$ |
| 89. | $NH_2$ | H | $CH_2CH=CHCO_2CH_2CH_3$ |
| 90. | $NH_2$ | H | $CH_2CH=CHCO_2H$ |
| 91. | $NHSO_2CH_3$ | H | $CH_2CH=CHCO_2CH_2CH_3$ |
| 92. | $NHSO_2CH_3$ | H | $CH_2CH=CHCO_2H$ |
| 93. | H | $OCH_2CH=CH_2$ | $CH_2CH=CHCO_2CH_2CH_3$ |
| 94. | H | $OCH_2CH=CH_2$ | $CH_2CH=CHCO_2H$ |
| 95. | H | $OCH_2C_6H_5$ | $CH_2CH=CHCO_2CH_2CH_3$ |
| 96. | H | $OCH_2C_6H_5$ | $CH_2CH=CHCO_2H$ |
| 97. | H | $OCH_2CH_2C_6H_5$ | $CH_2CH=CHCO_2CH_2CH_3$ |
| 98. | H | $OCH_2CH_2C_6H_5$ | $CH_2CH=CHCO_2H$ |
| 99. | H | $OCH_2CONH_2$ | $CH_2CH=CHCO_2CH_2CH_3$ |
| 100. | H | $OCH_2CONH_2$ | $CH_2CH=CHCO_2H$ |

TABLE III

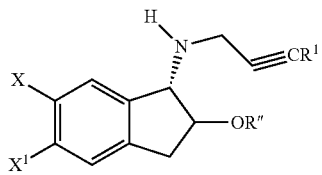

| Ex. # | X | X¹ | R¹ | R" |
|---|---|---|---|---|
| 1. | $OCH_2CH=CH_2$ | H | H | $CH_2-CO_2CH_2CH_3$ |
| 2. | $OCH_2CH=CH_2$ | H | $CH_3$ | $CH_2-CO_2H$ |
| 3. | $OCH_2C_6H_5$ | H | H | $CH_2-CO_2CH_2CH_3$ |
| 4. | $OCH_2C_6H_5$ | H | $CH_3$ | $CH_2-CO_2H$ |
| 5. | $OCH_2CH_2C_6H_5$ | H | H | $CH_2-CO_2CH_2CH_3$ |
| 6. | $OCH_2CH_2C_6H_5$ | H | $CH_3$ | $CH_2-CO_2H$ |
| 7. | $OCH_2-CONH_2$ | H | H | $CH_2-CO_2CH_2CH_3$ |
| 8. | $OCH_2-CONH_2$ | H | $CH_3$ | $CH_2-CO_2H$ |
| 9. | $NH_2$ | H | H | $CH_2-CO_2CH_2CH_3$ |
| 10. | $NH_2$ | H | $CH_3$ | $CH_2-CO_2H$ |
| 11. | $NHSO_2CH_3$ | H | H | $CH_2-CO_2CH_2CH_3$ |
| 12. | $NHSO_2CH_3$ | H | $CH_3$ | $CH_2-CO_2H$ |
| 13. | H | $OCH_2CH=CH_2$ | H | $CH_2-CO_2CH_2CH_3$ |
| 14. | H | $OCH_2CH=CH_2$ | $CH_3$ | $CH_2-CO_2H$ |
| 15. | H | $OCH_2C_6H_5$ | H | $CH_2-CO_2CH_2CH_3$ |
| 16. | H | $OCH_2C_6H_5$ | $CH_3$ | $CH_2-CO_2H$ |
| 17. | H | $OCH_2CH_2C_6H_5$ | H | $CH_2-CO_2CH_2CH_3$ |
| 18. | H | $OCH_2CH_2C_6H_5$ | $CH_3$ | $CH_2-CO_2H$ |
| 19. | H | $OCH_2-CONH_2$ | H | $CH_2-CO_2CH_2CH_3$ |
| 20. | H | $OCH_2-CONH_2$ | $CH_3$ | $CH_2-CO_2H$ |
| 21. | $OCH_2CH=CH_2$ | H | H | $CH_2CH_2-CO_2CH_2CH_3$ |
| 22. | $OCH_2CH=CH_2$ | H | $CH_3$ | $CH_2CH_2-CO_2H$ |
| 23. | $OCH_2C_6H_5$ | H | H | $CH_2CH_2-CO_2CH_2CH_3$ |
| 24. | $OCH_2C_6H_5$ | H | $CH_3$ | $CH_2CH_2-CO_2H$ |
| 25. | $OCH_2CH_2C_6H_5$ | H | H | $CH_2CH_2-CO_2CH_2CH_3$ |
| 26. | $OCH_2CH_2C_6H_5$ | H | $CH_3$ | $CH_2CH_2-CO_2H$ |
| 27. | $OCH_2-CONH_2$ | H | H | $CH_2CH_2-CO_2CH_2CH_3$ |
| 28. | $OCH_2-CONH_2$ | H | $CH_3$ | $CH_2CH_2-CO_2H$ |
| 35. | $NH_2$ | H | H | $CH_2CH_2-CO_2CH_2CH_3$ |
| 36. | $NH_2$ | H | $CH_3$ | $CH_2CH_2-CO_2H$ |
| 37. | $NHSO_2CH_3$ | H | H | $CH_2CH_2-CO_2CH_2CH_3$ |
| 38. | $NHSO_2CH_3$ | H | $CH_3$ | $CH_2CH_2-CO_2H$ |
| 39. | H | $OCH_2CH=CH_2$ | H | $CH_2CH_2-CO_2CH_2CH_3$ |
| 40. | H | $OCH_2CH=CH_2$ | $CH_3$ | $CH_2CH_2-CO_2H$ |
| 41. | H | $OCH_2C_6H_5$ | H | $CH_2CH_2-CO_2CH_2CH_3$ |
| 42. | H | $OCH_2C_6H_5$ | $CH_3$ | $CH_2CH_2-CO_2H$ |
| 43. | H | $OCH_2CH_2C_6H_5$ | H | $CH_2CH_2-CO_2CH_2CH_3$ |
| 44. | H | $OCH_2CH_2C_6H_5$ | $CH_3$ | $CH_2CH_2-CO_2H$ |
| 45. | H | $OCH_2-CONH_2$ | H | $CH_2CH_2-CO_2CH_2CH_3$ |

TABLE III-continued

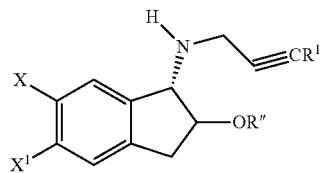

| Ex. # | X | X¹ | R¹ | R'' |
|---|---|---|---|---|
| 46. | H | $OCH_2$—$CONH_2$ | $CH_3$ | $CH_2CH_2$—$CO_2H$ |
| 47. | $OCH_2CH$=$CH_2$ | H | H | $CH_2CH_2P$—$O(OCH_2CH_3)_2$ |
| 48. | $OCH_2CH$=$CH_2$ | H | $CH_3$ | $CH_2CH_2P$—$O(OH)_2$ |
| 49. | $OCH_2C_6H_5$ | H | H | $CH_2CH_2P$—$O(OCH_2CH_3)_2$ |
| 50. | $OCH_2C_6H_5$ | H | $CH_3$ | $CH_2CH_2P$—$O(OH)_2$ |
| 51. | $OCH_2CH_2C_6H_5$ | H | H | $CH_2CH_2P$—$O(OCH_2CH_3)_2$ |
| 52. | $OCH_2CH_2C_6H_5$ | H | $CH_3$ | $CH_2CH_2P$—$O(OH)_2$ |
| 53. | $OCH_2$—$CONH_2$ | H | H | $CH_2CH_2P$—$O(OCH_2CH_3)_2$ |
| 54. | $OCH_2$—$CONH_2$ | H | $CH_3$ | $CH_2CH_2P$—$O(OH)_2$ |
| 55. | $NH_2$ | H | H | $CH_2CH_2P$—$O(OCH_2CH_3)_2$ |
| 56. | $NH_2$ | H | $CH_3$ | $CH_2CH_2P$—$O(OH)_2$ |
| 57. | $NHSO_2CH_3$ | H | H | $CH_2CH_2P$—$O(OCH_2CH_3)_2$ |
| 58. | $NHSO_2CH_3$ | H | $CH_3$ | $CH_2CH_2P$—$O(OH)_2$ |
| 59. | H | $OCH_2CH$=$CH_2$ | H | $CH_2CH_2P$—$O(OCH_2CH_3)_2$ |
| 60. | H | $OCH_2CH$=$CH_2$ | $CH_3$ | $CH_2CH_2P$—$O(OH)_2$ |
| 61. | H | $OCH_2C_6H_5$ | H | $CH_2CH_2P$—$O(OCH_2CH_3)_2$ |
| 62. | H | $OCH_2C_6H_5$ | $CH_3$ | $CH_2CH_2P$—$O(OH)_2$ |
| 63. | H | $OCH_2CH_2C_6H_5$ | H | $CH_2CH_2P$—$O(OCH_2CH_3)_2$ |
| 64. | H | $OCH_2CH_2C_6H_5$ | $CH_3$ | $CH_2CH_2P$—$O(OH)_2$ |
| 65. | H | $OCH_2$—$CONH_2$ | H | $CH_2CH_2P$—$O(OCH_2CH_3)_2$ |
| 66. | H | $OCH_2$—$CONH_2$ | $CH_3$ | $CH_2CH_2P$—$O(OH)_2$ |
| 67. | $OCH_2CH$=$CH_2$ | H | H | $CH_2CH$=$CH$—$CO_2CH_2CH_3$ |
| 68. | $OCH_2CH$=$CH_2$ | H | $CH_3$ | $CH_2CH$=$CH$—$CO_2H$ |
| 69. | $OCH_2C_6H_5$ | H | H | $CH_2CH$=$CH$—$CO_2CH_2CH_3$ |
| 70. | $OCH_2C_6H_5$ | H | $CH_3$ | $CH_2CH$=$CH$—$CO_2H$ |
| 71. | $OCH_2CH_2C_6H_5$ | H | H | $CH_2CH$=$CH$—$CO_2CH_2CH_3$ |
| 72. | $OCH_2CH_2C_6H_5$ | H | $CH_3$ | $CH_2CH$=$CH$—$CO_2H$ |
| 73. | $OCH_2$—$CONH_2$ | H | H | $CH_2CH$=$CH$—$CO_2CH_2CH_3$ |
| 74. | $OCH_2$—$CONH_2$ | H | $CH_3$ | $CH_2CH$=$CH$—$CO_2H$ |
| 75. | $NH_2$ | H | H | $CH_2CH$=$CH$—$CO_2CH_2CH_3$ |
| 76. | $NH_2$ | H | $CH_3$ | $CH_2CH$=$CH$—$CO_2H$ |
| 77. | $NHSO_2CH_3$ | H | H | $CH_2CH$=$CH$—$CO_2CH_2CH_3$ |
| 78. | $NHSO_2CH_3$ | H | $CH_3$ | $CH_2CH$=$CH$—$CO_2H$ |
| 79. | H | $OCH_2CH$=$CH_2$ | H | $CH_2CH$=$CH$—$CO_2CH_2CH_3$ |
| 80. | H | $OCH_2CH$=$CH_2$ | $CH_3$ | $CH_2CH$=$CH$—$CO_2H$ |
| 81. | H | $OCH_2C_6H_5$ | H | $CH_2CH$=$CH$—$CO_2CH_2CH_3$ |
| 82. | H | $OCH_2C_6H_5$ | $CH_3$ | $CH_2CH$=$CH$—$CO_2H$ |
| 83. | H | $OCH_2CH_2C_6H_5$ | H | $CH_2CH$=$CH$—$CO_2CH_2CH_3$ |
| 84. | H | $OCH_2CH_2C_6H_5$ | $CH_3$ | $CH_2CH$=$CH$—$CO_2H$ |
| 85. | H | $OCH_2$—$CONH_2$ | H | $CH_2CH$=$CH$—$CO_2CH_2CH_3$ |
| 86. | H | $OCH_2$—$CONH_2$ | $CH_3$ | $CH_2CH$=$CH$—$CO_2H$ |
| 87. | $OCH_2CH$=$CH_2$ | H | $CH_2$—$CO_2CH_2CH_3$ | $CH_3$ |
| 88. | $OCH_2CH$=$CH_2$ | H | $CH_2$—$CO_2H$ | $CH_3$ |
| 89. | $OCH_2C_6H_5$ | H | $CH_2$—$CO_2CH_2CH_3$ | $CH_3$ |
| 90. | $OCH_2C_6H_5$ | H | $CH_2$—$CO_2H$ | $CH_3$ |
| 91. | $OCH_2CH_2C_6H_5$ | H | $CH_2$—$CO_2CH_2CH_3$ | $CH_3$ |
| 92. | $OCH_2CH_2C_6H_5$ | H | $CH_2$—$CO_2H$ | $CH_3$ |
| 93. | $OCH_2$—$CONH_2$ | H | $CH_2$—$CO_2CH_2CH_3$ | $CH_3$ |
| 94. | $OCH_2$—$CONH_2$ | H | $CH_2$—$CO_2H$ | $CH_3$ |
| 95. | $NH_2$ | H | $CH_2$—$CO_2CH_2CH_3$ | $CH_3$ |
| 96. | $NH_2$ | H | $CH_2$—$CO_2H$ | $CH_3$ |
| 97. | $NHSO_2CH_3$ | H | $CH_2$—$CO_2CH_2CH_3$ | $CH_3$ |
| 98. | $NHSO_2CH_3$ | H | $CH_2$—$CO_2H$ | $CH_3$ |
| 99. | H | $OCH_2CH$=$CH_2$ | $CH_2$—$CO_2CH_2CH_3$ | $CH_3$ |
| 100. | H | $OCH_2CH$=$CH_2$ | $CH_2$—$CO_2H$ | $CH_3$ |
| 101. | H | $OCH_2C_6H_5$ | $CH_2$—$CO_2CH_2CH_3$ | $CH_3$ |
| 102. | H | $OCH_2C_6H_5$ | $CH_2$—$CO_2H$ | $CH_3$ |
| 103. | H | $OCH_2CH_2C_6H_5$ | $CH_2$—$CO_2CH_2CH_3$ | $CH_3$ |
| 104. | H | $OCH_2CH_2C_6H_5$ | $CH_2$—$CO_2H$ | $CH_3$ |
| 105. | H | $OCH_2$—$CONH_2$ | $CH_2$—$CO_2CH_2CH_3$ | $CH_3$ |
| 106. | H | $OCH_2$—$CONH_2$ | $CH_2$—$CO_2H$ | $CH_3$ |
| 107. | $OCH_2CH$=$CH_2$ | H | $CH_2CH_2P$—$O(OCH_2CH_3)_2$ | $CH_3$ |
| 108. | $OCH_2CH$=$CH_2$ | H | $CH_2CH_2P$—$O(OH)_2$ | $CH_3$ |
| 109. | $OCH_2C_6H_5$ | H | $CH_2CH_2P$—$O(OCH_2CH_3)_2$ | $CH_3$ |
| 110. | $OCH_2C_6H_5$ | H | $CH_2CH_2P$—$O(OH)_2$ | $CH_3$ |
| 111. | $OCH_2CH_2C_6H_5$ | H | $CH_2CH_2P$—$O(OCH_2CH_3)_2$ | $CH_3$ |
| 112. | $OCH_2CH_2C_6H_5$ | H | $CH_2CH_2P$—$O(OH)_2$ | $CH_3$ |
| 113. | $OCH_2$—$CONH_2$ | H | $CH_2CH_2P$—$O(OCH_2CH_3)_2$ | $CH_3$ |
| 114. | $OCH_2$—$CONH_2$ | H | $CH_2CH_2P$—$O(OH)_2$ | $CH_3$ |

TABLE III-continued

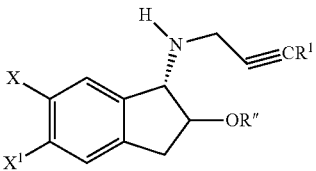

| Ex. # | X | X[1] | R[1] | R" |
|---|---|---|---|---|
| 115. | $NH_2$ | H | $CH_2CH_2P-O(OCH_2CH_3)_2$ | $CH_3$ |
| 116. | $NH_2$ | H | $CH_2CH_2P-O(OH)_2$ | $CH_3$ |
| 117. | $NHSO_2CH_3$ | H | $CH_2CH_2P-O(OCH_2CH_3)_2$ | $CH_3$ |
| 118. | $NHSO_2CH_3$ | H | $CH_2CH_2P-O(OH)_2$ | $CH_3$ |
| 119. | H | $OCH_2CH=CH_2$ | $CH_2CH_2P-O(OCH_2CH_3)_2$ | $CH_3$ |
| 120. | H | $OCH_2CH=CH_2$ | $CH_2CH_2P-O(OH)_2$ | $CH_3$ |
| 121. | H | $OCH_2C_6H_5$ | $CH_2CH_2P-O(OCH_2CH_3)_2$ | $CH_3$ |
| 122. | H | $OCH_2C_6H_5$ | $CH_2CH_2P-O(OH)_2$ | $CH_3$ |
| 123. | H | $OCH_2CH_2C_6H_5$ | $CH_2CH_2P-O(OCH_2CH_3)_2$ | $CH_3$ |
| 124. | H | $OCH_2CH_2C_6H_5$ | $CH_2CH_2P-O(OH)_2$ | $CH_3$ |
| 125. | H | $OCH_2-CONH_2$ | $CH_2CH_2P-O(OCH_2CH_3)_2$ | $CH_3$ |
| 126. | H | $OCH_2-CONH_2$ | $CH_2CH_2P-O(OH)_2$ | $CH_3$ |
| 127. | $OCH_2CH=CH_2$ | H | $CH_2-CO_2CH_2CH_3$ | $CH_2CH=CH_2$ |
| 128. | $OCH_2CH=CH_2$ | H | $CH_2-CO_2H$ | $CH_2CH=CH_2$ |
| 129. | $OCH_2C_6H_5$ | H | $CH_2-CO_2CH_2CH_3$ | $CH_2CH=CH_2$ |
| 130. | $OCH_2C_6H_5$ | H | $CH_2-CO_2H$ | $CH_2CH=CH_2$ |
| 131. | $OCH_2CH_2C_6H_5$ | H | $CH_2-CO_2CH_2CH_3$ | $CH_2CH=CH_2$ |
| 132. | $OCH_2CH_2C_6H_5$ | H | $CH_2-CO_2H$ | $CH_2CH=CH_2$ |
| 133. | $OCH_2-CONH_2$ | H | $CH_2-CO_2CH_2CH_3$ | $CH_2CH=CH_2$ |
| 134. | $OCH_2-CONH_2$ | H | $CH_2-CO_2H$ | $CH_2CH=CH_2$ |
| 135. | $NH_2$ | H | $CH_2-CO_2CH_2CH_3$ | $CH_2CH=CH_2$ |
| 136. | $NH_2$ | H | $CH_2-CO_2H$ | $CH_2CH=CH_2$ |
| 137. | $NHSO_2CH_3$ | H | $CH_2-CO_2CH_2CH_3$ | $CH_2CH=CH_2$ |
| 138. | $NHSO_2CH_3$ | H | $CH_2-CO_2H$ | $CH_2CH=CH_2$ |
| 139. | H | $OCH_2CH=CH_2$ | $CH_2-CO_2CH_2CH_3$ | $CH_2CH=CH_2$ |
| 140. | H | $OCH_2CH=CH_2$ | $CH_2-CO_2H$ | $CH_2CH=CH_2$ |
| 141. | H | $OCH_2C_6H_5$ | $CH_2-CO_2CH_2CH_3$ | $CH_2CH=CH_2$ |
| 142. | H | $OCH_2C_6H_5$ | $CH_2-CO_2H$ | $CH_2CH=CH_2$ |
| 143. | H | $OCH_2CH_2C_6H_5$ | $CH_2-CO_2CH_2CH_3$ | $CH_2CH=CH_2$ |
| 144. | H | $OCH_2CH_2C_6H_5$ | $CH_2-CO_2H$ | $CH_2CH=CH_2$ |
| 145. | H | $OCH_2-CONH_2$ | $CH_2-CO_2CH_2CH_3$ | $CH_2CH=CH_2$ |
| 146. | H | $OCH_2-CONH_2$ | $CH_2-CO_2H$ | $CH_2CH=CH_2$ |
| 147. | $OCH_2CH=CH_2$ | H | $CH_2CH_2P-O(OCH_2CH_3)_2$ | $CH_2CH=CH_2$ |
| 148. | $OCH_2CH=CH_2$ | H | $CH_2CH_2P-O(OH)_2$ | $CH_2CH=CH_2$ |
| 149. | $OCH_2C_6H_5$ | H | $CH_2CH_2P-O(OCH_2CH_3)_2$ | $CH_2CH=CH_2$ |
| 150. | $OCH_2C_6H_5$ | H | $CH_2CH_2P-O(OH)_2$ | $CH_2CH=CH_2$ |
| 151. | $OCH_2CH_2C_6H_5$ | H | $CH_2CH_2P-O(OCH_2CH_3)_2$ | $CH_2CH=CH_2$ |
| 152. | $OCH_2CH_2C_6H_5$ | H | $CH_2CH_2P-O(OH)_2$ | $CH_2CH=CH_2$ |
| 153. | $OCH_2-CONH_2$ | H | $CH_2CH_2P-O(OCH_2CH_3)_2$ | $CH_2CH=CH_2$ |
| 154. | $OCH_2-CONH_2$ | H | $CH_2CH_2P-O(OH)_2$ | $CH_2CH=CH_2$ |
| 155. | $NH_2$ | H | $CH_2CH_2P-O(OCH_2CH_3)_2$ | $CH_2CH=CH_2$ |
| 156. | $NH_2$ | H | $CH_2CH_2P-O(OH)_2$ | $CH_2CH=CH_2$ |
| 157. | $NHSO_2CH_3$ | H | $CH_2CH_2P-O(OCH_2CH_3)_2$ | $CH_2CH=CH_2$ |
| 158. | $NHSO_2CH_3$ | H | $CH_2CH_2P-O(OH)_2$ | $CH_2CH=CH_2$ |
| 159. | H | $OCH_2CH=CH_2$ | $CH_2CH_2P-O(OCH_2CH_3)_2$ | $CH_2CH=CH_2$ |
| 160. | H | $OCH_2CH=CH_2$ | $CH_2CH_2P-O(OH)_2$ | $CH_2CH=CH_2$ |
| 161. | H | $OCH_2C_6H_5$ | $CH_2CH_2P-O(OCH_2CH_3)_2$ | $CH_2CH=CH_2$ |
| 162. | H | $OCH_2C_6H_5$ | $CH_2CH_2P-O(OH)_2$ | $CH_2CH=CH_2$ |
| 163. | H | $OCH_2CH_2C_6H_5$ | $CH_2CH_2P-O(OCH_2CH_3)_2$ | $CH_2CH=CH_2$ |
| 164. | H | $OCH_2CH_2C_6H_5$ | $CH_2CH_2P-O(OH)_2$ | $CH_2CH=CH_2$ |
| 165. | H | $OCH_2-CONH_2$ | $CH_2CH_2P-O(OCH_2CH_3)_2$ | $CH_2CH=CH_2$ |
| 166. | H | $OCH_2-CONH_2$ | $CH_2CH_2P-O(OH)_2$ | $CH_2CH=CH_2$ |
| 167. | $OCH_2CH=CH_2$ | H | $CH_2-CO_2CH_2CH_3$ | $CH_2-CONH_2$ |
| 168. | $OCH_2CH=CH_2$ | H | $CH_2-CO_2H$ | $CH_2-CONH_2$ |
| 169. | $OCH_2C_6H_5$ | H | $CH_2-CO_2CH_2CH_3$ | $CH_2-CONH_2$ |
| 170. | $OCH_2C_6H_5$ | H | $CH_2-CO_2H$ | $CH_2-CONH_2$ |
| 171. | $OCH_2CH_2C_6H_5$ | H | $CH_2-CO_2CH_2CH_3$ | $CH_2-CONH_2$ |
| 172. | $OCH_2CH_2C_6H_5$ | H | $CH_2-CO_2H$ | $CH_2-CONH_2$ |
| 173. | $OCH_2-CONH_2$ | H | $CH_2-CO_2CH_2CH_3$ | $CH_2-CONH_2$ |
| 174. | $OCH_2-CONH_2$ | H | $CH_2-CO_2H$ | $CH_2-CONH_2$ |
| 175. | $NH_2$ | H | $CH_2-CO_2CH_2CH_3$ | $CH_2-CONH_2$ |
| 176. | $NH_2$ | H | $CH_2-CO_2H$ | $CH_2-CONH_2$ |
| 177. | $NHSO_2CH_3$ | H | $CH_2-CO_2CH_2CH_3$ | $CH_2-CONH_2$ |
| 178. | $NHSO_2CH_3$ | H | $CH_2-CO_2H$ | $CH_2-CONH_2$ |
| 179. | H | $OCH_2CH=CH_2$ | $CH_2-CO_2CH_2CH_3$ | $CH_2-CONH_2$ |
| 180. | H | $OCH_2CH=CH_2$ | $CH_2-CO_2H$ | $CH_2-CONH_2$ |
| 181. | H | $OCH_2C_6H_5$ | $CH_2-CO_2CH_2CH_3$ | $CH_2-CONH_2$ |
| 182. | H | $OCH_2C_6H_5$ | $CH_2-CO_2H$ | $CH_2-CONH_2$ |
| 183. | H | $OCH_2CH_2C_6H_5$ | $CH_2-CO_2CH_2CH_3$ | $CH_2-CONH_2$ |

TABLE III-continued

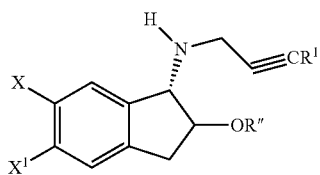

| Ex. # | X | X$^1$ | R$^1$ | R" |
|---|---|---|---|---|
| 184. | H | OCH$_2$CH$_2$C$_6$H$_5$ | CH$_2$—CO$_2$H | CH$_2$—CONH$_2$ |
| 185. | H | OCH$_2$—CONH$_2$ | CH$_2$—CO$_2$CH$_2$CH$_3$ | CH$_2$—CONH$_2$ |
| 186. | H | OCH$_2$—CONH$_2$ | CH$_2$—CO$_2$H | CH$_2$—CONH$_2$ |
| 187. | OCH$_2$CH=CH$_2$ | H | CH$_2$CH$_2$P—O(OCH$_2$CH$_3$)$_2$ | CH$_2$—CONH$_2$ |
| 188. | OCH$_2$CH=CH$_2$ | H | CH$_2$CH$_2$P—O(OH)$_2$ | CH$_2$—CONH$_2$ |
| 189. | OCH$_2$C$_6$H$_5$ | H | CH$_2$CH$_2$P—O(OCH$_2$CH$_3$)$_2$ | CH$_2$—CONH$_2$ |
| 190. | OCH$_2$C$_6$H$_5$ | H | CH$_2$CH$_2$P—O(OH)$_2$ | CH$_2$—CONH$_2$ |
| 191. | OCH$_2$CH$_2$C$_6$H$_5$ | H | CH$_2$CH$_2$P—O(OCH$_2$CH$_3$)$_2$ | CH$_2$—CONH$_2$ |
| 192. | OCH$_2$CH$_2$C$_6$H$_5$ | H | CH$_2$CH$_2$P—O(OH)$_2$ | CH$_2$—CONH$_2$ |
| 193. | OCH$_2$—CONH$_2$ | H | CH$_2$CH$_2$P—O(OCH$_2$CH$_3$)$_2$ | CH$_2$—CONH$_2$ |
| 194. | OCH$_2$—CONH$_2$ | H | CH$_2$CH$_2$P—O(OH)$_2$ | CH$_2$—CONH$_2$ |
| 195. | NH$_2$ | H | CH$_2$CH$_2$P—O(OCH$_2$CH$_3$)$_2$ | CH$_2$—CONH$_2$ |
| 196. | NH$_2$ | H | CH$_2$CH$_2$P—O(OH)$_2$ | CH$_2$—CONH$_2$ |
| 197. | NHSO$_2$CH$_3$ | H | CH$_2$CH$_2$P—O(OCH$_2$CH$_3$)$_2$ | CH$_2$—CONH$_2$ |
| 198. | NHSO$_2$CH$_3$ | H | CH$_2$CH$_2$P—O(OH)$_2$ | CH$_2$—CONH$_2$ |
| 199. | H | OCH$_2$CH=CH$_2$ | CH$_2$CH$_2$P—O(OCH$_2$CH$_3$)$_2$ | CH$_2$—CONH$_2$ |
| 200. | H | OCH$_2$CH=CH$_2$ | CH$_2$CH$_2$P—O(OH)$_2$ | CH$_2$—CONH$_2$ |
| 201. | H | OCH$_2$C$_6$H$_5$ | CH$_2$CH$_2$P—O(OCH$_2$CH$_3$)$_2$ | CH$_2$—CONH$_2$ |
| 202. | H | OCH$_2$C$_6$H$_5$ | CH$_2$CH$_2$P—O(OH)$_2$ | CH$_2$—CONH$_2$ |
| 203. | H | OCH$_2$CH$_2$C$_6$H$_5$ | CH$_2$CH$_2$P—O(OCH$_2$CH$_3$)$_2$ | CH$_2$—CONH$_2$ |
| 204. | H | OCH$_2$CH$_2$C$_6$H$_5$ | CH$_2$CH$_2$P—O(OH)$_2$ | CH$_2$—CONH$_2$ |
| 205. | H | OCH$_2$—CONH$_2$ | CH$_2$CH$_2$P—O(OCH$_2$CH$_3$)$_2$ | CH$_2$—CONH$_2$ |
| 206. | H | OCH$_2$—CONH$_2$ | CH$_2$CH$_2$P—O(OH)$_2$ | CH$_2$—CONH$_2$ |
| 207. | OCH$_2$CH=CH$_2$ | H | CH$_2$—CO$_2$CH$_2$CH$_3$ | CH$_2$C$_6$H$_5$ |
| 208. | OCH$_2$CH=CH$_2$ | H | CH$_2$—CO$_2$H | CH$_2$C$_6$H$_5$ |
| 209. | OCH$_2$C$_6$H$_5$ | H | CH$_2$—CO$_2$CH$_2$CH$_3$ | CH$_2$C$_6$H$_5$ |
| 210. | OCH$_2$C$_6$H$_5$ | H | CH$_2$—CO$_2$H | CH$_2$C$_6$H$_5$ |
| 211. | OCH$_2$CH$_2$C$_6$H$_5$ | H | CH$_2$—CO$_2$CH$_2$CH$_3$ | CH$_2$C$_6$H$_5$ |
| 212. | OCH$_2$CH$_2$C$_6$H$_5$ | H | CH$_2$—CO$_2$H | CH$_2$C$_6$H$_5$ |
| 213. | OCH$_2$—CONH$_2$ | H | CH$_2$—CO$_2$CH$_2$CH$_3$ | CH$_2$C$_6$H$_5$ |
| 214. | OCH$_2$—CONH$_2$ | H | CH$_2$—CO$_2$H | CH$_2$C$_6$H$_5$ |
| 215. | NH$_2$ | H | CH$_2$—CO$_2$CH$_2$CH$_3$ | CH$_2$C$_6$H$_5$ |
| 216. | NH$_2$ | H | CH$_2$—CO$_2$H | CH$_2$C$_6$H$_5$ |
| 217. | NHSO$_2$CH$_3$ | H | CH$_2$—CO$_2$CH$_2$CH$_3$ | CH$_2$C$_6$H$_5$ |
| 218. | NHSO$_2$CH$_3$ | H | CH$_2$—CO$_2$H | CH$_2$C$_6$H$_5$ |
| 219. | H | OCH$_2$CH=CH$_2$ | CH$_2$—CO$_2$CH$_2$CH$_3$ | CH$_2$C$_6$H$_5$ |
| 220. | H | OCH$_2$CH=CH$_2$ | CH$_2$—CO$_2$H | CH$_2$C$_6$H$_5$ |
| 221. | H | OCH$_2$C$_6$H$_5$ | CH$_2$—CO$_2$CH$_2$CH$_3$ | CH$_2$C$_6$H$_5$ |
| 222. | H | OCH$_2$C$_6$H$_5$ | CH$_2$—CO$_2$H | CH$_2$C$_6$H$_5$ |
| 223. | H | OCH$_2$CH$_2$C$_6$H$_5$ | CH$_2$—CO$_2$CH$_2$CH$_3$ | CH$_2$C$_6$H$_5$ |
| 224. | H | OCH$_2$CH$_2$C$_6$H$_5$ | CH$_2$—CO$_2$H | CH$_2$C$_6$H$_5$ |
| 225. | H | OCH$_2$—CONH$_2$ | CH$_2$—CO$_2$CH$_2$CH$_3$ | CH$_2$C$_6$H$_5$ |
| 226. | H | OCH$_2$—CONH$_2$ | CH$_2$—CO$_2$H | CH$_2$C$_6$H$_5$ |
| 227. | OCH$_2$CH=CH$_2$ | H | CH$_2$CH$_2$P—O(OCH$_2$CH$_3$)$_2$ | CH$_2$C$_6$H$_5$ |
| 228. | OCH$_2$CH=CH$_2$ | H | CH$_2$CH$_2$P—O(OH)$_2$ | CH$_2$C$_6$H$_5$ |
| 229. | OCH$_2$C$_6$H$_5$ | H | CH$_2$CH$_2$P—O(OCH$_2$CH$_3$)$_2$ | CH$_2$C$_6$H$_5$ |
| 230. | OCH$_2$C$_6$H$_5$ | H | CH$_2$CH$_2$P—O(OH)$_2$ | CH$_2$C$_6$H$_5$ |
| 231. | OCH$_2$CH$_2$C$_6$H$_5$ | H | CH$_2$CH$_2$P—O(OCH$_2$CH$_3$)$_2$ | CH$_2$C$_6$H$_5$ |
| 232. | OCH$_2$CH$_2$C$_6$H$_5$ | H | CH$_2$CH$_2$P—O(OH)$_2$ | CH$_2$C$_6$H$_5$ |
| 233. | OCH$_2$—CONH$_2$ | H | CH$_2$CH$_2$P—O(OCH$_2$CH$_3$)$_2$ | CH$_2$C$_6$H$_5$ |
| 234. | OCH$_2$—CONH$_2$ | H | CH$_2$CH$_2$P—O(OH)$_2$ | CH$_2$C$_6$H$_5$ |
| 235. | NH$_2$ | H | CH$_2$CH$_2$P—O(OCH$_2$CH$_3$)$_2$ | CH$_2$C$_6$H$_5$ |
| 236. | NH$_2$ | H | CH$_2$CH$_2$P—O(OH)$_2$ | CH$_2$C$_6$H$_5$ |
| 237. | NHSO$_2$CH$_3$ | H | CH$_2$CH$_2$P—O(OCH$_2$CH$_3$)$_2$ | CH$_2$C$_6$H$_5$ |
| 238. | NHSO$_2$CH$_3$ | H | CH$_2$CH$_2$P—O(OH)$_2$ | CH$_2$C$_6$H$_5$ |
| 239. | H | OCH$_2$CH=CH$_2$ | CH$_2$CH$_2$P—O(OCH$_2$CH$_3$)$_2$ | CH$_2$—CONH$_2$ |
| 240. | H | OCH$_2$CH=CH$_2$ | CH$_2$CH$_2$P—O(OH)$_2$ | CH$_2$—CONH$_2$ |
| 241. | H | OCH$_2$C$_6$H$_5$ | CH$_2$CH$_2$P—O(OCH$_2$CH$_3$)$_2$ | CH$_2$—CONH$_2$ |
| 242. | H | OCH$_2$C$_6$H$_5$ | CH$_2$CH$_2$P—O(OH)$_2$ | CH$_2$—CONH$_2$ |
| 243. | H | OCH$_2$CH$_2$C$_6$H$_5$ | CH$_2$CH$_2$P—O(OCH$_2$CH$_3$)$_2$ | CH$_2$—CONH$_2$ |
| 244. | H | OCH$_2$CH$_2$C$_6$H$_5$ | CH$_2$CH$_2$P—O(OH)$_2$ | CH$_2$—CONH$_2$ |
| 245. | H | OCH$_2$—CONH$_2$ | CH$_2$CH$_2$P—O(OCH$_2$CH$_3$)$_2$ | CH$_2$—CONH$_2$ |
| 246. | H | OCH$_2$—CONH$_2$ | CH$_2$CH$_2$P—O(OH)$_2$ | CH$_2$—CONH$_2$ |

TABLE IV

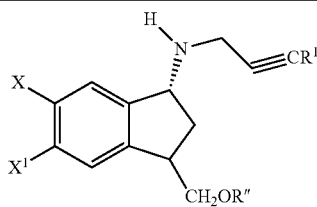

| Ex. # | X | X¹ | R¹ | R" |
|---|---|---|---|---|
| 1. | OCH$_2$CH=CH$_2$ | H | H | CH$_2$—CO$_2$CH$_2$CH$_3$ |
| 2. | OCH$_2$CH=CH$_2$ | H | CH$_3$ | CH$_2$—CO$_2$H |
| 3. | OCH$_2$C$_6$H$_5$ | H | H | CH$_2$—CO$_2$CH$_2$CH$_3$ |
| 4. | OCH$_2$C$_6$H$_5$ | H | CH$_3$ | CH$_2$—CO$_2$H |
| 5. | OCH$_2$CH$_2$C$_6$H$_5$ | H | H | CH$_2$—CO$_2$CH$_2$CH$_3$ |
| 6. | OCH$_2$CH$_2$C$_6$H$_5$ | H | CH$_3$ | CH$_2$—CO$_2$H |
| 7. | OCH$_2$—CONH$_2$ | H | H | CH$_2$—CO$_2$CH$_2$CH$_3$ |
| 8. | OCH$_2$—CONH$_2$ | H | CH$_3$ | CH$_2$—CO$_2$H |
| 9. | NH$_2$ | H | H | CH$_2$—CO$_2$CH$_2$CH$_3$ |
| 10. | NH$_2$ | H | CH$_3$ | CH$_2$—CO$_2$H |
| 11. | NHSO$_2$CH$_3$ | H | H | CH$_2$—CO$_2$CH$_2$CH$_3$ |
| 12. | NHSO$_2$CH$_3$ | H | CH$_3$ | CH$_2$—CO$_2$H |
| 13. | H | OCH$_2$CH=CH$_2$ | H | CH$_2$—CO$_2$CH$_2$CH$_3$ |
| 14. | H | OCH$_2$CH=CH$_2$ | CH$_3$ | CH$_2$—CO$_2$H |
| 15. | H | OCH$_2$C$_6$H$_5$ | H | CH$_2$—CO$_2$CH$_2$CH$_3$ |
| 16. | H | OCH$_2$C$_6$H$_5$ | CH$_3$ | CH$_2$—CO$_2$H |
| 17. | H | OCH$_2$CH$_2$C$_6$H$_5$ | H | CH$_2$—CO$_2$CH$_2$CH$_3$ |
| 18. | H | OCH$_2$CH$_2$C$_6$H$_5$ | CH$_3$ | CH$_2$—CO$_2$H |
| 19. | H | OCH$_2$—CONH$_2$ | H | CH$_2$—CO$_2$CH$_2$CH$_3$ |
| 20. | H | OCH$_2$—CONH$_2$ | CH$_3$ | CH$_2$—CO$_2$H |
| 21. | OCH$_2$CH=CH$_2$ | H | H | CH$_2$CH$_2$—CO$_2$CH$_2$CH$_3$ |
| 22. | OCH$_2$CH=CH$_2$ | H | CH$_3$ | CH$_2$CH$_2$—CO$_2$H |
| 23. | OCH$_2$C$_6$H$_5$ | H | H | CH$_2$CH$_2$—CO$_2$CH$_2$CH$_3$ |
| 24. | OCH$_2$C$_6$H$_5$ | H | CH$_3$ | CH$_2$CH$_2$—CO$_2$H |
| 25. | OCH$_2$CH$_2$C$_6$H$_5$ | H | H | CH$_2$CH$_2$—CO$_2$CH$_2$CH$_3$ |
| 26. | OCH$_2$CH$_2$C$_6$H$_5$ | H | CH$_3$ | CH$_2$CH$_2$—CO$_2$H |
| 27. | OCH$_2$—CONH$_2$ | H | H | CH$_2$CH$_2$—CO$_2$CH$_2$CH$_3$ |
| 28. | OCH$_2$—CONH$_2$ | H | CH$_3$ | CH$_2$CH$_2$—CO$_2$H |
| 29. | NH$_2$ | H | H | CH$_2$CH$_2$—CO$_2$CH$_2$CH$_3$ |
| 30. | NH$_2$ | H | CH$_3$ | CH$_2$CH$_2$—CO$_2$H |
| 31. | NHSO$_2$CH$_3$ | H | H | CH$_2$CH$_2$—CO$_2$CH$_2$CH$_3$ |
| 32. | NHSO$_2$CH$_3$ | H | CH$_3$ | CH$_2$CH$_2$—CO$_2$H |
| 33. | H | OCH$_2$CH=CH$_2$ | H | CH$_2$CH$_2$—CO$_2$CH$_2$CH$_3$ |
| 34. | H | OCH$_2$CH=CH$_2$ | CH$_3$ | CH$_2$CH$_2$—CO$_2$H |
| 35. | H | OCH$_2$C$_6$H$_5$ | H | CH$_2$CH$_2$—CO$_2$CH$_2$CH$_3$ |
| 36. | H | OCH$_2$C$_6$H$_5$ | CH$_3$ | CH$_2$CH$_2$—CO$_2$H |
| 37. | H | OCH$_2$CH$_2$C$_6$H$_5$ | H | CH$_2$CH$_2$—CO$_2$CH$_2$CH$_3$ |
| 38. | H | OCH$_2$CH$_2$C$_6$H$_5$ | CH$_3$ | CH$_2$CH$_2$—CO$_2$H |
| 39. | H | OCH$_2$—CONH$_2$ | H | CH$_2$CH$_2$—CO$_2$CH$_2$CH$_3$ |
| 40. | H | OCH$_2$—CONH$_2$ | CH$_3$ | CH$_2$CH$_2$—CO$_2$H |
| 41. | OCH$_2$CH=CH$_2$ | H | H | CH$_2$CH$_2$P—O(OCH$_2$CH$_3$)$_2$ |
| 42. | OCH$_2$CH=CH$_2$ | H | CH$_3$ | CH$_2$CH$_2$P—O(OH)$_2$ |
| 43. | OCH$_2$C$_6$H$_5$ | H | H | CH$_2$CH$_2$P—O(OCH$_2$CH$_3$)$_2$ |
| 44. | OCH$_2$C$_6$H$_5$ | H | CH$_3$ | CH$_2$CH$_2$P—O(OH)$_2$ |
| 45. | OCH$_2$CH$_2$C$_6$H$_5$ | H | H | CH$_2$CH$_2$P—O(OCH$_2$CH$_3$)$_2$ |
| 46. | OCH$_2$CH$_2$C$_6$H$_5$ | H | CH$_3$ | CH$_2$CH$_2$P—O(OH)$_2$ |
| 47. | OCH$_2$—CONH$_2$ | H | H | CH$_2$CH$_2$P—O(OCH$_2$CH$_3$)$_2$ |
| 48. | OCH$_2$—CONH$_2$ | H | CH$_3$ | CH$_2$CH$_2$P—O(OH)$_2$ |
| 49. | NH$_2$ | H | H | CH$_2$CH$_2$P—O(OCH$_2$CH$_3$)$_2$ |
| 50. | NH$_2$ | H | CH$_3$ | CH$_2$CH$_2$P—O(OH)$_2$ |
| 51. | NHSO$_2$CH$_3$ | H | H | CH$_2$CH$_2$P—O(OCH$_2$CH$_3$)$_2$ |
| 52. | NHSO$_2$CH$_3$ | H | CH$_3$ | CH$_2$CH$_2$P—O(OH)$_2$ |
| 53. | H | OCH$_2$CH=CH$_2$ | H | CH$_2$CH$_2$P—O(OCH$_2$CH$_3$)$_2$ |
| 54. | H | OCH$_2$CH=CH$_2$ | CH$_3$ | CH$_2$CH$_2$P—O(OH)$_2$ |
| 55. | H | OCH$_2$C$_6$H$_5$ | H | CH$_2$CH$_2$P—O(OCH$_2$CH$_3$)$_2$ |
| 56. | H | OCH$_2$C$_6$H$_5$ | CH$_3$ | CH$_2$CH$_2$P—O(OH)$_2$ |
| 57. | H | OCH$_2$CH$_2$C$_6$H$_5$ | H | CH$_2$CH$_2$P—O(OCH$_2$CH$_3$)$_2$ |
| 58. | H | OCH$_2$CH$_2$C$_6$H$_5$ | CH$_3$ | CH$_2$CH$_2$P—O(OH)$_2$ |
| 59. | H | OCH$_2$—CONH$_2$ | H | CH$_2$CH$_2$P—O(OCH$_2$CH$_3$)$_2$ |
| 60. | H | OCH$_2$—CONH$_2$ | CH$_3$ | CH$_2$CH$_2$P—O(OH)$_2$ |
| 61. | OCH$_2$CH=CH$_2$ | H | H | CH$_2$CH=CH—CO$_2$CH$_2$CH$_3$ |
| 62. | OCH$_2$CH=CH$_2$ | H | CH$_3$ | CH$_2$CH=CH—CO$_2$H |
| 63. | OCH$_2$C$_6$H$_5$ | H | H | CH$_2$CH=CH—CO$_2$CH$_2$CH$_3$ |
| 64. | OCH$_2$C$_6$H$_5$ | H | CH$_3$ | CH$_2$CH=CH—CO$_2$H |
| 65. | OCH$_2$CH$_2$C$_6$H$_5$ | H | H | CH$_2$CH=CH—CO$_2$CH$_2$CH$_3$ |
| 66. | OCH$_2$CH$_2$C$_6$H$_5$ | H | CH$_3$ | CH$_2$CH=CH—CO$_2$H |
| 67. | OCH$_2$—CONH$_2$ | H | H | CH$_2$CH=CH—CO$_2$CH$_2$CH$_3$ |

TABLE IV-continued

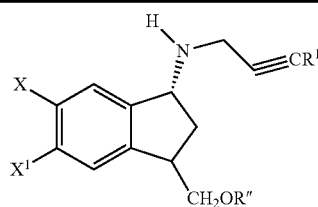

| Ex. # | X | X¹ | R¹ | R" |
|---|---|---|---|---|
| 68. | OCH₂—CONH₂ | H | CH₃ | CH₂CH=CH—CO₂H |
| 69. | NH₂ | H | H | CH₂CH=CH—CO₂CH₂CH₃ |
| 70. | NH₂ | H | CH₃ | CH₂CH=CH—CO₂H |
| 71. | NHSO₂CH₃ | H | H | CH₂CH=CH—CO₂CH₂CH₃ |
| 72. | NHSO₂CH₃ | H | CH₃ | CH₂CH=CH—CO₂H |
| 73. | H | OCH₂CH=CH₂ | H | CH₂CH=CH—CO₂CH₂CH₃ |
| 74. | H | OCH₂CH=CH₂ | CH₃ | CH₂CH=CH—CO₂H |
| 75. | H | OCH₂C₆H₅ | H | CH₂CH=CH—CO₂CH₂CH₃ |
| 76. | H | OCH₂C₆H₅ | CH₃ | CH₂CH=CH—CO₂H |
| 77. | H | OCH₂CH₂C₆H₅ | H | CH₂CH=CH—CO₂CH₂CH₃ |
| 78. | H | OCH₂CH₂C₆H₅ | CH₃ | CH₂CH=CH—CO₂H |
| 79. | H | OCH₂—CONH₂ | H | CH₂CH=CH—CO₂CH₂CH₃ |
| 80. | H | OCH₂—CONH₂ | CH₃ | CH₂CH=CH—CO₂H |
| 81. | OCH₂CH=CH₂ | H | CH₂—CO₂CH₂CH₃ | CH₃ |
| 82. | OCH₂CH=CH₂ | H | CH₂—CO₂H | CH₃ |
| 83. | OCH₂C₆H₅ | H | CH₂—CO₂CH₂CH₃ | CH₃ |
| 84. | OCH₂C₆H₅ | H | CH₂—CO₂H | CH₃ |
| 85. | OCH₂CH₂C₆H₅ | H | CH₂—CO₂CH₂CH₃ | CH₃ |
| 86. | OCH₂CH₂C₆H₅ | H | CH₂—CO₂H | CH₃ |
| 87. | OCH₂—CONH₂ | H | CH₂—CO₂CH₂CH₃ | CH₃ |
| 88. | OCH₂—CONH₂ | H | CH₂—CO₂H | CH₃ |
| 89. | NH₂ | H | CH₂—CO₂CH₂CH₃ | CH₃ |
| 90. | NH₂ | H | CH₂—CO₂H | CH₃ |
| 91. | NHSO₂CH₃ | H | CH₂—CO₂CH₂CH₃ | CH₃ |
| 92. | NHSO₂CH₃ | H | CH₂—CO₂H | CH₃ |
| 93. | H | OCH₂CH=CH₂ | CH₂—CO₂CH₂CH₃ | CH₃ |
| 94. | H | OCH₂CH=CH₂ | CH₂—CO₂H | CH₃ |
| 95. | H | OCH₂C₆H₅ | CH₂—CO₂CH₂CH₃ | CH₃ |
| 96. | H | OCH₂C₆H₅ | CH₂—CO₂H | CH₃ |
| 97. | H | OCH₂CH₂C₆H₅ | CH₂—CO₂CH₂CH₃ | CH₃ |
| 98. | H | OCH₂CH₂C₆H₅ | CH₂—CO₂H | CH₃ |
| 99. | H | OCH₂—CONH₂ | CH₂—CO₂CH₂CH₃ | CH₃ |
| 100. | H | OCH₂—CONH₂ | CH₂—CO₂H | CH₃ |
| 101. | OCH₂CH=CH₂ | H | CH₂CH₂P—O(OCH₂CH₃)₂ | CH₃ |
| 102. | OCH₂CH=CH₂ | H | CH₂CH₂P—O(OH)₂ | CH₃ |
| 103. | OCH₂C₆H₅ | H | CH₂CH₂P—O(OCH₂CH₃)₂ | CH₃ |
| 104. | OCH₂C₆H₅ | H | CH₂CH₂P—O(OH)₂ | CH₃ |
| 105. | OCH₂CH₂C₆H₅ | H | CH₂CH₂P—O(OCH₂CH₃)₂ | CH₃ |
| 106. | OCH₂CH₂C₆H₅ | H | CH₂CH₂P—O(OH)₂ | CH₃ |
| 107. | OCH₂—CONH₂ | H | CH₂CH₂P—O(OCH₂CH₃)₂ | CH₃ |
| 108. | OCH₂—CONH₂ | H | CH₂CH₂P—O(OH)₂ | CH₃ |
| 109. | NH₂ | H | CH₂CH₂P—O(OCH₂CH₃)₂ | CH₃ |
| 110. | NH₂ | H | CH₂CH₂P—O(OH)₂ | CH₃ |
| 111. | NHSO₂CH₃ | H | CH₂CH₂P—O(OCH₂CH₃)₂ | CH₃ |
| 112. | NHSO₂CH₃ | H | CH₂CH₂P—O(OH)₂ | CH₃ |
| 113. | H | OCH₂CH=CH₂ | CH₂CH₂P—O(OCH₂CH₃)₂ | CH₃ |
| 114. | H | OCH₂CH=CH₂ | CH₂CH₂P—O(OH)₂ | CH₃ |
| 115. | H | OCH₂C₆H₅ | CH₂CH₂P—O(OCH₂CH₃)₂ | CH₃ |
| 116. | H | OCH₂C₆H₅ | CH₂CH₂P—O(OH)₂ | CH₃ |
| 117. | H | OCH₂CH₂C₆H₅ | CH₂CH₂P—O(OCH₂CH₃)₂ | CH₃ |
| 118. | H | OCH₂CH₂C₆H₅ | CH₂CH₂P—O(OH)₂ | CH₃ |
| 119. | H | OCH₂—CONH₂ | CH₂CH₂P—O(OCH₂CH₃)₂ | CH₃ |
| 120. | H | OCH₂—CONH₂ | CH₂CH₂P—O(OH)₂ | CH₃ |
| 121. | OCH₂CH=CH₂ | H | CH₂—CO₂CH₂CH₃ | CH₂CH=CH₂ |
| 122. | OCH₂CH=CH₂ | H | CH₂—CO₂H | CH₂CH=CH₂ |
| 123. | OCH₂C₆H₅ | H | CH₂—CO₂CH₂CH₃ | CH₂CH=CH₂ |
| 124. | OCH₂C₆H₅ | H | CH₂—CO₂H | CH₂CH=CH₂ |
| 125. | OCH₂CH₂C₆H₅ | H | CH₂—CO₂CH₂CH₃ | CH₂CH=CH₂ |
| 126. | OCH₂CH₂C₆H₅ | H | CH₂—CO₂H | CH₂CH=CH₂ |
| 127. | OCH₂—CONH₂ | H | CH₂—CO₂CH₂CH₃ | CH₂CH=CH₂ |
| 128. | OCH₂—CONH₂ | H | CH₂—CO₂H | CH₂CH=CH₂ |
| 129. | NH₂ | H | CH₂—CO₂CH₂CH₃ | CH₂CH=CH₂ |
| 130. | NH₂ | H | CH₂—CO₂H | CH₂CH=CH₂ |
| 131. | NHSO₂CH₃ | H | CH₂—CO₂CH₂CH₃ | CH₂CH=CH₂ |
| 132. | NHSO₂CH₃ | H | CH₂—CO₂H | CH₂CH=CH₂ |
| 133. | H | OCH₂CH=CH₂ | CH₂—CO₂CH₂CH₃ | CH₂CH=CH₂ |
| 134. | H | OCH₂CH=CH₂ | CH₂—CO₂H | CH₂CH=CH₂ |

TABLE IV-continued

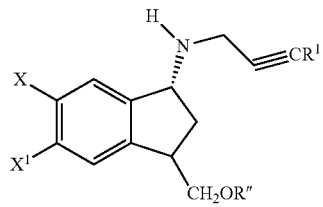

| Ex. # | X | X¹ | R¹ | R" |
|---|---|---|---|---|
| 135. | H | $OCH_2C_6H_5$ | $CH_2-CO_2CH_2CH_3$ | $CH_2CH=CH_2$ |
| 136. | H | $OCH_2C_6H_5$ | $CH_2-CO_2H$ | $CH_2CH=CH_2$ |
| 137. | H | $OCH_2CH_2C_6H_5$ | $CH_2-CO_2CH_2CH_3$ | $CH_2CH=CH_2$ |
| 138. | H | $OCH_2CH_2C_6H_5$ | $CH_2-CO_2H$ | $CH_2CH=CH_2$ |
| 139. | H | $OCH_2-CONH_2$ | $CH_2-CO_2CH_2CH_3$ | $CH_2CH=CH_2$ |
| 140. | H | $OCH_2-CONH_2$ | $CH_2-CO_2H$ | $CH_2CH=CH_2$ |
| 141. | $OCH_2CH=CH_2$ | H | $CH_2CH_2P-O(OCH_2CH_3)_2$ | $CH_2CH=CH_2$ |
| 142. | $OCH_2CH=CH_2$ | H | $CH_2CH_2P-O(OH)_2$ | $CH_2CH=CH_2$ |
| 143. | $OCH_2C_6H_5$ | H | $CH_2CH_2P-O(OCH_2CH_3)_2$ | $CH_2CH=CH_2$ |
| 144. | $OCH_2C_6H_5$ | H | $CH_2CH_2P-O(OH)_2$ | $CH_2CH=CH_2$ |
| 145. | $OCH_2CH_2C_6H_5$ | H | $CH_2CH_2P-O(OCH_2CH_3)_2$ | $CH_2CH=CH_2$ |
| 146. | $OCH_2CH_2C_6H_5$ | H | $CH_2CH_2P-O(OH)_2$ | $CH_2CH=CH_2$ |
| 147. | $OCH_2-CONH_2$ | H | $CH_2CH_2P-O(OCH_2CH_3)_2$ | $CH_2CH=CH_2$ |
| 148. | $OCH_2-CONH_2$ | H | $CH_2CH_2P-O(OH)_2$ | $CH_2CH=CH_2$ |
| 149. | $NH_2$ | H | $CH_2CH_2P-O(OCH_2CH_3)_2$ | $CH_2CH=CH_2$ |
| 150. | $NH_2$ | H | $CH_2CH_2P-O(OH)_2$ | $CH_2CH=CH_2$ |
| 151. | $NHSO_2CH_3$ | H | $CH_2CH_2P-O(OCH_2CH_3)_2$ | $CH_2CH=CH_2$ |
| 152. | $NHSO_2CH_3$ | H | $CH_2CH_2P-O(OH)_2$ | $CH_2CH=CH_2$ |
| 153. | H | $OCH_2CH=CH_2$ | $CH_2CH_2P-O(OCH_2CH_3)_2$ | $CH_2CH=CH_2$ |
| 154. | H | $OCH_2CH=CH_2$ | $CH_2CH_2P-O(OH)_2$ | $CH_2CH=CH_2$ |
| 155. | H | $OCH_2C_6H_5$ | $CH_2CH_2P-O(OCH_2CH_3)_2$ | $CH_2CH=CH_2$ |
| 156. | H | $OCH_2C_6H_5$ | $CH_2CH_2P-O(OH)_2$ | $CH_2CH=CH_2$ |
| 157. | H | $OCH_2CH_2C_6H_5$ | $CH_2CH_2P-O(OCH_2CH_3)_2$ | $CH_2CH=CH_2$ |
| 158. | H | $OCH_2CH_2C_6H_5$ | $CH_2CH_2P-O(OH)_2$ | $CH_2CH=CH_2$ |
| 159. | H | $OCH_2-CONH_2$ | $CH_2CH_2P-O(OCH_2CH_3)_2$ | $CH_2CH=CH_2$ |
| 160. | H | $OCH_2-CONH_2$ | $CH_2CH_2P-O(OH)_2$ | $CH_2CH=CH_2$ |
| 161. | $OCH_2CH=CH_2$ | H | $CH_2-CO_2CH_2CH_3$ | $CH_2-CONH_2$ |
| 162. | $OCH_2CH=CH_2$ | H | $CH_2-CO_2H$ | $CH_2-CONH_2$ |
| 163. | $OCH_2C_6H_5$ | H | $CH_2-CO_2CH_2CH_3$ | $CH_2-CONH_2$ |
| 164. | $OCH_2C_6H_5$ | H | $CH_2-CO_2H$ | $CH_2-CONH_2$ |
| 165. | $OCH_2CH_2C_6H_5$ | H | $CH_2-CO_2CH_2CH_3$ | $CH_2-CONH_2$ |
| 166. | $OCH_2CH_2C_6H_5$ | H | $CH_2-CO_2H$ | $CH_2-CONH_2$ |
| 167. | $OCH_2-CONH_2$ | H | $CH_2-CO_2CH_2CH_3$ | $CH_2-CONH_2$ |
| 168. | $OCH_2-CONH_2$ | H | $CH_2-CO_2H$ | $CH_2-CONH_2$ |
| 169. | $NH_2$ | H | $CH_2-CO_2CH_2CH_3$ | $CH_2-CONH_2$ |
| 170. | $NH_2$ | H | $CH_2-CO_2H$ | $CH_2-CONH_2$ |
| 171. | $NHSO_2CH_3$ | H | $CH_2-CO_2CH_2CH_3$ | $CH_2-CONH_2$ |
| 172. | $NHSO_2CH_3$ | H | $CH_2-CO_2H$ | $CH_2-CONH_2$ |
| 173. | H | $OCH_2CH=CH_2$ | $CH_2-CO_2CH_2CH_3$ | $CH_2-CONH_2$ |
| 174. | H | $OCH_2CH=CH_2$ | $CH_2-CO_2H$ | $CH_2-CONH_2$ |
| 175. | H | $OCH_2C_6H_5$ | $CH_2-CO_2CH_2CH_3$ | $CH_2-CONH_2$ |
| 176. | H | $OCH_2C_6H_5$ | $CH_2-CO_2H$ | $CH_2-CONH_2$ |
| 177. | H | $OCH_2CH_2C_6H_5$ | $CH_2-CO_2CH_2CH_3$ | $CH_2-CONH_2$ |
| 178. | H | $OCH_2CH_2C_6H_5$ | $CH_2-CO_2H$ | $CH_2-CONH_2$ |
| 179. | H | $OCH_2-CONH_2$ | $CH_2-CO_2CH_2CH_3$ | $CH_2-CONH_2$ |
| 180. | H | $OCH_2-CONH_2$ | $CH_2-CO_2H$ | $CH_2-CONH_2$ |
| 181. | $OCH_2CH=CH_2$ | H | $CH_2CH_2P-O(OCH_2CH_3)_2$ | $CH_2-CONH_2$ |
| 182. | $OCH_2CH=CH_2$ | H | $CH_2CH_2P-O(OH)_2$ | $CH_2-CONH_2$ |
| 183. | $OCH_2C_6H_5$ | H | $CH_2CH_2P-O(OCH_2CH_3)_2$ | $CH_2-CONH_2$ |
| 184. | $OCH_2C_6H_5$ | H | $CH_2CH_2P-O(OH)_2$ | $CH_2-CONH_2$ |
| 185. | $OCH_2CH_2C_6H_5$ | H | $CH_2CH_2P-O(OCH_2CH_3)_2$ | $CH_2-CONH_2$ |
| 186. | $OCH_2CH_2C_6H_5$ | H | $CH_2CH_2P-O(OH)_2$ | $CH_2-CONH_2$ |
| 187. | $OCH_2-CONH_2$ | H | $CH_2CH_2P-O(OCH_2CH_3)_2$ | $CH_2-CONH_2$ |
| 188. | $OCH_2-CONH_2$ | H | $CH_2CH_2P-O(OH)_2$ | $CH_2-CONH_2$ |
| 189. | $NH_2$ | H | $CH_2CH_2P-O(OCH_2CH_3)_2$ | $CH_2-CONH_2$ |
| 190. | $NH_2$ | H | $CH_2CH_2P-O(OH)_2$ | $CH_2-CONH_2$ |
| 191. | $NHSO_2CH_3$ | H | $CH_2CH_2P-O(OCH_2CH_3)_2$ | $CH_2-CONH_2$ |
| 192. | $NHSO_2CH_3$ | H | $CH_2CH_2P-O(OH)_2$ | $CH_2-CONH_2$ |
| 193. | H | $OCH_2CH=CH_2$ | $CH_2CH_2P-O(OCH_2CH_3)_2$ | $CH_2-CONH_2$ |
| 194. | H | $OCH_2CH=CH_2$ | $CH_2CH_2P-O(OH)_2$ | $CH_2-CONH_2$ |
| 195. | H | $OCH_2C_6H_5$ | $CH_2CH_2P-O(OCH_2CH_3)_2$ | $CH_2-CONH_2$ |
| 196. | H | $OCH_2C_6H_5$ | $CH_2CH_2P-O(OH)_2$ | $CH_2-CONH_2$ |
| 197. | H | $OCH_2CH_2C_6H_5$ | $CH_2CH_2P-O(OCH_2CH_3)_2$ | $CH_2-CONH_2$ |
| 198. | H | $OCH_2CH_2C_6H_5$ | $CH_2CH_2P-O(OH)_2$ | $CH_2-CONH_2$ |
| 199. | H | $OCH_2-CONH_2$ | $CH_2CH_2P-O(OCH_2CH_3)_2$ | $CH_2-CONH_2$ |
| 200. | H | $OCH_2-CONH_2$ | $CH_2CH_2P-O(OH)_2$ | $CH_2-CONH_2$ |
| 201. | $OCH_2CH=CH_2$ | H | $CH_2-CO_2CH_2CH_3$ | $CH_2C_6H_5$ |

TABLE IV-continued

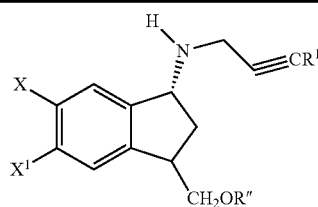

| Ex. # | X | X¹ | R¹ | R″ |
|---|---|---|---|---|
| 202. | $OCH_2CH=CH_2$ | H | $CH_2-CO_2H$ | $CH_2C_6H_5$ |
| 203. | $OCH_2C_6H_5$ | H | $CH_2-CO_2CH_3$ | $CH_2C_6H_5$ |
| 204. | $OCH_2C_6H_5$ | H | $CH_2-CO_2H$ | $CH_2C_6H_5$ |
| 205. | $OCH_2CH_2C_6H_5$ | H | $CH_2-CO_2CH_2CH_3$ | $CH_2C_6H_5$ |
| 206. | $OCH_2CH_2C_6H_5$ | H | $CH_2-CO_2H$ | $CH_2C_6H_5$ |
| 207. | $OCH_2-CONH_2$ | H | $CH_2-CO_2CH_2CH_3$ | $CH_2C_6H_5$ |
| 208. | $OCH_2-CONH_2$ | H | $CH_2-CO_2H$ | $CH_2C_6H_5$ |
| 209. | $NHSO_2CH_3$ | H | $CH_2-CO_2CH_2CH_3$ | $CH_2C_6H_5$ |
| 210. | $NHSO_2CH_3$ | H | $CH_2-CO_2H$ | $CH_2C_6H_5$ |
| 211. | H | $OCH_2CH=CH_2$ | $CH_2-CO_2CH_2CH_3$ | $CH_2C_6H_5$ |
| 212. | H | $OCH_2CH=CH_2$ | $CH_2-CO_2H$ | $CH_2C_6H_5$ |
| 213. | H | $OCH_2C_6H_5$ | $CH_2-CO_2CH_2CH_3$ | $CH_2C_6H_5$ |
| 214. | H | $OCH_2C_6H_5$ | $CH_2-CO_2H$ | $CH_2C_6H_5$ |
| 215. | H | $OCH_2CH_2C_6H_5$ | $CH_2-CO_2CH_2CH_3$ | $CH_2C_6H_5$ |
| 216. | H | $OCH_2CH_2C_6H_5$ | $CH_2-CO_2H$ | $CH_2C_6H_5$ |
| 217. | H | $OCH_2-CONH_2$ | $CH_2-CO_2CH_2CH_3$ | $CH_2C_6H_5$ |
| 218. | H | $OCH_2-CONH_2$ | $CH_2-CO_2H$ | $CH_2C_6H_5$ |
| 219. | $OCH_2CH=CH_2$ | H | $CH_2CH_2P-O(OCH_2CH_3)_2$ | $CH_2C_6H_5$ |
| 220. | $OCH_2CH=CH_2$ | H | $CH_2CH_2P-O(OH)_2$ | $CH_2C_6H_5$ |
| 221. | $OCH_2C_6H_5$ | H | $CH_2CH_2P-O(OCH_2CH_3)_2$ | $CH_2C_6H_5$ |
| 222. | $OCH_2C_6H_5$ | H | $CH_2CH_2P-O(OH)_2$ | $CH_2C_6H_5$ |
| 223. | $OCH_2CH_2C_6H_5$ | H | $CH_2CH_2P-O(OCH_2CH_3)_2$ | $CH_2C_6H_5$ |
| 224. | $OCH_2CH_2C_6H_5$ | H | $CH_2CH_2P-O(OH)_2$ | $CH_2C_6H_5$ |
| 225. | $OCH_2-CONH_2$ | H | $CH_2CH_2P-O(OCH_2CH_3)_2$ | $CH_2C_6H_5$ |
| 226. | $OCH_2-CONH_2$ | H | $CH_2CH_2P-O(OH)_2$ | $CH_2C_6H_5$ |
| 227. | $NH_2$ | H | $CH_2CH_2P-O(OCH_2CH_3)_2$ | $CH_2C_6H_5$ |
| 228. | $NH_2$ | H | $CH_2CH_2P-O(OH)_2$ | $CH_2C_6H_5$ |
| 229. | $NHSO_2CH_3$ | H | $CH_2CH_2P-O(OCH_2CH_3)_2$ | $CH_2C_6H_5$ |
| 230. | $NHSO_2CH_3$ | H | $CH_2CH_2P-O(OH)_2$ | $CH_2C_6H_5$ |
| 231. | H | $OCH_2CH=CH_2$ | $CH_2CH_2P-O(OCH_2CH_3)_2$ | $CH_2-CONH_2$ |
| 232. | H | $OCH_2CH=CH_2$ | $CH_2CH_2P-O(OH)_2$ | $CH_2-CONH_2$ |
| 233. | H | $OCH_2C_6H_5$ | $CH_2CH_2P-O(OCH_2CH_3)_2$ | $CH_2-CONH_2$ |
| 234. | H | $OCH_2C_6H_5$ | $CH_2CH_2P-O(OH)_2$ | $CH_2-CONH_2$ |
| 235. | H | $OCH_2CH_2C_6H_5$ | $CH_2CH_2P-O(OCH_2CH_3)_2$ | $CH_2-CONH_2$ |
| 236. | H | $OCH_2CH_2C_6H_5$ | $CH_2CH_2P-O(OH)_2$ | $CH_2-CONH_2$ |
| 237. | H | $OCH_2-CONH_2$ | $CH_2CH_2P-O(OCH_2CH_3)_2$ | $CH_2-CONH_2$ |
| 238. | H | $OCH_2-CONH_2$ | $CH_2CH_2P-O(OH)_2$ | $CH_2-CONH_2$ |

TABLE Va

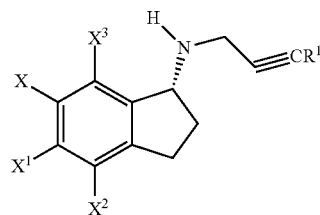

| Ex. # | X | X¹ | X² | X³ | R¹ |
|---|---|---|---|---|---|
| 1. | $OCH_2CO_2-CH_2CH_3$ | H | H | H | H |
| 2. | $OCH_2CO_2-CH_2CH_3$ | H | H | H | $CH_3$ |
| 3. | $OCH_2CO_2H$ | H | H | H | H |
| 4. | $OCH_2CO_2H$ | H | H | H | $CH_3$ |
| 5. | $OCH_2CH_2-CO_2CH_2CH_3$ | H | H | H | H |
| 6. | $OCH_2CH_2-CO_2CH_2CH_3$ | H | H | H | $CH_3$ |
| 7. | $OCH_2CH_2-CO_2H$ | H | H | H | H |
| 8. | $OCH_2CH_2-CO_2H$ | H | H | H | $CH_3$ |
| 9. | $OCH_2CH=CH-CO_2CH_2CH_3$ | H | H | H | H |
| 10. | $OCH_2CH=CH-CO_2CH_2CH_3$ | H | H | H | $CH_3$ |
| 11. | $OCH_2CH=CH-CO_2H$ | H | H | H | H |

TABLE Va-continued

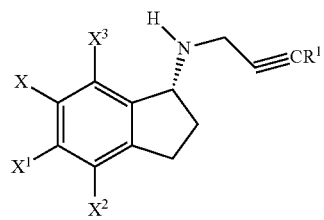

| Ex. # | X | $X^1$ | $X^2$ | $X^3$ | $R^1$ |
|---|---|---|---|---|---|
| 12. | $OCH_2CH=CH-CO_2H$ | H | H | H | $CH_3$ |
| 13. | $OCH_2CH_2-PO(OCH_2CH_3)_2$ | H | H | H | H |
| 14. | $OCH_2CH_2-PO(OCH_2CH_3)_2$ | H | H | H | $CH_3$ |
| 15. | $OCH_2CH_2-PO(OH)_2$ | H | H | H | H |
| 16. | $OCH_2CH_2-PO(OH)_2$ | H | H | H | $CH_3$ |
| 17. | H | $OCH_2CO_2-CH_2CH_3$ | H | H | H |
| 18. | H | $OCH_2CO_2-CH_2CH_3$ | H | H | $CH_3$ |
| 19. | H | $OCH_2CO_2H$ | H | H | H |
| 20. | H | $OCH_2CO_2H$ | H | H | $CH_3$ |
| 21. | H | $OCH_2CH_2CO_2-CH_2CH_3$ | H | H | H |
| 22. | H | $OCH_2CH_2CO_2-CH_2CH_3$ | H | H | $CH_3$ |
| 23. | H | $OCH_2CH_2CO_2H$ | H | H | H |
| 24. | H | $OCH_2CH_2CO_2H$ | H | H | $CH_3$ |
| 25. | H | $OCH_2CH=CH-CO_2CH_2CH_3$ | H | H | H |
| 26. | H | $OCH_2CH=CH-CO_2CH_2CH_3$ | H | H | $CH_3$ |
| 27. | H | $OCH_2CH=CH-CO_2H$ | H | H | H |
| 28. | H | $OCH_2CH=CH-CO_2H$ | H | H | $CH_3$ |
| 29. | H | $OCH_2CH_2-PO(OCH_2CH_3)_2$ | H | H | H |
| 30. | H | $OCH_2CH_2-PO(OCH_2CH_3)_2$ | H | H | $CH_3$ |
| 31. | H | $OCH_2CH_2-PO(OH)_2$ | H | H | H |
| 32. | H | $OCH_2CH_2-PO(OH)_2$ | H | H | $CH_3$ |
| 33. | H | H | $OCH_2CO_2-CH_2CH_3$ | H | H |
| 34. | H | H | $OCH_2CO_2-CH_2CH_3$ | H | $CH_3$ |
| 35. | H | H | $OCH_2CO_2H$ | H | H |
| 36. | H | H | $OCH_2CO_2H$ | H | $CH_3$ |
| 37. | H | H | $OCH_2CH_2-CO_2CH_2CH_3$ | H | H |
| 38. | H | H | $OCH_2CH_2-CO_2CH_2CH_3$ | H | $CH_3$ |
| 39. | H | H | $OCH_2CH_2-CO_2H$ | H | H |
| 40. | H | H | $OCH_2CH_2-CO_2H$ | H | $CH_3$ |
| 41. | H | H | $OCH_2-CH=CH-CO_2CH_2CH_3$ | H | H |
| 42. | H | H | $OCH_2-CH=CH-CO_2CH_2CH_3$ | H | $CH_3$ |
| 43. | H | H | $OCH_2-CH=CHCO_2H$ | H | H |
| 44. | H | H | $OCH_2-CH=CHCO_2H$ | H | $CH_3$ |
| 45. | H | H | $OCH_2CH_2PO-(OCH_2CH_3)_2$ | H | H |
| 46. | H | H | $OCH_2CH_2PO-(OCH_2CH_3)_2$ | H | $CH_3$ |
| 47. | H | H | $OCH_2CH_2-PO(OH)_2$ | H | H |
| 48. | H | H | $OCH_2CH_2-PO(OH)_2$ | H | $CH_3$ |
| 49. | H | H | H | $OCH_2CO_2-CH_2CH_3$ | H |
| 50. | H | H | H | $OCH_2CO_2-CH_2CH_3$ | $CH_3$ |
| 51. | H | H | H | $OCH_2CO_2H$ | H |
| 52. | H | H | H | $OCH_2CO_2H$ | $CH_3$ |
| 53. | H | H | H | $OCH_2CH_2-CO_2CH_2CH_3$ | H |
| 54. | H | H | H | $OCH_2CH_2-CO_2CH_2CH_3$ | $CH_3$ |
| 55. | H | H | H | $OCH_2CH_2-CO_2H$ | H |
| 56. | H | H | H | $OCH_2CH_2-CO_2H$ | $CH_3$ |
| 57. | H | H | H | $OCH_2-CH=CH-CO_2CH_2CH_3$ | H |
| 58. | H | H | H | $OCH_2-CH=CH-CO_2CH_2CH_3$ | $CH_3$ |
| 59. | H | H | H | $OCH_2-CH=CHCO_2H$ | H |
| 60. | H | H | H | $OCH_2-CH=CHCO_2H$ | $CH_3$ |
| 61. | H | H | H | $OCH_2CH_2PO-(OCH_2CH_3)_2$ | H |
| 62. | H | H | H | $OCH_2CH_2PO-(OCH_2CH_3)_2$ | $CH_3$ |
| 63. | H | H | H | $OCH_2CH_2-PO(OH)_2$ | H |
| 64. | H | H | H | $OCH_2CH_2-PO(OH)_2$ | $CH_3$ |

TABLE Vb

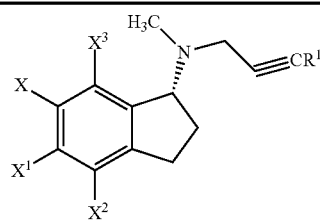

| Ex. # | X | X¹ | X² | X³ | R¹ |
|---|---|---|---|---|---|
| 1. | OCH₂CO₂—CH₂CH₃ | H | H | H | H |
| 2. | OCH₂CO₂—CH₂CH₃ | H | H | H | CH₃ |
| 3. | OCH₂CO₂H | H | H | H | H |
| 4. | OCH₂CO₂H | H | H | H | CH₃ |
| 5. | OCH₂CH₂—CO₂CH₂CH₃ | H | H | H | H |
| 6. | OCH₂CH₂—CO₂CH₂CH₃ | H | H | H | CH₃ |
| 7. | OCH₂CH₂—CO₂H | H | H | H | H |
| 8. | OCH₂CH₂—CO₂H | H | H | H | CH₃ |
| 9. | OCH₂CH=CH—CO₂CH₂CH₃ | H | H | H | H |
| 10. | OCH₂CH=CH—CO₂CH₂CH₃ | H | H | H | CH₃ |
| 11. | OCH₂CH=CH—CO₂H | H | H | H | H |
| 12. | OCH₂CH=CH—CO₂H | H | H | H | CH₃ |
| 13. | OCH₂CH₂—PO(OCH₂CH₃)₂ | H | H | H | H |
| 14. | OCH₂CH₂—PO(OCH₂CH₃)₂ | H | H | H | CH₃ |
| 15. | OCH₂CH₂—PO(OH)₂ | H | H | H | H |
| 16. | OCH₂CH₂—PO(OH)₂ | H | H | H | CH₃ |
| 17. | H | OCH₂CO₂—CH₂CH₃ | H | H | H |
| 18. | H | OCH₂CO₂—CH₂CH₃ | H | H | CH₃ |
| 19. | H | OCH₂CO₂H | H | H | H |
| 20. | H | OCH₂CO₂H | H | H | CH₃ |
| 21. | H | OCH₂CH₂CO₂—CH₂CH₃ | H | H | H |
| 22. | H | OCH₂CH₂CO₂—CH₂CH₃ | H | H | CH₃ |
| 23. | H | OCH₂CH₂CO₂H | H | H | H |
| 24. | H | OCH₂CH₂CO₂H | H | H | CH₃ |
| 25. | H | OCH₂CH=CH—CO₂CH₂CH₃ | H | H | H |
| 26. | H | OCH₂CH=CH—CO₂CH₂CH₃ | H | H | CH₃ |
| 27. | H | OCH₂CH=CH—CO₂H | H | H | H |
| 28. | H | OCH₂CH=CH—CO₂H | H | H | CH₃ |
| 29. | H | OCH₂CH₂—PO(OCH₂CH₃)₂ | H | H | H |
| 30. | H | OCH₂CH₂—PO(OCH₂CH₃)₂ | H | H | CH₃ |
| 31. | H | OCH₂CH₂—PO(OH)₂ | H | H | H |
| 32. | H | OCH₂CH₂—PO(OH)₂ | H | H | CH₃ |
| 33. | H | H | OCH₂CO₂—CH₂CH₃ | H | H |
| 34. | H | H | OCH₂CO₂—CH₂CH₃ | H | CH₃ |
| 35. | H | H | OCH₂CO₂H | H | H |
| 36. | H | H | OCH₂CO₂H | H | CH₃ |
| 37. | H | H | OCH₂CH₂—CO₂CH₂CH₃ | H | H |
| 38. | H | H | OCH₂CH₂—CO₂CH₂CH₃ | H | CH₃ |
| 39. | H | H | OCH₂CH₂—CO₂H | H | H |
| 40. | H | H | OCH₂CH₂—CO₂H | H | CH₃ |
| 41. | H | H | OCH₂—CH=CH—CO₂CH₂CH₃ | H | H |
| 42. | H | H | OCH₂—CH=CH—CO₂CH₂CH₃ | H | CH₃ |
| 43. | H | H | OCH₂—CH=CHCO₂H | H | H |
| 44. | H | H | OCH₂—CH=CHCO₂H | H | CH₃ |
| 45. | H | H | OCH₂CH₂PO—(OCH₂CH₃)₂ | H | H |
| 46. | H | H | OCH₂CH₂PO—(OCH₂CH₃)₂ | H | CH₃ |
| 47. | H | H | OCH₂CH₂—PO(OH)₂ | H | H |
| 48. | H | H | OCH₂CH₂—PO(OH)₂ | H | CH₃ |
| 49. | H | H | H | OCH₂CO₂—CH₂CH₃ | H |
| 50. | H | H | H | OCH₂CO₂—CH₂CH₃ | CH₃ |
| 51. | H | H | H | OCH₂CO₂H | H |
| 52. | H | H | H | OCH₂CO₂H | CH₃ |
| 53. | H | H | H | OCH₂CH₂—CO₂CH₂CH₃ | H |
| 54. | H | H | H | OCH₂CH₂—CO₂CH₂CH₃ | CH₃ |
| 55. | H | H | H | OCH₂CH₂—CO₂H | H |
| 56. | H | H | H | OCH₂CH₂—CO₂H | CH₃ |
| 57. | H | H | H | OCH₂—CH=CH—CO₂CH₂CH₃ | H |
| 58. | H | H | H | OCH₂—CH=CH—CO₂CH₂CH₃ | CH₃ |
| 59. | H | H | H | OCH₂—CH=CHCO₂H | H |
| 60. | H | H | H | OCH₂—CH=CHCO₂H | CH₃ |
| 61. | H | H | H | OCH₂CH₂PO—(OCH₂CH₃)₂ | H |
| 62. | H | H | H | OCH₂CH₂PO—(OCH₂CH₃)₂ | CH₃ |
| 63. | H | H | H | OCH₂CH₂—PO(OH)₂ | H |
| 64. | H | H | H | OCH₂CH₂—PO(OH)₂ | CH₃ |

TABLE VIIa

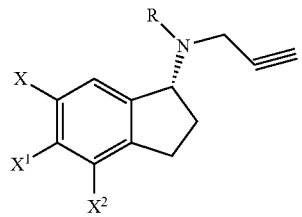

| Ex. # | X | X¹ | X² | R |
|---|---|---|---|---|
| 1. | OCH$_2$CH=CH$_2$ | H | H | H |
| 2. | OCH$_2$CH=CH$_2$ | H | H | CH$_3$ |
| 3. | NHSO$_2$CH$_3$ | H | H | H |
| 4. | NHSO$_2$CH$_3$ | H | H | CH$_3$ |
| 5. | OCH$_2$C$_6$H$_5$ | H | H | H |
| 6. | OCH$_2$C$_6$H$_5$ | H | H | CH$_3$ |
| 7. | OCH$_2$C$_6$H$_4$—Cl(3) | H | H | H |
| 8. | OCH$_2$C$_6$H$_4$—Cl(3) | H | H | CH$_3$ |
| 9. | OCH$_2$C$_6$H$_4$—Cl(4) | H | H | H |
| 10. | OCH$_2$C$_6$H$_4$—Cl(4) | H | H | CH$_3$ |
| 11. | OCH$_2$C$_6$H$_4$—F(3) | H | H | H |
| 12. | OCH$_2$C$_6$H$_4$—F(3) | H | H | CH$_3$ |
| 13. | OCH$_2$C$_6$H$_4$—F(4) | H | H | H |
| 14. | OCH$_2$C$_6$H$_4$—F(4) | H | H | CH$_3$ |
| 15. | OCH$_2$C$_6$H$_4$—CF$_3$(3) | H | H | H |
| 16. | OCH$_2$C$_6$H$_4$—CF$_3$(3) | H | H | CH$_3$ |
| 17. | OCH$_2$C$_6$H$_4$—CF$_3$(4) | H | H | H |
| 18. | OCH$_2$C$_6$H$_4$—CF$_3$(4) | H | H | CH$_3$ |
| 19. | OCH$_2$C$_6$H$_4$—NO$_2$(3) | H | H | H |
| 20. | OCH$_2$C$_6$H$_4$—NO$_2$(3) | H | H | CH$_3$ |
| 21. | OCH$_2$C$_6$H$_4$—NO$_2$(4) | H | H | H |
| 22. | OCH$_2$C$_6$H$_4$—NO$_2$(4) | H | H | CH$_3$ |
| 23. | OCH$_2$C$_6$H$_4$—NHSO$_2$CH$_3$(3) | H | H | H |
| 24. | OCH$_2$C$_6$H$_4$—NHSO$_2$CH$_3$(3) | H | H | CH$_3$ |
| 25. | OCH$_2$C$_6$H$_4$—NHSO$_2$CH$_3$(4) | H | H | H |
| 26. | OCH$_2$C$_6$H$_4$—NHSO$_2$CH$_3$(4) | H | H | CH$_3$ |
| 27. | OCH$_2$C$_6$H$_4$—CN(3) | H | H | H |
| 28. | OCH$_2$C$_6$H$_4$—CN(3) | H | H | CH$_3$ |
| 29. | OCH$_2$C$_6$H$_4$—CN(4) | H | H | H |
| 30. | OCH$_2$C$_6$H$_4$—CN(4) | H | H | CH$_3$ |
| 31. | OCH$_2$C$_6$H$_4$—CONH$_2$(3) | H | H | H |
| 32. | OCH$_2$C$_6$H$_4$—CONH$_2$(3) | H | H | CH$_3$ |
| 33. | OCH$_2$C$_6$H$_4$—CONH$_2$(4) | H | H | H |
| 34. | OCH$_2$C$_6$H$_4$—CONH$_2$(4) | H | H | CH$_3$ |
| 35. | OCH$_2$C$_6$H$_4$—CH$_2$CN(3) | H | H | H |
| 36. | OCH$_2$C$_6$H$_4$—CH$_2$CN(3) | H | H | CH$_3$ |
| 37. | OCH$_2$C$_6$H$_4$—CH$_2$CN(4) | H | H | H |
| 38. | OCH$_2$C$_6$H$_4$—CH$_2$CN(4) | H | H | CH$_3$ |
| 39. | OCH$_2$C$_6$H$_4$—CH$_2$CONH$_2$(3) | H | H | H |
| 40. | OCH$_2$C$_6$H$_4$—CH$_2$CONH$_2$(3) | H | H | CH$_3$ |
| 41. | OCH$_2$C$_6$H$_4$—CH$_2$CONH$_2$(4) | H | H | H |
| 42. | OCH$_2$C$_6$H$_4$—CH$_2$CONH$_2$(4) | H | H | CH$_3$ |
| 43. | OCH$_2$C$_6$H$_4$—OCH$_2$CN(3) | H | H | H |
| 44. | OCH$_2$C$_6$H$_4$—OCH$_2$CN(3) | H | H | CH$_3$ |
| 45. | OCH$_2$C$_6$H$_4$—OCH$_2$CN(4) | H | H | H |
| 46. | OCH$_2$C$_6$H$_4$—OCH$_2$CN(4) | H | H | CH$_3$ |
| 47. | OCH$_2$C$_6$H$_4$—OCH$_2$CONH$_2$(3) | H | H | H |
| 48. | OCH$_2$C$_6$H$_4$—OCH$_2$CONH$_2$(3) | H | H | CH$_3$ |
| 49. | OCH$_2$C$_6$H$_4$—OCH$_2$CONH$_2$(4) | H | H | H |
| 50. | OCH$_2$C$_6$H$_4$—OCH$_2$CONH$_2$(4) | H | H | CH$_3$ |
| 51. | OCH$_2$C$_6$H$_3$—(CN)$_2$(3,5) | H | H | H |
| 52. | OCH$_2$C$_6$H$_3$—(CN)$_2$(3,5) | H | H | CH$_3$ |
| 53. | OCH$_2$C$_6$H$_3$—(CN)$_2$(3,5) | H | H | H |
| 54. | OCH$_2$C$_6$H$_3$—(CN)$_2$(3,5) | H | H | CH$_3$ |
| 55. | OCH$_2$C$_6$H$_3$—(CONH$_2$)$_2$(3,5) | H | H | H |
| 56. | OCH$_2$C$_6$H$_3$—(CONH$_2$)$_2$(3,5) | H | H | CH$_3$ |
| 57. | OCH$_2$C$_6$H$_3$—(CONH$_2$)$_2$(3,5) | H | H | H |
| 58. | OCH$_2$C$_6$H$_3$—(CONH$_2$)$_2$(3,5) | H | H | CH$_3$ |
| 59. | OCH$_2$CH$_2$C$_6$H$_5$ | H | H | H |
| 60. | OCH$_2$CH$_2$C$_6$H$_5$ | H | H | CH$_3$ |
| 61. | OCH$_2$C$_6$H$_4$C$_6$H$_4$CN(2) | H | H | H |
| 62. | OCH$_2$C$_6$H$_4$C$_6$H$_4$CN(2) | H | H | CH$_3$ |
| 63. | OCH$_2$C$_6$H$_4$C$_6$H$_4$CONH$_2$(2) | H | H | H |
| 64. | OCH$_2$C$_6$H$_4$C$_6$H$_4$CONH$_2$(2) | H | H | CH$_3$ |

TABLE VIIb

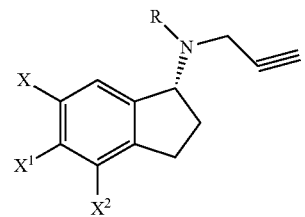

| Ex. # | X¹ | X | X² | R |
|---|---|---|---|---|
| 1. | OCH$_2$CH=CH$_2$ | H | H | H |
| 2. | OCH$_2$CH=CH$_2$ | H | H | CH$_3$ |
| 3. | NHSO$_2$CH$_3$ | H | H | H |
| 4. | NHSO$_2$CH$_3$ | H | H | CH$_3$ |
| 5. | OCH$_2$C$_6$H$_5$ | H | H | H |
| 6. | OCH$_2$C$_6$H$_5$ | H | H | CH$_3$ |
| 7. | OCH$_2$C$_6$H$_4$—Cl(3) | H | H | H |
| 8. | OCH$_2$C$_6$H$_4$—Cl(3) | H | H | CH$_3$ |
| 9. | OCH$_2$C$_6$H$_4$—Cl(4) | H | H | H |
| 10. | OCH$_2$C$_6$H$_4$—Cl(4) | H | H | CH$_3$ |
| 11. | OCH$_2$C$_6$H$_4$—F(3) | H | H | H |
| 12. | OCH$_2$C$_6$H$_4$—F(3) | H | H | CH$_3$ |
| 13. | OCH$_2$C$_6$H$_4$—F(4) | H | H | H |
| 14. | OCH$_2$C$_6$H$_4$—F(4) | H | H | CH$_3$ |
| 15. | OCH$_2$C$_6$H$_4$—CF$_3$(3) | H | H | H |
| 16. | OCH$_2$C$_6$H$_4$—CF$_3$(3) | H | H | CH$_3$ |
| 17. | OCH$_2$C$_6$H$_4$—CF$_3$(4) | H | H | H |
| 18. | OCH$_2$C$_6$H$_4$—CF$_3$(4) | H | H | CH$_3$ |
| 19. | OCH$_2$C$_6$H$_4$—NO$_2$(3) | H | H | H |
| 20. | OCH$_2$C$_6$H$_4$—NO$_2$(3) | H | H | CH$_3$ |
| 21. | OCH$_2$C$_6$H$_4$—NO$_2$(4) | H | H | H |
| 22. | OCH$_2$C$_6$H$_4$—NO$_2$(4) | H | H | CH$_3$ |
| 23. | OCH$_2$C$_6$H$_4$—NHSO$_2$CH$_3$(3) | H | H | H |
| 24. | OCH$_2$C$_6$H$_4$—NHSO$_2$CH$_3$(3) | H | H | CH$_3$ |
| 25. | OCH$_2$C$_6$H$_4$—NHSO$_2$CH$_3$(4) | H | H | H |
| 26. | OCH$_2$C$_6$H$_4$—NHSO$_2$CH$_3$(4) | H | H | CH$_3$ |
| 27. | OCH$_2$C$_6$H$_4$—CN(3) | H | H | H |
| 28. | OCH$_2$C$_6$H$_4$—CN(3) | H | H | CH$_3$ |
| 29. | OCH$_2$C$_6$H$_4$—CN(4) | H | H | H |
| 30. | OCH$_2$C$_6$H$_4$—CN(4) | H | H | CH$_3$ |
| 31. | OCH$_2$C$_6$H$_4$—CONH$_2$(3) | H | H | H |
| 32. | OCH$_2$C$_6$H$_4$—CONH$_2$(3) | H | H | CH$_3$ |
| 33. | OCH$_2$C$_6$H$_4$—CONH$_2$(4) | H | H | H |
| 34. | OCH$_2$C$_6$H$_4$—CONH$_2$(4) | H | H | CH$_3$ |
| 35. | OCH$_2$C$_6$H$_4$—CH$_2$CN(3) | H | H | H |
| 36. | OCH$_2$C$_6$H$_4$—CH$_2$CN(3) | H | H | CH$_3$ |
| 37. | OCH$_2$C$_6$H$_4$—CH$_2$CN(4) | H | H | H |
| 38. | OCH$_2$C$_6$H$_4$—CH$_2$CN(4) | H | H | CH$_3$ |
| 39. | OCH$_2$C$_6$H$_4$—CH$_2$CONH$_2$(3) | H | H | H |
| 40. | OCH$_2$C$_6$H$_4$—CH$_2$CONH$_2$(3) | H | H | CH$_3$ |
| 41. | OCH$_2$C$_6$H$_4$—CH$_2$CONH$_2$(4) | H | H | H |
| 42. | OCH$_2$C$_6$H$_4$—CH$_2$CONH$_2$(4) | H | H | CH$_3$ |
| 43. | OCH$_2$C$_6$H$_4$—OCH$_2$CN(3) | H | H | H |
| 44. | OCH$_2$C$_6$H$_4$—OCH$_2$CN(3) | H | H | CH$_3$ |
| 45. | OCH$_2$C$_6$H$_4$—OCH$_2$CN(4) | H | H | H |
| 46. | OCH$_2$C$_6$H$_4$—OCH$_2$CN(4) | H | H | CH$_3$ |
| 47. | OCH$_2$C$_6$H$_4$—OCH$_2$CONH$_2$(3) | H | H | H |
| 48. | OCH$_2$C$_6$H$_4$—OCH$_2$CONH$_2$(3) | H | H | CH$_3$ |
| 49. | OCH$_2$C$_6$H$_4$—OCH$_2$CONH$_2$(4) | H | H | H |
| 50. | OCH$_2$C$_6$H$_4$—OCH$_2$CONH$_2$(4) | H | H | CH$_3$ |
| 51. | OCH$_2$C$_6$H$_3$—(CN)$_2$(3,5) | H | H | H |
| 52. | OCH$_2$C$_6$H$_3$—(CN)$_2$(3,5) | H | H | CH$_3$ |
| 53. | OCH$_2$C$_6$H$_3$—(CN)$_2$(3,5) | H | H | H |
| 54. | OCH$_2$C$_6$H$_3$—(CN)$_2$(3,5) | H | H | CH$_3$ |
| 55. | OCH$_2$C$_6$H$_3$—(CONH$_2$)$_2$(3,5) | H | H | H |
| 56. | OCH$_2$C$_6$H$_3$—(CONH$_2$)$_2$(3,5) | H | H | CH$_3$ |
| 57. | OCH$_2$C$_6$H$_3$—(CONH$_2$)$_2$(3,5) | H | H | H |
| 58. | OCH$_2$C$_6$H$_3$—(CONH$_2$)$_2$(3,5) | H | H | CH$_3$ |
| 59. | OCH$_2$CH$_2$C$_6$H$_5$ | H | H | H |
| 60. | OCH$_2$CH$_2$C$_6$H$_5$ | H | H | CH$_3$ |
| 61. | OCH$_2$C$_6$H$_4$C$_6$H$_4$CN(2) | H | H | H |
| 62. | OCH$_2$C$_6$H$_4$C$_6$H$_4$CN(2) | H | H | CH$_3$ |
| 63. | OCH$_2$C$_6$H$_4$C$_6$H$_4$CONH$_2$(2) | H | H | H |
| 64. | OCH$_2$C$_6$H$_4$C$_6$H$_4$CONH$_2$(2) | H | H | CH$_3$ |

TABLE VIIc

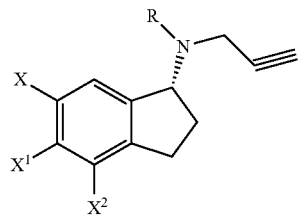

| Ex. # | $X^2$ | X | $X^1$ | R |
|---|---|---|---|---|
| 1. | $OCH_2CH=CH_2$ | H | H | H |
| 2. | $OCH_2CH=CH_2$ | H | H | $CH_3$ |
| 3. | $NHSO_2CH_3$ | H | H | H |
| 4. | $NHSO_2CH_3$ | H | H | $CH_3$ |
| 5. | $OCH_2C_6H_5$ | H | H | H |
| 6. | $OCH_2C_6H_5$ | H | H | $CH_3$ |
| 7. | $OCH_2C_6H_4$—Cl(3) | H | H | H |
| 8. | $OCH_2C_6H_4$—Cl(3) | H | H | $CH_3$ |
| 9. | $OCH_2C_6H_4$—Cl(4) | H | H | H |
| 10. | $OCH_2C_6H_4$—Cl(4) | H | H | $CH_3$ |
| 11. | $OCH_2C_6H_4$—F(3) | H | H | H |
| 12. | $OCH_2C_6H_4$—F(3) | H | H | $CH_3$ |
| 13. | $OCH_2C_6H_4$—F(4) | H | H | H |
| 14. | $OCH_2C_6H_4$—F(4) | H | H | $CH_3$ |
| 15. | $OCH_2C_6H_4$—$CF_3$(3) | H | H | H |
| 16. | $OCH_2C_6H_4$—$CF_3$(3) | H | H | $CH_3$ |
| 17. | $OCH_2C_6H_4$—$CF_3$(4) | H | H | H |
| 18. | $OCH_2C_6H_4$—$CF_3$(4) | H | H | $CH_3$ |
| 19. | $OCH_2C_6H_4$—$NO_2$(3) | H | H | H |
| 20. | $OCH_2C_6H_4$—$NO_2$(3) | H | H | $CH_3$ |
| 21. | $OCH_2C_6H_4$—$NO_2$(4) | H | H | H |
| 22. | $OCH_2C_6H_4$—$NO_2$(4) | H | H | $CH_3$ |
| 23. | $OCH_2C_6H_4$—$NHSO_2CH_3$(3) | H | H | H |
| 24. | $OCH_2C_6H_4$—$NHSO_2CH_3$(3) | H | H | $CH_3$ |
| 25. | $OCH_2C_6H_4$—$NHSO_2CH_3$(4) | H | H | H |
| 26. | $OCH_2C_6H_4$—$NHSO_2CH_3$(4) | H | H | $CH_3$ |
| 27. | $OCH_2C_6H_4$—CN(3) | H | H | H |
| 28. | $OCH_2C_6H_4$—CN(3) | H | H | $CH_3$ |
| 29. | $OCH_2C_6H_4$—CN(4) | H | H | H |
| 30. | $OCH_2C_6H_4$—CN(4) | H | H | $CH_3$ |
| 31. | $OCH_2C_6H_4$—$CONH_2$(3) | H | H | H |
| 32. | $OCH_2C_6H_4$—$CONH_2$(3) | H | H | $CH_3$ |
| 33. | $OCH_2C_6H_4$—$CONH_2$(4) | H | H | H |
| 34. | $OCH_2C_6H_4$—$CONH_2$(4) | H | H | $CH_3$ |
| 35. | $OCH_2C_6H_4$—$CH_2CN$(3) | H | H | H |
| 36. | $OCH_2C_6H_4$—$CH_2CN$(3) | H | H | $CH_3$ |
| 37. | $OCH_2C_6H_4$—$CH_2CN$(4) | H | H | H |
| 38. | $OCH_2C_6H_4$—$CH_2CN$(4) | H | H | $CH_3$ |
| 39. | $OCH_2C_6H_4$—$CH_2CONH_2$(3) | H | H | H |
| 40. | $OCH_2C_6H_4$—$CH_2CONH_2$(3) | H | H | $CH_3$ |
| 41. | $OCH_2C_6H_4$—$CH_2CONH_2$(4) | H | H | H |
| 42. | $OCH_2C_6H_4$—$CH_2CONH_2$(4) | H | H | $CH_3$ |
| 43. | $OCH_2C_6H_4$—$OCH_2CN$(3) | H | H | H |
| 44. | $OCH_2C_6H_4$—$OCH_2CN$(3) | H | H | $CH_3$ |
| 45. | $OCH_2C_6H_4$—$OCH_2CN$(4) | H | H | H |
| 46. | $OCH_2C_6H_4$—$OCH_2CN$(4) | H | H | $CH_3$ |
| 47. | $OCH_2C_6H_4$—$OCH_2CONH_2$(3) | H | H | H |
| 48. | $OCH_2C_6H_4$—$OCH_2CONH_2$(3) | H | H | $CH_3$ |
| 49. | $OCH_2C_6H_4$—$OCH_2CONH_2$(4) | H | H | H |
| 50. | $OCH_2C_6H_4$—$OCH_2CONH_2$(4) | H | H | $CH_3$ |
| 51. | $OCH_2C_6H_3$—$(CN)_2$(3,5) | H | H | H |
| 52. | $OCH_2C_6H_3$—$(CN)_2$(3,5) | H | H | $CH_3$ |
| 53. | $OCH_2C_6H_3$—$(CN)_2$(3,5) | H | H | H |
| 54. | $OCH_2C_6H_3$—$(CN)_2$(3,5) | H | H | $CH_3$ |
| 55. | $OCH_2C_6H_3$—$(CONH_2)_2$(3,5) | H | H | H |
| 56. | $OCH_2C_6H_3$—$(CONH_2)_2$(3,5) | H | H | $CH_3$ |
| 57. | $OCH_2C_6H_3$—$(CONH_2)_2$(3,5) | H | H | H |
| 58. | $OCH_2C_6H_3$—$(CONH_2)_2$(3,5) | H | H | $CH_3$ |
| 59. | $OCH_2CH_2C_6H_5$ | H | H | H |
| 60. | $OCH_2CH_2C_6H_5$ | H | H | $CH_3$ |
| 61. | $OCH_2C_6H_4C_6H_4CN$(2) | H | H | H |
| 62. | $OCH_2C_6H_4C_6H_4CN$(2) | H | H | $CH_3$ |
| 63. | $OCH_2C_6H_4C_6H_4CONH_2$(2) | H | H | H |
| 64. | $OCH_2C_6H_4C_6H_4CONH_2$(2) | H | H | $CH_3$ |

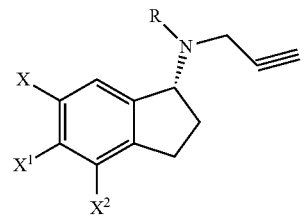

* * * * *

UNITED STATES PATENT AND TRADEMARK OFFICE
CERTIFICATE OF CORRECTION

PATENT NO. : 8,541,475 B2  
APPLICATION NO. : 12/650642  
DATED : September 24, 2013  
INVENTOR(S) : John Francis McElroy et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 304 days.

Signed and Sealed this  
Third Day of March, 2015

Michelle K. Lee  
*Deputy Director of the United States Patent and Trademark Office*